US008765727B2

(12) United States Patent
Combs et al.

(10) Patent No.: US 8,765,727 B2
(45) Date of Patent: Jul. 1, 2014

(54) MACROCYCLIC COMPOUNDS AND THEIR USE AS KINASE INHIBITORS

(75) Inventors: Andrew Paul Combs, Kennett Square, PA (US); Richard B. Sparks, Boothwyn, PA (US); Eddy Wai Tsun Yue, Landenberg, PA (US); Hao Feng, Aston, PA (US); Michael Jason Bower, Newark, DE (US); Wenyu Zhu, Media, PA (US)

(73) Assignee: Incyte Corporation, Wilmington, DE (US)

( * ) Notice: Subject to any disclaimer, the term of this patent is extended or adjusted under 35 U.S.C. 154(b) by 848 days.

(21) Appl. No.: 12/692,078

(22) Filed: Jan. 22, 2010

(65) Prior Publication Data

US 2011/0251215 A9    Oct. 13, 2011

Related U.S. Application Data

(60) Provisional application No. 61/146,824, filed on Jan. 23, 2009.

(51) Int. Cl.
*A61K 31/33* (2006.01)
*C07D 487/00* (2006.01)

(52) U.S. Cl.
USPC .......................... 514/183; 540/471; 540/472

(58) Field of Classification Search
None
See application file for complete search history.

(56) References Cited

U.S. PATENT DOCUMENTS

| 7,598,257 B2 | 10/2009 | Rodgers et al. |
| 2004/0198737 A1 | 10/2004 | Cox et al. |

FOREIGN PATENT DOCUMENTS

| WO | 9962908 | 12/1999 | |
| WO | 9965909 | 12/1999 | |
| WO | 0142246 | 6/2001 | |
| WO | 2004026881 | 4/2004 | |
| WO | 2004072063 | 8/2004 | |
| WO | 2004079326 | 9/2004 | |
| WO | 2004099204 | 11/2004 | |
| WO | 2004099205 | 11/2004 | |
| WO | 2004105765 | 12/2004 | |
| WO | WO 2005005551 | * 1/2005 | .............. C09B 62/04 |
| WO | 2005058913 | 6/2005 | |
| WO | 2006061415 | 6/2006 | |
| WO | 2007003525 | 1/2007 | |
| WO | 2009112439 | 9/2009 | |
| WO | 2009132202 | 10/2009 | |

OTHER PUBLICATIONS

"Cancer Prevention Overview", http://www.cancer.gov/cancertopics/pdq/prevention/overview/patient, accessed Apr. 9, 2012.*

Blume-Jensen et al., "Oncogenic kinase signalling," Nature (2001) 411(6835):355-365.
Bolen "Non-receptor tyrosine protein kinases," Oncogene (1993) 8(8):2025-31.
Boudny et al., "JAK/STAT signaling pathways and cancer*," Neoplasma (2002) 49(6):349-355.
Bowman et al. "STATs in oncogenesis," Oncogene (2000) 19(21):2474-2488.
Candotti et al., "Structural and functional basis for JAK3-deficient severe combined immunodeficiency." Blood (1997) 90(10):3996-4003.
Candotti et al. "Molecular aspects of primary immunodeficiencies: lessons from cytokine and other signaling pathways." J Clin Invest (2002) 109(10):1261-9.
Cetkovic-Cvrlje et al. "Targeting JAK3 with JANEX-1 for prevention of autoimmune type 1 diabetes in NOD mice," Clin Immunol (2003) 106(3):213-25.
Godshall et al., "Jaks, STATs, Cytokines, and Sepsis," Clin Diagn Lab Immunol (2002) 9(6):1153-9.
Gottlieb et al., "Psoriasis: emerging therapeutic strategies," Nat Rev Drug Disc. (2005) 4(1):19-34.
Kawamura et al., "Molecular cloning of L-JAK, a Janus family protein-tyrosine kinase expressed in natural killer cells and activated leukocytes," Proc Natl Acad Sci USA (1994) 91(14):6374-8.
Kimball et al., "Safety and efficacy of ABT-874, a fully human interleukin 12/23 monoclonal antibody, in the treatment of moderate to severe chronic plaque psoriasis: results of a randomized, placebo-controlled, phase 2 trial," Arch Dermatol. (2008) 144(2):200-7.
Lemp, "The Definition and Classification of Dry Eye Disease: Report of the Definition and Classification Subcommittee of the International Dry Eye WorkShop," The Ocular Surface (2007) 5(2)75-92.
Levin et al., "Activating mutation in the tyrosine kinase JAK2 in polycythemia vera, essential thrombocythemia, and myeloid metaplasia with myelofibrosis," Cancer Cell (2005) 7(4):387-397.
Macchi et al. "Mutations of Jak-3 gene in patients with autosomal severe combined immune deficiency (SCID)," Nature (1995) 337(6544):65-68.

(Continued)

*Primary Examiner* — Noble Jarrell
(74) *Attorney, Agent, or Firm* — Pepper Hamilton LLP

(57) ABSTRACT

The present invention relates to macrocyclic compounds of Formula I:

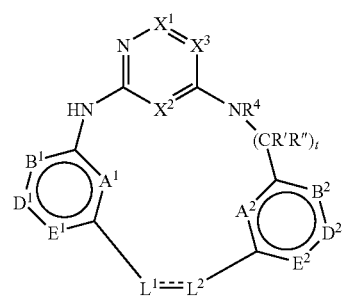

or pharmaceutically acceptable salts thereof or quaternary ammonium salts thereof wherein constituent members are provided herewith, as well as their compositions and methods of use, which are JAK/ALK inhibitors useful in the treatment of JAK/ALK-associated diseases including, for example, inflammatory and autoimmune disorders, as well as cancer.

64 Claims, No Drawings

(56) References Cited

OTHER PUBLICATIONS

Manning, G. et al., "The protein kinase complement of the human genome," Science (2002) 298(5600):1912-1934.

Madhusudan et al., "Tyrosine kinase inhibitors in cancer therapy," Clin Biochem. (2004) 37(7):618-35.

Neubauer et al. "Jak2 deficiency defines an essential developmental checkpoint in definitive hematopoiesis," (1998) Cell 93(3):397-409.

Ortmann, R. A., T. Cheng, et al. (2000). "Janus kinases and signal transducers and activators of transcription: their roles in cytokine signaling, development and immunoregulation." Arthritis Res 2(1):16-32.

Parganas et al., "Jak2 is essential for signaling through a variety of cytokine receptors," Cell (1998) 93(3):385-95.

Pedranzini et al., "Pyridone 6, a pan-Janus-activated kinase inhibitor, induces growth inhibition of multiple myeloma cells," Cancer Research (2006) 66(19):9714-21.

Pernis et al. "JAK-STAT signaling in asthma," J Clin Invest (2002) 109(10):1279-83.

Rodig et al. "Disruption of the Jak1 gene demonstrates obligatory and non-redundant roles of the Jaks in cytokine-induced biologic responses," Cell (1998) 93(3):373-83.

Saemann et al. "Prevention of CD40-triggered dendritic cell maturation and induction of T-cell hyporeactivity by targeting of Janus kinase 3," Am J Transplant (2003) 3(11):1341-9.

Scott et al., "Jaks STATs, Cytokines, and Sepsis," Clinical and Diagnostic Laboratory Immunology (2002) 9 (6):1153-1159.

Soda et al, "Identification of the transforming EML4-ALK fusion gene in non-small-cell lung cancer," Nature (2007)448 (7153):561-566.

Tefferi "JAK and MPL mutations in myeloid malignancies," Leukemia & Lymphoma (2008) 49(3):388-397.

Takemoto et al. "Proliferation of adult T cell leukemia/lymphoma cells is associated with the constitutive activation of JAK/STAT proteins," Proc Natl Acad Sci USA (1997) 94(25):13897-902.

Schindler et al., "Cytokines and STAT signaling," Adv Pharmacol. (2000) 47:113-74.

Nickoloff et al., Recent insights into the immunopathogenesis of psoriasis provide new therapeutic opportunities, JCI (2004) 113(12):1664-1675.

Seto et al,. "Enhanced Th2 cell-mediated allergic inflammation in Tyk2-deficient mice," J Immunol (2003) 170 (2):1077-83.

International Search Report dated Jul. 7, 2010 received in International Application No. PCT/US2010/021720.

Non-Final Office Action dated Feb. 28, 2012 received in copending U.S. Appl. No. 12/429,014.

Final Office Action dated Oct. 16, 2012 received in copending U.S. Appl. No. 12/429,014.

Final Office Action dated Nov. 12, 2013 received in copending U.S. Appl. No. 12/429,014.

* cited by examiner

MACROCYCLIC COMPOUNDS AND THEIR USE AS KINASE INHIBITORS

This application claims benefit of priority to U.S. provisional patent application Ser. No. 61/146,824 filed Jan. 23, 2009, which is hereby incorporated by reference in its entirety.

FIELD OF THE INVENTION

The present invention relates to macrocyclic compounds, and compositions thereof as well as methods of use the same for treatment of Janus Kinase and/or Anaplastic Lymphoma Kinase (JAK/ALK)-associated diseases including, for example, inflammatory disorders, autoimmune disorders, skin disorders, myeloid proliferative disorders, as well as cancer.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or other substrates such as lipids) and thereby modulating the cellular activities of the substrates in various biological contexts. In addition to the functions in normal tissues/organs, many protein kinases also play a central role in a host of human diseases including cancer. A subset of protein kinases (also referred to as oncogenic protein kinases), when dysregulated, can cause tumor formation and inappropriate tumor cell survival and proliferation, and further contribute to tumor progression [See e.g. Blume-Jensen P. et al, Nature 2001, 411(6835):355-365]. Thus far, oncogenic protein kinases represent one of the largest and most attractive groups of protein targets for cancer intervention and drug development.

Protein kinases can be categorized as receptor type and non-receptor type. Receptor tyrosine kinases (RTKs) have an extracellular portion, a transmembrane domain, and an intracellular portion, while non-receptor tyrosine kinases are entirely intracellular. RTK mediated signal transduction is typically initiated by extracellular interaction with a specific growth factor (ligand), typically followed by receptor dimerization, stimulation of the intrinsic protein tyrosine kinase activity, and receptor transphosphorylation. Binding sites are thereby created for intracellular signal transduction molecules and lead to the formation of complexes with a spectrum of cytoplasmic signaling molecules that facilitate cellular responses such as cell survival, proliferation, differentiation, metabolic effects, and changes in the extracellular microenvironment.

At present, at least nineteen (19) distinct RTK subfamilies have been identified. One RTK subfamily, designated the HER subfamily, includes EGFR, HER2, HER3 and HER4, and bind such ligands as epithelial growth factor (EGF), TGF-α, amphiregulin, HB-EGF, betacellulin and heregulin. A second family of RTKs, designated the insulin subfamily, includes the INS-R, the IGF-1R and the IR-R. A third family, the "PDGF" subfamily, includes the PDGF alpha and beta receptors, CSFIR, c-kit and FLK-II. Another subfamily of RTKs, referred to as the FLK subfamily, encompasses the Kinase insert Domain-Receptor fetal liver kinase-1 (KDR/FLK-1), the fetal liver kinase 4 (FLK-4) and the fms-like tyrosine kinase 1 (flt-1). Two other subfamilies of RTKs have been designated as the FGF receptor family (FGFR1, FGFR2, FGFR3 and FGFR4) and the Met subfamily (c-Met, Ron and Sea). For a detailed discussion of protein kinases, see for example, Blume-Jensen, P. et al., Nature. 2001, 411(6835): 355-365, and Manning, G. et al., Science. 2002, 298(5600): 1912-1934.

The non-receptor type of tyrosine kinases are also composed of numerous sub-families, including Src, Btk, Abl, Fak, and Jak. Each of these subfamilies can be further subdivided into multiple members that have been frequently linked to oncogenesis. The Src family, for example, is the largest and includes Src, Fyn, Lck and Fgr among others. For a detailed discussion of these kinases, see Bolen J B, "Non-receptor tyrosine protein kinases," Oncogene., 1993, 8(8):2025-31.

A significant number of tyrosine kinases (both receptor and nonreceptor) are associated with cancer (see Madhusudan S, Ganesan T S. Tyrosine kinase inhibitors in cancer therapy. Clin Biochem. 2004, 37(7):618-35.). Clinical studies suggest that overexpression or dysregulation of tyrosine kinases may also be of prognostic value. For example, members of the HER family of RTKs have been associated with poor prognosis in breast, colorectal, head and neck and lung cancer. Mutation of c-Kit tyrosine kinase has been associated with decreased survival in gastrointestinal stromal tumors. In acute myelogenous leukemia (AML), Flt-3 mutation predicts shorter disease free survival. VEGFR expression, which is important for tumor angiogenesis, is associated with a lower survival rate in lung cancer. Tie-1 kinase expression inversely correlates with survival in gastric cancer. BCR-Abl expression is an important predictor of response in chronic myelogenous leukemia (CML) and Src tyrosine kinase is an indicator of poor prognosis in all stages of colorectal cancer.

The immune system responds to injury and threats from pathogens. Cytokines are low-molecular weight polypeptides or glycoproteins that stimulate biological responses in virtually all cell types. For example, cytokines regulate many of the pathways involved in the host inflammatory response to sepsis. Cytokines influence cell differentiation, proliferation and activation, and they can modulate both proinflammatory and anti-inflammatory responses to allow the host to react appropriately to pathogens.

Binding of a cytokine to its cell surface receptor initiates intracellular signaling cascades that transduce the extracellular signal to the nucleus, ultimately leading to changes in gene expression. The pathway involving the Janus kinase family of protein tyrosine kinases (JAKs) and Signal Transducers and Activators of Transcription (STATs) is engaged in the signaling of a wide range of cytokines. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs, and other proteins, recognize these phosphotyrosine motifs and are recruited to the receptor where they are activated by a JAK-dependent tyrosine phosphorylation events. Upon activation, STATs dissociate from the receptors and translocate to the nucleus to bind to specific DNA sites and alter transcription [Scott, M. J., C. J. Godshall, et al. (2002). "Jaks, STATs, Cytokines, and Sepsis." Clin Diagn Lab Immunol 9(6): 1153-9].

The Janus Kinase (JAK) family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra).

While JAK1, JAK2 and TYK2 are widely expressed, JAK3 is reported to be preferentially expressed in natural killer (NK) cells and activated T cells, suggesting a role in lymphoid activation (Kawamura, M., D. W. McVicar, et al. (1994). "Molecular cloning of L-JAK, a Janus family protein-tyrosine kinase expressed in natural killer cells and activated leukocytes." *Proc Natl Acad Sci USA* 91(14): 6374-8).

Not only do the cytokine-stimulated immune and inflammatory responses contribute to normal host defense, they also play roles in the pathogenesis of diseases. Pathologies such as severe combined immunodeficiency (SCID) can arise from hypoactivity, e.g. the inability of various cytokines to signal through JAK3 (Macchi, et al. Nature, 337:65-68, 1995). In contrast, hyperactive or inappropriate immune/inflammatory responses can contribute to the pathology of autoimmune diseases such as rheumatoid and psoriatic arthritis, asthma and systemic lupus erythematosus, inflammatory bowel disease, multiple sclerosis, type I diabetes mellitus, myasthenia gravis, thyroiditis, immunoglobulin nephropathies, myocarditis as well as illnesses such as scleroderma and osteoarthritis (Ortmann, R. A., T. Cheng, et al. (2000). "Janus kinases and signal transducers and activators of transcription: their roles in cytokine signaling, development and immunoregulation." *Arthritis Res* 2(1): 16-32). Furthermore, syndromes with a mixed presentation of autoimmune and immunodeficiency disease are quite common (Candotti, F., L. Notarangelo, et al. (2002). "Molecular aspects of primary immunodeficiencies: lessons from cytokine and other signaling pathways." *J Clin Invest* 109(10): 1261-9). Thus, therapeutic agents are typically aimed at augmentation or suppression of the immune and inflammatory pathways, accordingly.

Deficiencies in expression of various JAK family members have been associated with pathologies in rodents. Jak1−/− mice are runted at birth, fail to nurse, and die perinatally (Rodig, S. J., M. A. Meraz, et al. (1998). "Disruption of the Jak1 gene demonstrates obligatory and non-redundant roles of the Jaks in cytokine-induced biologic responses." *Cell* 93(3): 373-83). Jak2−/− mouse embryos are anemic and die around day 12.5 postcoitum due to the absence of definitive erythropoiesis. In addition, JAK2 deficiency resulted in cell-type specific deficiencies in the signaling of some cytokines such as those required for definitive erythropoiesis (Neubauer, H., A. Cumano, et al. (1998). Cell 93(3): 397-409; Parganas, E., D. Wang, et al. (1998). *Cell* 93(3): 385-95.). JAK3 appears to play a role in normal development and function of B and T lymphocytes. Mutations of JAK3 are reported to be responsible for autosomal recessive severe combined immunodeficiency (SCID) in humans (Candotti, F., S. A. Oakes, et al. (1997). "Structural and functional basis for JAK3-deficient severe combined immunodeficiency." *Blood* 90(10): 3996-4003).

The JAK/STAT pathway, and in particular all four members of the JAK family, are believed to play a role in the pathogenesis of the asthmatic response, chronic obstructive pulmonary disease, bronchitis other related inflammatory diseases of the lower respiratory tract, inflammatory diseases or conditions of the upper respiratory tract such as those affecting the nose and sinuses (e.g. rhinitis, sinusitis) whether classically allergic reactions or not, Systemic Inflammatory Response Syndrome (SIRS), and septic shock. See e.g., Pernis, A. B. and P. B. Rothman, "JAK—STAT signaling in asthma," J Clin Invest 109(10): 1279-83 (2002); and Seto, Y., H. Nakajima, et al, "Enhanced Th2 cell-mediated allergic inflammation in Tyk2-deficient mice." J Immunol 170(2): 1077-83 (2003).

The JAK/STAT pathway has also been implicated to play a role in inflammatory diseases/conditions of the eye including, but not limited to, dry eye disorder, iritis, uveitis, scleritis, conjunctivitis, as well as chronic allergic responses. Therefore, inhibition of JAK kinases may have a beneficial role in the therapeutic treatment of these diseases.

As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye WorkShop", *The Ocular Surface,* 5(2), 75-92 April 2007, which is incorporated herein by reference in its entirety. Dry eye is also sometimes referred to as keratoconjunctivitis sicca. In some embodiments, the treatment of the dry eye disorder involves ameliorating a particular symptom of dry eye disorder, such as eye discomfort, visual disturbance, tear film instability, tear hyperosmolarity, and inflammation of the ocular surface.

The JAK/STAT pathway also plays a role in cancers of the immune system. In adult T cell leukemia/lymphoma (ATLL), human CD4+ T cells acquire a transformed phenotype, an event that correlates with acquisition of constitutive phosphorylation of JAKs and STATs. Furthermore, an association between JAK3 and STAT-1, STAT-3, and STAT-5 activation and cell-cycle progression was demonstrated by both propidium iodide staining and bromodeoxyuridine incorporation in cells of four ATLL patients tested. These results imply that JAK/STAT activation is associated with expansion of leukemic cells and that therapeutic approaches aimed at JAK/STAT inhibition may be considered to halt neoplastic growth (Takemoto, S., J. C. Mulloy, et al. (1997). "Proliferation of adult T cell leukemia/lymphoma cells is associated with the constitutive activation of JAK/STAT proteins." *Proc Natl Acad Sci USA* 94(25): 13897-902).

Blocking cytokine and growth factor signal transduction at the level of the JAK kinases holds promise for the treatment of a number of human cancers. For example, cytokines of the interleukin 6 (IL-6) family, which activate the signal transducer gp130, are major survival and growth factors for human multiple myeloma (MM) cells. The signal transduction of gp130 is believed to involve JAK1, JAK2 and Tyk2 and the downstream effectors STAT3 and the mitogen-activated protein kinase (MAPK) and AKT pathways. In IL-6-dependent MM cell lines treated with the JAK2 inhibitor pyridone 6 STAT3 phosphorylation and tumor cell proliferation and survival were inhibited (Pedranzini, L, et al, Cancer Research 66:9714-21, 2006.

Activation of JAK/STAT in cancers may occur by multiple mechanisms including cytokine stimulation (e.g. IL-6 or GM-CSF) or by a reduction in the endogenous suppressors of JAK signaling such as SOCS (suppressor of cytokine signaling) or PIAS (protein inhibitor of activated STAT) (Boudny, V., and Kovarik, J., *Neoplasm.* 49:349-355, 2002). Importantly, activation of STAT signaling, as well as other pathways downstream of JAKs (e.g. Akt), has been correlated with poor prognosis in many cancer types (Bowman, T., et al. *Oncogene* 19:2474-2488, 2000). Moreover, elevated levels of circulating cytokines that signal through JAK/STAT may adversely impact patient health as they are thought to play a causal role in cachexia and/or chronic fatigue. As such, JAK inhibition may be therapeutic for the treatment of cancer patients for reasons that extend beyond potential anti-tumor activity. The cachexia indication may gain further mechanistic support with the realization that the satiety factor leptin signals through JAKs.

Pharmacological targeting of Janus kinase 3 (JAK3) has been employed successfully to control allograft rejection and graft versus host disease (GVHD). In addition to its involvement in signaling of cytokine receptors, JAK3 is also engaged in the CD40 signaling pathway of peripheral blood monocytes. During CD40-induced maturation of myeloid dendritic cells (DCs), JAK3 activity is induced, and increases in costimulatory molecule expression, IL-12 production, and potent allogeneic stimulatory capacity are observed. A rationally designed JAK3 inhibitor WHI-P-154 prevented these effects arresting the DCs at an immature level, suggesting that immunosuppressive therapies targeting the tyrosine kinase JAK3 may also affect the function of myeloid cells (Saemann, M. D., C. Diakos, et al. (2003). "Prevention of CD40-triggered dendritic cell maturation and induction of T-cell hyporeactivity by targeting of Janus kinase 3." *Am J Transplant* 3(11): 1341-9). In the mouse model system, JAK3 was also shown to be an important molecular target for treatment of autoimmune insulin-dependent (type 1) diabetes mellitus. The rationally designed JAK3 inhibitor JANEX-1 exhibited potent immunomodulatory activity and delayed the onset of diabetes in the NOD mouse model of autoimmune type 1 diabetes (Cetkovic-Cvrlje, M., A. L. Dragt, et al. (2003). "Targeting JAK3 with JANEX-1 for prevention of autoimmune type 1 diabetes in NOD mice." *Clin Immunol* 106(3): 213-25).

It has been suggested that inhibition of JAK2 tyrosine kinase can be beneficial for patients with myeloproliferative disorders. (Levin, et al., *Cancer Cell, vol.* 7, 2005: 387-397) Myeloproliferative disorders (MPD) include polycythemia vera (PV), essential thrombocythemia (ET), myelofibrosis with myeloid metaplasia (MMM), chronic myelogenous leukemia (CML), chronic myelomonocytic leukemia (CMML), hypereosinophilic syndrome (HES), systemic mast cell disease (SMCD) and the like. Although myeloproliferative disorders (such as PV, ET and MMM) are thought to be caused by acquired somatic mutation in hematopoietic progenitors, the genetic basis for these diseases has not been known. However, it has been reported that hematopoietic cells from a majority of patients with PV and a significant number of patients with ET and MMM possess a recurrent somatic activating mutation in the JAK2 tyrosine kinase. It has also been reported that inhibition of the JAK2V617F kinase with a small molecule inhibitor leads to inhibition of proliferation of hematopoietic cells, suggesting that the JAK2 tyrosine kinase is a potential target for pharmacologic inhibition in patients with PV, ET and MMM. In addition, mutations in the receptor for thrombopoietin have also been described in MPD patients and due to the requirement of JAK2 for this receptor to signal, inhibition of JAKs may be therapeutic (Tefferi, A. *Leukemia & Lymphoma*, March 2008; 49(3): 388-397).

Inhibition of the JAK kinases is also envisioned to have therapeutic benefits in patients suffering from skin immune disorders such as psoriasis, and skin sensitization. In psoriasis vulgaris, the most common form of psoriasis, it has been generally accepted that activated T lymphocytes are important for the maintenance of the disease and its associated psoriatic plaques (Gottlieb, A. B., et al, *Nat Rev Drug Disc.,* 4:19-34). Psoriatic plaques contain a significant immune infiltrate, including leukocytes and monocytes, as well as multiple epidermal layers with increased keratinocyte proliferation. While the initial activation of immune cells in psoriasis occurs by an ill defined mechanism, the maintenance is believed to be dependent on a number of inflammatory cytokines, in addition to various chemokines and growth factors (JCI, 113:1664-1675). Many of these, including interleukins-2, -4, -6, -7, -12, -15, -18, and -23 as well as GM-CSF and IFNg, signal through the Janus (JAK) kinases (*Adv Pharmacol.* 2000; 47:113-74). As such, blocking signal transduction at the level of JAK kinases may result in therapeutic benefits in patients suffering from psoriasis or other immune disorders of the skin (Kimbal, A. B., et al. Arch Dermatol. 2008 February; 144(2):200-7).

It has been known that certain therapeutics can cause immune reactions such as skin rash or diarrhea in some patients. For instance, administration of some of the new targeted anti-cancer agents such as Iressa, Erbitux, and Tarceva has induced acneiform rash with some patients. Another example is that some therapeutics used topically induce skin irritation, skin rash, contact dermatitis or allergic contact sensitization. For some patients, these immune reactions may be bothersome, but for others, the immune reactions such as rash or diarrhea may result in the inability to continue treatment. Although the driving force behind these immune reactions has not been elucidated completely at the present time, these immune reactions are likely linked to immune infiltrate.

Inhibitors of Janus kinases or related kinases are widely sought and several publications report effective classes of compounds. For example, certain inhibitors are reported in WO 99/65909, US 2004/0198737; WO 2004/099204; WO 2004/099205; and WO 01/42246. Heteroaryl substituted pyrroles and other compounds are reported in WO 2004/72063 and WO 99/62908. For another example, certain JAK inhibitors, including pyrrolopyridine and pyrrolopyrimidines, are reported in U.S. Ser. No. 11/637, 545, filed Dec. 12, 2006.

Anaplastic lymphoma kinase (ALK), is a receptor tyrosine kinase, believed to play an important role in the development and function of the nervous system. ALK is normally expressed in the central nervous system, with peak expression during the neonatal period. However, due to chromosomal translocations, ALK is also aberrantly expressed and activated in some cancers in the form of oncogenic fusion proteins. ALK fusion proteins are responsible for approximately 5-10% of all non-Hodgkin's lymphomas. Additional mutations/translocations and increased expression have also been identified in lung cancer and neurological tumors (Soda, M., et al. Nature 448:561-566, 2007 and Mosse, Y P, AACR 2008). Accordingly, ALK inhibitors are useful for the treatment of ALK-related tumors, including anaplastic large cell lymphomas and non-Hodgkin lymphomas in addition to skin diseases and lung cancers.

The annual incidence of ALK positive lymphomas is about 100,000 worldwide. ALK is an excellent candidate for therapeutic intervention, as it plays an essential role in oncogenicity and its normal expression is mostly restricted to the central nervous system.

Hence, a specific ALK inhibitor could be an efficient treatment for ALK positive lymphomas with few associated clinical side effects. Accordingly, potential ALK inhibitors are highly desirable as potential treatments of ALK-related diseases/tumors. For example, certain ALK inhibitors such staurosporine derivatives are reported in WO2004079326.

Thus, new or improved agents which inhibit kinases such as Janus kinases and/or ALK are continually needed for developing new and more effective pharmaceuticals to treat cancer, myeloproliferative disorders, autoimmune diseases, and inflammatory diseases, to name a few. The compounds, compositions and methods described herein are directed toward these needs and other ends.

SUMMARY OF THE INVENTION

The present invention provides, inter alia, compounds of Formula I:

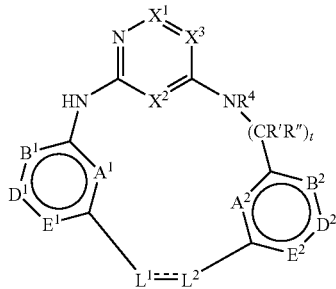

or pharmaceutically acceptable salts thereof or quaternary ammonium salts thereof, wherein constituent members are provided below.

The present invention further provides pharmaceutical compositions comprising a compound of Formula I, or pharmaceutically acceptable salt thereof, and at least one pharmaceutically acceptable carrier.

The present invention further provides methods of modulating an activity of one or more JAK/ALK kinases, comprising contacting the kinases with a compound of Formula I, or pharmaceutically acceptable salt of the same.

The present invention further provides methods of inhibiting an activity of one or more JAK/ALK kinases, comprising contacting the kinases with a compound of Formula I, or pharmaceutically acceptable salt of the same.

The present invention further provides methods of treating one or more of the various JAK/ALK-associated conditions, diseases and disorders named herein by administering to a patient a therapeutically effective amount of a compound of Formula I, or pharmaceutically acceptable salt of the same.

The present invention further provides compounds of Formula I, or pharmaceutically acceptable salts thereof, for use in therapy.

The present invention further provides use of the compounds of Formula I, or pharmaceutically acceptable salts thereof, for the manufacture/preparation of a medicament for use in therapy.

DETAILED DESCRIPTION

The present invention provides, inter alia, compounds of Formula I:

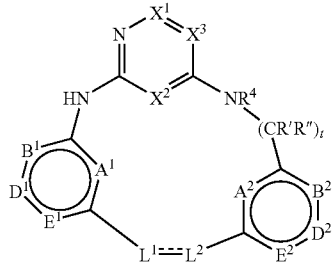

or pharmaceutically acceptable salts thereof or quaternary ammonium salts thereof, wherein:

----- represents a single bond or a double bond;

$X^1$ is N or $CR^1$;

$X^2$ is N or $CR^2$;

$X^3$ is N or $CR^3$;

$A^1$ and $A^2$ are each, independently, selected from $CR^2$, N, $NR^6$, O, and S;

$B^1$, $B^2$, $E^1$, and $E^2$ are each, independently, selected from $CR^5$, N, $NR^6$, O, and S;

$D^1$ and $D^2$ are each, independently, selected from a bond, $CR^5$, N, $NR^6$, O, and S;

wherein the ring containing $A^1$, $B^1$, $D^1$, and $E^1$ is a 5- or 6-membered aromatic ring and wherein the ring containing $A^2$, $B^2$, $D^2$, and $E^2$ is a 5- or 6-membered aromatic ring;

$L^1$ and $L^2$ are each, independently selected from a bond, $-(CR^7R^8)_n-$, $-O-(CR^7R^8)_m-CR^{10}=$, $-S-(CR^7R^8)_m-CR^{10}=$, $-(CR^7R^8)_m-CR^{10}=$, $-(CR^7R^8)_m-NR^9-$, $-(CR^7R^8)_m-N=$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-NR^9C(O)NR^9-$, $-(CR^7R^8)_m-OC(O)NR^9-$, $-(CR^7R^8)_m-NR^9C(O)O-$, $-(CR^7R^8)_m-NR^9-S(O)_2NR^9-$, $-(CR^7R^8)_m-S(O)NR^9-$, and $-(CR^7R^8)_m-S(O)_2NR^9-$;

wherein at least one of $L^1$ and $L^2$ is other than a bond;

R' and R" are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

or R' and R" together with the C atom to which they are attached form a 3-, 4-, 5-, 6-, 7-, 8-, 9- or 10-membered cycloalkyl group or heterocycloalkyl group, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2 NR^{c2}R^{d2}$;

R$^1$ and R$^3$ are each, independently, selected from H, halo, C$_{1-6}$ alkyl, C$_{2-6}$ alkenyl, C$_{2-6}$ alkynyl, C$_{1-6}$ haloalkyl, CN, NO$_2$, SF$_5$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

each R$^2$ is, independently, selected from H, halo, C$_{1-6}$ alkyl, C$_{2-6}$ alkenyl, C$_{2-6}$ alkynyl, C$_{1-6}$ haloalkyl, CN, NO$_2$, SF$_5$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

each R$^5$ is, independently, H, Cy$^1$, halo, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, halosulfanyl, CN, NO$_2$, SF$_5$, OR$^{a1}$, SR$^{a1}$, C(O)R$^{b1}$, C(O)NR$^{c1}$R$^{d1}$, C(S)R$^{b1}$, C(S)NR$^{c1}$R$^{d1}$, C(O)OR$^{a1}$, OC(O)R$^{b1}$, —W$^1$-Q$^1$-Y$^1$—Z$^1$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(S)R$^{b1}$, NR$^{c1}$C(S)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, or P(O)OR$^{e1}$OR$^{f1}$, wherein each of said C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, or heterocycloalkylalkyl, is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, Cy$^1$, halosulfanyl, CN, NO$_2$, SF$_5$, OR$^{a1}$, SR$^{a1}$, C(O)R$^{b1}$, C(O)NR$^{c1}$R$^{d1}$, C(S)R$^{b1}$, C(S)NR$^{c1}$R$^{d1}$, C(O)OR$^{a1}$, OC(O)R$^{b1}$, —W$^1$-Q$^1$-Y$^1$—Z$^1$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(S)R$^{b1}$, NR$^{c1}$C(S)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$; or two adjacent R$^5$ on the same ring can link to form a fused cycloalkyl or fused heterocycloalkyl group, each optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, halosulfanyl, Cy$^1$, CN, NO$_2$, OR$^{a1}$, SR$^{a1}$, C(O)R$^{b1}$, C(O)NR$^{c1}$R$^{d1}$, SF$_5$, C(S)R$^{b1}$, C(S)NR$^{c1}$R$^{d1}$, C(O)OR$^{a1}$, OC(O)R$^{b1}$, —W$^1$-Q$^1$-Y$^1$—Z$^1$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(S)R$^{b1}$, NR$^{c1}$C(S)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$, wherein each of said C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, or heterocycloalkylalkyl, is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, Cy$^1$, —W$^1$-Q$^1$-Y$^1$—Z$^1$, halosulfanyl, CN, NO$_2$, SF$_5$, OR$^{a1}$, SR$^{a1}$, C(O)R$^{b1}$, C(O)NR$^{c1}$R$^{d1}$, C(O)OR$^{a1}$, OC(O)R$^{b1}$, OCH$_2$C(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)$_2$R$^{b1}$, NR$^{c2}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$;

R$^4$ and R$^6$ are each, independently, selected from H, Cy$^2$, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, —W$^2$—X$^2$—Y$^2$—Z$^2$, C(O)R$^{b1}$, C(O)NR$^{c1}$R$^{d1}$, C(O)OR$^{a2}$, C(=NR$^g$)NR$^{c1}$R$^{d1}$, S(O)R$^{b1}$, S(O)NR$^{c1}$R$^{d1}$, S(O)$_2$R$^{b1}$, S(O)$_2$ NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$, wherein each of said C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, Cy$^2$, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, —W$^2$-Q$^2$-Y$^2$—Z$^2$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c2}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$;

R$^7$, R$^8$, and R$^{10}$ are each, independently, selected from H, Cy$^3$, halo, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, —W$^3$-Q$^3$-Y$^3$—Z$^3$, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a2}$, C(=NR$^{g1}$)NR$^{c1}$R$^{d1}$, NR$^{c1}$C(=NR$^{g1}$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c2}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$, wherein each of said C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, Cy$^3$, —W$^3$-Q$^3$-Y$^3$—Z$^3$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$;

each R$^9$ is, independently, H, Cy$^4$, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, —W$^4$-Q$^4$-Y$^4$—Z$^4$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{g1}$)NR$^{c1}$R$^{d1}$, S(O)R$^{b1}$, S(O)NR$^{c1}$R$^{d1}$, S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, or P(O)OR$^{e1}$OR$^{f1}$ wherein each of said C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, Cy$^4$, —W$^4$-Q$^4$-Y$^4$—Z$^4$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^{g1}$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$;

R$^{11a}$, R$^{11b}$, R$^{12a}$, R$^{12b}$, and R$^{13}$ are each, independently, selected from H, Cy$^3$, halo, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)

$R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, —$W^3$-$Q^3$-$Y^3$—$Z^3$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$W^1$, $W^2$, $W^3$, $W^4$, and $W^5$ are each, independently, selected from absent, $W^6$, $C_{1-6}$ alkylenyl, $C_{2-6}$ alkenylenyl, $C_{2-6}$ alkynylenyl, $(CR^{11a}R^{11b})_{p1}O(CR^{11a}R^{11b})_{p2}$, $(CR^{11a}R^{11b})_{p1}S(CR^{11a}R^{11b})_{p2}$, $(CR^{11a}R^{11b})_{p1}NR^e(CR^{11a}R^{11b})_{p2}$, $(CR^{11a}R^{11b})_{p1}C(O)(CR^{11a}R^{11b})_{p2}$, $(CR^{11a}R^{11b})_{p1}C(S)(CR^{11a}R^{11b})_{p2}$, $(CR^{11a}R^{11b})_{p1}C(O)O(CR^{11a}R^{11b})_{p2}$, $(CR^{11a}R^{11b})_{p1}C(O)NR^e(CR^{11a}R^{11b})_{p2}$, $(CR^{11a}R^{11b})_{p1}C(S)NR^e(CR^{11a}R^{11b})_{p2}$, $(CR^{11a}R^{11b})_{p1}S(O)(CR^{11a}R^{11b})_{p2}$, $(CR^{11a}R^{11b})_{p1}S(O)_2(CR^{11a}R^{11b})_{p2}$, $(CR^{11a}R^{11b})_{p1}S(O)NR^e(CR^{11a}R^{11b})_{p2}$, $(CR^{11a}R^{11b})_{p1}S(O)_2NR^e(CR^{11a}R^{11b})_{p2}$, $(CR^{11a}R^{11b})_{p1}NR^cC(O)NR^f(CR^{11a}R^{11b})_{p2}$, $(CR^{11a}R^{11b})_{p1}NR^eC(S)NR^f(CR^{11a}R^{11b})_{p2}$, $(CR^{11a}R^{11b})_{p1}NR^eS(O)_2NR^f(CR^{11a}R^{11b})_{p2}$, $(CR^{11a}R^{11b})_{p1}C(=NR^g)NR^e(CR^{11a}R^{11b})_{p2}$, $(CR^{11a}R^{11b})_{p1}NR^eC(=NR^g)NR^f(CR^{11a}R^{11b})_{p2}$, $O(CR^{11a}R^{11b})_{q1}C(O)$, $S(CR^{11a}R^{11b})_{q1}C(O)$, $NR^e(CR^{11a}R^{11b})_{q1}C(O)$, $C(O)(CR^{11a}R^{11b})_{q1}C(O)$, $NR^e(CR^{11a}R^{11b})_{q1}NR^f$, $O(CR^{11a}R^{11b})_{q1}NR^f$, and $O(CR^{11a}R^{11b})_{q1}O$, wherein each of the $C_{1-6}$ alkylenyl, $C_{2-6}$ alkenylenyl and $C_{2-6}$ alkynylenyl is optionally substituted by 1, 2, or 3 substituents independently selected from halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

each $W^6$ is independently selected from $NR^{e100}C(O)NR^{f100}$ and $NR^{e200}C(O)CR^{13}R^{f200}$, wherein $R^{e100}$ and $R^{f100}$ together with the intervening NC(O)N moiety to which they are attached form a 4-7 membered heterocycloalkyl group which is optionally substituted by 1, 2, or 3 substituents each independently selected from $C_{1-6}$ alkyl, $C_{1-6}$ haloalkyl, $C_{2-6}$ alkenyl, $C_{2-6}$ alkynyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$, and wherein $R^{e200}$ and $R^{f200}$ together with the intervening $NC(O)CR^{13}$ moiety to which they are attached form a 4-7 membered heterocycloalkyl group which is optionally substituted by 1, 2, or 3 substituents each independently selected from $C_{1-6}$ alkyl, $C_{1-6}$ haloalkyl, $C_{2-6}$ alkenyl, $C_{2-6}$ alkynyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$Q^1$, $Q^2$, $Q^3$, $Q^4$, and $Q^5$ are each, independently, selected from aryl, cycloalkyl, heteroaryl, heterocycloalkyl, arylalkyl, heteroarylalkyl, cycloalkylalkyl, and heterocycloalkylalkyl, each optionally substituted by 1, 2, 3, 4, or 5 substituents independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$Y^1$, $Y^2$, $Y^3$, $Y^4$, and $Y^5$ are each, independently, selected from absent, $C_{1-6}$ alkylenyl, $C_{2-6}$ alkenylenyl, $C_{2-6}$ alkynylenyl, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(S)(CR^{12a}R^{12b})_{p4}$, $(CR^{12a}R^{12b})_{p3}C(O)O(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}C(S)NR^e(CR^{12a}R^{12b})_{p4}$, $(CR^{12a}R^{12b})_{p3}S(O)(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)NR^e(CR^{12a}R^{12b})_{p4}$, $(CR^{12a}R^{12b})_{p3}S(O)_2NR^e(CR^{12a}R^{12b})_{p4}$, $(CR^{12a}R^{12b})_{p3}NR^eC(O)NR^f(CR^{12a}R^{12b})_{p4}$, $(CR^{12a}R^{12b})_{p3}NR^eC(S)NR^f(CR^{12a}R^{12b})_{p4}$, $(CR^{12a}R^{12b})_{p3}NR^eS(O)_2NR^f(CR^{12a}R^{12b})_{p4}$, $(CR^{12a}R^{12b})_{p3}C(=NR^g)NR^e(CR^{12a}R^{12b})_{p4}$, $(CR^{12a}R^{12b})_{p3}NR^eC(=NR^g)NR^f(CR^{12}R^{12b})_{p4}$, $O(CR^{12a}R^{12b})_{q2}C(O)$, $S(CR^{12a}R^{12b})_{q2}C(O)$, $NR^e(CR^{12a}R^{12b})_{q2}C(O)$, $NR^e(CR^{12a}R^{12b})_{q2}NR^f$, $O(CR^{12a}R^{12b})_{q2}NR^f$, and $O(CR^{12a}R^{12b})_{q2}O$, wherein each of the $C_{1-6}$ alkylenyl, $C_{2-6}$ alkenylenyl and $C_{2-6}$ alkynylenyl is optionally substituted by 1, 2 or 3 substituents independently selected from $C_{1-6}$ alkyl, $C_{1-6}$ haloalkyl, $C_{2-6}$ alkenyl, $C_{2-6}$ alkynyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$Z^1$, $Z^2$, $Z^3$, $Z^4$, and $Z^5$ are each, independently, selected from H, halo, CN, $NO_2$, OH, $C_{1-6}$ alkoxy, $C_{1-6}$ haloalkoxy, amino, $C_{1-6}$ alkylamino, $C_{2-8}$ dialkylamino, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $NR^cS(O)_2R^b$, $NR^cS(O)_2NR^cR^d$; $S(O)R^b$, $S(O)NR^cR^d$, $S(O)_2R^b$, and $S(O)_2NR^cR^d$;

$Cy^1$, $Cy^2$, $Cy^3$, and $Cy^4$ are each, independently, selected from aryl, cycloalkyl, heteroaryl, and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $SF_5$, $Cy^5$, -$L^{b1}$-$Cy^5$, —$W^5$-$Q^5$-$Y^5$—$Z^5$, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$Cy^5$ and $Cy^6$ are each, independently, selected from aryl, cycloalkyl, heteroaryl, and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, arylalkyl, heteroarylalkyl, cycloalkylalkyl, heterocycloalkylalkyl, halosulfanyl, CN, $NO_2$, $OR^{a2}$, $SR^{a2}$, $SF_5$, $C(O)R^{b2}$, $C(O)NR^{c2}R^{d2}$, $C(S)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)$ NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

L$^{b1}$ and L$^{b2}$ are each, independently, selected from C$_{1-4}$ alkylenyl, O, S, C(O), C(S), C(O)NR$^{c2}$, C(S)NR$^{c2}$, C(O)O, OC(O)NR$^{c2}$, NR$^{c2}$, NR$^{c2}$C(O)NR$^{d2}$, NR$^{c2}$C(S)NR$^{d2}$, C(=NR$^g$)NR$^{c2}$, NR$^{c2}$C(=NR$^g$)NR$^{d2}$, NR$^{c2}$S(O)$_2$NR$^{d2}$, S(O), S(O)NR$^{c2}$, S(O)$_2$, and S(O)$_2$NR$^{c2}$, wherein said C$_{1-4}$ alkylenyl is optionally substituted by 1, 2, 3, 4, 5, 6, 7, or 8 substituents each independently selected from halo, CN, C$_{1-6}$ alkyl, C$_{1-6}$ haloalkyl, OH, C$_{1-6}$ alkoxy, C$_{1-6}$ haloalkoxy, NH$_2$, NH(C$_{1-4}$ alkyl), and N(C$_{1-4}$ alkyl)$_2$;

R$^{a1}$, R$^{b1}$, R$^{c1}$, and R$^{d1}$ are each, independently, selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from C$_{1-6}$ alkyl, halo, CN, Cy$^6$, -L$^{b2}$-Cy$^6$, OR$^{a2}$, SR$^{a2}$, SF$_5$, C(O)R$^{b2}$, C(O)NR$^{c2}$R$^{d2}$, C(S)R$^{b2}$, C(S)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O) NR$^{c2}$R$^{d2}$, NR$^{c2}$C(S)R$^{b2}$, NR$^{c2}$C(S)NR$^{c2}$R$^{d2}$, NR$^{c2}$C(O) OR$^{a2}$, C(=NR$^g$)NR$^{c2}$R$^{d2}$, NR$^{c2}$C(=NR$^g$)NR$^{c2}$R$^{d2}$, NR$^{c2}$S (O)$_2$NR$^{c2}$R$^{d2}$, S(O)R$^{b2}$, S(O)NR$^{c2}$R$^{d2}$, S(O)$_2$R$^{b2}$, NR$^{c2}$S (O)$_2$ R$^{b2}$, and S(O)$_2$NR$^{c2}$R$^{d2}$;

or R$^{c1}$ and R$^{d1}$ together with the N atom to which they are attached form a 4-, 5-, 6- or 7-membered heterocycloalkyl group or heteroaryl group, each optionally substituted with 1, 2, or 3 substituents independently selected from C$_{1-6}$ alkyl, C$_{1-6}$ haloalkyl, halo, CN, Cy$^6$, -L$^{b2}$-Cy$^6$, OR$^{a2}$, SR$^{a2}$, SF$_5$, C(O)R$^{b2}$, C(O)NR$^{c2}$R$^{d2}$, C(S)R$^{b2}$, C(S)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(S)R$^{b2}$, NR$^{c2}$C(S)NR$^{c2}$R$^{d2}$, NR$^{c2}$C(O)OR$^{a2}$, C(=NR$^g$)NR$^{c2}$R$^{d2}$, NR$^{c2}$C(=NR$^g$) NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

each R$^{e1}$ is, independently, H, C$_{1-6}$ alkyl, C$_{1-6}$ haloalkyl, C$_{2-6}$ alkenyl, (C$_{1-6}$ alkoxy)-C$_{1-6}$ alkyl, C$_{2-6}$ alkynyl, aryl, cycloalkyl, heteroaryl, heterocycloalkyl, arylalkyl, cycloalkylalkyl, heteroarylalkyl, or heterocycloalkylalkyl;

each R$^{f1}$ is, independently, H, C$_{1-6}$ alkyl, C$_{1-6}$ haloalkyl, C$_{2-6}$ alkenyl, C$_{2-6}$ alkynyl, aryl, cycloalkyl, heteroaryl, or heterocycloalkyl;

R$^{a2}$, R$^{b2}$, R$^{c2}$, and R$^{d2}$ are each, independently, selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

or R$^{c2}$ and R$^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

each R$^a$ is independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl is optionally substituted with 1, 2, 3, 4, or 5 substituents independently selected from OH, CN, amino, halo, C$_{1-6}$ alkyl, C$_{1-6}$ haloalkyl, C$_{1-6}$ hydroxylalkyl, C$_{1-6}$ cyanoalkyl, C$_{1-6}$ alkoxy, C$_{1-6}$ haloalkoxy, C$_{2-8}$ alkoxyalkoxy, aryl, arylalkyl, heteroaryl, heteroarylalkyl, cycloalkyl, and heterocycloalkyl;

each R$^b$ is independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, CN, amino, halo, C$_{1-6}$ alkyl, C$_{1-6}$ haloalkyl, C$_{1-6}$ hydroxylalkyl, C$_{1-6}$ cyanoalkyl, C$_{1-6}$ alkoxy, C$_{1-6}$ haloalkoxy, C$_{2-8}$ alkoxyalkoxy, aryl, arylalkyl, heteroaryl, heteroarylalkyl, cycloalkyl, and heterocycloalkyl;

R$^c$ and R$^d$ are independently selected from H, C$_{1-10}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the C$_{1-10}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents independently selected from OH, CN, amino, halo, C$_{1-6}$ alkyl, C$_{1-6}$ haloalkyl, C$_{1-6}$ hydroxylalkyl, C$_{1-6}$ cyanoalkyl, C$_{1-6}$ alkoxy, C$_{1-6}$ haloalkoxy, C$_{2-8}$ alkoxyalkoxy, aryl, arylalkyl, heteroaryl, heteroarylalkyl, cycloalkyl, and heterocycloalkyl;

or R$^c$ and R$^d$ together with the N atom to which they are attached form a 4-, 5-, 6- or 7-membered heterocycloalkyl group that is optionally substituted with 1, 2, 3, 4, or 5 substituents independently selected from OH, CN, amino, halo, C$_{1-6}$ alkyl, C$_{1-6}$ haloalkyl, C$_{1-6}$ hydroxylalkyl, C$_{1-6}$ cyanoalkyl, C$_{1-6}$ alkoxy, C$_{1-6}$ haloalkoxy, C$_{2-8}$ alkoxyalkoxy, aryl, arylalkyl, heteroaryl, heteroarylalkyl, cycloalkyl, and heterocycloalkyl; and R$^e$ and R$^f$ are each, independently, selected from H, C$_{1-10}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the C$_{1-10}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted by OH, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl, or heterocycloalkyl;

R$^g$, R$^{g1}$, and R$^{g2}$ are each, independently, H, CN, or NO$_2$;
each p1 is, independently, 0, 1, or 2;
each p2 is, independently, 0, 1, or 2;
each p3 is, independently, 0, 1, or 2;
each p4 is, independently, 0, 1, or 2;
each q1 is, independently, 1 or 2;
each q2 is, independently, 1 or 2;
each n is, independently, 1, 2, or 3;
each m is, independently, 0, 1, or 2; and
t is 1, 2, 3, or 4.

In some embodiments, the compound of Formula I or pharmaceutically acceptable salt thereof or quaternary ammonium salt thereof is other than (9S)-6-Chloro-9-methyl-15-oxa-2,4,8,23-tetraazatetracyclo[15.3.1.1(3,7).1(10,14)]tricosa-1(21), 3(23), 4, 6, 10(22), 11,13,17,19-nonaene, or pharmaceutically acceptable salt thereof or quaternary ammonium salt thereof.

In some embodiments, the compound of Formula I or pharmaceutically acceptable salt thereof or quaternary ammonium salt thereof is other than N-[6-Chloro-2,4,8,19,23-pentaazatetracyclo[15.3.1.1(3,7).1(10,14)]tricosa-1(21), 3(23), 4, 6, 10(22), 11,13,17,19-nonaen-13-yl]benzamide, or pharmaceutically acceptable salt thereof or quaternary ammonium salt thereof.

In some embodiments, the compound of Formula I or pharmaceutically acceptable salt thereof or quaternary ammonium salt thereof is other than N-[6-Chloro-2,4,8,19,23-pentaazatetracyclo[15.3.1.1(3,7).1(10,14)]tricosa-1(21), 3(23), 4, 6, 10(22), 11,13,17,19-nonaen-13-yl]-2-cyanobenzenesulfonamide, or pharmaceutically acceptable salt thereof or quaternary ammonium salt thereof.

In some embodiments, $A^1$ and $A^2$ are each, independently, selected from $CR^2$, N, NH, $N(CH_3)$, O, and S. In some embodiments, one of $A^1$ and $A^2$ is selected from NH, $N(CH_3)$, O, and S. In some embodiments, both $A^1$ and $A^2$ are independently selected from NH, $N(CH_3)$, O, and S.

In some embodiments, $A^1$ and $A^2$ are each, independently, selected from $CR^2$ and N. In some further embodiments, $A^1$ and $A^2$ are each, independently, selected from $CR^2$.

In some embodiments, the ring containing $A^1$, $B^1$, $D^1$, and $E^1$ is a 6-membered aromatic ring; $B^1$, $D^1$, and $E^1$ are each, independently, $CR^5$ or N; and $A^1$ is $CR^2$ or N.

In some embodiments, the ring containing $A^1$, $B^1$, $D^1$, and $E^1$ is a 6-membered aromatic ring; $B^1$, $D^1$, and $E^1$ are each, independently, $CR^5$; and $A^1$ is $CR^2$.

In some embodiments, the ring containing $A^1$, $B^1$, $D^1$, and $E^1$ is a benzene ring (and the benzene is optionally substituted with $R^2$ and optionally substituted with 1, 2, or 3 $R^5$.)

In some embodiments, the ring containing $A^1$, $B^1$, $D^1$, and $E^1$ is a 6-membered aromatic ring wherein at least one of $A^1$, $B^1$, $D^1$, and $E^1$ is N (and the 6-membered aromatic ring such can be optionally substituted, i.e., optionally substituted with $R^2$ and optionally substituted with one or more $R^5$). In some further embodiments, the 6-membered aromatic ring is selected from pyridine, pyrimidine, and pyrazine rings (and the 6-membered aromatic rings such as pyridine, pyrimidine, and pyrazine can be substituted or unsubstituted). In yet further embodiments, the 6-membered aromatic ring is selected from optionally substituted pyridine and pyrimidine rings. In some embodiments, the 6-membered aromatic ring is an optionally substituted pyridine ring. In some embodiments wherein the ring containing $A^1$, $B^1$, $D^1$, and $E^1$ is an optionally substituted pyridine ring, $D^1$ is N. In some embodiments wherein the ring containing $A^1$, $B^1$, $D^1$, and $E^1$ is an optionally substituted pyridine ring, $E^1$ is N. In some embodiments wherein the ring containing $A^1$, $B^1$, $D^1$, and $E^1$ is an optionally substituted pyridine ring, $B^1$ is N. In some embodiments wherein the ring containing $A^1$, $B^1$, $D^1$, and $E^1$ is an optionally substituted pyridine ring, $A^1$ is N. In some embodiments, the 6-membered aromatic ring is an optionally substituted pyrimidine ring.

In some embodiments, the ring containing $A^1$, $B^1$, $D^1$, and $E^1$ is a 5-membered aromatic ring (and the aromatic ring is optionally substituted). In some further embodiments, the 5-membered aromatic ring is selected from 1H-pyrrole, furan, thiophene, 1H-imidazole, 1H-pyrazole, oxazole, thiazole, isoxazole, and isothiazole (and the 5-membered aromatic rings can be substituted or unsubstituted). In yet further embodiments, the 5-membered aromatic ring is selected from 1H-pyrrole, furan, and thiophene (and the 5-membered aromatic rings can be optionally substituted). In still further embodiments, the 5-membered aromatic ring is an optionally substituted thiophene ring In some embodiments, the ring containing $A^2$, $B^2$, $D^2$, and $E^2$ is a 6-membered aromatic ring; $B^2$, $D^2$, and $E^2$ are each, independently, $CR^5$ or N; and $A^2$ is $CR^2$ or N. In some further embodiments, $E^2$ is $CR^5$ wherein the $R^5$ of $E^2$ is other than H. In some other further embodiments, $D^2$ is $CR^5$ wherein the $R^5$ of $D^2$ is other than H. In some other further embodiments, $B^2$ is $CR^5$ wherein the $R^5$ of $B^2$ is other than H.

In some embodiments, the ring containing $A^2$, $B^2$, $D^2$, and $E^2$ is a 6-membered aromatic ring; $B^2$, $D^2$, and $E^2$ are each, independently, $CR^5$; and $A^2$ is $CR^2$. In some embodiments, the ring containing $A^2$, $B^2$, $D^2$, and $E^2$ is a benzene ring (and the benzene ring is optionally substituted).

In some embodiments, the ring containing $A^2$, $B^2$, $D^2$, and $E^2$ is a 6-membered aromatic ring, wherein at least one of $A^2$, $B^2$, $D^2$, and $E^2$ is N. In some further embodiments, the 6-membered aromatic ring is selected from pyridine, pyrimidine, and pyrazine rings (and the 6-membered aromatic rings can be optionally substituted, i.e., optionally substituted with $R^2$ and optionally substituted with one or more $R^5$). In yet further embodiments, the 6-membered aromatic ring is selected from optionally substituted pyridine and pyrimidine rings. In some embodiments, the 6-membered aromatic ring is an optionally substituted pyridine ring. In some embodiments, the 6-membered aromatic ring is an optionally substituted pyrimidine ring.

In some embodiments, the ring containing $A^2$, $B^2$, $D^2$, and $E^2$ is a 5-membered aromatic ring (and the aromatic ring is optionally substituted). In some further embodiments, the 5-membered aromatic ring is selected from 1H-pyrrole, furan, thiophene, 1H-imidazole, 1H-pyrazole, oxazole, thiazole, isoxazole, and isothiazole rings (and the 5-membered aromatic rings can be substituted or unsubstituted). In yet further embodiments, the 5-membered aromatic ring is selected from 1H-pyrrole, furan, and thiophene rings (and the 5-membered aromatic rings can be optionally substituted). In still further embodiments, the 5-membered aromatic ring is an optionally substituted thiophene ring.

In some embodiments, $X^1$ is $CR^1$.
In some embodiments, $X^1$ is N.
In some embodiments, $X^2$ is $CR^2$.
In some embodiments, $X^2$ is N.
In some embodiments, $X^3$ is $CR^3$.
In some embodiments, $X^3$ is C-halo. In some embodiments, $X^3$ is C—F, C—Cl, or C—Br.
In some embodiments, $X^3$ is C—Cl.
In some embodiments, $X^3$ is C—Br.
In some embodiments, $X^3$ is C—Cl.
In some embodiments, $X^3$ is N.

In some embodiments, R' and R" are each, independently, selected from H, halo, $C_{1-4}$ alkyl, $C_{2-4}$ alkenyl, $C_{2-4}$ alkynyl, $C_{1-4}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c1}S(O)_2NR^{c1}R^{d1}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, R' and R" are each, independently, selected from H, $C_{1-6}$ alkyl, and $C_{1-6}$ haloalkyl. In some further embodiments, R' and R" are each, independently, selected from H, $C_{1-3}$ alkyl, and $C_{1-3}$ haloalkyl. In yet further embodiments, R' and R" are each, independently, selected from H and $C_{1-3}$ alkyl. In still further embodiments, R' and R" are each, independently, selected from H and methyl. In some embodiments, R' and R" are both H.

In some embodiments, R' and R" are each, independently, selected from H, halo, $C_{1-4}$ alkyl, $C_{2-4}$ alkenyl, $C_{2-4}$ alkynyl, and $C_{1-4}$ haloalkyl. In some further embodiments, R' and R" are each, independently, selected from H, $C_{1-4}$ alkyl, and $C_{1-4}$ haloalkyl.

In some embodiments, R' and R" are each, independently, selected from H and $C_{1-4}$ alkyl. In some further embodiments, R' and R" are each, independently, selected from H and methyl.

In some embodiments, R' and R" are each, independently, selected from H and $C_{1-3}$ alkyl. In some further embodiments, at least one of R' and R" is $C_{1-3}$ alkyl. In yet further embodiments, R' and R" are both, independently, $C_{1-3}$ alkyl.

In some embodiments, at least one of R' and R" is methyl.
In some embodiments, one of R' and R" is methyl.
In some embodiments, R' and R" are both H.

In some embodiments, R' and R" together with the C atom to which they are attached form a 3-, 4-, 5-, 6-, 7-, 8-, 9- or 10-membered cycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, R' and R" together with the C atom to which they are attached form a 3-, 4-, 5-, 6-, 7-, 8-, 9- or 10-membered cycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $C_{1-6}$ alkoxy, $C_{1-6}$ haloalkoxy, $-NH_2$, $-NH(C_{1-6}$ alkyl), and $N(C_{1-6}$ alkyl)$_2$. In some further embodiments, R' and R" together with the C atom to which they are attached form a 3-, 4-, 5-, 6-, 7-, 8-, 9- or 10-membered cycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $C_{1-6}$ alkoxy, and $C_{1-6}$ haloalkoxy.

In some embodiments, R' and R" together with the C atom to which they are attached form a 3-, 4-, 5-, 6-, 7-, or 8-membered cycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $C_{1-6}$ alkoxy, and $C_{1-6}$ haloalkoxy.

In some embodiments, R' and R" together with the C atom to which they are attached form a 3-, 4-, 5-, 6-, 7-, 8-, 9- or 10-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, R' and R" together with the C atom to which they are attached form a 3-, 4-, 5-, 6-, 7-, 8-, 9- or 10-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $C_{1-6}$ alkoxy, $C_{1-6}$ haloalkoxy, $-NH_2$, $-NH(C_{1-6}$ alkyl), and $N(C_{1-6}$ alkyl)$_2$. In some further embodiments, R' and R" together with the C atom to which they are attached form a 3-, 4-, 5-, 6-, 7-, 8-, 9- or 10-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $C_{1-6}$ alkoxy, and $C_{1-6}$ haloalkoxy.

In some further embodiments, R' and R" together with the C atom to which they are attached form a 3-, 4-, 5-, 6-, 7-, or 8-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $C_{1-6}$ alkoxy, and $C_{1-6}$ haloalkoxy.

In some embodiments, $R^1$ is selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, and $NR^{c2}R^{d2}$.

In some embodiments, $R^1$ is selected from H, halo, $C_{1-6}$ alkyl, $C_{1-6}$ haloalkyl, CN, $NO_2$, $-O-(C_{1-6}$ alkyl), and $-O-(C_{1-6}$ haloalkyl).

In some embodiments, $R^1$ is selected from H, halo, $C_{1-6}$ alkyl, and $C_{1-6}$ haloalkyl.

In some embodiments, $R^1$ is selected from H, halo, $C_{1-3}$ alkyl, and $C_{1-3}$ haloalkyl. In some embodiments, $R^1$ is selected from H, F, Cl, Br, methyl, ethyl, 1-propyl, 2-propyl, and $C_{1-2}$ haloalkyl. In some embodiments, $R^1$ is selected from H, F, Cl, Br, methyl, ethyl, 1-propyl, 2-propyl, and $CF_3$. In some embodiments, $R^1$ is selected from H, F, Cl, Br, methyl, and $CF_3$.

In some embodiments, $R^1$ is $SF_5$.

In some embodiments, $R^1$ is selected from H, F, Cl, Br, methyl, ethyl, and $C_{1-2}$ haloalkyl.

In some embodiments, $R^1$ is selected from H, F, Cl, and Br.

In some embodiments, $R^1$ is selected from H, $CH_3$ and $CF_3$. In some further embodiments, $R^1$ is H or $CH_3$. In yet further embodiments, $R^1$ is H.

In some embodiments, each $R^2$ is, independently, selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2NR^{c2}R^{d2}$, $NR^{c2}S(O)_2R^{b2}$, and $NR^{c2}R^{d2}$.

In some embodiments, each $R^2$ is, independently, selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2NR^{c2}R^{d2}$, $NR^{c2}S(O)_2R^{b2}$, and, $NR^{c2}R^{d2}$.

In some embodiments, each $R^2$ is, independently, selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, and $NR^{c2}R^{d2}$.

In some embodiments, each $R^2$ is, independently, selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, and $NR^{c2}R^{d2}$.

In some embodiments, each $R^2$ is, independently, selected from H, halo, $C_{1-6}$ alkyl, $C_{1-6}$ haloalkyl, CN, $NO_2$, amino, $C_{1-4}$ alkylamino, $C_{2-8}$ dialkylamino, $NHC(=O)-(C_{1-4}$ alkyl), $NHC(=O)O$-(arylalkyl), $NHC(=O)O-(C_{1-4}$ alkyl), $NHC(=O)O$-(arylalkyl), $NHC(=O)NH_2$, $NHC(=O)NH-(C_{1-4}$ alkyl), $NHC(=O)N-(C_{1-4}$ alkyl)$_2$, $NHC(=O)NH$-(arylalkyl), $NHS(=O)_2-(C_{1-4}$ alkyl), and $NHS(=O)_2$-(arylalkyl).

In some embodiments, each $R^2$ is, independently, selected from H, halo, $C_{1-6}$ alkyl, $C_{1-6}$ haloalkyl, amino, $C_{1-4}$ alkylamino, $C_{2-8}$ dialkylamino, $NHC(=O)-(C_{1-4}$ alkyl), $NHC(=O)O$-(arylalkyl), $NHC(=O)O-(C_{1-4}$ alkyl), $NHC(=O)O$-(arylalkyl), $NHC(=O)NH_2$, $NHC(=O)NH-(C_{1-4}$ alkyl), $NHC(=O)N-(C_{1-4}$ alkyl)$_2$, $NHC(=O)NH$-(arylalkyl), $NHS(=O)_2-(C_{1-4}$ alkyl), and $NHS(=O)_2$-(arylalkyl).

In some embodiments, each $R^2$ is, independently, selected from H, halo, $C_{1-6}$ alkyl, and $C_{1-6}$ haloalkyl.

In some embodiments, each $R^2$ is, independently, selected from H, halo, $C_{1-3}$ alkyl, and $C_{1-3}$ haloalkyl. In some embodiments, each $R^2$ is, independently, selected from H, F, Cl, Br, methyl, ethyl, 1-propyl, 2-propyl, and $C_{1-2}$ haloalkyl. In some embodiments, each $R^2$ is, independently, selected from H, F, Cl, Br, methyl, ethyl, 1-propyl, 2-propyl, and $CF_3$. In some embodiments, each $R^2$ is, independently, selected from H, F, Cl, Br, methyl, and $CF_3$.

In some embodiments, each $R^2$ is, independently, selected from H, $CH_3$, $CF_3$, and halo. In some embodiments, each $R^2$ is, independently, selected from H, F, Cl, $CH_3$, and $CF_3$. In some further embodiments, each $R^2$ is, independently, selected from H, F, and Cl. In yet further embodiments, each $R^2$ is, independently, selected from H and F.

In some embodiments, each $R^2$ is, independently, selected from H, $CH_3$ and $CF_3$. In some further embodiments, each $R^2$ is H.

In some embodiments, $R^3$ is selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2NR^{c2}R^{d2}$, $NR^{c2}S(O)_2R^{b2}$, and $NR^{c2}R^{d2}$.

In some embodiments, $R^3$ is selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, and $NR^{c2}R^{d2}$.

In some embodiments, $R^3$ is selected from H, halo, $C_{1-6}$ alkyl, $C_{1-6}$ haloalkyl, amino, $C_{1-4}$ alkylamino, and $C_{2-8}$ dialkylamino.

In some embodiments, $R^3$ is selected from H, halo, $C_{1-3}$ alkyl, $C_{1-3}$ haloalkyl, $NH_2$, $NH(C_{1-3}$ alkyl), and $N(C_{1-3}$ alkyl$)_2$. In some embodiments, $R^3$ is selected from H, F, Cl, Br, methyl, ethyl, 1-propyl, 2-propyl, $C_{1-2}$ haloalkyl, $NH_2$, $NH(C_{1-3}$ alkyl), and $N(C_{1-3}$ alkyl$)_2$. In some embodiments, $R^3$ is selected from H, F, Cl, Br, methyl, ethyl, 1-propyl, 2-propyl, $CF_3$, $NH_2$, $NH(C_{1-3}$ alkyl), and $N(C_{1-3}$ alkyl$)_2$. In some embodiments, $R^3$ is selected from H, Cl, Br, methyl, $CF_3$, $NH_2$, $NH(C_{1-3}$ alkyl), and $N(C_{1-3}$ alkyl$)_2$.

In some embodiments, $R^3$ is selected from H, halo, $C_{1-6}$ alkyl, and $C_{1-6}$ haloalkyl.

In some embodiments, $R^3$ is selected from H, halo, $C_{1-3}$ alkyl, and $C_{1-3}$ haloalkyl. In some embodiments, $R^3$ is selected from H, F, Cl, Br, methyl, ethyl, 1-propyl, 2-propyl, and $C_{1-2}$ haloalkyl. In some embodiments, $R^3$ is selected from H, F, Cl, Br, methyl, ethyl, 1-propyl, 2-propyl, and $CF_3$. In some embodiments, $R^3$ is selected from H, F, Cl, Br, methyl, and $CF_3$.

In some embodiments, $R^3$ is selected from F, Cl, Br, and $CF_3$. In some further embodiments, $R^3$ is selected from F, Cl, and Br. In yet further embodiments, $R^3$ is selected from F, Cl, and Br.

In some embodiments, $R^3$ is F. In some embodiments, $R^3$ is Cl. In some embodiments, $R^3$ is Br.

In some embodiments, $R^3$ is $SF_5$.

In some embodiments, $R^1$ and $R^3$ are each, independently, selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2NR^{c2}R^{d2}$, $NR^{c2}S(O)_2R^{b2}$, and $NR^{c2}R^{d2}$.

In some embodiments, $R^1$ and $R^3$ are each, independently, selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, and $NR^{c2}R^{d2}$.

In some embodiments, $R^1$ and $R^3$ are each, independently, selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, and $NR^{c2}R^{d2}$.

In some embodiments, $R^1$ and $R^3$ are each, independently, selected from H, halo, $C_{1-6}$ alkyl, $C_{1-6}$ haloalkyl, CN, $NO_2$, $SF_5$, amino, $C_{1-4}$ alkylamino, $C_{2-8}$ dialkylamino, NHC(=O)—($C_{1-4}$ alkyl), NHC(=O)O-(arylalkyl), NHC(=O)O—($C_{1-4}$ alkyl), NHC(=O)O-(arylalkyl), NHC(=O)$NH_2$, NHC(=O)NH—($C_{1-4}$ alkyl), NHC(=O)N—($C_{1-4}$ alkyl$)_2$, NHC(=O)NH-(arylalkyl), NHS(=O)$_2$—($C_{1-4}$ alkyl), and NHS(=O)$_2$-(arylalkyl).

In some embodiments, $R^1$ and $R^3$ are each, independently, selected from H, halo, $C_{1-6}$ alkyl, $C_{1-6}$ haloalkyl, amino, $C_{1-4}$ alkylamino, $C_{2-8}$ dialkylamino, NHC(=O)—($C_{1-4}$ alkyl), NHC(=O)O-(arylalkyl), NHC(=O)O—($C_{1-4}$ alkyl), NHC(=O)O-(arylalkyl), NHC(=O)$NH_2$, NHC(=O)NH—($C_{1-4}$ alkyl), NHC(=O)N—($C_{1-4}$ alkyl$)_2$, NHC(=O)NH-(arylalkyl), NHS(=O)$_2$—($C_{1-4}$ alkyl), and NHS(=O)$_2$-(arylalkyl).

In some embodiments, $R^1$ and $R^3$ are each, independently, selected from H, halo, $C_{1-6}$ alkyl, and $C_{1-6}$ haloalkyl.

In some embodiments, $R^1$ and $R^3$ are each, independently, selected from H, halo, $C_{1-3}$ alkyl, and $C_{1-3}$ haloalkyl. In some embodiments, $R^1$ and $R^3$ are each, independently, selected from H, F, Cl, Br, methyl, ethyl, 1-propyl, 2-propyl, and $C_{1-2}$ haloalkyl. In some embodiments, $R^1$ and $R^3$ are each, independently, selected from H, F, Cl, Br, methyl, ethyl, 1-propyl, 2-propyl, and $CF_3$. In some embodiments, $R^1$ and $R^3$ are each, selected from H, F, Cl, Br, methyl, and $CF_3$.

In some embodiments, $R^1$ is selected from H and $C_{1-3}$ alkyl; and $R^3$ is selected from halo, $C_{1-3}$ alkyl, and $C_{1-3}$ haloalkyl.

In some embodiments, $R^1$ is H; and $R^3$ is selected from halo and $C_{1-3}$ alkyl.

In some embodiments, $R^1$ is H; and $R^3$ is halo.

In some embodiments, one of $R^1$ and $R^3$ is $SF_5$. In some further embodiments, $R^3$ is $SF_5$.

In some embodiments, $R^1$ and $R^2$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, $R^1$ and $R^2$ are each, independently, selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2NR^{c2}R^{d2}$, $NR^{c2}S(O)_2R^{b2}$, and $NR^{c2}R^{d2}$.

In some embodiments, $R^1$ and $R^2$ are each, independently, selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, and $NR^{c2}R^{d2}$. In some further embodiments, $R^1$ and $R^2$ are each, independently, selected from H, halo, $C_{1-6}$ alkyl, and $C_{1-6}$ haloalkyl. In some embodiments, $R^1$ and $R^2$ are each, independently, selected from H, methyl, and ethyl. In some embodiments, $R^1$ and $R^2$ are each, independently, selected from H and methyl. In some further embodiments, $R^1$ and $R^2$ are H.

In some embodiments, $R^1$ and $R^2$ are each, independently, selected from H, F, Cl, Br, methyl, ethyl, and $C_{1-2}$ haloalkyl. In some further embodiments, $R^1$ and $R^2$ are each, independently, selected from H, F, Cl, methyl, and $CF_3$. In yet further embodiments, $R^1$ and $R^2$ are each, independently, selected from H and methyl. In still further embodiments, $R^1$ and $R^2$ are each H.

In some embodiments, $X^1$ is $CR^1$; $X^2$ is N; and $X^3$ is $CR^3$. In some further embodiments, $R^1$ is selected from H and $C_{1-3}$ alkyl; and $R^3$ is selected from halo, $C_{1-3}$ alkyl, and $C_{1-3}$ haloalkyl. In yet further embodiments, $R^1$ is H; and $R^3$ is halo. In still further embodiments, $R^1$ is H; and $R^3$ is F, Cl, or Br. In further embodiments, $R^1$ is H; and $R^3$ is Cl.

In some embodiments, $R^4$ is H or $C_{1-6}$ alkyl. In some embodiments, $R^4$ is H.

In some embodiments, $R^4$ is H or $C_{1-3}$ alkyl. In some further embodiments, $R^4$ is $C_{1-3}$ alkyl. In yet further embodiments, $R^4$ is methyl.

In some embodiments, $L^1$ and $L^2$ are each, independently, selected from a bond, $-(CR^7R^8)_n-$, $-O-(CR^7R^8)_m-CR^{10}=$, $-S-(CR^7R^8)_m-CR^{10}=$, $-(CR^7R^8)_m-CR^{10}=$, $-(CR^7R^8)_m-NR^9-$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-NR^9C(O)NR^9-$, $-(CR^7R^8)_m-OC(O)NR^9-$, $-(CR^7R^8)_m-NR^9C(O)O-$, $-(CR^7R^8)_m-NR^9S(O)_2NR^9-$, $-(CR^7R^8)_m-S(O)NR^9-$, and $-(CR^7R^8)_m-S(O)_2NR^9-$.

In some embodiments, $L^1$ and $L^2$ are each, independently, selected from a bond, $-(CR^7R^8)_n-$, $-(CR^7R^8)_m-CR^{10}=$, $-O-(CR^7R^8)_m-CR^{10}=$, $-S-(CR^7R^8)_m-CR^{10}=$, $-(CR^7R^8)_m-NR^9-$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-S(O)NR^9-$, and $-(CR^7R^8)_m-S(O)_2NR^9-$.

In some embodiments, $L^1$ and $L^2$ are each, independently, selected from a bond, $-(CR^7R^8)_n-$, $-(CR^7R^8)_m-CR^{10}=$, $-(CR^7R^8)_m-NR^9-$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-S(O)NR^9-$, and $-(CR^7R^8)_m-S(O)_2NR^9-$.

As used herein, when one of $L^1$ and $L^2$ is selected from $-O-(CR^7R^8)_m-CR^{10}=$, $-S-(CR^7R^8)_m-CR^{10}=$, $-(CR^7R^8)_m-CR^{10}=$, and $-(CR^7R^8)_m-N=$, the other is also selected from $-O-(CR^7R^8)_m-CR^{10}=$, $-S-(CR^7R^8)_m-CR^{10}=$, $-(CR^7R^8)_m-CR^{10}=$, and $-(CR^7R^8)_m-N=$ (although $L^1$ and $L^2$ can be the same or different in such embodiments). In such embodiments, the moiety formed by $L^1$ and $L^2$ together can include a moiety of "$-CR^{10}=CR^{10}-$" or "$-CR^{10}=N-$". In some further embodiments, the moiety formed by $L^1$ and $L^2$ together includes a moiety of $-CR^{10}=CR^{10}-$. In some embodiments, $L^1$ and $L^2$ together form $-(CR^7R^8)_m-CR^{10}=CR^{10}-(CR^7R^8)_m-$, $-O-(CR^7R^8)_m-CR^{10}=CR^{10}-(CR^7R^8)_m-$, $-S-(CR^7R^8)_m-CR^{10}=CR^{10}-(CR^7R^8)_m-$, $-O-(CR^7R^8)_m-CR^{10}=CR^{10}-(CR^7R^8)_m-O-$, $-O-(CR^7R^8)_m-CR^{10}=CR^{10}-(CR^7R^8)_m-S-$, or $-S-(CR^7R^8)_m-CR^{10}=CR^{10}-(CR^7R^8)_m-S-$.

In some embodiments, $L^1$ and $L^2$ are each, independently, selected from a bond, $-(CR^7R^8)_n-$, and $-(CR^7R^8)_m-CR^{10}=$.

In some embodiments, $L^1$ and $L^2$ together form $-(CR^7R^8)_m-CR^{10}=CR^{10}-(CR^7R^8)_m-$ or $-(CR^7R^8)_m-(CR^7R^8)_n-$.

In some embodiments, $L^1$ and $L^2$ together form $-CR^{10}=CR^{10}-$, $-(CR^7R^8)_2-$, or $-(CR^7R^8)_3-$.

In some embodiments, $L^1$ and $L^2$ together form $-CR^{10}=CR^{10}-$ or $-(CR^7R^8)_2-$. In some embodiments, $L^1$ and $L^2$ together form $-CH=CH-$ or $-CH_2-CH_2-$.

In some embodiments, $L^1$ and $L^2$ together form $-CH=CH-$. In some embodiments, $L^1$ and $L^2$ together form $-CH_2-CH_2-$.

In some embodiments, $L^1$ and $L^2$ together form $-(CR^7R^8)_n-$. In some further embodiments, $L^1$ and $L^2$ together form $-(CR^7R^8)-$, $-(CR^7R^8)_2-$, or $-(CR^7R^8)_3-$. In yet further embodiments, $L^1$ and $L^2$ together form $-CH_2-$, $-(CH_2)_2-$, or $-(CH_2)_3-$.

In some embodiments, $L^1$ and $L^2$ together form $-(CR^7R^8)_2-$. In further embodiments, $L^1$ and $L^2$ together form $-(CH_2)_2-$.

In some embodiments, $L^1$ and $L^2$ together form $-(CR^7R^8)_3-$. In some embodiments, $L^1$ and $L^2$ together form $-(CH_2)_3-$.

In some embodiments, $L^1$ and $L^2$ together form $-(CR^7R^8)_4-$, $-(CR^7R^8)_5-$, or $-(CR^7R^8)_6-$. In some embodiments, $L^1$ and $L^2$ together form $-(CH_2)_4-$, $-(CH_2)_5-$, or $-(CH_2)_6-$.

In some embodiments, one of $L^1$ and $L^2$ is selected from $-(CR^7R^8)_m-O-$, $-(CR^7R^8)_m-S-$, $-(CR^7R^8)_m-S(O)-$, and $-(CR^7R^8)_m-S(O)_2-$; and the other is selected from a bond, $-(CR^7R^8)_n-$, $-(CR^7R^8)_m-O-$, $-(CR^7R^8)_m-S-$, $-(CR^7R^8)_m-S(O)-$, and $-(CR^7R^8)_m-S(O)_2-$.

In some embodiments, $L^1$ and $L^2$ together form $-O-(CR^7R^8)_m-(CR^7R^8)_n-$.

In some embodiments, $L^1$ and $L^2$ together form $-O-(CR^7R^8)-$, $-O-(CR^7R^8)_2-$, or $-O-(CR^7R^8)_3-$.

In some embodiments, $L^1$ and $L^2$ together form $-O-CH_2-$, $-O-(CH_2)_2-$, or $-O-(CH_2)_3-$.

In some embodiments, $L^1$ is $-(CR^7R^8)-$, $-(CR^7R^8)_2-$, or $-(CR^7R^8)_3-$; and $L^2$ is $-O-$.

In some embodiments:
$L^1$ and $L^2$ together form $-(CR^7R^8)_{t1}-S-$, $-(CR^7R^8)_{t1}-O-$, $-(CR^7R^8)_{t1}-S(O)-$, $-(CR^7R^8)_{t1}-S(O)_2-$, $-S-(CR^7R^8)_{t2}-S-$, $-O-(CR^7R^8)_{t2}-S-$, $-O-(CR^7R^8)_{t2}-S(O)-$, $-O-(CR^7R^8)_{t2}-S(O)_2-$, $-S-S-$, $-(CR^7R^8)_{t3}-O-(CR^7R^8)_{t4}-$, $-(CR^7R^8)_{t3}-S-(CR^7R^8)_{t4}-$, $-(CR^7R^8)_{t3}-S(O)-(CR^7R^8)_{t4}-$, or $-(CR^7R^8)_{t3}-S(O)_2-(CR^7R^8)_{t4}-$;

t1 is 1, 2, or 3;
t2 is 1, 2, 3 or 4;
t3 is 1, 2, or 3; and
t4 is 1 or 2.

In some embodiments:
$L^1$ and $L^2$ together form $-(CR^7R^8)_{t1}-S-$, $-(CR^7R^8)_{t1}-O-$, $-(CR^7R^8)_{t1}-S(O)-$, $-(CR^7R^8)_{t1}-S(O)_2-$, $-S-(CR^7R^8)_{t2}-S-$, $-O-(CR^7R^8)_{t2}-S-$, $-O-(CR^7R^8)_{t2}-S(O)-$, $-O-(CR^7R^8)_{t2}-S(O)_2-$, or $-S-S-$;

t1 is 1, 2, or 3; and
t2 is 1, 2, 3 or 4;

In some embodiments:
$L^1$ and $L^2$ together form $-(CR^7R^8)_{t3}-O-(CR^7R^8)_{t4}-$, $-(CR^7R^8)_{t3}-S-(CR^7R^8)_{t4}-$, $-(CR^7R^8)_{t3}-S(O)-(CR^7R^8)_{t4}-$, or $-(CR^7R^8)_{t3}-S(O)_2-(CR^7R^8)_{t4}-$,
t3 is 1, 2, or 3; and
t4 is 1 or 2.

In some embodiments, $L^1$ and $L^2$ together form $-S-S-$, $-(CR^7R^8)-S-$, $-(CR^7R^8)-S(O)-$, $-(CR^7R^8)-S(O)_2-$, $-(CR^7R^8)-O-$, $-(CR^7R^8)_2-O-$, $-O-(CR^7R^8)-O-$, $-O-(CR^7R^8)_2-S-$, $-O-(CR^7R^8)_2-S(O)-$, or $-O-(CR^7R^8)_2-S(O)_2-$.

In some embodiments, $L^1$ and $L^2$ together form $-S-S-$, $-(CH_2)-S-$, $-(CH_2)-S(O)-$, $-(CH_2)-S(O)_2-$, $-(CH_2)-O-$, $-(CH_2)_2-O-$, $-O-(CH_2)_2-O-$, $-O-(CH_2)_2-S-$, $-O-(CH_2)_2-S(O)-$, or $-O-

$(CH_2)_2$—$S(O)_2$—. In some embodiments, $L^1$ and $L^2$ together form S—S. In some embodiments, $L^1$ and $L^2$ together form —$(CH_2)$—S—, —$(CH_2)$—S(O)—, —$(CH_2)$—$S(O)_2$—, —$(CH_2)$—O—, —$(CH_2)_2$—O—, —O—$(CH_2)_2$—O—, —O—$(CH_2)_2$—S—, —O—$(CH_2)_2$—S(O)—, or —O—$(CH_2)_2$—$S(O)_2$—.

In some embodiments, $L^1$ and $L^2$ together form —$(CR^7R^8)$—O—, —$(CR^7R^8)$—S—, —$(CR^7R^8)$—S(O)—, —$(CR^7R^8)$—$S(O)_2$—, —$(CR^7R^8)_2$—O—, —$(CR^7R^8)_2$—S—, —$(CR^7R^8)_2$—S(O)—, —$(CR^7R^8)_2$—$S(O)_2$—, —O—$(CR^7R^8)_3$—, —S—$(CR^7R^8)_3$—, —S(O)—$(CR^7R^8)_3$—, or —$S(O)_2$—$(CR^7R^8)_3$—.

In some embodiments, $L^1$ and $L^2$ together form —$(CH_2)$—O—, —$(CH_2)$—S—, —$(CH_2)$—S(O)—, or —$(CH_2)$—$S(O)_2$—. In some embodiments, $L^1$ and $L^2$ together form —$(CH_2)$—O— or —$(CH_2)$—S—.

In some embodiments, $L^1$ and $L^2$ together form —$(CH_2)$—O—.

In some embodiments, $L^1$ and $L^2$ together form —$(CH_2)$—S—.

In some embodiments, $L^1$ and $L^2$ together form —$(CH_2)$—S(O)—.

In some embodiments, $L^1$ and $L^2$ together form —$(CH_2)$—$S(O)_2$—.

In some embodiments, $L^1$ and $L^2$ together form —$(CH_2)_2$—O—, —$(CH_2)_2$—S—, —$(CH_2)_2$—S(O)—, or —$(CH_2)_2$—$S(O)_2$—. In some embodiments, $L^1$ and $L^2$ together form —$(CH_2)_2$—O— or —$(CH_2)_2$—S—.

In some embodiments, $L^1$ and $L^2$ together form —$(CH_2)_2$—O.

In some embodiments, $L^1$ and $L^2$ together form —$(CH_2)_2$—S—.

In some embodiments, $L^1$ and $L^2$ together form —$(CH_2)_2$—S(O)—.

In some embodiments, $L^1$ and $L^2$ together form —$(CH_2)_2$—$S(O)_2$—.

In some embodiments, $L^1$ and $L^2$ together form —$(CH_2)_3$—O—, —$(CH_2)_3$—S—, —$(CH_2)_3$—S(O)—, or —$(CH_2)_3$—$S(O)_2$—. In some embodiments, $L^1$ and $L^2$ together form —$(CH_2)_3$—O— or —$(CH_2)_3$—S—.

In some embodiments, $L^1$ and $L^2$ together form —$(CH_2)_3$—O—.

In some embodiments, $L^1$ and $L^2$ together form —$(CH_2)_3$—S—.

In some embodiments, $L^1$ and $L^2$ together form —$(CH_2)_3$—S(O)—.

In some embodiments, $L^1$ and $L^2$ together form —$(CH_2)_3$—$S(O)_2$—.

In some embodiments, $L^1$ and $L^2$ together form —$(CR^7R^8)$—O—$(CR^7R^8)$—, —$(CR^7R^8)$—S—$(CR^7R^8)$—, —$(CR^7R^8)$—S(O)—$(CR^7R^8)$—, —$(CR^7R^8)$—$S(O)_2$—$(CR^7R^8)$—, —$(CR^7R^8)$—O—$(CR^7R^8)_2$—, —$(CR^7R^8)$—S—$(CR^7R^8)_2$—, —$(CR^7R^8)$—S(O)—$(CR^7R^8)_2$—, —$(CR^7R^8)$—$S(O)_2$—$(CR^7R^8)_2$—, —$(CR^7R^8)_2$—O—$(CR^7R^8)_2$—, —$(CR^7R^8)_2$—S—$(CR^7R^8)_2$—, —$(CR^7R^8)_2$—S(O)—$(CR^7R^8)_2$—, or —$(CR^7R^8)_2$—$S(O)_2$—$(CR^7R^8)_2$—.

In some embodiments, $L^1$ and $L^2$ together form —$(CH_2)$—O—$(CH_2)$—, —$(CH_2)$—S—$(CH_2)$—, —$(CH_2)$—S(O)—$(CH_2)$—, —$(CH_2)$—$S(O)_2$—$(CH_2)$—, —$(CH_2)$—O—$(CH_2)_2$—, —$(CH_2)$—S—$(CH_2)_2$—, —$(CH_2)$—S(O)—$(CH_2)_2$—, —$(CH_2)$—$S(O)_2$—$(CH_2)_2$—, —$(CH_2)_2$—O—$(CH_2)_2$—, —$(CH_2)_2$—S—$(CH_2)_2$—, —$(CH_2)_2$—S(O)—$(CH_2)_2$—, or —$(CH_2)_2$—$S(O)_2$—$(CH_2)_2$—.

In some embodiments, $L^1$ and $L^2$ together form —$(CH_2)$—O—$(CH_2)$— or —$(CH_2)$—S—$(CH_2)$—.

In some embodiments, $L^1$ and $L^2$ together form —$(CH_2)$—O—$(CH_2)$—.

In some embodiments, $L^1$ and $L^2$ together form —$(CH_2)$—S—$(CH_2)$—.

In some embodiments, $L^1$ and $L^2$ together form —$(CH_2)$—O—$(CH_2)_2$— or —$(CH_2)$—S—$(CH_2)_2$—.

In some embodiments, $L^1$ and $L^2$ together form —$(CH_2)$—O—$(CH_2)_2$—.

In some embodiments, $L^1$ and $L^2$ together form —$(CH_2)$—S—$(CH_2)_2$—.

In some embodiments, $L^1$ and $L^2$ together form —$(CH_2)_2$—O—$(CH_2)_2$— or —$(CH_2)_2$—S—$(CH_2)_2$—.

In some embodiments, $L^1$ and $L^2$ together form —$(CH_2)_2$—O—$(CH_2)_2$—

In some embodiments, $L^1$ and $L^2$ together form —$(CH_2)_2$—S—$(CH_2)_2$—.

In some embodiments, $L^1$ and $L^2$ together form —O—$(CR^7R^8)$—O—, —O—$(CR^7R^8)_2$—O—, or —O—$(CR^7R^8)_3$—O—.

In some embodiments, $L^1$ and $L^2$ together form —O—$(CH_2)$—O—, —O—$(CH_2)_2$—O—, or —O—$(CH_2)_3$—O—. In some further embodiments, $L^1$ and $L^2$ together form —O—$(CH_2)_2$—O—.

In some embodiments, $L^1$ and $L^2$ together form S—S, —$(CH_2)$—S—, —$(CH_2)$—S(O)—, —$(CH_2)$—$S(O)_2$—, —$(CH_2)$—O—, —$(CH_2)_2$—O—, —$(CH_2)_3$—O—, —O—$(CH_2)_2$—O—, —O—$(CH_2)_2$—S—, —O—$(CH_2)_2$—S(O)—, or —O—$(CH_2)_2$—$S(O)_2$—.

In some embodiments, $L^1$ and $L^2$ together form —$(CH_2)$—S—, —$(CH_2)$—S(O)—, —$(CH_2)$—$S(O)_2$—, —$(CH_2)$—O—, —$(CH_2)_2$—O—, —$(CH_2)_3$—O—, —O—$(CH_2)_2$—O—, —O—$(CH_2)_2$—S—, —O—$(CH_2)_2$—S(O)—, or —O—$(CH_2)_2$—$S(O)_2$—.

In some embodiments, $L^1$ and $L^2$ together form —$(CH_2)$—O—, —$(CH_2)_2$—O—, or —$(CH_2)_3$—O—. In some embodiments, $L^1$ is —$(CH_2)$—, —$(CH_2)_2$—, or —$(CH_2)_3$—; and $L^2$ is —O—.

In some embodiments, $L^1$ and $L^2$ together form —O—$(CH_2)_2$—O—, —O—$(CH_2)_2$—S—, —O—$(CH_2)_2$—S(O)—, —O—$(CH_2)_2$—$S(O)_2$—, —S—$(CH_2)_2$—S—, —S(O)—$(CH_2)_2$—S(O)—, or —$S(O)_2$—$(CH_2)_2$—$S(O)_2$—.

In some embodiments, $L^1$ and $L^2$ together form —O—$(CH_2)_2$—O—, —O—$(CH_2)_2$—S—, —O—$(CH_2)_2$—S(O)—, or —O—$(CH_2)_2$—$S(O)_2$—.

In some embodiments, $L^1$ and $L^2$ together form —O—$(CH_2)_2$—O—.

In some embodiments, $L^1$ and $L^2$ together form —O—$(CH_2)_2$—S—.

In some embodiments, $L^1$ and $L^2$ together form —O—$(CH_2)_2$—S(O)—.

In some embodiments, $L^1$ and $L^2$ together form —O—$(CH_2)_2$—$S(O)_2$—.

In some embodiments, one of $L^1$ and $L^2$ is selected from —$(CR^7R^8)_m$—$NR^9$—, —$(CR^7R^8)_m$—$S(O)_2$—, —$(CR^7R^8)_m$—C(O)—, —C(O)$NR^9$—, —$(CR^7R^8)_m$—S(O)$NR^9$—, and —$(CR^7R^8)_m$—$S(O)_2NR^9$—; and the other is selected from a bond, —$(CR^7R^8)_n$—, —$(CR^7R^8)_m$—$NR^9$—, —$(CR^7R^8)_m$—$S(O)_2$—, —$(CR^7R^8)_m$—C(O)—, —C(O)$NR^9$—, —$(CR^7R^8)_m$—S(O)$NR^9$—, and —$(CR^7R^8)_m$—$S(O)_2NR^9$—.

In some embodiments, $L^1$ and $L^2$ together form —$(CR^7R^8)_{t5}$—C(O)—, —$(CR^7R^8)_{t5}$—C(O)$NR^9$—, —C(O)$NR^9$—$(CR^7R^8)_{t5}$—, —C(O)$NR^9$—, —$S(O)_2NR^9$—$(CR^7R^8)_{t5}$—, —$(CR^7R^8)_{t5}$—$S(O)_2NR^9$—, or —$S(O)_2NR^9$—, wherein t5 is 1, 2, or 3.

In some embodiments, $L^1$ and $L^2$ together form —$(CR^7R^8)_2$—C(O)—, —C(O)$NR^9$—$(CR^7R^8)$—, —C(O)$NR^9$—, —$(CR^7R^8)$—$S(O)_2NR^9$—, —$S(O)_2NR^9$—$(CR^7R^8)$—, or —$S(O)_2NR^9$—.

In some embodiments, $L^1$ and $L^2$ together form —$(CH_2)_2$—C(O)—, —C(O)NH—$(CH_2)$—, —C(O)NH—, —S(O)$_2$NH—$(CH_2)$—, —$(CH_2)$—S(O)$_2$NH—, or —S(O)$_2$NH—.

In some embodiments, $L^1$ and $L^2$ together form —C(O)NH— or —S(O)$_2$NH—.

In some embodiments, $L^1$ is —C(O)— and $L^2$ is —NH—.

In some embodiments, wherein $L^1$ is —S(O)$_2$— and $L^2$ is —NH—.

In some embodiments, $L^1$ and $L^2$ together form —$(CR^7R^8)_{t5}$—C(O)—, —C(O)NR$^9$—, or —S(O)$_2$NR$^9$—, and wherein t5 is 1, 2, or 3.

In some embodiments, $L^1$ and $L^2$ together form —$(CR^7R^8)$—C(O)—, —$(CR^7R^8)_2$—C(O)—, or —$(CR^7R^8)_3$—C(O)—. In some embodiments, $L^1$ and $L^2$ together form —$(CR^7R^8)$—C(O)—. In some embodiments, $L^1$ and $L^2$ together form —$(CR^7R^8)_2$—C(O)—. In some embodiments, $L^1$ and $L^2$ together form —$(CR^7R^8)_3$—C(O)—.

In some embodiments, $L^1$ and $L^2$ together form —$(CH_2)$—C(O)—, —$(CH_2)_2$—C(O)—, or —$(CH_2)_3$—C(O)—. In some embodiments, $L^1$ and $L^2$ together form —$(CH_2)$—C(O)—. In some embodiments, $L^1$ and $L^2$ together form —$(CH_2)_2$—C(O)—. In some embodiments, $L^1$ and $L^2$ together form —$(CH_2)_3$—C(O)—.

In some embodiments, $L^1$ and $L^2$ together form —$(CR^7R^8)$—C(O)NR$^9$—, —C(O)NR$^9$—$(CR^7R^8)$—, or —C(O)NR$^9$—. In some embodiments, $L^1$ and $L^2$ together form —$(CH_2)$—C(O)NR$^9$—, —C(O)NR$^9$—$(CH_2)$—, or —C(O)NR$^9$—. In some embodiments, $L^1$ and $L^2$ together form —$(CH_2)$—C(O)NH—, —C(O)NH—$(CH_2)$—, or —C(O)NH—. In some embodiments, $L^1$ and $L^2$ together form —C(O)NH—$(CH_2)$—, or —C(O)NH—.

In some embodiments, $L^1$ and $L^2$ together form —$(CH_2)$—C(O)NH—.

In some embodiments, $L^1$ and $L^2$ together form —C(O)NH—$(CH_2)$—.

In some embodiments, $L^1$ and $L^2$ together form —C(O)NH—.

In some embodiments, $L^1$ and $L^2$ together form —$(CR^7R^8)_{t7}$—C(O)NR$^9$—$(CR^7R^8)_{t8}$, wherein t7 is 1 or 2 and t8 is 1 or 2. In some embodiments, $L^1$ and $L^2$ together form —$(CR^7R^8)$—C(O)NR$^9$—$(CR^7R^8)$—. In some embodiments, $L^1$ and $L^2$ together form —$(CH_2)$—C(O)NH—$(CH_2)$—.

In some embodiments, $L^1$ and $L^2$ together form —S(O)$_2$NR$^9$—$(CR^7R^8)_{t5}$—, —$(CR^7R^8)_{t5}$—S(O)$_2$NR$^9$—, or —S(O)$_2$NR$^9$—, wherein t5 is 1, 2, or 3.

In some embodiments, $L^1$ and $L^2$ together form —S(O)$_2$NR$^9$—$(CR^7R^8)$—, —$(CR^7R^8)$—S(O)$_2$NR$^9$—, or —S(O)$_2$NR$^9$—. In some further embodiments, R$^9$ is H or $C_{1-3}$ alkyl.

In some embodiments, $L^1$ and $L^2$ together form —S(O)$_2$NR$^9$—$(CH_2)$—, —$(CH_2)$—S(O)$_2$NR$^9$—, or —S(O)$_2$NR$^9$—. In some further embodiments, $L^1$ and $L^2$ together form —S(O)$_2$NH—$(CH_2)$—, —$(CH_2)$—S(O)$_2$NH—, or —S(O)$_2$NH—.

In some embodiments, $L^1$ and $L^2$ together form —S(O)$_2$NH—$(CH_2)$—.

In some embodiments, $L^1$ and $L^2$ together form —$(CH_2)$—S(O)$_2$NH—.

In some embodiments, $L^1$ and $L^2$ together form —S(O)$_2$NH—.

In some embodiments, $L^1$ and $L^2$ together form —$(CR^7R^8)_{t7}$—S(O)$_2$NR$^9$—$(CR^7R^8)_{t8}$—, wherein t7 is 1 or 2 and t8 is 1 or 2. In some embodiments, $L^1$ and $L^2$ together form —$(CR^7R^8)$—S(O)$_2$NR$^9$—$(CR^7R^8)$.

In some embodiments, $L^1$ and $L^2$ together form —$(CH_2)$—S(O)$_2$NR$^9$—$(CH_2)$—.

In some embodiments, $L^1$ and $L^2$ together form —$(CR^7R^8)_m$—NR$^9$—C(O)NR$^9$—, —$(CR^7R^8)_m$—O—C(O)NR$^9$—, or —O—C(O)NR$^9$—$(CR^7R^8)_m$—.

In some embodiments, $L^1$ and $L^2$ together form —$(CR^7R^8)$—NR$^9$—C(O)NR$^9$—, —$(CR^7R^8)$—O—C(O)NR$^9$—, —O—C(O)NR$^9$—$(CR^7R^8)$—, —NR$^9$—C(O)NR$^9$—, or —O—C(O)NR$^9$—.

In some embodiments, $L^1$ and $L^2$ together form —$(CH_2)$—NR$^9$—C(O)NR$^9$—. In some embodiments, $L^1$ and $L^2$ together form —$(CH_2)$—NH—C(O)NH—.

In some embodiments, $L^1$ and $L^2$ together form —$(CR^7R^8)$—O—C(O)NR$^9$—. In some embodiments, $L^1$ and $L^2$ together form —$(CH_2)$—O—C(O)NH—.

In some embodiments, $L^1$ and $L^2$ together form —O—C(O)NR$^9$—$(CR^7R^8)$—. In some embodiments, $L^1$ and $L^2$ together form —O—C(O)NH—$(CH_2)$—.

In some embodiments, $L^1$ and $L^2$ together form —NR$^9$—C(O)NR$^9$—, or —O—C(O)NR$^9$—.

In some embodiments, $L^1$ and $L^2$ together form —NH—C(O)NH—.

In some embodiments, $L^1$ and $L^2$ together form —O—C(O)NH—.

In some embodiments, $L^1$ and $L^2$ together form —$(CR^7R^8)_m$—NR$^9$—$(CR^7R^8)_n$—.

In some embodiments, $L^1$ and $L^2$ together form —NR$^9$—$(CR^7R^8)_n$—. In some embodiments, $L^1$ and $L^2$ together form —NR$^9$—$(CR^7R^8)$—. In some embodiments, $L^1$ and $L^2$ together form —NR$^9$—$(CR^7R^8)_2$—. In some embodiments, $L^1$ and $L^2$ together form —NR$^9$—$(CR^7R^8)_3$—.

In some embodiments, $L^1$ and $L^2$ together form —NR$^9$—$(CH_2)_n$—. In some embodiments, $L^1$ and $L^2$ together form —NR$^9$—$(CH_2)$—. In some embodiments, $L^1$ and $L^2$ together form —NR$^9$—$(CH_2)_2$—. In some embodiments, $L^1$ and $L^2$ together form —NR$^9$—$(CH_2)_3$—.

In some embodiments, $L^1$ and $L^2$ together form —$(CR^7R^8)_{m2}$—NR$^9$—$(CR^7R^8)_n$—, wherein m2 is 1 or 2. In some embodiments, $L^1$ and $L^2$ together form —$(CR^7R^8)$—NR$^9$—$(CR^7R^8)$—, —$(CR^7R^8)$—NR$^9$—$(CR^7R^8)_2$—, or —$(CR^7R^8)_2$—NR$^9$—$(CR^7R^8)_2$—. In some further embodiments, $L^1$ and $L^2$ together form —$(CR^7R^8)$—NR$^9$—$(CR^7R^8)$— or —$(CR^7R^8)$—NR$^9$—$(CR^7R^8)_2$—. In some further embodiments, R$^9$ is H or $C_{1-3}$ alkyl.

In some embodiments, $L^1$ and $L^2$ together form —$(CH_2)_{m2}$—NR$^9$—$(CH_2)_n$—, wherein m2 is 1 or 2. In some embodiments, $L^1$ and $L^2$ together form —$(CH_2)$—NR$^9$—$(CH_2)$—, —$(CH_2)$—NR$^9$—$(CH_2)_2$—, or —$(CH_2)_2$—NR$^9$—$(CH_2)_2$—. In some further embodiments, $L^1$ and $L^2$ together form —$(CH_2)$—NR$^9$—$(CH_2)$— or —$(CH_2)$—NR$^9$—$(CH_2)_2$—. In some further embodiments, R$^9$ is H or $C_{1-3}$ alkyl.

In some embodiments, $L^1$ and $L^2$ together form —$(CR^7R^8)$—NR$^9$—$(CR^7R^8)$—. In some embodiments, $L^1$ and $L^2$ together form —$(CH_2)$—NR$^9$—$(CH_2)$—.

In some embodiments, $L^1$ and $L^2$ together form —NR$^9$—$(CR^7R^8)_{t9}$—O— wherein t9 is 1, 2, or 3. In some embodiments, $L^1$ and $L^2$ together form —NR$^9$—$(CR^7R^8)$—O—. In some embodiments, $L^1$ and $L^2$ together form —NR$^9$—$(CR^7R^8)_2$—O—. In some embodiments, $L^1$ and $L^2$ together form —NR$^9$—$(CR^7R^8)_3$—O—.

In some embodiments, $L^1$ and $L^2$ together form —NR$^9$—$(CH_2)$—O—.

In some embodiments, $L^1$ and $L^2$ together form —NR$^9$—$(CH_2)_2$—O—.

In some embodiments, $L^1$ and $L^2$ together form —NR$^9$—$(CH_2)_3$—O—.

In some embodiments, $L^1$ and $L^2$ together form —$(CR^7R^8)_m$—CR$^{10}$=CR$^{10}$—$(CR^7R^8)_m$—, —$(CR^7R^8)_m$—

$-(CR^7R^8)_n-$, $-NR^9C(O)NR^9$, $-NR^9C(O)NR^9-(CR^7R^8)-$, $-NR^9C(O)NR^9-(CR^7R^8)_2-$, $-(CR^7R^8)-NR^9C(O)NR^9-(CR^7R^8)-$, $-(CR^7R^8)-NR^9C(O)NR^9-(CR^7R^8)_2-$, $-(CR^7R^8)_2-NR^9C(O)NR^9-(CR^7R^8)_2-$, $-OC(O)NR^9-$, $-OC(O)NR^9-(CR^7R^8)-$, $-OC(O)NR^9-(CR^7R^8)_2-$, $-(CR^7R^8)-OC(O)NR^9-$, $-(CR^7R^8)_2-OC(O)NR^9-$, $-(CR^7R^8)-OC(O)NR^9-(CR^7R^8)-$, $-(CR^7R^8)-OC(O)NR^9-(CR^7R^8)_2-$, $-(CR^7R^8)_2-OC(O)NR^9-(CR^7R^8)-$, $-(CR^7R^8)_2-OC(O)NR^9-(CR^7R^8)_2-$, $-NR^9S(O)_2NR^9$, $-NR^9S(O)_2NR^9-(CR^7R^8)-$, $-NR^9S(O)_2NR^9-(CR^7R^8)_2-$, $-(CR^7R^8)-NR^9S(O)_2NR^9-(CR^7R^8)-$, $-(CR^7R^8)-NR^9S(O)_2NR^9-(CR^7R^8)_2-$, or $-(CR^7R^8)_2-NR^9S(O)_2NR^9-(CR^7R^8)_2-$.

In some embodiments, $L^1$ and $L^2$ together form $-NR^9C(O)NR^9$, $-NR^9C(O)NR^9-(CR^7R^8)-$, $-NR^9C(O)NR^9-(CR^7R^8)_2-$, $-(CR^7R^8)-NR^9C(O)NR^9-(CR^7R^8)-$, $-(CR^7R^8)-NR^9C(O)NR^9-(CR^7R^8)_2-$, $-(CR^7R^8)_2-NR^9C(O)NR^9-(CR^7R^8)_2-$, $-OC(O)NR^9-$, $-OC(O)NR^9-(CR^7R^8)-$, $-OC(O)NR^9-(CR^7R^8)_2-$, $-(CR^7R^8)-OC(O)NR^9-$, $-(CR^7R^8)_2-OC(O)NR^9-$, $-(CR^7R^8)-OC(O)NR^9-(CR^7R^8)-$, $-(CR^7R^8)-OC(O)NR^9-(CR^7R^8)_2-$, $-(CR^7R^8)_2-OC(O)NR^9-(CR^7R^8)-$, $-(CR^7R^8)_2-OC(O)NR^9-(CR^7R^8)_2-$, $-NR^9S(O)_2NR^9$, $-NR^9S(O)_2NR^9-(CR^7R^8)-$, $-NR^9S(O)_2NR^9-(CR^7R^8)_2-$, $-(CR^7R^8)-NR^9S(O)_2NR^9-(CR^7R^8)-$, $-(CR^7R^8)-NR^9S(O)_2NR^9-(CR^7R^8)_2-$, or $-(CR^7R^8)_2-NR^9S(O)_2NR^9-(CR^7R^8)_2-$.

In some embodiments, $L^1$ and $L^2$ together form $-NR^9C(O)NR^9$, $-NR^9C(O)NR^9-(CH_2)-$, $-NR^9C(O)NR^9-(CH_2)_2-$, $-(CH_2)-NR^9C(O)NR^9-(CH_2)-$, $-(CH_2)-NR^9C(O)NR^9-(CH_2)_2-$, $-(CH_2)_2-NR^9C(O)NR^9-(CH_2)_2-$, $-OC(O)NR^9-$, $-OC(O)NR^9-(CH_2)-$, $-OC(O)NR^9-(CH_2)_2-$, $-(CH_2)-OC(O)NR^9-$, $-(CH_2)_2-OC(O)NR^9-$, $-(CH_2)-OC(O)NR^9-(CH_2)-$, $-(CH_2)-OC(O)NR^9-(CH_2)_{27}$, $-(CH_2)_2-OC(O)NR^9-(CH_2)-$, $-(CH_2)_2-OC(O)NR^9-(CH_2)_2-$, $-NR^9S(O)_2NR^9$, $-NR^9S(O)_2NR^9-(CH_2)-$, $-NR^9S(O)_2NR^9-(CH_2)_2-$, $-(CH_2)-NR^9S(O)_2NR^9-(CH_2)-$, $-(CH_2)-NR^9S(O)_2NR^9-(CH_2)_2-$, or $-(CH_2)_2-NR^9S(O)_2NR^9-(CH_2)_2-$.

In some embodiments, one of $L^1$ and $L^2$ is selected from $-(CR^7R^8)_m-NR^9C(O)NR^9-$, $-(CR^7R^8)_m-OC(O)NR^9-$, $-(CR^7R^8)_m-NR^9C(O)O-$, and $-(CR^7R^8)_m-NR^9-S(O)_2NR^9-$; and the other is selected from a bond, $-(CR^7R^8)_n-$, $-(CR^7R^8)_m-NR^9-$, $-(CR^7R^8)_m-O-$, $-(CR^7R^8)_m-S-$, $-(CR^7R^8)_m-S(O)_2-$, $-(CR^7R^8)_m-C(O)-$, $-C(O)NR^9-$, $-(CR^7R^8)_m-S(O)NR^9-$, and $-(CR^7R^8)_m-S(O)_2NR^9-$.

In some embodiments, one of $L^1$ and $L^2$ is selected from $-(CR^7R^8)_m-NR^9C(O)NR^9-$, $-(CR^7R^8)_m-OC(O)NR^9-$, $-(CR^7R^8)_m-NR^9C(O)O-$, and $-(CR^7R^8)_m-NR^9-S(O)_2NR^9-$; and the other is selected from a bond, and $-(CR^7R^8)_n-$.

In some embodiments, $L^1$ and $L^2$ together form $-(CR^7R^8)_m-NR^9C(O)NR^9-(CR^7R^8)_m-$, $-(CR^7R^8)_m-OC(O)NR^9-(CR^7R^8)_m-$, or $-(CR^7R^8)_m-NR^9-S(O)_2NR^9-(CR^7R^8)_m-$.

In some embodiments, $L^1$ and $L^2$ together form $-(CR^7R^8)_m-NR^9C(O)NR^9-(CR^7R^8)_m-$. In some embodiments, $L^1$ and $L^2$ together form $-NR^9C(O)NR^9$, $-NR^9C(O)NR^9-(CR^7R^8)_{m2}-$, or $-(CR^7R^8)_{m1}-NR^9C(O)NR^9-(CR^7R^8)_{m2}-$, wherein m1 and m2 are each, independently 1 or 2.

In some embodiments, $L^1$ and $L^2$ together form $-NR^9C(O)NR^9-$.

In some embodiments, $L^1$ and $L^2$ together form $-NR^9C(O)NR^9-(CR^7R^8)-$, $-NR^9C(O)NR^9-(CR^7R^8)_2-$, $-(CR^7R^8)-NR^9C(O)NR^9-(CR^7R^8)-$, $-(CR^7R^8)-NR^9C(O)NR^9-(CR^7R^8)_2-$, or $-(CR^7R^8)_2-NR^9C(O)NR^9-(CR^7R^8)_2-$.

In some embodiments, $L^1$ and $L^2$ together form $-(CH_2)_m-NR^9C(O)NR^9-(CH_2)_m-$. In some embodiments, $L^1$ and $L^2$ together form $-NR^9C(O)NR^9$, $-NR^9C(O)NR^9-(CH_2)_{m2}-$, or $-(CH_2)_{m1}-NR^9C(O)NR^9-(CH_2)_{m2}-$ wherein m1 and m2 are each, independently 1 or 2.

In some embodiments, $L^1$ and $L^2$ together form $-NR^9C(O)NR^9-(CH_2)-$, $-NR^9C(O)NR^9-(CH_2)_2-$, $-(CH_2)-NR^9C(O)NR^9-(CH_2)-$, $-(CH_2)-NR^9C(O)NR^9-(CH_2)_2-$, or $-(CH_2)_2-NR^9C(O)NR^9-(CH_2)_2-$.

In some embodiments, $L^1$ and $L^2$ together form $-(CR^7R^8)_m-OC(O)NR^9-(CR^7R^8)_m-$.

In some embodiments, $L^1$ and $L^2$ together form $-OC(O)NR^9-$.

In some embodiments, $L^1$ and $L^2$ together form $-OC(O)NR^9-(CR^7R^8)-$, $-OC(O)NR^9-(CR^7R^8)_2-$, $-(CR^7R^8)-OC(O)NR^9-$, $-(CR^7R^8)_2-OC(O)NR^9-$, $-(CR^7R^8)-OC(O)NR^9-(CR^7R^8)-$, $-(CR^7R^8)-OC(O)NR^9-(CR^7R^8)_2-$, $-(CR^7R^8)_2-OC(O)NR^9-(CR^7R^8)-$, or $-(CR^7R^8)_2-OC(O)NR^9-(CR^7R^8)_2-$.

In some embodiments, $L^1$ and $L^2$ together form $-OC(O)NR^9-(CH_2)-$, $-OC(O)NR^9-(CH_2)_2-$, $-(CH_2)-OC(O)NR^9-$, $-(CH_2)_2-OC(O)NR^9-$, $-(CH_2)-OC(O)NR^9-(CH_2)-$, $-(CH_2)-OC(O)NR^9-(CH_2)_2-$, $-(CH_2)_2-OC(O)NR^9-(CH_2)-$, or $-(CH_2)_2-OC(O)NR^9-(CH_2)_2-$.

In some embodiments, $L^1$ and $L^2$ together form $-(CR^7R^8)_m-NR^9S(O)_2NR^9-(CR^7R^8)_m-$. In some embodiments, $L^1$ and $L^2$ together form $-NR^9S(O)_2NR^9-$, $-NR^9S(O)_2NR^9-(CR^7R^8)_{m2}-$, or $-(CR^7R^8)_{m1}-NR^9S(O)_2NR^9-(CR^7R^8)_{m2}-$, wherein m1 and m2 are each, independently 1 or 2.

In some embodiments, $L^1$ and $L^2$ together form $-NR^9S(O)_2NR^9-$.

In some embodiments, $L^1$ and $L^2$ together form $-NR^9S(O)_2NR^9-(CR^7R^8)-$, $-NR^9S(O)_2NR^9-(CR^7R^8)_2-$, $-(CR^7R^8)-NR^9S(O)_2NR^9-(CR^7R^8)-$, $-(CR^7R^8)-NR^9S(O)_2NR^9-(CR^7R^8)_2-$, or $-(CR^7R^8)_2-NR^9S(O)_2NR^9-(CR^7R^8)_2-$.

As used herein, unless specifically indicated, a linkage—a moiety that links two other moieties—can be attached to the other two moieties in either direction, if the linkage is asymmetric. For example, the moiety formed by $L^1$ and $L^2$ together in compounds of Formula I can be linked to the ring containing $A^1$, $B^1$, $D^1$, and $E^1$ and the containing $A^2$, $B^2$, $D^2$, and $E^2$ in either direction. For example, when $L^1$ and $L^2$ together form $-O-(CH_2)_2-S-$, the sulfur atom (S) can be linked to the ring containing $A^1$, $B^1$, $D^1$, and $E^1$, and oxygen atom (O) to the ring containing $A^2$, $B^2$, $D^2$, and $E^2$. Alternatively, when $L^1$ and $L^2$ together form $-O-(CH_2)_2-S-$, the oxygen atom (O) can be linked to the ring containing $A^1$, $B^1$, $D^1$, and $E^1$, and the sulfur atom (S) to the ring containing $A^2$, $B^2$, $D^2$, and $E^2$. For another example, when $W^1$ in $-W^1-Q^1-Y^1-Z^1$ is $O(CR^{11a}R^{11b})_{q1}NR^f$, $W^1$ can be linked to $Q^1$ either via the O or the N atom.

In some embodiments, $R^7$, $R^8$, and $R^{10}$ are each, independently, selected from H, halo, $C_{1-6}$ alkyl, $C_{2-6}$ alkenyl, $C_{2-6}$ alkynyl, $C_{1-6}$ haloalkyl, cycloalkyl, CN, $NO_2$, $OR^{a1}$, $SR^{a1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $C(O)R^{b1}$, $C(O)NR^{c1}R^{d1}$, $C(O)OR^{a1}$, $NR^{c1}C(O)R^{b1}$, $NR^{c1}C(O)NR^{c1}R^{d1}$, and $NR^{c1}R^{d1}$, wherein each of said $C_{1-6}$ alkyl, $C_{2-6}$ alkenyl, $C_{2-6}$ alkynyl, $C_{1-6}$ haloalkyl and cycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, cycloalkyl, CN, $NO_2$, $OR^{a1}$, $SR^{a1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $C(O)R^{b1}$, $C(O)NR^{c1}R^{d1}$, $C(O)OR^{a1}$, $NR^{c1}C(O)R^{b1}$, $NR^{c1}C(O)NR^{c1}R^{d1}$, and $NR^{c1}R^{d1}$.

In some embodiments, $R^7$, $R^8$, and $R^{10}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, and $NR^{c1}R^{d1}$.

In some embodiments, $R^7$, $R^8$, and $R^{10}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, and $SR^{a1}$.

In some embodiments, $R^7$, $R^8$, and $R^{10}$ are each, independently, selected from H, halo, $C_{1-6}$ alkyl, $C_{1-6}$ haloalkyl, CN, $NO_2$, $OR^{a1}$, and $SR^{a1}$.

In some embodiments, $R^7$, $R^8$, and $R^{10}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, or $NR^{c1}R^{d1}$.

In some embodiments, $R^7$, $R^8$, and $R^{10}$ are each, independently, selected from H, halo, $C_{1-6}$ alkyl, CN, $NO_2$, OH, $C_{1-6}$ alkoxy, $C_{1-6}$ haloalkoxy, and $C_{2-8}$ alkoxyalkoxy. In some embodiments, $R^7$, $R^8$, and $R^{10}$ are each, independently, selected from H, $C_{1-4}$ alkyl, OH, $C_{1-6}$ alkoxy, $C_{1-6}$ haloalkoxy, and $C_{2-8}$ alkoxyalkoxy.

In some embodiments, $R^7$ and $R^8$ are each, independently, selected from H, halo, $C_{1-6}$ alkyl, CN, $NO_2$, OH, $C_{1-6}$ alkoxy, $C_{1-6}$ haloalkoxy, and $C_{2-8}$ alkoxyalkoxy. In some further embodiments, $R^7$ and $R^8$ are each, independently, selected from H, halo, $C_{1-4}$ alkyl, CN, $NO_2$, $C_{1-4}$ alkoxy, $C_{1-4}$ haloalkoxy, and $C_{2-8}$ alkoxyalkoxy. In some further embodiments, $R^7$ and $R^8$ are each, independently, selected from H, halo, $C_{1-4}$ alkyl, OH, $C_{1-4}$ alkoxy, $C_{1-4}$ haloalkoxy, and $C_{2-8}$ alkoxyalkoxy. In some further embodiments, $R^7$ and $R^8$ are each, independently, selected from H, OH, $C_{1-4}$ alkoxy, $C_{1-4}$ haloalkoxy, and $C_{2-8}$ alkoxyalkoxy. In some further embodiments, $R^7$ and $R^8$ are each, independently, selected from H, OH, and $C_{2-8}$ alkoxyalkoxy.

In some embodiments, $R^7$ and $R^8$ are each, independently, selected from H and $C_{1-6}$ alkyl. In some further embodiments, $R^7$ and $R^8$ are each, independently, selected from H and $C_{1-4}$ alkyl.

In some embodiments, $R^7$ and $R^8$ are each, independently, selected from H and $C_{1-3}$ alkyl. In some further embodiments, $R^7$ and $R^8$ are each, independently, selected from H and $CH_3$.

In some embodiments, $R^7$ and $R^8$ are both H. In some embodiments, $R^7$ and $R^8$ are both $CH_3$. In some embodiments, one of $R^7$ and $R^8$ is H and the other is $CH_3$.

In some embodiments, each $R^9$ is, independently, H, $C_{1-6}$ alkyl, $C_{1-6}$ haloalkyl, $C(O)R^{b1}$, $C(O)NR^{c1}R^{d1}$, or $C(O)OR^{a1}$. In some further embodiments, each $R^9$ is, independently, H, $C_{1-6}$ alkyl, $C_{1-6}$ haloalkyl, $C(O)R^{b1}$, or $C(O)NR^{c1}R^{d1}$.

In some embodiments, each $R^9$ is, independently, H, $C_{1-6}$ alkyl, $C_{1-6}$ haloalkyl, $C(=O)-(C_{1-6}$ alkyl), $C(=O)$-(arylalkyl), $C(=O)NH_2$, $C(=O)NH(C_{1-6}$ alkyl), $C(=O)N(C_{1-6}$ alkyl)$_2$, $C(=O)O-(C_{1-6}$ alkyl), or $C(=O)O$-(arylalkyl). In some embodiments, each $R^9$ is, independently, H, $C_{1-6}$ alkyl, $C_{1-6}$ haloalkyl, $C(=O)-(C_{1-6}$ alkyl), $C(=O)$-(arylalkyl), $C(=O)NH_2$, $C(=O)NH(C_{1-6}$ alkyl), or $C(=O)N(C_{1-4}$ alkyl)$_2$. In some embodiments, each $R^9$ is independently, H or $C_{1-6}$ alkyl. In some embodiments, each $R^9$ is independently, H or $C_{1-4}$ alkyl. In some embodiments, each $R^9$ is independently, H or $C_{1-3}$ alkyl. In some embodiments, each $R^9$ is H. In some embodiments, each $R^9$ is, independently, $C_{1-3}$ alkyl. In some embodiments, each $R^9$ is methyl.

In some embodiments, each $R^{10}$ is, independently, selected from H, halo, and $C_{1-6}$ alkyl. In some embodiments, each $R^{10}$ is, independently, selected from H and $C_{1-6}$ alkyl. In some embodiments, each $R^{10}$ is, independently, selected from H and $C_{1-4}$ alkyl. In some further embodiments, each $R^{10}$ is H.

In some embodiments, each $R^5$ is, independently, selected from H, halo, $C_{1-6}$ alkyl, $C_{1-6}$ haloalkyl, $Cy^1$, $—W^1-Q^1-Y^1—Z^1$, CN, $NO_2SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $S(O)_2R^{b1}$, $NR^{c1}S(O)_2NR^{c1}R^{d1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$ alkynyl, or $C_{1-6}$ haloalkyl is optionally substituted by 1, 2, 3, 4, or 5 substituents each independently selected from halo, $C_{1-6}$ alkyl, $C_{2-6}$ alkenyl, $C_{2-6}$ alkynyl, $C_{1-6}$ haloalkyl, halosulfanyl, $Cy^1$, $—W^1-Q^1-Y^1—Z^1$, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments, each $R^5$ is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, $C_{2-6}$ alkynyl, or $C_{1-6}$ haloalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments:

each $R^5$ is, independently, selected from H, halo, $C_{1-6}$ alkyl, $C_{2-6}$ alkenyl, $C_{2-6}$ alkynyl, $C_{1-6}$ haloalkyl, $Cy^3$, $—W^1-Q^1-Y^1—Z^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$alkynyl, or $C_{1-6}$ haloalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$; or each $R^5$ is, independently, selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, $C_{2-6}$ alkynyl, or $C_{1-6}$ haloalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$R^{a1}$, $R^{b1}$, $R^{c1}$, and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, NO$_2$, OH, SH, O($C_{1-4}$ alkyl), O($C_{1-4}$ haloalkyl), O(aryl), O(arylalkyl), S($C_{1-4}$alkyl), S($C_{1-4}$haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)NH$_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)NH$_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl);

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, NO$_2$, OH, SH, O($C_{1-4}$ alkyl), O($C_{1-4}$ haloalkyl), O(aryl), O(arylalkyl), S($C_{1-4}$ alkyl), S($C_{1-4}$haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)NH$_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)NH$_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl).

In some embodiments:

each $R^5$ is, independently, selected from H, halo, $C_{1-6}$ alkyl, $C_{1-6}$ haloalkyl, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)NR$^{c1}$R$^{d1}$, NR$^{c1}$S(O)$_2$NR$^{c1}$R$^{d1}$, S(O)$_2$R$^{b1}$, NR$^{c1}$S(O)$_2$R$^{b1}$, and S(O)$_2$NR$^{c1}$R$^{d1}$, wherein said $C_{1-6}$ alkyl, $C_{2-6}$ alkenyl, $C_{2-6}$ alkynyl, or $C_{1-6}$ haloalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, SF$_5$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$;

$R^{a1}$, $R^{b1}$, $R^{c1}$, and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, NO$_2$, OH, SH, O($C_{1-4}$ alkyl), O($C_{1-4}$ haloalkyl), O(aryl), O(arylalkyl), S($C_{1-4}$ alkyl), S($C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)NH$_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)NH$_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$NH$_2$, S(=O)$_2$NH($C_{1-4}$ alkyl) and S(=O)$_2$NH(arylalkyl);

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, NO$_2$, OH, SH, O($C_{1-4}$ alkyl), O($C_{1-4}$ haloalkyl), O(aryl), O(arylalkyl), S($C_{1-4}$ alkyl), S($C_{1-4}$haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)NH$_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)NH$_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$NH$_2$, S(=O)$_2$NH($C_{1-4}$ alkyl) and S(=O)$_2$NH(arylalkyl).

In some embodiments, at least one of $R^5$ is selected C(O)NR$^{c1}$R$^{d1}$ or NR$^{c1}$R$^{d1}$, wherein:

$R^{c1}$ and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, NO$_2$, OH, SH, O($C_{1-4}$ alkyl), O($C_{1-4}$ haloalkyl), O(aryl), O(arylalkyl), S($C_{1-4}$ alkyl), S($C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)NH$_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)NH$_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$NH$_2$, S(=O)$_2$NH($C_{1-4}$ alkyl) and S(=O)$_2$NH(arylalkyl);

or $R^{c1}$ and $R^{d1}$ together with the N atom to which they are attached form pyrrolidinyl, piperidinyl, piperazinyl, or morpholinyl, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, NO$_2$, OH, SH, O($C_{1-4}$ alkyl), O($C_{1-4}$haloalkyl), O(aryl), O(arylalkyl), S($C_{1-4}$ alkyl), S($C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)NH$_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)NH$_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$NH$_2$, S(=O)$_2$NH($C_{1-4}$ alkyl) and S(=O)$_2$NH(arylalkyl).

In some embodiments, at least one of $R^5$ is selected C(O)NR$^{c1}$R$^{d1}$ or NR$^{c1}$R$^{d1}$, wherein:

R$^{c1}$ and R$^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, NO$_2$, OH, SH, O($C_{1-4}$ alkyl), O($C_{1-4}$ haloalkyl), O(aryl), O(arylalkyl), S($C_{1-4}$ alkyl), S($C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)NH$_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)NH$_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$NH$_2$, S(=O)$_2$NH($C_{1-4}$ alkyl) and S(=O)$_2$NH(arylalkyl);

or R$^{c1}$ and R$^{d1}$ together with the N atom to which they are attached form pyrrolidinyl, piperidinyl or morpholinyl, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, NO$_2$, OH, SH, O($C_{1-4}$ alkyl), O($C_{1-4}$ haloalkyl), O(aryl), O(arylalkyl), S($C_{1-4}$ alkyl), S($C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)NH$_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)NH$_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$NH$_2$, S(=O)$_2$NH($C_{1-4}$ alkyl) and S(=O)$_2$NH(arylalkyl).

In some embodiments, each $R^5$ is, independently, selected from H, halo, $C_{1-6}$ alkyl, $C_{1-6}$ haloalkyl, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)NR$^{c1}$R$^{d1}$, NR$^{c1}$S(O)$_2$NR$^{c1}$R$^{d1}$, S(O)$_2$R$^{b1}$, NR$^{c1}$S(O)$_2$R$^{b1}$, and S(O)$_2$NR$^{c1}$R$^{d1}$.

In some embodiments, each $R^5$ is, independently, selected from H, halo, $C_{1-6}$ alkyl, $C_{1-6}$ haloalkyl, CN, NO$_2$, SF$_5$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$.

In some embodiments, each $R^5$ is independently selected from H, halo, $C_{1-6}$ alkyl, $C_{1-6}$ haloalkyl, CN, NO$_2$, OR$^{a1}$, NR$^{c1}$R$^{d1}$, NR$^{c1}$C(O)NR$^{c1}$R$^{d1}$, NR$^{c1}$S(O)$_2$R$^{b1}$, NR$^{c1}$S(O)$_2$NR$^{c1}$R$^{d1}$, S(O)R$^{b1}$, S(O)$_2$R$^{b1}$, and S(O)$_2$NR$^{c1}$R$^{d1}$.

In some embodiments, each $R^5$ is independently selected from H, halo, $C_{1-6}$ alkyl, $C_{1-6}$ haloalkyl, CN, NO$_2$, OR$^{a1}$, NR$^{c1}$R$^{d1}$, NR$^{c1}$C(O)NR$^{c1}$R$^{d1}$, NR$^{c1}$S(O)$_2$R$^{b1}$, S(O)R$^{b1}$, S(O)$_2$R$^{b1}$, and S(O)$_2$NR$^{c1}$R$^{d1}$.

In some embodiments, each $R^5$ is independently selected from H, $C_{1-6}$ alkyl, COOH, C(=O)—($C_{1-4}$ alkyl), S(=O)$_2$—($C_{1-4}$ alkyl), S(=O)$_2$NH$_2$, S(=O)$_2$NH($C_{1-4}$ alkyl), NR$^{c1}$C(O)NR$^{c1}$R$^{d1}$, NR$^{c1}$S(O)$_2$NR$^{c1}$R$^{d1}$, C(O)NR$^{c1}$R$^{d1}$, and NR$^{c1}$R$^{d1}$.

In some embodiments, each $R^5$ is independently selected from H, $C_{1-6}$ alkyl, COOH, C(=O)—($C_{1-4}$ alkyl), S(=O)$_2$—($C_{1-4}$ alkyl), S(=O)$_2$NH$_2$, S(=O)$_2$NH($C_{1-4}$ alkyl), C(O)NR$^{c1}$R$^{d1}$ and NR$^{c1}$R$^{d1}$, wherein:

R$^{c1}$ and R$^{d1}$ are each, independently, selected from H, $C_{1-6}$ alkyl, aryl, heteroaryl, arylalkyl, and heteroarylalkyl, wherein each of said $C_{1-6}$ alkyl, aryl, heteroaryl, arylalkyl, heteroarylalkyl is optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, heteroaryl, OH, O($C_{1-4}$alkyl), O($C_{1-4}$haloalkyl), piperidinyl, pyrrolidinyl, morpholinyl, and piperizinyl optionally substituted with $C_{1-4}$ alkyl, aryl, or arylalkyl;

or R$^{c1}$ and R$^{d1}$ together with the N atom to which they are attached form pyrrolidinyl, piperidinyl, piperazinyl, or morpholinyl, each optionally substituted with 1, 2, or 3 substituents independently selected from $C_{1-4}$ alkyl, $C_{1-4}$ haloalkyl, $C_{1-4}$ hydroxylalkyl, aryl, arylalkyl, heteroaryl, heteroarylalkyl, OH, O($C_{1-4}$ alkyl), and O($C_{1-4}$haloalkyl).

In some embodiments, two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$.

In some embodiments, two adjacent $R^5$ on the ring containing $A^1$, $B^1$, $D^1$, and $E^1$ can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$.

In some embodiments, two adjacent $R^5$ on the ring containing $A^2$, $B^2$, $D^2$, and $E^2$ can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, $NR^{c1}C(=NR^{g1})NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments, at least one $R^5$ is other than H. In some embodiments, at least one $R^5$ on the ring containing $A^1$, $B^1$, $D^1$, and $E^1$ is other than H. In some embodiments, at least one $R^5$ on the ring containing $A^2$, $B^2$, $D^2$, and $E^2$ is other than H. In some embodiments, one or two $R^5$ on the ring containing $A^1$, $B^1$, $D^1$, and $E^1$ are other than H. In some embodiments, one $R^5$ on the ring containing $A^1$, $B^1$, $D^1$, and $E^1$ is other than H. In some embodiments, one or two $R^5$ on the ring containing $A^2$, $B^2$, $D^2$, and $E^2$ are other than H. In some embodiments, one $R^5$ on the ring containing $A^2$, $B^2$, $D^2$, and $E^2$ is other than H.

In some embodiments, at least one $R^5$ is selected from halo, $C_{1-6}$ alkyl, $C_{1-6}$ haloalkyl, cycloalkyl, aryl, heteroaryl, heterocycloalkylalkyl, $Cy^1$, $-W^1-Q^1-Y^1-Z^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{1-6}$ haloalkyl, cycloalkyl, aryl, heteroaryl, or heterocycloalkylalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$.

In some embodiments, at least one $R^5$ is selected from halo, $C_{1-6}$ alkyl, aryl, heteroaryl, heterocycloalkylalkyl, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, aryl, heteroaryl, or heterocycloalkylalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$.

In some embodiments, at least one $R^5$ is selected from $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments, at least one $R^5$ is $Cy^1$ or $-W^1-Q^1-Y^1-Z^1$.

In some embodiments, at least one $R^5$ is $Cy^1$. In some embodiments, at least one $R^5$ on the ring containing $A^1$, $B^1$, $D^1$, and $E^1$ is $Cy^1$. In some other embodiments, at least one $R^5$ on the ring containing $A^2$, $B^2$, $D^2$, and $E^2$ is $Cy^1$.

In some embodiments, at least one $R^5$ is $-W^1-Q^1-Y^1-Z^1$. In some embodiments, at least one $R^5$ on the ring containing $A^1$, $B^1$, $D^1$, and $E^1$ is $-W^1-Q^1-Y^1-Z^1$. In some other embodiments, at least one $R^5$ on the ring containing $A^2$, $B^2$, $D^2$, and $E^2$ is $-W^1-Q^1-Y^1-Z^1$.

In some embodiments, at least one $R^5$ on the ring containing $A^1$, $B^1$, $D^1$, and $E^1$ or on the ring containing $A^2$, $B^2$, $D^2$, and $E^2$ is $-W^1-Q^1-Y^1-Z^1$ that is selected from $-(CR^{11a}R^{11b})_{p1}-Q^1-Y^1-Z^1$, $-(CR^{11a}R^{11b})_{p1}O(CR^{11a}R^{11b})_{p2}-Q^1-Y^1-Z^1$, $-(CR^{11a}R^{11b})_{p1}S(CR^{11a}R^{11b})_{p2}-Q^1-Y^1-Z^1$, $-(CR^{11a}R^{11b})_{p1}S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}NR^e(CR^{11a}R^{11b})_{p2}-Q^1-Y^1-Z^1$, $-NR^eS(O)(CR^{11a}R^{11b})_{p1}-Q^1-Y^1-Z^1$, $-S(O)NR^e(CR^{11a}R^{11b})_{p2}-Q^1-Y^1-Z^1$, $-NR^eS(O)_2(CR^{11a}R^{11b})_{p1}-Q^1-Y^1-Z^1$, $-S(O)_2NR^e(CR^{11a}R^{11b})_{p2}-Q^1-Y^1-Z^1$, $NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, and $NR^eC(O)NR^f(CR^{11a}R^{11b})_{p2}-Q^1-Y^1-Z^1$.

In some embodiments, at least one $R^5$ on the ring containing $A^1$, $B^1$, $D^1$, and $E^1$ or on the ring containing $A^2$, $B^2$, $D^2$, and $E^2$ is $-(CR^{11a}R^{11b})_{p1}O(CR^{11a}R^{11b})_{p2}-Q^1-Y^1-Z^1$, $-(CR^{11a}R^{11b})_{p1}S(CR^{11a}R^{11b})_{p2}-Q^1-Y^1-Z^1$, $-(CR^{11a}R^{11b})_{p1}S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}NR^e(CR^{11a}R^{11b})_{p2}-Q^1-Y^1-Z^1$, $-NR^eS(O)(CR^{11a}R^{11b})_{p1}-Q^1-Y^1-Z^1$, $-S(O)NR^e(CR^{11a}R^{11b})_{p2}-Q^1-Y^1-Z^1$, $NR^eS(O)_2(CR^{11a}R^{11b})_{p1}-Q^1-Y^1-Z^1$, $-S(O)_2NR^e(CR^{11a}R^{11b})_{p2}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

In some embodiments, at least one of $Q^1$, $Q^2$, $Q^3$, $Q^4$, and $Q^5$ is selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, $Q^1$, $Q^2$, $Q^3$, $Q^4$, and $Q^5$ are each, independently, selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, at least one of $Q^1$, $Q^2$, $Q^3$, $Q^4$, and $Q^5$ is selected from aryl and heteroaryl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, at least one of $Q^1$, $Q^2$, $Q^3$, $Q^4$, and $Q^5$ is aryl optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, at least one of $Q^1$, $Q^2$, $Q^3$, $Q^4$, and $Q^5$ is heteroaryl optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, at least one $Q^1$ is selected from aryl and heteroaryl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, each $Q^1$ is independently selected from aryl and heteroaryl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In some further embodiments, each $Q^1$ is independently selected from such optionally substituted cycloalkyl. In other further embodiments, each $Q^1$ is independently selected from such optionally substituted heterocycloalkyl.

In some embodiments, at least one $Q^1$ is heteroaryl optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, each $Q^1$ is independently heteroaryl optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some further embodiments, each $Q^1$ is independently selected from such optionally substituted cycloalkyl. In other further embodiments, each $Q^1$ is independently selected from such optionally substituted heterocycloalkyl.

In some embodiments, at least one $Q^1$ is aryl optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, each $Q^1$ is independently aryl optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some further embodiments, each $Q^1$ is independently selected from such optionally substituted cycloalkyl. In other further embodiments, each $Q^1$ is independently selected from such optionally substituted heterocycloalkyl.

In some embodiments, at least one $Q^1$ is selected from cycloalkyl and heterocycloalkyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, each $Q^1$ is independently selected from cycloalkyl and heterocycloalkyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some further embodiments, each $Q^1$ is independently selected from such optionally substituted cycloalkyl. In other further embodiments, each $Q^1$ is independently selected from such optionally substituted heterocycloalkyl.

In some embodiments, at least one $Q^1$ is selected from heterocycloalkyl optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, each $Q^1$ is independently selected from heterocycloalkyl optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, at least one $Q^1$ is selected from cycloalkyl optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, each $Q^1$ is independently selected from cycloalkyl optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, each $Q^1$ is independently selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some further embodiments, each $Q^1$ is independently selected from cyclopropyl, cyclobutyl, cyclopentyl, and cyclohexyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In other further embodiments, each $Q^1$ is independently selected from azetidinyl, pyrrolidinyl, piperidinyl, and piperazinyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some embodiments, at least one $Q^1$ is selected from such optionally substituted cyclopropyl, cyclobutyl, cyclopentyl, cyclohexyl, azetidinyl, pyrrolidinyl, piperidinyl, or piperazinyl.

In some embodiments, each $Q^1$ is independently selected from cyclobutyl, cyclopentyl, cyclohexyl, pyrrolidinyl, piperidinyl, and piperazinyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some embodiments, at least one $Q^1$ is selected from such optionally substituted cyclobutyl, cyclopentyl, cyclohexyl, pyrrolidinyl, piperidinyl, or piperazinyl.

In some embodiments, each $Q^1$ is independently selected from cyclopropyl, cyclobutyl, cyclopentyl, cyclohexyl, azetidinyl, pyrrolidinyl, and piperidinyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some embodiments, at least one $Q^1$ is selected from such optionally substituted cyclopropyl, cyclobutyl, cyclopentyl, cyclohexyl, azetidinyl, pyrrolidinyl, or piperidinyl.

In some embodiments, each $Q^1$ is independently selected from pyrrolidinyl, piperidinyl, and piperazinyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some embodiments, at least one Q$^1$ is selected from such optionally substituted pyrrolidinyl, piperidinyl, or piperazinyl.

In some embodiments, each Q$^1$ is independently selected from pyrrolidinyl, and piperidinyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some embodiments, at least one Q$^1$ is selected from such optionally substituted pyrrolidinyl or piperidinyl.

In some embodiments, at least one R$^5$ is —W$^6$-Q$^1$-Y$^1$—Z$^1$.

In some embodiments, at least one R$^5$ is —(CR$^{11a}$R$^{11b}$)$_{p1}$S(CR$^{11a}$R$^{11b}$)$_{p2}$-Q$^1$-Y$^1$—Z$^1$, —(CR$^{11a}$R$^{11b}$)$_{p1}$S(O)(CR$^{11a}$R$^{11b}$)$_{p2}$-Q$^1$-Y$^1$—Z$^1$, —(CR$^{11a}$R$^{11b}$)$_{p1}$S(O)$_2$(CR$^{11a}$R$^{11b}$)$_{p2}$-Q$^1$-Y$^1$—Z$^1$, —(CR$^{11a}$R$^{11b}$)$_{p1}$S(O)NR$^e$(CR$^{11a}$R$^{11b}$)$_{p2}$-Q$^1$-Y$^1$—Z$^1$, —(CR$^{11a}$R$^{11b}$)$_{p2}$NR$^e$S(O)(CR$^{11a}$R$^{11b}$)$_{p1}$-Q$^1$-Y$^1$—Z$^1$, (CR$^{11a}$R$^{11b}$)$_{p1}$S(O)$_2$NR$^e$(CR$^{11a}$R$^{11b}$)$_{p2}$-Q$^1$-Y$^1$—Z$^1$, or —(CR$^{11a}$R$^{11b}$)$_{p2}$NR$^e$S(O)$_2$(CR$^{11a}$R$^{11b}$)$_{p1}$-Q$^1$-Y$^1$—Z$^1$.

In some embodiments, at least one Y$^1$ is selected from absent, (CR$^{12a}$R$^{12b}$)$_{p3}$O(CR$^{12a}$R$^{12b}$)$_{p4}$, (CR$^{12a}$R$^{12b}$)$_{p3}$S(CR$^{12a}$R$^{12b}$)$_{p4}$, (CR$^{12a}$R$^{12b}$)$_{p3}$NR$^e$(CR$^{12a}$R$^{12b}$)$_{p4}$, (CR$^{12a}$R$^{12b}$)$_{p3}$C(O)(CR$^{12a}$R$^{12b}$)$_{p4}$, (CR$^{12a}$R$^{12b}$)$_{p3}$C(O)NR$^e$(CR$^{12a}$R$^{12b}$)$_{p4}$, (CR$^{12a}$R$^{12b}$)$_{p3}$S(O)$_2$(CR$^{12a}$R$^{12b}$)$_{p4}$, (CR$^{12a}$R$^{12b}$)$_{p3}$S(O)$_2$NR$^e$(CR$^{12a}$R$^{12b}$)$_{p4}$, In some embodiments, each Y$^1$ is independently selected from absent, (CR$^{12a}$R$^{12b}$)$_{p3}$O(CR$^{12a}$R$^{12b}$)$_{p4}$, (CR$^{12a}$R$^{12b}$)$_{p3}$S(CR$^{12a}$R$^{12b}$)$_{p4}$, (CR$^{12a}$R$^{12b}$)$_{p3}$NR$^e$(CR$^{12a}$R$^{12b}$)$_{p4}$, (CR$^{12a}$R$^{12b}$)$_{p3}$C(O)(CR$^{12a}$R$^{12b}$)$_{p4}$, (CR$^{12a}$R$^{12b}$)$_{p3}$C(O)NR$^e$(CR$^{12a}$R$^{12b}$)$_{p4}$, (CR$^{12a}$R$^{12b}$)$_{p3}$S(O)$_2$(CR$^{12a}$R$^{12b}$)$_{p4}$, (CR$^{12a}$R$^{12b}$)$_{p3}$S(O)$_2$NR$^e$(CR$^{12a}$R$^{12b}$)$_{p4}$, and (CR$^{12a}$R$^{12b}$)$_{p3}$NR$^e$C(O)NR$^f$(CR$^{12a}$R$^{12b}$)$_{p4}$.

In some embodiments, at least one Z$^1$ is selected from C$_{1-6}$ alkyl, C$_{1-6}$ haloalkyl, aryl, cycloalkyl, heteroaryl and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, each Z$^1$ is independently selected from C$_{1-6}$ alkyl, C$_{1-6}$ haloalkyl, aryl, cycloalkyl, heteroaryl and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, at least one Z$^1$ is selected from aryl, cycloalkyl, heteroaryl and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)NR$^c$R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, each Z$^1$ is independently selected from aryl, cycloalkyl, heteroaryl and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)NR$^c$R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, at least one Z$^1$ is selected from aryl, cycloalkyl, heteroaryl and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, each Z$^1$ is independently selected from aryl, cycloalkyl, heteroaryl and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, at least one Z$^1$ is selected from heteroaryl and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, each Z$^1$ is independently selected from heteroaryl and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, at least one Z$^1$ is selected from aryl and heteroaryl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, each Z$^1$ is independently selected from aryl and heteroaryl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, each R$^6$ is, independently, H, C$_{1-6}$ alkyl, C$_{2-6}$ alkenyl, C$_{2-6}$ alkynyl, C$_{1-6}$ haloalkyl, C(O)R$^{b1}$, C(O)NR$^{c1}$R$^{d1}$, C(O)OR$^{a1}$, S(O)R$^{b1}$, S(O)$_2$R$^{b1}$, or S(O)$_2$NR$^{c1}$R$^{d1}$. In some further embodiments, each R$^6$ is, independently, H, C$_{1-6}$ alkyl, C$_{2-6}$ alkenyl, C$_{2-6}$ alkynyl, or C$_{1-6}$ haloalkyl. In yet further embodiments, each R$^6$ is, independently, H or C$_{1-6}$ alkyl. In still further embodiments, each R$^6$ is H or C$_{1-3}$ alkyl.

In some embodiments, each R$^6$ is, independently, H, C$_{1-3}$ alkyl, C$_{2-3}$ alkenyl, C$_{2-3}$ alkynyl, or C$_{1-3}$ haloalkyl. In some further embodiments, each $R^6$ is, independently, H, $C_{1-3}$ alkyl, or $C_{1-3}$ haloalkyl. In some further embodiments, each $R^6$ is, independently, $C_{1-3}$ alkyl.

In some embodiments, each $R^6$ is, independently, H or methyl. In some embodiments, each $R^6$ is H. In some other embodiments, one $R^6$ is methyl.

In some embodiments, $R^{11a}$, $R^{11b}$, $R^{12a}$, and $R^{12b}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c2}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$ alkynyl, or $C_{1-6}$ haloalkyl, is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, $R^{11a}$, $R^{11b}$, $R^{12a}$, and $R^{12b}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, OH, $C_{1-6}$ alkoxy, $C_{1-6}$ haloalkoxy, $C_{2-8}$ alkoxyalkyl, cycloalkyl, heterocycloalkyl, $C(O)OR^{a1}$, $C(O)NR^{c1}R^{d1}$, amino, $C_{1-6}$ alkylamino and $C_{2-8}$ dialkylamino.

In some embodiments, $R^{11a}$, $R^{11b}$, $R^{12a}$, and $R^{12b}$ are each, independently, selected from H, and $C_{1-6}$ alkyl. In some further embodiments, at least one of $R^{11a}$, $R^{11b}$, $R^{12a}$, and $R^{12b}$ is selected from $C_{1-6}$ alkyl.

In some embodiments, $R^{11a}$, $R^{11b}$, $R^{12a}$, and $R^{12}$ are each, independently, selected from H and $C_{1-3}$ alkyl. In some embodiments, $R^{11a}$, $R^{11b}$, $R^{12a}$, and $R^{12b}$ are each, independently, selected from H and $CH_3$.

In some embodiments, each $R^{13}$ is independently selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2 NR^{c1}R^{d1}$, wherein each of said $C_{1-6}$ alkyl, $C_{2-6}$ alkenyl, $C_{2-6}$ alkynyl, or $C_{1-6}$ haloalkyl, is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2 NR^{c1}R^{d1}$, $P(R^{f1})_2$, $P(OR^{e1})_2$.

In some embodiments, each $R^{13}$ is independently selected from H, halo, $C_{1-6}$ alkyl, $C_{2-6}$ alkenyl, $C_{2-6}$ alkynyl, $C_{1-6}$ haloalkyl, CN, $NO_2$, OH, $C_{1-6}$ alkoxy, $C_{1-6}$ haloalkoxy, $C_{2-8}$ alkoxyalkyl, cycloalkyl, heterocycloalkyl, $C(O)OR^{a1}$, $C(O)NR^{c1}R^{d1}$, amino, $C_{1-6}$ alkylamino and $C_{2-8}$ dialkylamino. In some further embodiments, each $R^{13}$ is H or $C_{1-6}$ alkyl. In yet further embodiments, each $R^{13}$ is H.

In some embodiments, each p1 is, independently, 0 or 1. In some other embodiments, each p1 is, independently, 1 or 2.

In some embodiments, each p2 is, independently, 0 or 1. In some other embodiments, each p2 is, independently, 1 or 2.

In some embodiments, each p3 is, independently, 0 or 1. In some other embodiments, each p3 is, independently, 1 or 2.

In some embodiments, each p4 is, independently, 0 or 1. In some other embodiments, each p4 is, independently, 1 or 2.

In some embodiments, each q1 is 1. In some other embodiments, each q1 is 2.

In some embodiments, each q2 is 1. In some other embodiments, each q2 is 2.

In some embodiments, each n is, independently, 1 or 2. In some embodiments, n is 1. In some embodiments, n is 2.

In some embodiments, n is 3.

In some embodiments, each m is 0 or 1. In some embodiments, m is 0. In some embodiments, m is 1.

In some embodiments, m is 2.

In some embodiments, t is 1.

In some embodiments, t is 2.

In some embodiments, t is 3.

In some embodiments, $-(CR'R'')_t-$ is $-CH_2-$, $-CH(CH_3)-$, $-C(CH_3)_2-$, $-(CH_2)_2-$, $-[CH(CH_3)]_2-$, $-(CH_2)_3-$ or $-[CH(CH_3)]_3-$.

In some embodiments, $-(CR'R'')_t-$ is $-CH_2-$, $-CH(CH_3)-$, $-(CH_2)_2-$, or $-(CH_2)_3-$.

In some embodiments, $X^1$ is CH; $X^2$ is N; $X^3$ is $CR^3$; $R^3$ is halo; $R^4$ is H or $C_{1-3}$ alkyl; and at least one $R^5$ is selected from $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, $S(O)_2NR^{c1}R^{d1}$, $Cy^1$, and $-W^1-Q^1-Y^1-Z^1$. In some further embodiments, at least one $R^5$ is $-W^1-Q^1-Y^1-Z^1$. In some further embodiments, at least one $R^5$ on the ring containing $A^1$, $B^1$, $D^1$, and $E^1$ is $-W^1-Q^1-Y^1-Z^1$. In some other embodiments, at least one $R^5$ on the ring containing $A^2$, $B^2$, $D^2$, and $E^2$ is $-W^1-Q^1-Y^1-Z^1$. In further embodiments, each $Q^1$ is independently selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In yet further embodiments, each $Q^1$ is independently selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, the ring containing $A^1$, $B^1$, $D^1$, and $E^1$ is a 6-membered aromatic ring; $B^1$, $D^1$, and $E^1$ are each, independently, $CR^5$ or N; $A^1$ is $CR^2$ or N; and at least one of $A^1$, $B^1$, $D^1$, and $E^1$ is N.

In some embodiments, the ring containing $A^2$, $B^2$, $D^2$, and $E^2$ is a 6-membered aromatic ring; $B^2$, $D^2$, and $E^2$ are each, independently, $CR^5$ or N; $A^2$ is $CR^2$ or N; and at least one of $A^2$, $B^2$, $D^2$, and $E^2$ is N.

In some embodiments, the ring containing $A^1$, $B^1$, $D^1$, and $E^1$ is a 6-membered aromatic ring; $B^1$, $D^1$, and $E^1$ are each, independently, $CR^5$ or N; $A^1$ is $CR^2$ or N; the ring containing $A^2$, $B^2$, $D^2$, and $E^2$ is a 6-membered aromatic ring; $B^2$, $D^2$, and $E^2$ are each, independently, $CR^5$ or N; and $A^2$ is $CR^2$ or N. In some further embodiments, at least one of $A^1$, $B^1$, $D^1$, and $E^1$ is N. In other further embodiments, at least one of $A^2$, $B^2$, $D^2$, and $E^2$ is N.

In some embodiments, the ring containing $A^1$, $B^1$, $D^1$, and $E^1$ is a pyridine ring, wherein said pyridine ring is optionally substituted by $R^2$ and optionally by 1 or 2 $R^5$; and the ring containing $A^2$, $B^2$, $D^2$, and $E^2$ is a benzene ring, wherein said benzene ring optionally substituted by $R^2$ and optionally by 1, 2, or 3 $R^5$.

In some embodiments, the ring containing $A^1$, $B^1$, $D^1$, and $E^1$ is a pyridine ring, wherein said pyridine ring is optionally substituted by 1 or 2 $R^5$; and the ring containing $A^2$, $B^2$, $D^2$, and $E^2$ is a benzene ring, wherein said benzene ring substituted by $—W^1-Q^1-Y^1—Z^1$ and optionally substituted by 1 or 2 $R^5$. In further embodiments, at least one $Q^1$ is selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In yet further embodiments, at least one $Q^1$ is selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, the compound of Formula I of the present invention is a compound of Formula II:

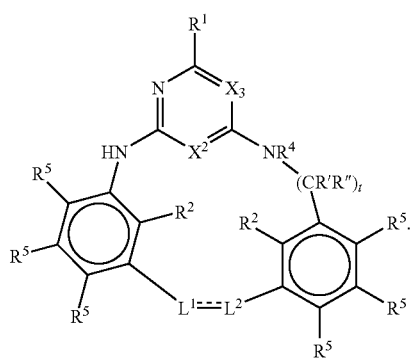

II

In some embodiments of the compounds of Formula II, $R^1$ is selected from H and $C_{1-3}$ alkyl; each $R^2$ is, independently, selected from H, F, Cl, $CH_3$, and $CF_3$; $R^3$ is selected from halo, $C_{1-3}$ alkyl, and $C_{1-3}$ haloalkyl; $R^4$ is H or $C_{1-3}$ alkyl; and R' and R" are each, independently, H or $C_{1-3}$ alkyl.

In some embodiments of the compounds of Formula II, $R^1$ is selected from H and $C_{1-3}$ alkyl; each $R^2$ is, independently, selected from H, F, Cl, $CH_3$, and $CF_3$; $R^3$ is selected from halo, $C_{1-3}$ alkyl, and $C_{1-3}$ haloalkyl; $R^4$ is H or methyl; and R' and R" are each, independently, H or methyl.

In some embodiments of the compounds of Formula II, $R^1$ is selected from H and methyl; each $R^2$ is H; $R^3$ is halo; $R^4$ is H or methyl; and R' and R" are each, independently, H or methyl.

In some embodiments, the compound of Formula I of the present invention is a compound of formula IIa:

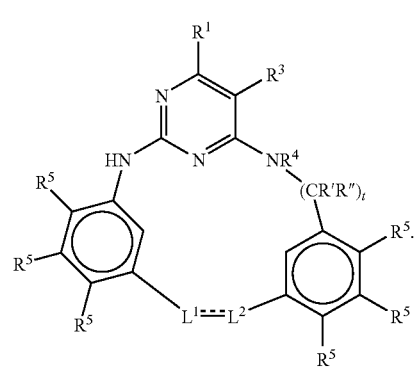

IIa

In some embodiments of the compounds of Formula II or IIa:
R' and R" are each, independently, selected from H and $C_{1-3}$ alkyl;
R' is selected from H and $C_{1-3}$ alkyl;
$R^3$ is selected from halo, $C_{1-3}$ alkyl, and $C_{1-3}$ haloalkyl; and
$R^4$ is H or $C_{1-3}$ alkyl;

In some embodiments of the compounds of Formula II or IIa:
R' and R" are each, independently, selected from H and methyl;
$R^1$ is H and;
$R^3$ is halo; and
$R^4$ is H.

In some embodiments of the compounds of Formula II or IIa:
R' and R" are both H;
$R^1$ is H and;
$R^3$ is Cl; and
$R^4$ is H.

In some embodiments, the compound of Formula I of the present invention is a compound of Formula IIb:

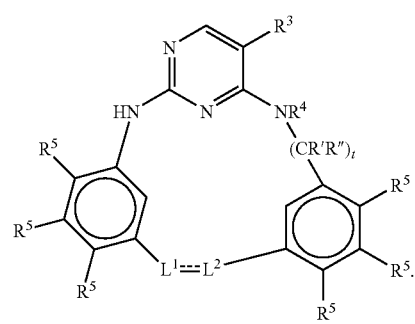

IIb

In some embodiments of the compounds of Formula IIb:
R' and R" are each, independently, selected from H and $C_{1-3}$ alkyl;
$R^3$ is selected from halo, $C_{1-3}$ alkyl, and $C_{1-3}$ haloalkyl; and
$R^4$ is H or $C_{1-3}$ alkyl;

In some embodiments of the compounds of Formula II or IIa:
R' and R" are each, independently, selected from H and methyl;
$R^3$ is halo; and
$R^4$ is H.

In some embodiments of the compounds of Formula II or IIa:
R' and R" are both H;
$R^3$ is Cl; and
$R^4$ is H.

In some embodiments of the compounds of Formula II, IIa, or IIb, each $R^5$ is, independently, selected from H, halo, $C_{1-6}$ alkyl, $C_{1-6}$ haloalkyl, CN, $NO_2$, $SF_5$, $Cy^1$, $-W^1$-$Q^1$-$Y^1$-$Z^1$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $NR^{c1}C(O)NR^{c1}R^{d1}$, $NR^{c1}S(O)_2NR^{c1}R^{d1}$, $S(O)R^{b1}$, $S(O)_2R^{b1}$, and $S(O)_2NR^{c1}R^{d1}$. In some further embodiments, each $R^5$ is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $NR^{c1}C(O)NR^{c1}R^{d1}$, $NR^{c1}S(O)_2NR^{c1}R^{d1}$, $S(O)R^{b1}$, $S(O)_2R^{b1}$, and $S(O)_2NR^{c1}R^{d1}$. In yet further embodiments, each $R^5$ is independently selected from H, halo, $C_{1-6}$ alkyl, $C_{1-3}$ haloalkyl, CN, $NO_2$, $OR^{a1}$, $NR^{c1}R^{d1}$, $NR^{c1}C(O)NR^{c1}R^{d1}$, $NR^{c1}S(O)_2R^{b1}$, $NR^{c1}S(O)_2NR^{c1}R^{d1}$, $S(O)R^{b1}$, $S(O)_2R^{b1}$, and $S(O)_2NR^{c1}R^{d1}$.

In some embodiments of the compounds of Formula II, IIa, or IIb, $L^1$ and $L^2$ are each, independently, selected from a bond, $-(CR^7R^8)_n-$, $-O-(CR^7R^8)_m-CR^{10}=$, $-S-(CR^7R^8)-CR^{10}=$, $-(CR^7R^8)_m-CR^{10}=$, $-(CR^7R^8)_m-NR^9-$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-NR^9-$, $-(CR^7R^8)_m-OC(O)NR^9-$, $-(CR^7R^8)_m-NR^9C(O)O-$, $-(CR^7R^8)_m-NR^9-S(O)_2NR^9-$, $-(CR^7R^8)_m-S(O)NR^9-$, and $-(CR^7R^8)_m-S(O)_2NR^9-$.

In some embodiments of the compounds of Formula II, IIa, or IIb, $L^1$ and $L^2$ together form $-(CR^7R^8)_m-CR^{10}=CR^{10}-(CR^7R^8)_m-$ or $-(CR^7R^8)_m-(CR^7R^8)_n-$.

In some embodiments of the compounds of Formula II, IIa, or IIb, $L^1$ and $L^2$ together form $-(CR^7R^8)-$, $-(CR^7R^8)_2-$, or $-(CR^7R^8)_3-$. In some further embodiments, IIa, or IIb, $L^1$ and $L^2$ together form $-CH_2-$, $-(CH_2)_2-$, or $-(CH_2)_3-$.

In some embodiments of the compounds of Formula II, IIa, or IIb, one of $L^1$ and $L^2$ is selected from $-(CR^7R^8)_m-O-$, $-(CR^7R^8)_m-S-$, $-(CR^7R^8)_m-S(O)-$, and $-(CR^7R^8)_m-S(O)_2-$; and the other is selected from a bond, $-(CR^7R^8)_n-$, $-(CR^7R^8)_m-O-$, $-(CR^7R^8)_m-S-$, $-(CR^7R^8)_m-S(O)-$, and $-(CR^7R^8)_m-S(O)_2-$.

In some embodiments of the compounds of Formula II, IIa, or IIb:
$L^1$ and $L^2$ together form $-(CR^7R^8)_{t1}-S-$, $-(CR^7R^8)_{t1}-O-$, $-(CR^7R^8)_{t1}-S(O)-$, $-(CR^7R^8)_{t1}-S(O)_2-$, $-S-(CR^7R^8)_{t2}-S-$, $-O-(CR^7R^8)_{t2}-S-$, $-O-(CR^7R^8)_{t2}-S(O)-$, $-O-(CR^7R^8)_{t2}-S(O)_2-$, $-S-S-$, $-(CR^7R^8)_{t3}-O-(CR^7R^8)_{t4}-$, $-(CR^7R^8)_{t3}-S-(CR^7R^8)_{t4}-$, $-(CR^7R^8)_{t3}S(O)-(CR^7R^8)_{t4}-$, or $-(CR^7R^8)_{t3}-S(O)_2-(CR^7R^8)_{t4}-$;
t1 is 1, 2, or 3;
t2 is 1 2, 3, or 4;
t3 is 1, 2, or 3; and
t4 is 1 or 2.

In some embodiments of the compounds of Formula II, IIa, or IIb, $L^1$ and $L^2$ together form $-O-(CR^7R^8)-$, $-O-(CR^7R^8)_2-$, or $-O-(CR^7R^8)_3-$. In some further embodiments, $L^1$ and $L^2$ together form $-O-CH_2-$, $-O-(CH_2)_2-$, or $-O-(CH_2)_3-$.

In some embodiments of the compounds of Formula II, IIa, or IIb, $L^1$ is $-(CR^7R^8)-$, $-(CR^7R^8)_2-$, or $-(CR^7R^8)_3-$; and $L^2$ is $-O-$.

In some embodiments of the compounds of Formula II, IIa, or IIb, $L^1$ and $L^2$ together form $-O-(CR^7R^8)-O-$, $-O-(CR^7R^8)_2-O-$, or $-O-(CR^7R^8)_3-O-$.

In some embodiments of the compounds of Formula II, IIa, or IIb, $L^1$ and $L^2$ together form $-(CH_2)-S-$, $-(CH_2)-S(O)-$, $-(CH_2)-S(O)_2-$, $-(CH_2)-O-$, $-(CH_2)_2-O-$, $-(CH_2)_3-O-$, $-O-(CH_2)_2-O-$, $-O-(CH_2)_2-S-$, $-O-(CH_2)_2-S(O)-$, or $-O-(CH_2)_2-S(O)_2-$.

In some embodiments of the compounds of Formula II, IIa, or IIb, one of $L^1$ and $L^2$ is selected from $-(CR^7R^8)_m-NR^9-$, $-(CR^7R^8)_m-S(O)_2-$, $-(CR^7R^8)_m-C(O)-$, $-C(O)NR^9-$, $-(CR^7R^8)_m-NR^9C(O)NR^9-$, $-(CR^7R^8)_m-OC(O)NR^9-$, $-(CR^7R^8)_m-NR^9C(O)O-$, $-(CR^7R^8)_m-NR^9-S(O)_2NR^9-$, $-(CR^7R^8)_m-S(O)NR^9-$, and $-(CR^7R^8)_m-S(O)_2NR^9-$; and the other is selected from a bond, $-(CR^7R^8)_n-$, $-(CR^7R^8)_m-NR^9-$, $-(CR^7R^8)_m-S(O)_2-$, $-(CR^7R^8)_m-C(O)-$, $-C(O)NR^9-$, $-(CR^7R^8)_m-S(O)NR^9-$, and $-(CR^7R^8)_m-S(O)_2NR^9-$.

In some embodiments of the compounds of Formula II, IIa, or IIb, $L^1$ and $L^2$ together form $-(CR^7R^8)_2-C(O)-$, $-C(O)NR^9-(CR^7R^8)-$, $-C(O)NR^9-$, $-(CR^7R^8)-S(O)_2NR^9-$, $-S(O)_2NR^9-(CR^7R^8)-$, or $-S(O)_2NR^9-$. In some further embodiments, $L^1$ and $L^2$ together form $-C(O)NH-$ or $-S(O)_2NH-$.

In some embodiments, the compound of Formula I of the present invention is a compound of Formula IIIa:

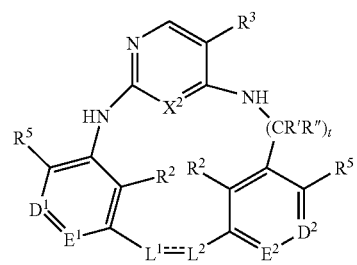

IIIa wherein $D^1$, $E^1$, $D^2$, and $E^2$ are each, independently, $CR^5$ or N.

In some embodiments, the compound of Formula I of the present invention is a compound of Formula IIIb:

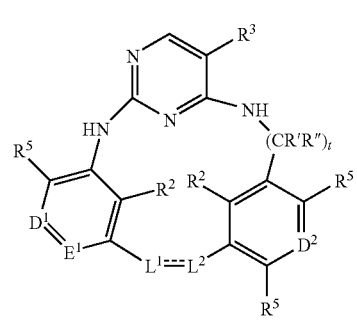

IIIb wherein $D^1$, $E^1$, and $D^2$ are each, independently, $CR^5$ or N.

In some embodiments, the compound of Formula I of the present invention is a compound of Formula IIIc:

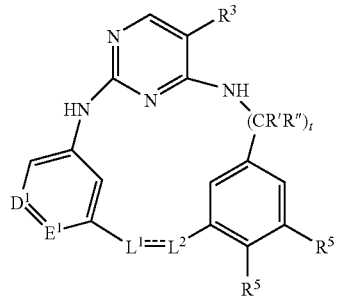

IIIc wherein $D^1$ and $E^1$ are each, independently, $CR^5$ or N.

In some embodiments, the compound of Formula I of the present invention is a compound of Formula IIId:

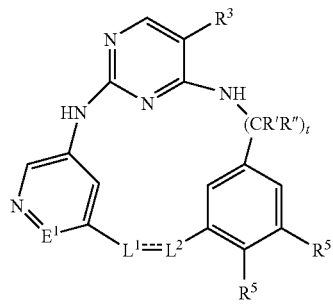

IIId wherein $E^1$ is $CR^5$ or N.

In some embodiments, the compound of Formula I of the present invention is a compound of Formula IIIe:

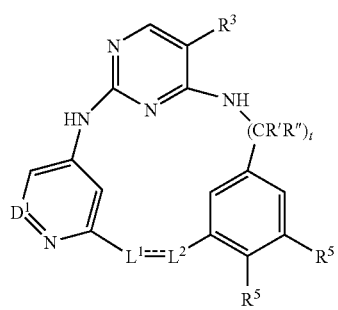

IIIe wherein $D^1$ is $CR^5$ or N.

In some embodiments, the compound of Formula I of the present invention is a compound of Formula IIIf:

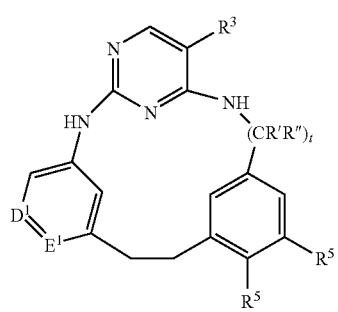

IIIf wherein $D^1$ and $E^1$ are each, independently, $CR^5$ or N.

In some embodiments, the compound of Formula I of the present invention is a compound of Formula IIIg:

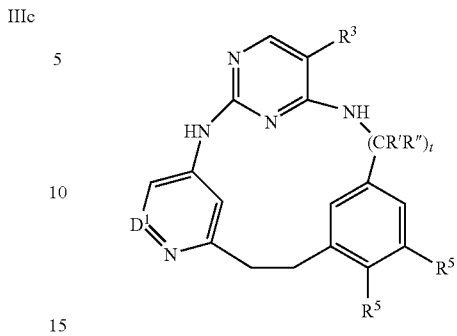

IIIg wherein $D^1$ is $CR^5$ or N.

In some embodiments, the compound of Formula I of the present invention is a compound of Formula IIIh:

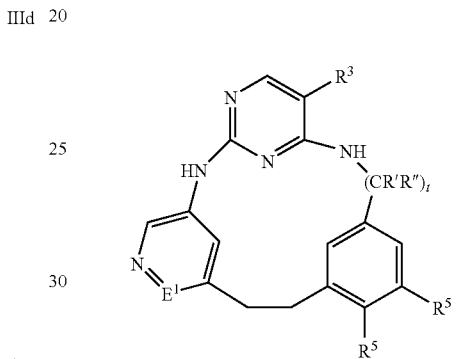

IIIh wherein $E^1$ is $CR^5$ or N.

In some embodiments, the compound of Formula I of the present invention is a compound of Formula IVa:

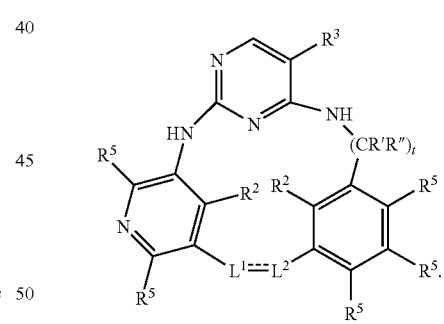

IVa

In some embodiments, the compound of Formula I of the present invention is a compound of Formula IVb:

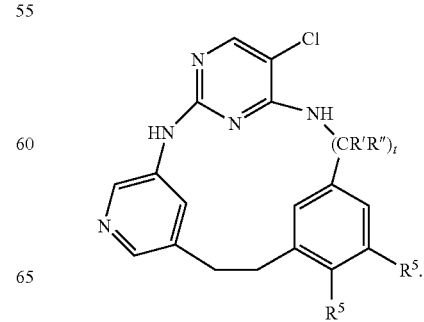

IVb

In some embodiments, the compound of Formula I of the present invention is a compound of Formula IVc:

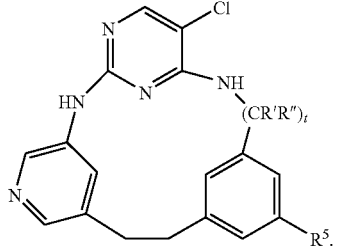

IVc

In some embodiments, the compound of Formula I of the present invention is a compound of Formula IVd:

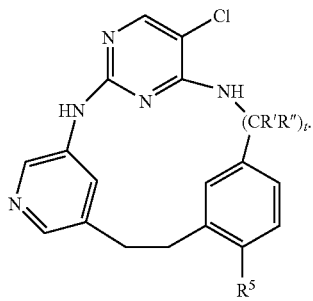

IVd

In some embodiments, the compound of Formula I of the present invention is a compound of Formula IVe:

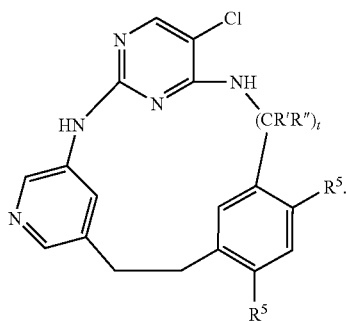

IVe

In some embodiments of the compound of Formula IIIa, IIIb, IIIc, IIId, IIIe, or IVa, $L^1$ and $L^2$ are each, independently, selected from a bond, —$(CR^7R^8)_n$—, —O—$(CR^7R^8)_m$—$CR^{10}$=, —S—$(CR^7R^8)$—$CR^{10}$=, —$(CR^7R^8)_m$—$CR^{10}$=, —$(CR^7R^8)_m$—$NR^9$—, —$(CR^7R^8)_m$—O—, —$(CR^7R^8)_m$—S—, —$(CR^7R^8)_m$—S(O)—, —$(CR^7R^8)_m$—S(O)$_2$—, —$(CR^7R^8)_m$—C(O)—, —C(O)$NR^9$—, —$(CR^7R^8)_m$—C(O)O—, —$(CR^7R^8)_m$—$NR^9$C(O)$NR^9$—, —$(CR^7R^8)_m$—OC(O)$NR^9$—, —$(CR^7R^8)_m$—$NR^9$C(O)O—, —$(CR^7R^8)_m$—$NR^9$—S(O)$_2$$NR^9$—, —$(CR^7R^8)_m$—S(O)$NR^9$—, and —$(CR^7R^8)_m$—S(O)$_2$$NR^9$—.

In some embodiments of the compound of Formula IIIa, IIIb, IIIc, IIId, IIIe, or IVa, $L^1$ and $L^2$ together form —$(CR^7R^8)_m$—$CR^{10}$=$CR^{10}$—$(CR^7R^8)_m$— or —$(CR^7R^8)_m$—, $(CR^7R^8)_n$—.

In some embodiments of the compound of Formula IIIa, IIIb, IIIc, IIId, IIIe, or IVa, $L^1$ and $L^2$ together form —$(CR^7R^8)$—, —$(CR^7R^8)_2$—, or —$(CR^7R^8)_3$—. In some further embodiments, IIa, or IIb, $L^1$ and $L^2$ together form —$CH_2$—, —$(CH_2)_2$—, or —$(CH_2)_3$—.

In some embodiments of the compound of Formula IIIa, IIIb, IIIc, IIId, IIIe, or IVa, one of $L^1$ and $L^2$ is selected from —$(CR^7R^8)_m$—O—, —$(CR^7R^8)_m$—S—, —$(CR^7R^8)_m$—S(O)—, and —$(CR^7R^8)_m$—S(O)$_2$—; and the other is selected from a bond, —$(CR^7R^8)_n$—, —$(CR^7R^8)_m$—O—, —$(CR^7R^8)_m$—S—, —$(CR^7R^8)_m$—S(O)—, and —$(CR^7R^8)_m$—S(O)$_2$—.

In some embodiments of the compounds of Formula II, IIa, or IIb:

$L^1$ and $L^2$ together form —$(CR^7R^8)_{t1}$—S—, —$(CR^7R^8)_{t1}$—O—, —$(CR^7R^8)_{t1}$—S(O)—, —$(CR^7R^8)_{t1}$—S(O)$_2$—, —S—$(CR^7R^8)_2$—S—, —O—$(CR^7R^8)_2$—S—, —O—$(CR^7R^8)_2$—S(O)—, —O—$(CR^7R^8)_2$—S(O)$_2$—, —S—S—, —$(CR^7R^8)_{t3}$—O—$(CR^7R^8)_{t4}$—, —$(CR^7R^8)_{t3}$—S—$(CR^7R^8)_{t4}$—, —$(CR^7R^8)_{t3}$—S(O)—$(CR^7R^8)_{t4}$—, or —$(CR^7R^8)_{t3}$—S(O)$_2$—$(CR^7R^8)_{t4}$—;

t1 is 1, 2, or 3;
t2 is 1 2, 3, or 4;
t3 is 1, 2, or 3; and
t4 is 1 or 2.

In some embodiments of the compound of Formula IIIa, IIIb, IIIc, IIId, IIIe, or IVa, $L^1$ and $L^2$ together form —O—$(CR^7R^8)$—, —O—$(CR^7R^8)_2$—, or —O—$(CR^7R^8)_3$—. In some further embodiments, $L^1$ and $L^2$ together form —O—$CH_2$—, —O—$(CH_2)_2$—, or —O—$(CH_2)_3$—.

In some embodiments of the compound of Formula IIIa, IIIb, IIIc, IIId, IIIe, or IVa, $L^1$ is —$(CR^7R^8)$—, —$(CR^7R^8)_2$—, or —$(CR^7R^8)_3$—; and $L^2$ is —O—.

In some embodiments of the compound of Formula IIIa, IIIb, IIIc, IIId, IIIe, or IVa, $L^1$ and $L^2$ together form —O—$(CR^7R^8)$—O—, —O—$(CR^7R^8)_2$—O—, or —O—$(CR^7R^8)_3$—O—.

In some embodiments of the compound of Formula IIIa, IIIb, IIIc, IIId, IIIe, or IVa, $L^1$ and $L^2$ together form —$(CH_2)$—S—, —$(CH_2)$—S(O)—, —$(CH_2)$—S(O)$_2$—, —$(CH_2)$—O—, —$(CH_2)_2$—O—, —$(CH_2)_3$—O—, —O—$(CH_2)_2$—O—, —O—$(CH_2)_2$—S—, —O—$(CH_2)_2$—S(O)—, or —O—$(CH_2)_2$—S(O)$_2$—.

In some embodiments of the compound of Formula IIIa, IIIb, IIIc, IIId, IIIe, or IVa, one of $L^1$ and $L^2$ is selected from —$(CR^7R^8)_m$—$NR^9$—, —$(CR^7R^8)_m$—S(O)$_2$—, —$(CR^7R^8)_m$—C(O)—, —C(O)$NR^9$—, —$(CR^7R^8)_m$—$NR^9$C(O)$NR^9$—, —$(CR^7R^8)_m$—OC(O)$NR^9$—, —$(CR^7R^8)_m$—$NR^9$C(O)O—, —$(CR^7R^8)_m$—$NR^9$—S(O)$_2$$NR^9$—, —$(CR^7R^8)_m$—S(O)$NR^9$—, and —$(CR^7R^8)_m$—S(O)$_2$$NR^9$—; and the other is selected from a bond, —$(CR^7R^8)_n$—, —$(CR^7R^8)_m$—$NR^9$—, —$(CR^7R^8)_m$—S(O)$_2$—, —$(CR^7R^8)_m$—C(O)—, —C(O)$NR^9$—, —$(CR^7R^8)_m$—S(O)$NR^9$—, and —$(CR^7R^8)_m$—S(O)$_2$ $NR^9$—.

In some embodiments of the compound of Formula IIIa, IIIb, IIIc, IIId, IIIe, or IVa, $L^1$ and $L^2$ together form —$(CR^7R^8)_2$—C(O)—, —C(O)$NR^9$—$(CR^7R^8)$—, —C(O)$NR^9$—, —$(CR^7R^8)$—S(O)$_2$$NR^9$—, —S(O)$_2$$NR^9$—$(CR^7R^8)$—, or —S(O)$_2$$NR^9$—. In some further embodiments, $L^1$ and $L^2$ together form —C(O)NH— or —S(O)$_2$NH—.

In some embodiments of the compound of Formula II, IIa, IIb, IIIa, IIIb, IIIc, IIId, IIIe, IIIf, IIIg, IIIh, IVa, IVb, IVc, IVd, or IVe, R' and R" are each, independently, selected from H and $C_{1-3}$ alkyl; $R^1$ is selected from H and $C_{1-3}$ alkyl; $R^3$ is selected from halo, $C_{1-3}$ alkyl, and $C_{1-3}$ haloalkyl; and $R^4$ is H or $C_{1-3}$ alkyl;

In some embodiments of the compound of Formula II, IIa, IIb, IIIa, IIIb, IIIc, IIId, IIIe, IIIf, IIIg, IIIh, IVa, IVb, IVc, IVd, or IVe, R' and R" are each, independently, selected from H and methyl; $R^1$ is H; $R^3$ is halo; and $R^4$ is H.

In some embodiments of the compound of Formula II, IIa, IIb, IIIa, IIIb, IIIc, IIId, IIIe, IIIf, IIIg, IIIh, IVa, IVb, IVc, IVd, or IVe, R' and R" are both H; $R^1$ is H and; $R^3$ is Cl; and $R^4$ is H.

In some embodiments of the compound of Formula II, IIa, IIb, IIIa, IIIb, IIIc, IIId, IIIe, IIIf, IIIg, IIIh, IVa, IVb, IVc, IVd, or IVe, $R^1$ is selected from H and $C_{1-3}$ alkyl; each $R^2$ is, independently, selected from H, F, Cl, $CH_3$, and $CF_3$; $R^3$ is selected from halo, $C_{1-3}$ alkyl, and $C_{1-3}$ haloalkyl; $R^4$ is H or methyl; and R' and R" are each, independently, H or methyl.

In some embodiments of the compound of Formula II, IIa, IIb, IIIa, IIIb, IIIc, IIId, IIIe, IIIf, IIIg, IIIh, IVa, IVb, IVc, IVd, or IVe, $R^1$ is selected from H and methyl; each $R^2$ is H; $R^3$ is halo; $R^4$ is H or methyl; and R' and R" are each, independently, H or methyl.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof:

each $R^5$ is, independently, H, $Cy^3$, halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, or —$W^1$-$Q^1$-$Y^1$—$Z^1$;

or two adjacent $R^5$ on the same ring link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, halosulfanyl, $Cy^1$, CN, $NO_2$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, —$W^1$-$Q^1$-$Y^1$—$Z^1$, $OC(O)NR^{c1}R^{d1}$, $NR^{c1}R^{d1}$, $NR^{c1}C(O)R^{b1}$.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, at least one $R^5$ is —$W^1$-$Q^1$-$Y^1$—$Z^1$. In some further embodiments, at least one $R^5$ on the ring containing $A^2$, $B^2$, $D^2$, and $E^2$ is —$W^1$-$Q^1$-$Y^1$—$Z^1$.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, at least one $R^5$ is $Cy^1$.

In some embodiments of the compound of Formula II, IIa, III), IIIa, IIIb, IIIc, IIId, Hie, IIIf, IIIg, IIIh, IVa, IVb, IVc, IVd, or IVe, or pharmaceutically acceptable salt thereof, at least one $R^5$ is —$(CR^{11a}R^{11b})_{p1}$-$Q^1$-$Y^1$-$Z^1$, —$(CR^{11a}R^{11b})_{p1}$O$(CR^{11a}R^{11b})_{p2}$-$Q^1$-$Y^1$—$Z^1$, —$(CR^{11a}R^{11b})_{p1}$S$(CR^{11a}R^{11b})_{p2}$-$Q^1$-$Y^1$—$Z^1$, —$(CR^{11a}R^{11b})_{p1}$S(O)$(CR^{11a}R^{11b})_{p2}$-$Q^1$-$Y^1$—$Z^1$, —$(CR^{11a}R^{11b})_{p1}$S(O)$_2$(($CR^{11a}R^{11b})_{p2}$-$Q^1$-$Y^1$—$Z^1$, —$(CR^{11a}R^{11b})_{p1}$NR$^e$($CR^{11a}R^{11b})_{p2}$-$Q^1$-$Y^1$—$Z^1$, —NR$^e$S(O)$(CR^{11a}R^{11b})_{p1}$-$Q^1$-$Y^1$—$Z^1$, —S(O)NR$^e$($CR^{11a}R^{11b})_{p2}$-$Q^1$-$Y^1$—$Z^1$, —NR$^e$S(O)$_2$ $(CR^{11a}R^{11b})_{p1}$-$Q^1$-$Y^1$—$Z^1$, —S(O)$_2$NR$^e$($CR^{11a}R^{11b})_{p2}$-$Q^1$-$Y^1$—$Z^1$, —NR$^e$C(O)$(CR^{11a}R^{11b})_{p1}$-$Q^1$-$Y^1$—$Z^1$, —C(O)NR$^e$($CR^{11a}R^{11b})_{p2}$-$Q^1$-$Y^1$—$Z^1$, or —NR$^e$C(O)NR$^f$($CR^{11a}R^{11b})_{p2}$-$Q^1$-$Y^1$—$Z^1$. In some further embodiments, each $Q^1$ is independently selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In yet further embodiments, each $Q^1$ is independently selected from cyclopentyl, cyclohexyl, pyrrolidinyl, and piperidinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compound of Formula II, IIa, IIb, IIIa, IIIb, IIIc, IIId, IIe, IIIf, IIIg, IIIh, IVa, IVb, IVc, IVd, or IVe, or pharmaceutically acceptable salt thereof, at least one $R^5$ is -$Q^1$-$Y^1$—$Z^1$, —$(CR^{11a}R^{11b})_{p1}$O$(CR^{11a}R^{11b})_{p2}$-$Q^1$-$Y^1$—$Z^1$, —$(CR^{11a}R^{11b})_{p1}$S$(CR^{11a}R^{11b})_{p2}$-$Q^1$-$Y^1$—$Z^1$, —$(CR^{11a}R^{11b})_{p1}$S(O)$(CR^{11a}R^{11b})_{p2}$-$Q^1$-$Y^1$—$Z^1$, —$(CR^{11a}R^{11b})_{p1}$S(O)$_2$($CR^{11a}R^{11b})_{p2}$-$Q^1$-$Y^1$—$Z^1$, —$(CR^{11a}R^{11b})_{p1}$NR$^e$($CR^{11a}R^{11b})_{p2}$-$Q^1$-$Y^1$—$Z^1$, —NR$^e$S(O)$(CR^{11a}R^{11b})_{p1}$-$Q^1$-$Y^1$—$Z^1$, —S(O)NR$^e$($CR^{11a}R^{11b})_{p2}$-$Q^1$-$Y^1$—$Z^1$, —NR$^e$S(O)$_2$($CR^{11a}R^{11b})_{p1}$-$Q^1$-$Y^1$—$Z^1$, —S(O)$_2$NR$^e$($CR^{11a}R^{11b})_{p2}$-$Q^1$-$Y^1$—$Z^1$, —NR$^e$C(O)$(CR^{11a}R^{11b})_{p1}$-$Q^1$-$Y^1$—$Z^1$, —C(O)NR$^e$($CR^{11a}R^{11b})_{p2}$-$Q^1$-$Y^1$—$Z^1$, or —NR$^e$C(O)NR$^f$($CR^{11a}R^{11b})_{p2}$-$Q^1$-$Y^1$—$Z^1$, In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, at least one $R^5$ is —$(CR^{11a}R^{11b})_{p1}$O$(CR^{11a}R^{11b})_{p2}$-$Q^1$-$Y^1$—$Z^1$, —$(CR^{11a}R^{11b})_{p1}$S$(CR^{11a}R^{11b})_{p2}$-$Q^1$-$Y^1$—$Z^1$, —$(CR^{11a}R^{11b})_{p1}$S(O)$(CR^{11a}R^{11b})_{p2}$-$Q^1$-$Y^1$—$Z^1$, —$(CR^{11a}R^{11b})_{p1}$S(O)$_2$(($CR^{11a}R^{11b})_{p2}$-$Q^1$-$Y^1$—$Z^1$, —$(CR^{11a}R^{11b})_{p1}$NR$^e$($CR^{11a}R^{11b})_{p2}$-$Q^1$-$Y^1$—$Z^1$, —NR$^e$S(O)$(CR^{11a}R^{11b})_{p1}$-$Q^1$-$Y^1$—$Z^1$, —S(O)NR$^e$($CR^{11a}R^{11b})_{p2}$-$Q^1$-$Y^1$—$Z^1$, —NR$^e$S(O)$_2$($CR^{11a}R^{11b})_{p1}$-$Q^1$-$Y^1$—$Z^1$, —S(O)$_2$NR$^e$($CR^{11a}R^{11b})_{p2}$-$Q^1$-$Y^1$—$Z^1$, —NR$^e$C(O)$(CR^{11a}R^{11b})_{p1}$-$Q^1$-$Y^1$—$Z^1$, —C(O)NR$^e$($CR^{11a}R^{11b})_{p2}$-$Q^1$-$Y^1$—$Z^1$, or —NR$^e$C(O)NR$^f$($CR^{11a}R^{11b})_{p2}$-$Q^1$-$Y^1$—$Z^1$. In some further embodiments, each $Q^1$ is independently selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In yet further embodiments, each $Q^1$ is independently selected from cyclopentyl, cyclohexyl, pyrrolidinyl, and piperidinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, at least one $R^5$ is —$W^6$-$Q^1$-$Y^1$—$Z^1$. In some further embodiments, at least one $R^5$ on the ring containing $A^2$, $B^2$, $D^2$, and $E^2$ is —$W^6$-$Q^1$-$Y^1$—$Z^1$.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, at least one $R^5$ is -$Q^1$-$Y^1$—$Z^1$, —$(CR^{11a}R^{11b})_{p1}$S$(CR^{11a}R^{11b})_{p2}$-$Q^1$-$Y^1$—$Z^1$, —$((CR^{11a}R^{11b})_{p1}$S(O)$(CR^{11a}R^{11b})_{p2}$-$Q^1$-$Y^1$—$Z^1$, —$(CR^{11a}R^{11b})_{p1}$S(O)$_2$(($CR^{11a}R^{11b})_{p2}$-$Q^1$-$Y^1$—$Z^1$, —$(CR^{11a}R^{11b})_{p1}$S(O)NR$^e$($CR^{11a}R^{11b})_{p2}$-$Q^1$-$Y^1$—$Z^1$, —$(CR^{11a}R^{11b})_{p2}$NR$^e$S(O)$(CR^{11a}R^{11b})_{p1}$-$Q^1$-$Y^1$—$Z^1$, —$(CR^{11a}R^{11b})_{p1}$S(O)$_2$NR$^e$($CR^{11a}R^{11b})_{p2}$-$Q^1$-$Y^1$—$Z^1$, or —$(CR^{11a}R^{11b})_{p2}$NR$^e$S(O)$_2$($CR^{11a}R^{11b})_{p1}$-$Q^1$-$Y^1$—$Z^1$.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, at least one $R^5$ is $-(CR^{11a}R^{11b})_{p1}S(CR^{11a}R^{11b})_{p2}-Q^1-Y^1-Z^1$, $-(CR^{11a}R^{11b})_{p1}S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}S(O)NR^e(CR^{11a}R^{11b})_{p2}-Q^1-Y^1-Z^1$, $-(CR^{11a}R^{11b})_{p2}NR^eS(O)(CR^{11a}R^{11b})_{p1}-Q^1-Y^1-Z^1$, $(CR^{11a}R^{11b})_{p1}S(O)_2NR^e(CR^{11a}R^{11b})_{p2}-Q^1-Y^1-Z^1$, or $-(CR^{11a}R^{11b})_{p2}NR^eS(O)_2(CR^{11a}R^{11b})_{p1}-Q^1-Y^1-Z^1$.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, each $Q^1$ is independently selected from aryl and heteroaryl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, each $Q^1$ is independently selected from cycloakyl or heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, each $Q^1$ is independently selected from cycloakyl optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, each $Q^1$ is independently selected from heterocycloalkyl optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, each $Q^1$ is independently selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In some further embodiments, each $Q^1$ is independently selected from cyclopropyl, cyclobutyl, cyclopentyl, and cyclohexyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In other further embodiments, each $Q^1$ is independently selected from azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, each $Y^1$ is independently selected from absent, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, each $Z^1$ is independently selected from $C_{1-6}$ alkyl, $C_{2-6}$ alkenyl, $C_{2-6}$ alkynyl, $C_{1-6}$ haloalkyl, aryl, cycloalkyl, heteroaryl and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^eC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, each $Z^1$ is independently selected from $C_{1-6}$ alkyl, $C_{1-6}$ haloalkyl, aryl, cycloalkyl, heteroaryl and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^eC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments of the compound of Formula II, IIa, IIb, IIIa, IIIb, IIIc, IIId, IIIe, IIIf, IIIg, IIIh, IVa, IVb, IVc, IVd, or IVe, or pharmaceutically acceptable salt thereof, each $Z^1$ is independently selected from aryl, cycloalkyl, heteroaryl and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, each of $R^5$, $R^6$, $-W^1-Q^1-Y^1-Z^1$, $Cy^1$, and $R^{a1}$ can be a different moiety selected from the Markush group defining the variable. For another example, where a structure is described having two R groups that are simultaneously present on the same compound; the two R groups can represent different moieties selected from the Markush group defined for R. In another example, when an optionally multiple substituent is designated in the form:

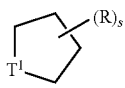

then it is understood that substituent R can occur s number of times on the ring, and R can be a different moiety at each occurrence. Further, in the above example, should the variable $T^1$ be defined to include hydrogens, such as when $T^1$ is said to be $CH_2$, NH, etc., any floating substituent such as R in the above example, can replace a hydrogen of the $T^1$ variable as well as a hydrogen in any other non-variable component of the ring.

As used herein, the term "adjacent" in describing the relative positions of two substitution groups on a same ring structure refers to two substitution groups that are respectively attached to two ring-forming atoms of the same ring, wherein the two-ring forming atoms are directly connected through a chemical bond. For example, in the following structure:

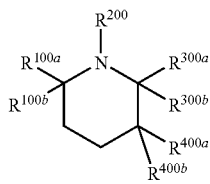

$R^{100a}$ and $R^{200}$ are two adjacent groups. For another example, each of $R^{200}$, $R^{400a}$, and $R^{400b}$ is an adjacent group of $R^{300a}$. For yet another example, each of $R^{200}$, $R^{400a}$, and $R^{400b}$ is an adjacent group of $R^{300b}$.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

As used herein, the term "alkyl" is meant to refer to a saturated hydrocarbon group which is straight-chained or branched. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylene" refers to a divalent alkyl linking group. An example of alkylene is methylene ($CH_2$).

As used herein, "alkenyl" refers to an alkyl group having one or more double carbon-carbon bonds. Example alkenyl groups include, but are not limited to, ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include, but are not limited to, ethynyl, propynyl, and the like. The term "alkynylenyl" refers to a divalent linking alkynyl group.

As used herein, "haloalkyl" refers to an alkyl group having one or more halogen substituents. Example haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. In some embodiments, aryl groups have from 6 to about 10 carbon atoms.

As used herein, "cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic (e.g., having 2, 3 or 4 fused rings) ring systems as well as spiro ring systems. A cycloalkyl group can contain from 3 to about 15, from 3 to about 10, from 3 to about 8, from 3 to about 6, from 4 to about 6, from 3 to about 5, or from 5 to about 6 ring-forming carbon atoms. Ring-forming carbon atoms of a cycloalkyl group can be optionally substituted by oxo or sulfido. Example cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, "heteroaryl" groups refer to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms each independently selected from sulfur, oxygen, and nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 1 to about 5, from about 1 to about 4, from about 1 to about 3, from about 1 to about 2, carbon atoms as ring-forming atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles having up to 20 ring-forming atoms including cyclized alkyl, alkenyl, and alkynyl groups where one or more of the ring-forming carbon atoms is replaced by a heteroatom such as an O, N, or S atom. Hetercycloalkyl groups can be mono or polycyclic (e.g., both fused and spiro systems). Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, pyrrolidin-2-one-3-yl, and the like. Ring-forming carbon atoms and heteroatoms of a heterocycloalkyl group can be optionally substituted by oxo or sulfido. For example, a ring-forming S atom can be substituted by 1 or 2 oxo [i.e., form a S(O) or S(O)$_2$]. For another example, a ring-forming C atom can be substituted by oxo (i.e., form carbonyl). Also included in the definition of heterocycloalkyl are moieties that have one or more aromatic rings fused (i.e., having a bond in common with) to the nonaromatic heterocyclic ring, for example pyridinyl, thiophenyl, phthalimidyl, naphthalimidyl, and benzo derivatives of heterocycles such as indolene, isoindolene, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. Ring-forming carbon atoms and heteroatoms of the heterocycloalkyl group can be optionally substituted by oxo or sulfido. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "halosulfanyl" refers to a sulfur group having one or more halogen substituents. Example halosulfanyl groups include pentahalosulfanyl groups such as SF$_5$.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-haloalkyl group. An example haloalkoxy group is OCF$_3$.

As used herein, "cyanoalkyl" refers to an alkyl group substituted by a cyano group (CN). One example of cyanoalkyl is —CH$_2$—CN.

As used herein, "alkoxyalkoxy" refers to an alkoxy group substituted by an alkoxy group. One example of alkoxyalkoxy is —OCH$_2$CH$_2$—OCH$_3$.

As used herein, "arylalkyl" refers to a C$_{1-6}$ alkyl substituted by aryl and "cycloalkylalkyl" refers to C$_{1-6}$ alkyl substituted by cycloalkyl.

As used herein, "heteroarylalkyl" refers to a C$_{1-6}$ alkyl group substituted by a heteroaryl group, and "heterocycloalkylalkyl" refers to a C$_{1-6}$ alkyl substituted by heterocycloalkyl.

As used herein, "amino" refers to NH$_2$.

As used herein, "alkylamino" refers to an amino group substituted by an alkyl group.

As used herein, "dialkylamino" refers to an amino group substituted by two alkyl groups.

As used herein, "hydroxylalkyl" or "hydroxylalkyl" refers to an alkyl group substituted by a hydroxyl group. An example is —CH$_2$OH or —CH$_2$CH$_2$OH.

As used here, C(O) refers to C(=O).
As used here, C(S) refers to C(=S).
As used here, S(O) refers to S(=O).
As used here, S(O)$_2$ refers to S(=O)$_2$.

As used used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group (i.e., CH$_3$) is optionally substituted, then 3 hydrogen atoms on the carbon atom can be replaced with substituent groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention further include hydrates and solvates, as well as anhydrous and non-solvated forms.

The term, "compound," as used herein is meant to include all stereoisomers, geometric isomers, tautomers, and isotopes of the structures depicted.

All compounds and pharmaceutically acceptable salts thereof, can be prepared or present together with other substances such as water and solvents (e.g. hydrates and solvates) or can be isolated.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, or salts thereof, are substantially isolated. By "substantially isolated" is meant that the compound is at least partially or substantially separated from the environment in which is formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Compounds of the invention are intended to include compounds with stable structures. As used herein, "stable compound" and "stable structure" are meant to indicate a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The present invention also includes quaternary ammonium salts of the compounds described herein, where the compounds are primary amines, secondary amines, or tertiary amines. As used herein, "quaternary ammonium salts" refers to derivatives of the disclosed primary amine, secondary amine, or tertiary amine compounds wherein the parent amine compounds are modified by converting the amines to quaternary ammonium cations via alkylation (and the cations are balanced by anions such as $Cl^-$, $CH_3COO^-$, or $CF_3COO^-$), for example methylation or ethylation.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC) or thin layer chromatography (TLC).

The compounds of invention can be prepared according to the synthetic procedures described below in the Example section.

As shown in Scheme 1a, macrocycle 1-2 of the present invention (wherein $R^4$ can be H, methyl, ethyl, or the like) can be synthesized by cyclizing precursor 1-1 [wherein $Lg^1$ is a leaving group such as halo (e.g., chloro)] under acidic condition, or basic condition, or in the presence of a transition metal catalysis [such as a Palladium catalyst (e.g., $Pd(PPh_3)_4$) or a Pd(II) catalyst] to afford the desired macrocycle 1-2. Precursors 1-1 [wherein $Lg^1$ is a leaving group such as halo (e.g. chloro)], 1-1a [wherein $Lg^1$ is a leaving group such as halo (e.g., chloro)], 1-3 [wherein $Lg^1$ is a leaving group such as halo (e.g., chloro)], and 1-3a [wherein $Lg^1$ is a leaving group such as halo (e.g., chloro)] can undergo similar transformations to afford products 1-2, 1-4, and 1-4 (wherein $R^4$ can be H, methyl, ethyl, or the like) respectively.

Scheme 1a
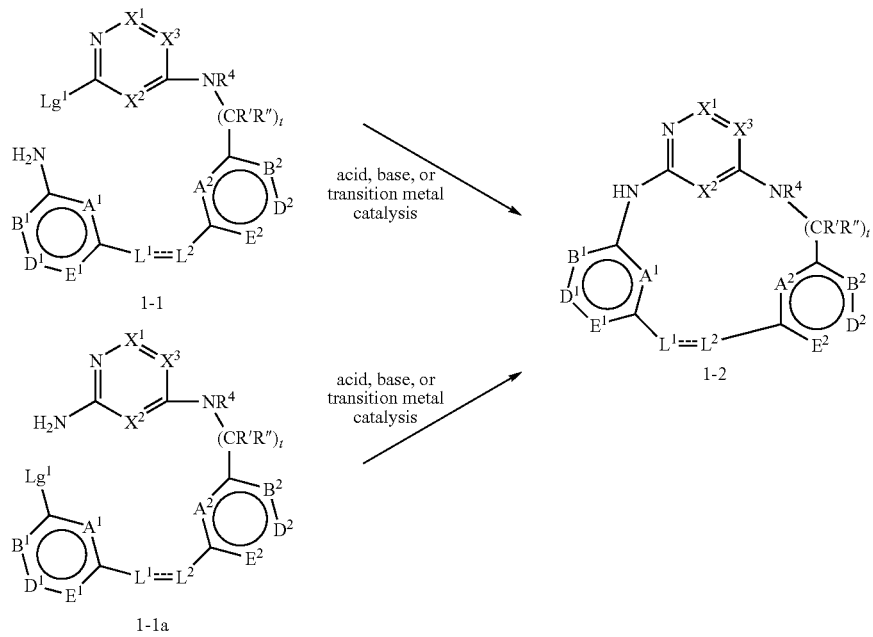
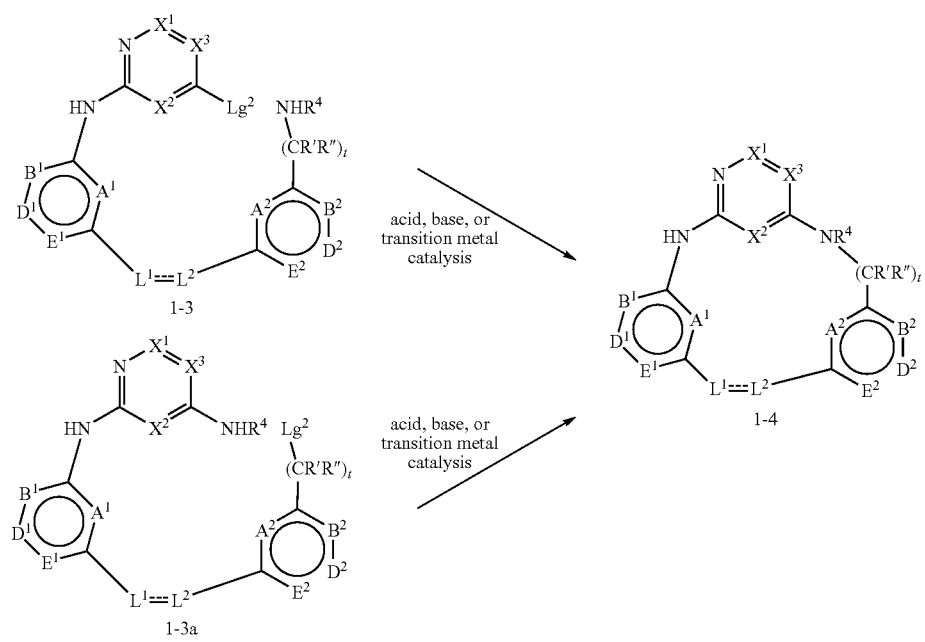

As shown in Scheme 1b, bis-olefin precursor 1-5 [wherein $L^{1f}$ and $L^{2f}$ can be independently selected from $-(CR^7R^8)_m-$, $-(CR^7R^8)_m-O-$, or $-(CR^7R^8)_m-S-$] can be cyclized in the presence of a metathesis catalyst (ruthenium, such as the Grubbs catalysts or molybdenum catalysts, such as the Hoveyda catalysts) to afford the desired macrocycle 1-6 that contains an olefin moiety of $CR^{10}=CR^{10}$. The olefin moiety of compound 1-6 can be further reduced under suitable hydrogenation conditions [such as in the presence of a palladium catalyst (e.g., 5% Pd/C)] to afford macrocycle 1-7.

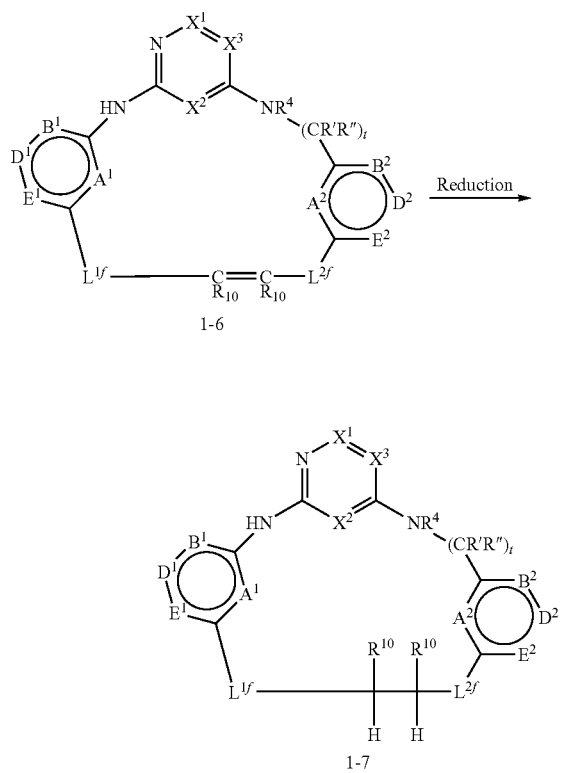

Scheme 1b

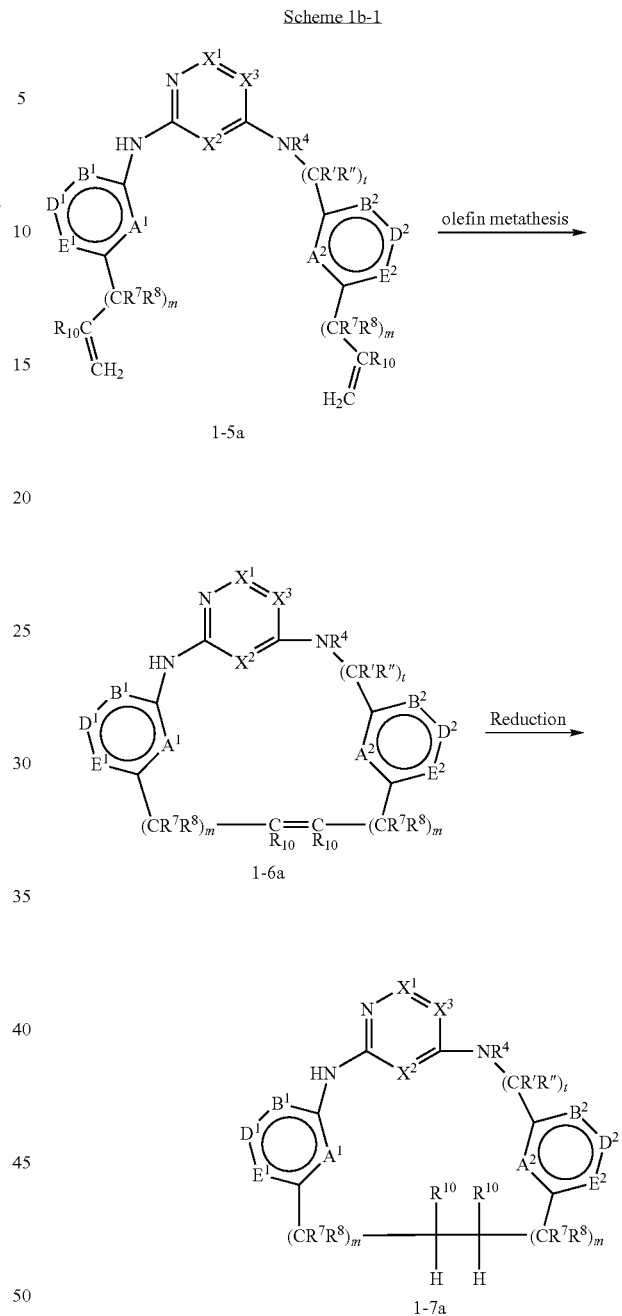

Scheme 1b-1

As shown in Scheme 1b-1, macrocycle 1-7a can be obtained similarly according to the transformations described in Scheme 1b.

Acyclic precursors 1-1, 1-1a, 1-3, and 1-3a can be synthesized by a variety of appropriate ways that would be recognized by those skilled in organic synthesis. For example, compound 2-1 [wherein $R^{101}$ is H or an amine protecting group (such as tert-butyloxycarbonyl or BOC); $R^4$ can be H, methyl, ethyl, or the like] can be reacted with substituted heteroaromatic compound 2-2 [wherein $Lg^1$ and $Lg^2$ are each, independently, a leaving group such as halo (e.g., chloro)] in the presence of a suitable base (such as a inorganic base, for example a metal carbonate (e.g., potassium carbonate), a metal hydride (e.g., sodium hydride), a metal hydroxide (e.g., sodium hydroxide), a metal alkoxide (e.g., sodium ethoxide)] and/or in the presence of a transition metal catalyst for example a palladium catalyst [e.g., $Pd(PPh_3)_4$].

Scheme 2

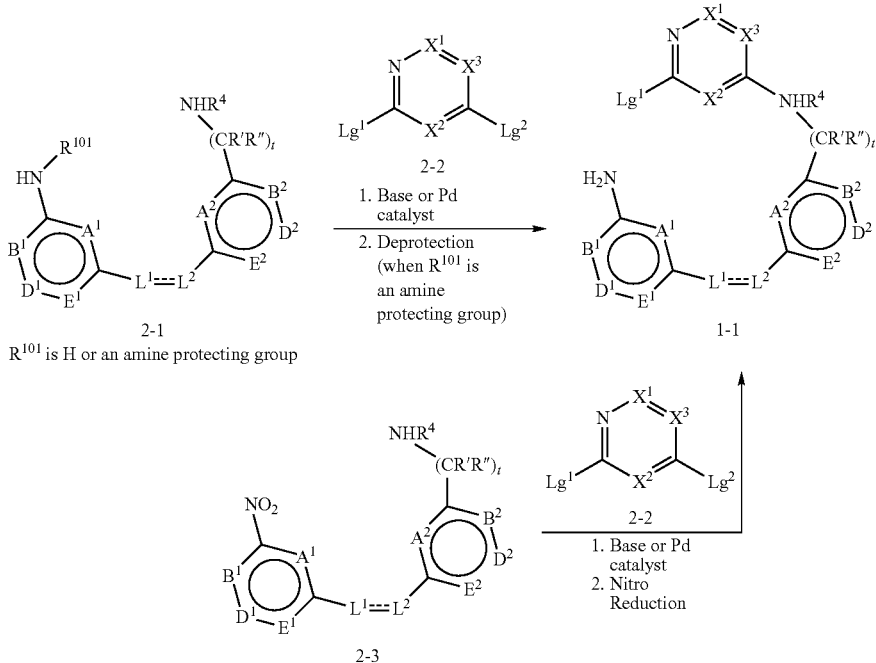

Precursors for the macrocycles of the present invention (for example, precursors 1-1, 1-1a, 1-3, 1-3a, and 1-5) can be prepared by a variety of methods. For example, Mitsunobu coupling, thioether formation, amine alkylation, amide formation, sulfonamide formation, urea formation and carbamate formation can be utilized in synthesizing these compounds. Some non-limiting examples are depicted in the following schemes.

As shown in Scheme 3a, compound 3-1 [wherein $R^{201}$ can be $NO_2$ or $NHR^{101}$; $R^{101}$ can be H or $Pg^4$; $Pg^4$ is an amine protecting group (such as tert-butyloxycarbonyl or BOC); $L^{1a}$ can be —$(CR^7R^8)_m$— (such as a bond or methylene) or $L^{1a}$ is selected from —$(CR^7R^8)_n$—, —$(CR^7R^8)_{m1}$—$NR^9$—, —$(CR^7R^8)_{m1}$—O—, —$(CR^7R^8)_{m1}$—S—, —$(CR^7R^8)_{m1}$—S(O)—, —$(CR^7R^8)_{m1}$—S(O)$_2$—, —$(CR^7R^8)_{m1}$—C(O)—, —$(CR^7R^8)_{m1}$—C(O)O—, —$(CR^7R^8)_{m1}$—$NR^9$C(O)$NR^9$—, —$(CR^7R^8)_{m1}$—OC(O)$NR^9$—, —$(CR^7R^8)_{m1}$—$NR^9$C(O)O—, —$(CR^7R^8)_{m1}$—$NR^9$—S(O)$_2$$NR^9$—, —$(CR^7R^8)_{m1}$—S(O)$NR^9$—, and —$(CR^7R^8)_{m1}$—S(O)$_2$$NR^9$—, wherein m1 is 1 or 2] can be reacted with compound 3-2 [wherein $R^{252}$ can be $NHR^4$ or $NO_2$ wherein the $NHR^4$ can also be protected by an appropriate protecting group; $R^4$ can be H, methyl, ethyl, or the like; $L^{2a}$ is selected from —$(CR^7R^8)_n$—, —$(CR^7R^8)_{m1}$—$NR^9$—, —$(CR^7R^8)_{m1}$—O—, —$(CR^7R^8)_{m1}$—S—, —$(CR^7R^8)_{m1}$—S(O)—, —$(CR^7R^8)_{m1}$—S(O)$_2$—, —$(CR^7R^8)_{m1}$—C(O)—, —$(CR^7R^8)_{m1}$—C(O)O—, —$(CR^7R^8)_{m1}$—$NR^9$C(O)$NR^9$—, —$(CR^7R^8)_{m1}$—OC(O)$NR^9$—, —$(CR^7R^8)_{m1}$—$NR^9$C(O)O—, —$(CR^7R^8)_{m1}$—$NR^9$—S(O)$_2$$NR^9$—, —$(CR^7R^8)_{m1}$—S(O)$NR^9$—, and —$(CR^7R^8)_{m1}$—S(O)$_2$$NR^9$—, wherein m1 is 1 or 2; or $L^{2a}$ can be —$(CR^7R^8)_m$— (such as a bond or methylene)] under Mitsunobu coupling reaction conditions to afford compound 3-3 [wherein $L^{1a}$ can be —$(CR^7R^8)_m$— and $L^{2a}$ is selected from —$(CR^7R^8)_n$—, —$(CR^7R^8)_{m1}$—$NR^9$—, —$(CR^7R^8)_{m1}$—O—, —$(CR^7R^8)_{m1}$—S—, —$(CR^7R^8)_{m1}$—S(O)—, —$(CR^7R^8)_{m1}$—S(O)$_2$—, —$(CR^7R^8)_{m1}$—C(O)—, —$(CR^7R^8)_{m1}$—C(O)O—, —$(CR^7R^8)_{m1}$—$NR^9$C(O)$NR^9$—, —$(CR^7R^8)_{m1}$—OC(O)$NR^9$—, —$(CR^7R^8)_{m1}$—$NR^9$C(O)O—, —$(CR^7R^8)_{m1}$—$NR^9$—S(O)$_2$$NR^9$—, —$(CR^7R^8)_{m1}$—S(O)$NR^9$—, and —$(CR^7R^8)_{m1}$—S(O)$_2$$NR^9$—, wherein m1 is 1 or 2; or $L^{2a}$ can be —$(CR^7R^8)_m$— and $L^{1a}$ is selected from —$(CR^7R^8)_n$—, —$(CR^7R^8)_{m1}$—$NR^9$—, —$(CR^7R^8)_{m1}$—O—, —$(CR^7R^8)_{m1}$—S—, —$(CR^7R^8)_{m1}$—S(O)—, —$(CR^7R^8)_{m1}$—S(O)$_2$—, —$(CR^7R^8)_{m1}$—C(O)—, —$(CR^7R^8)_{m1}$—C(O)O—, —$(CR^7R^8)_{m1}$—$NR^9$C(O)$NR^9$—, —$(CR^7R^8)_{m1}$—OC(O)$NR^9$—, —$(CR^7R^8)_{m1}$—$NR^9$C(O)O—, —$(CR^7R^8)_{m1}$—$NR^9$—S(O)$_2$$NR^9$—, —$(CR^7R^8)_{m1}$—S(O)$NR^9$—, and —$(CR^7R^8)_{m1}$—S(O)$_2$$NR^9$—, wherein m1 is 1 or 2.]. Compound 3-3 can undergo further chemical transformations if and when appropriate. For example, when $R^{252}$ of compound 3-3 is protected (i.e., $NR^4Pg^4$), it can be deprotected according to the amine protecting group $Pg^4$. For another example, when $R^{252}$ of compound 3-3 is $NO_2$, it can be reduced to $NH_2$ under suitable conditions.

Compounds 3-4 and 3-5 [wherein $Lg^3$ is a leaving group such as halo (e.g., Br or Cl); $R^{201}$, $L^{1a}$, and $L^{2a}$ can be the same as those in compounds 3-1 and 3-2] can be reacted under basic conditions to afford compound 3-6. Alternatively compound 3-6 can be obtained by reacting compound 3-7 with compound 3-8 (wherein $Lg^3$, $R^{201}$, $L^{1a}$, and $L^{2a}$ can be the same as those in compounds 3-4 and 3-5). The $NO_2$ of compound 3-6 can be reduced to $NH_2$ under suitable conditions.

Scheme 3a

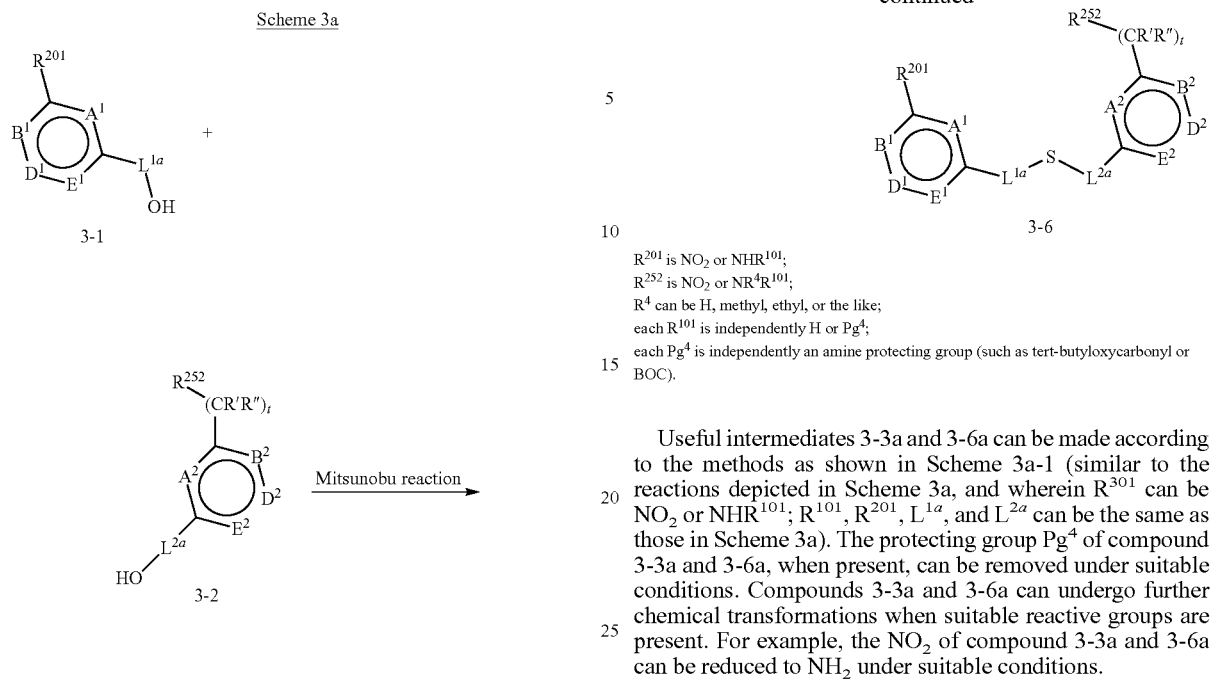

$R^{201}$ is $NO_2$ or $NHR^{101}$;
$R^{252}$ is $NO_2$ or $NR^4R^{101}$;
$R^4$ can be H, methyl, ethyl, or the like;
each $R^{101}$ is independently H or $Pg^4$;
each $Pg^4$ is independently an amine protecting group (such as tert-butyloxycarbonyl or BOC).

Useful intermediates 3-3a and 3-6a can be made according to the methods as shown in Scheme 3a-1 (similar to the reactions depicted in Scheme 3a, and wherein $R^{301}$ can be $NO_2$ or $NHR^{101}$; $R^{101}$, $R^{201}$, $L^{1a}$, and $L^{2a}$ can be the same as those in Scheme 3a). The protecting group $Pg^4$ of compound 3-3a and 3-6a, when present, can be removed under suitable conditions. Compounds 3-3a and 3-6a can undergo further chemical transformations when suitable reactive groups are present. For example, the $NO_2$ of compound 3-3a and 3-6a can be reduced to $NH_2$ under suitable conditions.

Scheme 3a-1

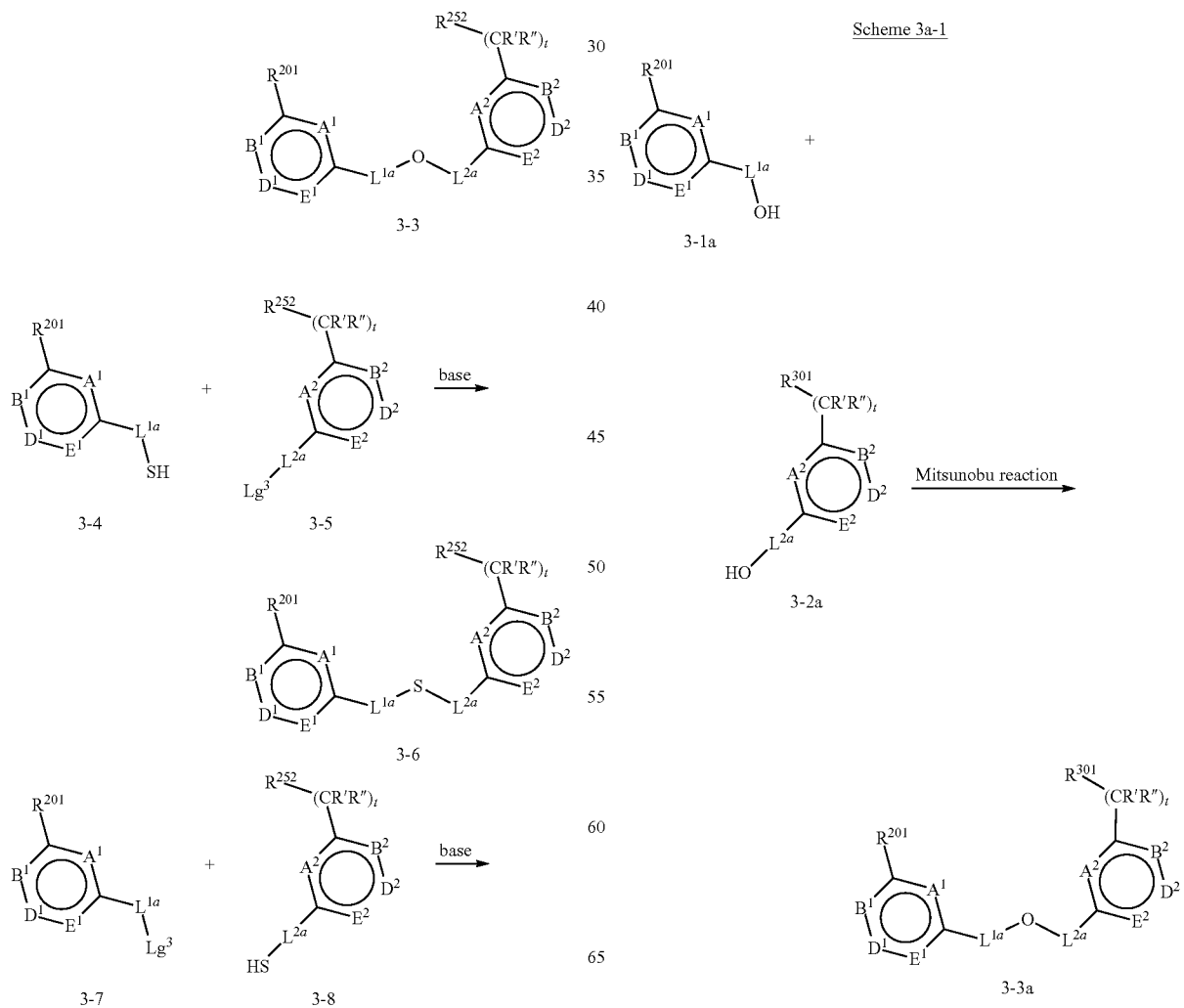

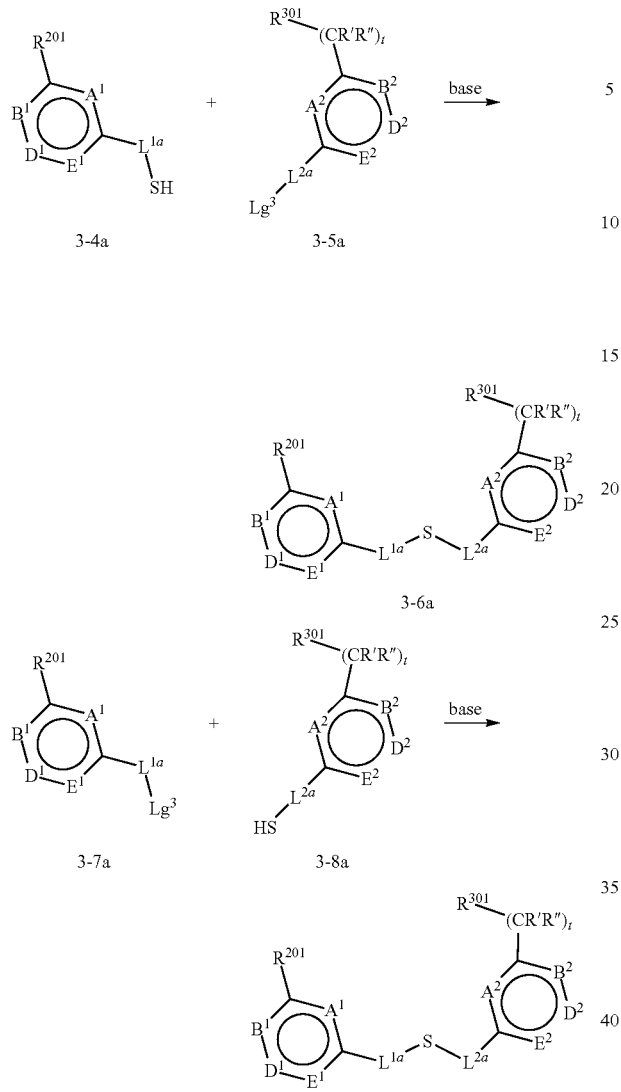

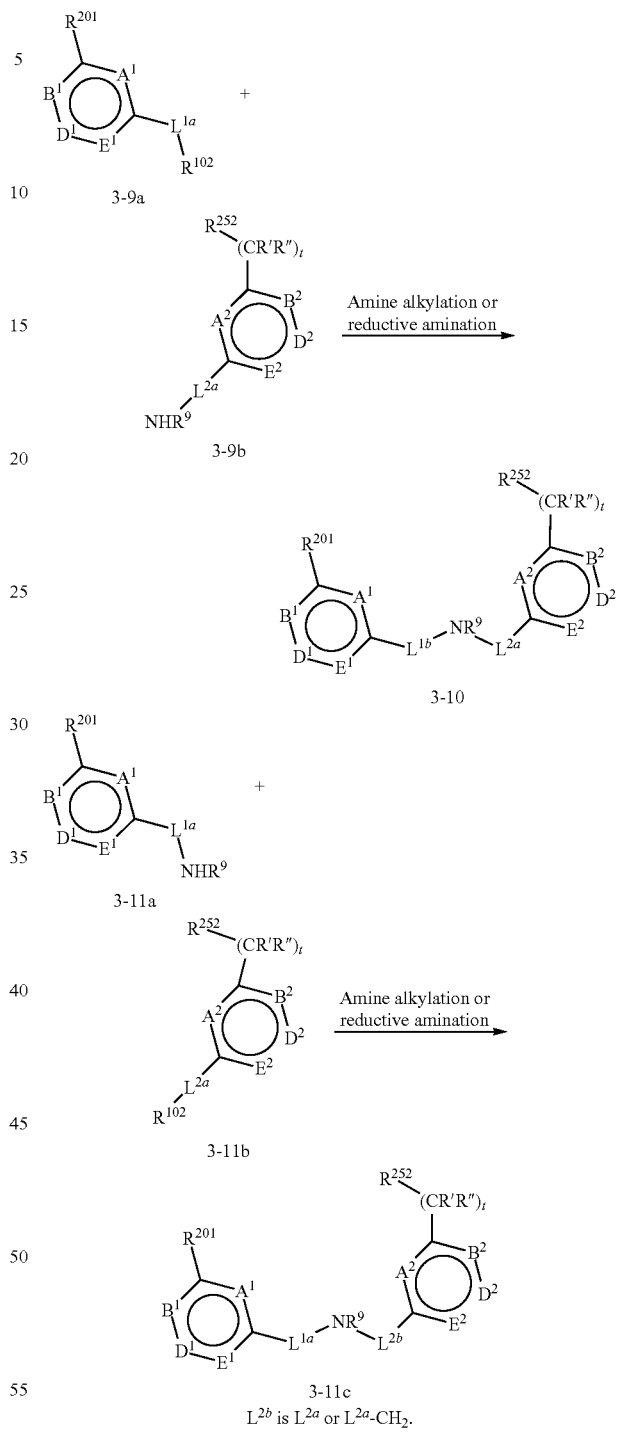

$R^{201}$ is $NO_2$ or $NHR^{101}$;
$R^{301}$ is $NO_2$ or $NHR^{101}$;
each $R^{101}$ is independently H or $Pg^4$;
and each $Pg^4$ is independently an amine protecting group (such as tert-butyloxycarbonyl or BOC).

As shown in Scheme 3b, compounds 3-9a and 3-9b [wherein $R^{201}$, $L^{1a}$, and $L^{2a}$ can be the same as those in compounds 3-4 and 3-5] can be reacted under appropriate conditions to afford compound 3-10. For example, when $R^{102}$ is $Lg^3$ (a leaving group), amine alkylation can be carried out under basic conditions. When $R^{102}$ is —C(=O)H (i.e., compound 3-9a is an aldehyde), reductive aminations can be carried out. Similarly, compound 3-11c can be obtained by reacting compound 3-11a with compound 3-11b [wherein $L^{1a}$ and $L^{2a}$ can be the same as those in compounds 3-4 and 3-5] under suitable conditions. The protecting group $Pg^4$ of compound 3-10 or 3-11c can be removed under suitable conditions. Compounds 3-10 and 3-11c can undergo further chemical transformations when suitable reactive groups are present. For example, when $R^{252}$ is $NO_2$, it can be reduced to $NH_2$ under suitable conditions.

$L^{2b}$ is $L^{2a}$ or $L^{2a}$-$CH_2$.

$R^{201}$ is $NO_2$ or $NHR^{101}$;
$R^{252}$ is $NO_2$ or $NR^4R^{101}$;
each $R^{101}$ is independently H or $Pg^4$;
each $Pg^4$ is independently an amine protecting group (such as tert-butyloxycarbonyl or BOC);
$R^{102}$ is $Lg^3$ or —C(=O)H;
$Lg^3$ is a leaving group such as halo (e.g., Br or Cl); and
$L^{1b}$ is $L^{1a}$-$CH_2$.

Useful intermediates 3-10-1 and 3-11c-1 can be made according to the methods outlined in Scheme 3b-1 (similar to the reactions depicted in Scheme 3b, and wherein $L^{1a}$ and $L^{2a}$ can be the same as those in Scheme 3a). The protecting group $Pg^4$ of compound 3-10-1 and 3-11c-1 can be removed under suitable conditions. Compounds 3-10-1 and 3-11c-1 can undergo further chemical transformations when suitable reactive groups are present. For example, the $NO_2$ of compound 3-10-1 and 3-11c-1 can be reduced to $NH_2$ under suitable conditions.

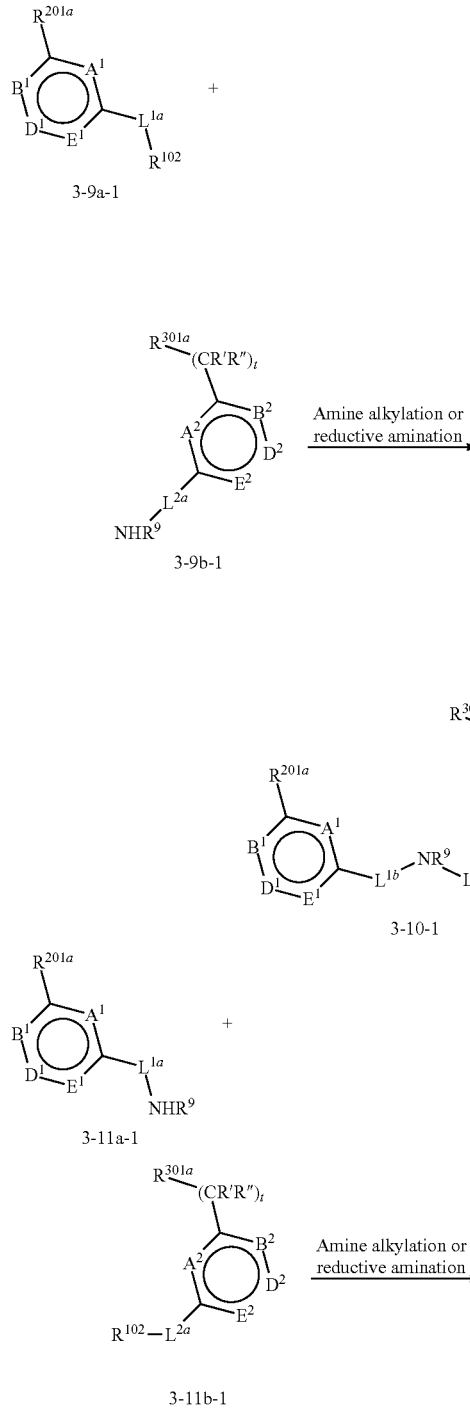

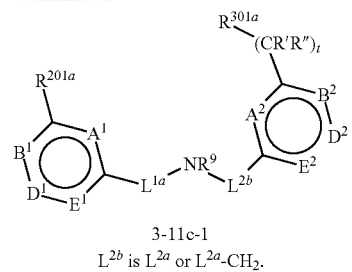

3-11c-1

$L^{2b}$ is $L^{2a}$ or $L^{2a}$-$CH_2$.

$R^{201a}$ is $NO_2$ or $NHPg^4$;
$R^{301a}$ is $NO_2$ or $NR^4Pg^4$;
each $Pg^4$ is independently an amine protecting group (such as tert-butyloxycarbonyl or BOC);
$R^{102}$ is $Lg^3$ or —C(═O)H;
$Lg^3$ is a leaving group such as halo (e.g., Br or Cl); and
$L^{1b}$ is $L^{1a}$ or $L^{1a}$-$CH_2$.

As shown in Scheme 3c, amide compounds 3-12c, 3-13c, 3-14c, and 3-15c [wherein $Pg^4$, $R^{252}$, $L^{1a}$, and $L^{2a}$ can be the same as those in Scheme 3a] can be obtained from an appropriate acid such as acid 3-12a, 3-13b, 3-14b, or 3-15a and an appropriate amine such as amine 3-12b, 3-13a, 3-14a, or 3-15b by standard coupling reactions [such as in the presence of an amide coupling reagent such as benzotriazol-1-yloxy-tris(dimethylamino)phosphonium hexafluorophosphate (BOP), 2-(1H-benzotriazol-1-yl)-1,1,3,3-tetramethyluronium hexafluorophosphate (HBTU), O-(7-azabenzotriazol1-yl)-N,N,N',N'-tetramethyluronium hexafluorophosphate (HATU), 1-ethyl-3-(3-dimethylaminopropyl)carbodiimide (EDC), or dicyclohexylcarbodiimide (DCC), and in the presence of a suitable base such as triethylamine, diisopropylethylamine, N-methylmorpholine, or N-N-dimethylaminopyridine]. Alternatively, the acid 3-12a, 3-13b, 3-14b, or 3-15a can be converted to a more reactivate species such as an acid halide (e.g., acid chloride) or a mixed anhydride, and the more reactive species can be reacted with the appropriate amine 3-12b, 3-13a, 3-14a, or 3-15b respectively.

The protecting group $Pg^4$ of compound 3-12c, 3-13c, 3-14c, or 3-15c can be removed under suitable conditions. Compounds 3-12c, 3-13c, 3-14c, and 3-15c can undergo further transformation when suitable reactive groups are present. For example, when $R^{252}$ is $NO_2$, it can be reduced to $NH_2$ under suitable conditions.

Scheme 3c

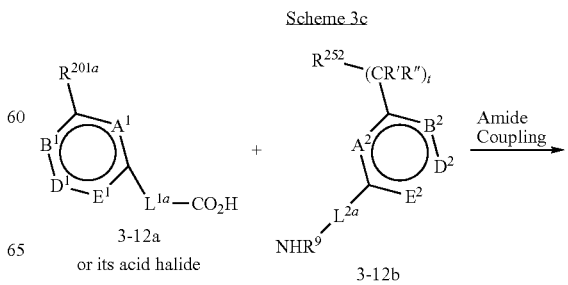

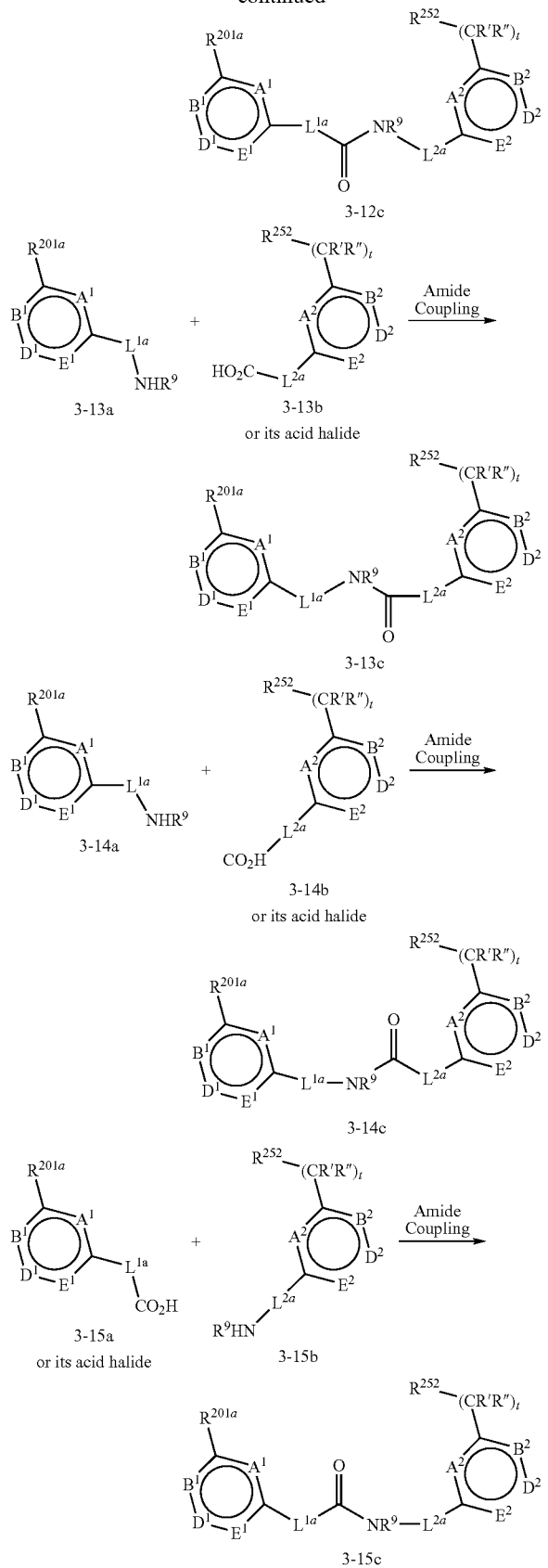

Useful intermediates 3-12c-1, 3-13c-1, 3-14c-1, and 3-15c-1 [wherein $Pg^4$, $L^{1a}$, and $L^{2a}$ can be the same as those in Scheme 3a] can be made according to the methods outlined in Scheme 3c-1 (similar to the reactions depicted in Scheme 3c). The protecting group $Pg^4$ of compounds 3-12c-1, 3-13c-1, 3-14c-1, and 3-15c-1 can be removed under suitable conditions. Compounds 3-12c-1, 3-13c-1, 3-14c-1, and 3-15c-1 can undergo further chemical transformations when suitable reactive groups are present. For example, the $NO_2$ of compounds 3-12c-1, 3-13c-1, 3-14c-1, and 3-15c-1 can be reduced to $NH_2$ under suitable conditions.

Scheme 3c-1

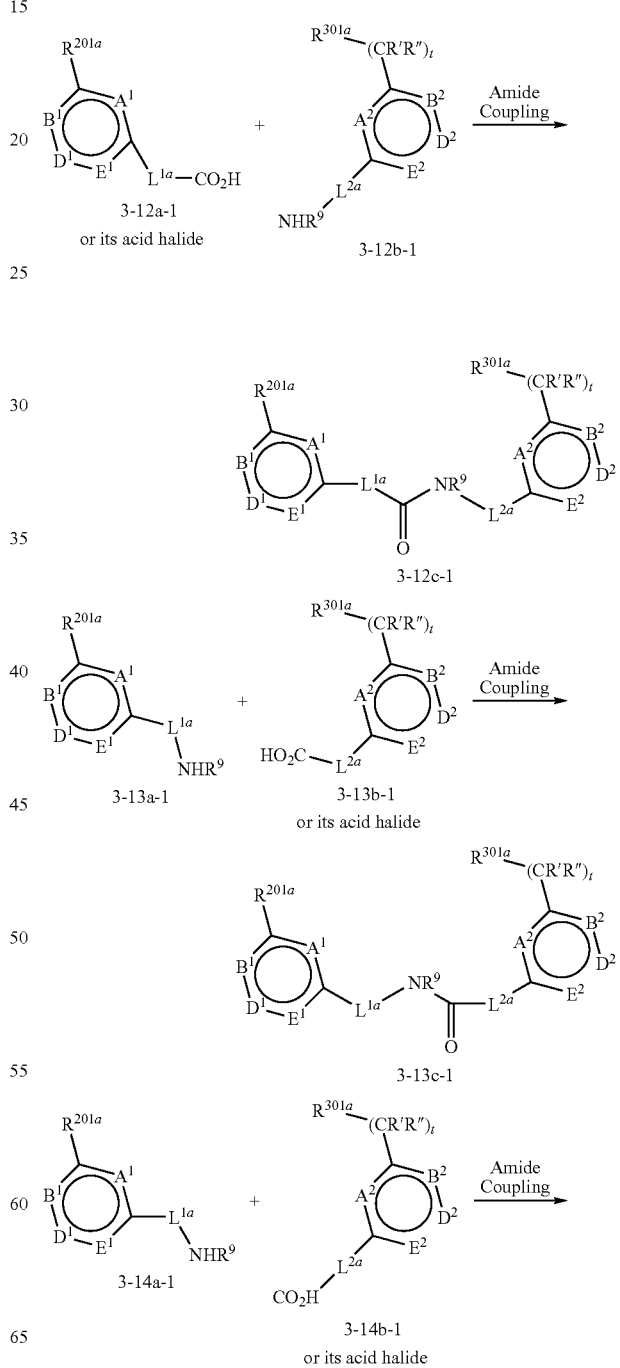

$R^{201a}$ is $NO_2$ or $NHPg^4$; and
$Pg^4$ is an amine protecting group (such as tert-butyloxycarbonyl or BOC).

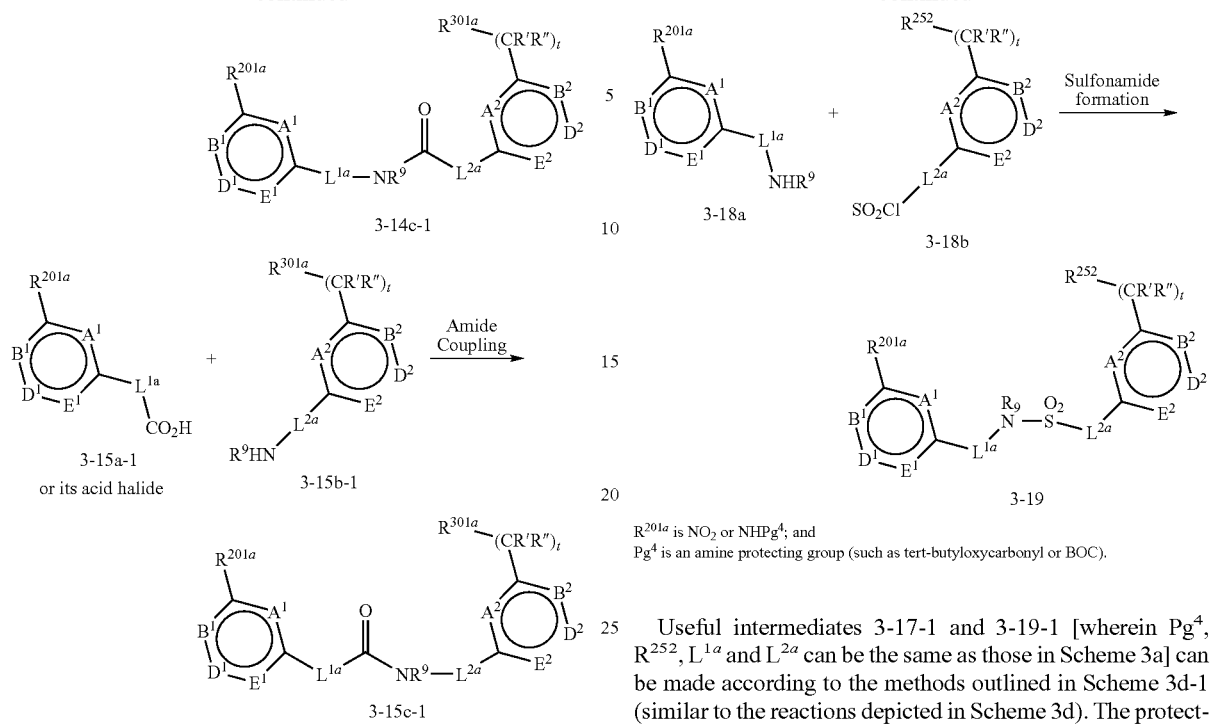

$R^{201a}$ is $NO_2$ or $NHPg^4$;
$R^{301a}$ is $NO_2$ or $NR^4Pg^4$;
each $Pg^4$ is independently an amine protecting group (such as tert-butyloxycarbonyl or BOC).

As shown in Scheme 3d, sulfonamide compounds 3-17 and 3-19 [wherein $Pg^4$, $R^{252}$, $L^{1a}$, and $L^{2a}$ can be the same as those in Scheme 3a] can be obtained by reacting an appropriate sulfonyl halide (such as chloride) with an appropriate amine. The protecting group $Pg^4$ of compounds 3-17 or 3-19 can be removed under suitable conditions. Compounds 3-17 and 3-19 can undergo further chemical transformations when suitable reactive groups are present. For example, when $R^{252}$ is $NO_2$, it can be reduced to $NH_2$ under suitable conditions.

$R^{201a}$ is $NO_2$ or $NHPg^4$; and
$Pg^4$ is an amine protecting group (such as tert-butyloxycarbonyl or BOC).

Useful intermediates 3-17-1 and 3-19-1 [wherein $Pg^4$, $R^{252}$, $L^{1a}$ and $L^{2a}$ can be the same as those in Scheme 3a] can be made according to the methods outlined in Scheme 3d-1 (similar to the reactions depicted in Scheme 3d). The protecting group $Pg^4$ of compounds 3-17-1 and 3-19-1 can be removed under suitable conditions. Compounds 3-17-1 and 3-19-1 can undergo further chemical transformations when suitable reactive groups are present. For example, the $NO_2$ of compounds 3-17-1 and 3-19-1 can be reduced to $NH_2$ under suitable conditions.

Scheme 3d

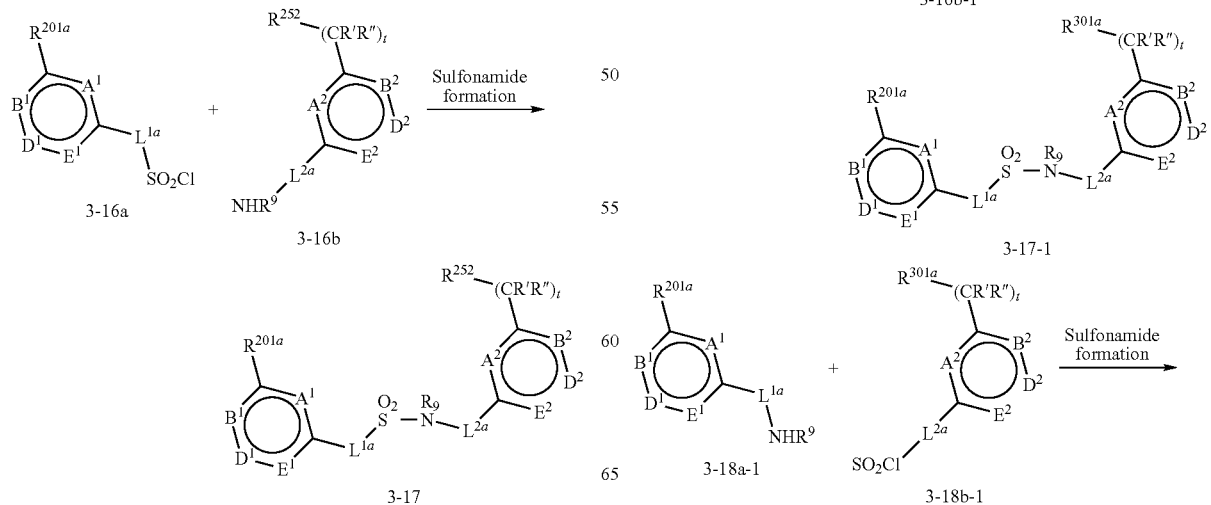

Scheme 3d-1

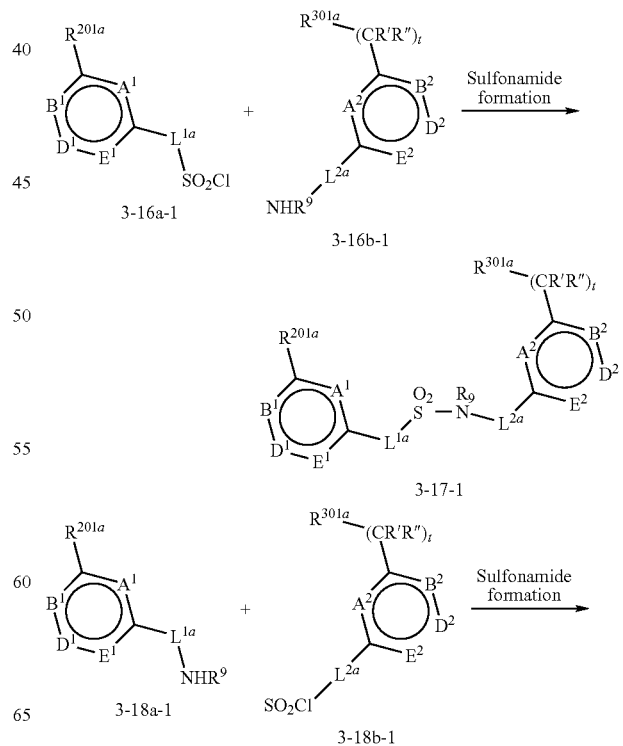

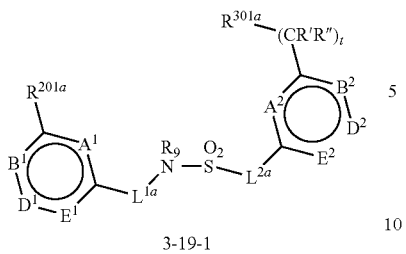

3-19-1

$R^{201a}$ is NO$_2$ or NHPg$^4$;
$R^{301a}$ is NO$_2$ or NHPg$^4$;
each Pg$^4$ is independently an amine protecting group (such as tert-butyloxycarbonyl or BOC).

As shown in Scheme 3e, urea compound 3-21 [wherein $R^{201a}$, Pg$^4$, and $R^{252}$ can be the same as those in Scheme 3d; and $L^{1d}$ and $L^{2d}$ can be each, independently, —(CR$^7$R$^8$)$_m$— (such as a bond or methylene)] can be obtained by reacting two appropriate amines with phosgene [C(=O)Cl$_2$] or a phosgene equivalent [e.g., triphosgene, ethyl chloroformate, trichloromethyl chloroformate, or phenyl chlorocarbonate]. Similarly, carbamates 3-23 and 3-25 can be made by reacting an appropriate amine and an appropriate alcohol with phosgene or its equivalent. Sulfamide 3-25c can be made by reacting amines 3-25a and 3-25b with SO$_2$Cl$_2$ or its equivalent (such as other thionyl halides, e.g., SO$_2$Br$_2$). The protecting group Pg$^4$ of compounds 3-21, 3-23, or 3-25 can be removed under suitable conditions. Compounds 3-21, 3-23, and 3-25 can undergo further chemical transformations when suitable reactive groups are present. For example, when $R^{252}$ (and/or $R^{201a}$) is NO$_2$, it can be reduced to NH$_2$ under suitable conditions.

Scheme 3e

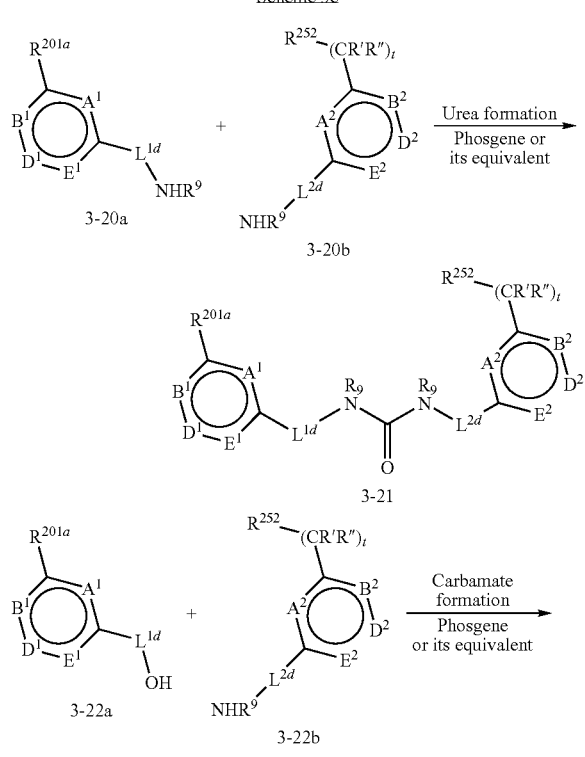

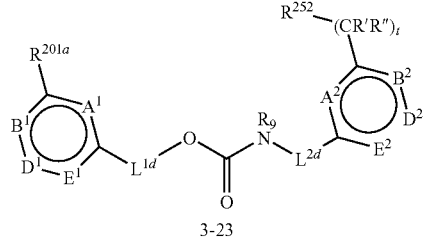

$R^{201a}$ is NO$_2$ or NHPg$^4$; and
Pg$^4$ is an amine protecting group (such as tert-butyloxycarbonyl or BOC).

Useful intermediates 3-21-1, 3-23-1, 3-25-1, or 3-25-1c [wherein Pg$^4$, $L^{1d}$, and $L^{2d}$ can be the same as those in Scheme 3e] can be made according to the methods outlined in Scheme 3e-1 (similar to the reactions depicted in Scheme 3e). The protecting group Pg$^4$ of compounds 3-21, 3-23, or 3-25 can be removed under suitable conditions. Compounds 3-21, 3-23, or 3-25 can undergo further chemical transformations when suitable reactive groups are present. For example, the NO$_2$ of compound 3-21, 3-23, or 3-25 can be reduced to NH$_2$ under suitable conditions.

Scheme 3e-1

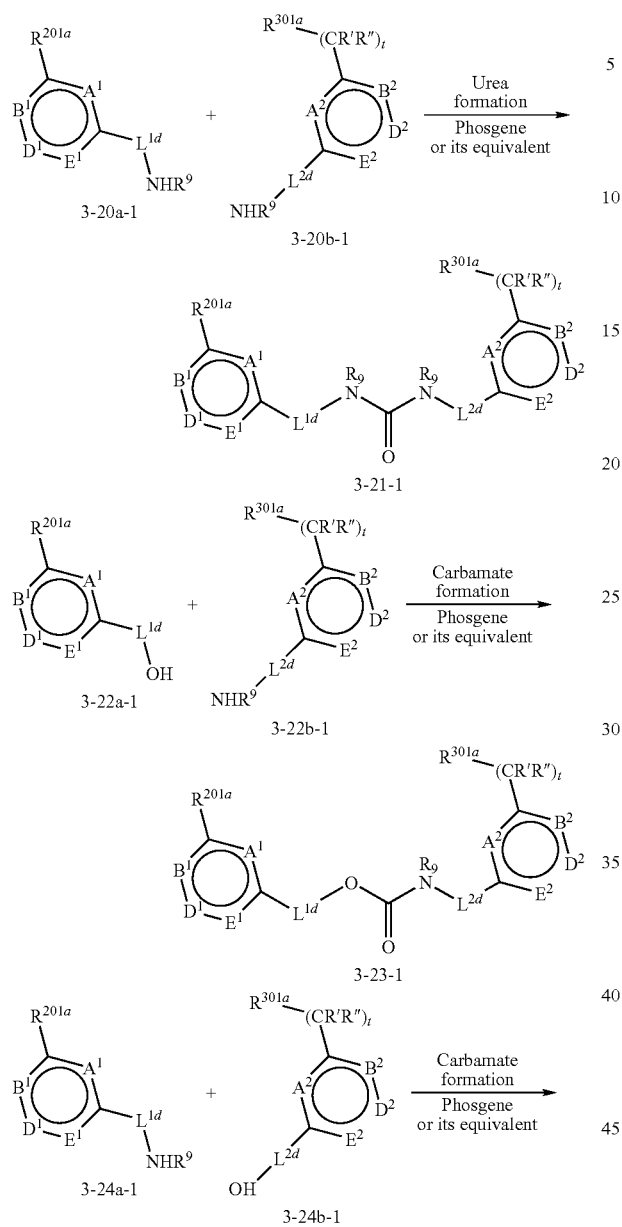

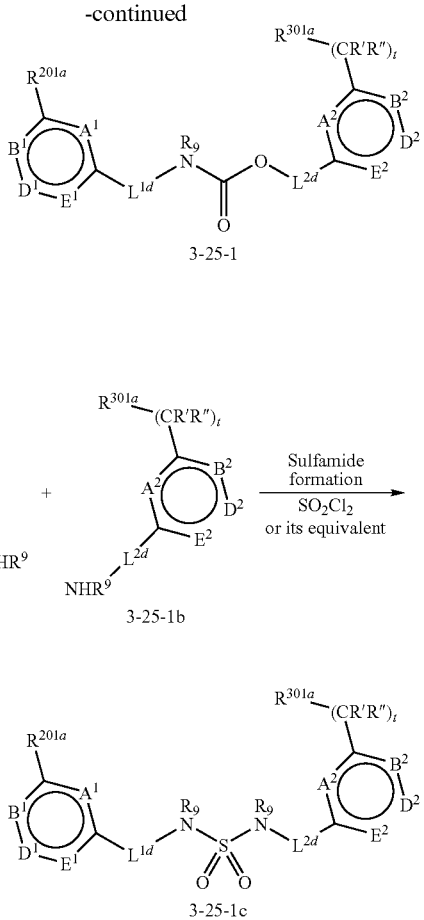

$R^{201a}$ is $NO_2$ or $NHPg^4$;
$R^{301a}$ is $NO_2$ or $NHPg^4$; and
each $Pg^4$ is independently an amine protecting group (such as tert-butyloxycarbonyl or BOC).

A more detailed scheme (similar to Scheme 3d-1) is provided in Scheme 3f. Sulfonamide 3-27 [wherein $L^{1a}$, and $L^{2a}$ can be the same as those in Scheme 3a] can be obtained by reacting sulfonyl halide 3-26a (such as chloride) with amine 3-26b. The $NO_2$ of compound 3-27 can be reduced to $NH_2$, for example in the presence of $Fe/CH_3COOH$, to afford compound 3-27a. The Boc group of compound 3-27 can be removed, for example, in the presence of HCl, to afford compound 3-27b.

Scheme 3f

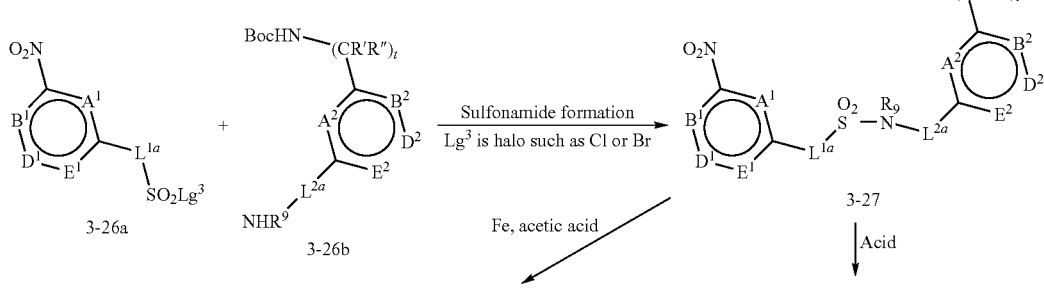

81

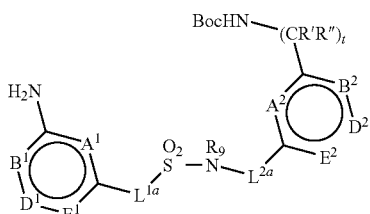

3-27a

82

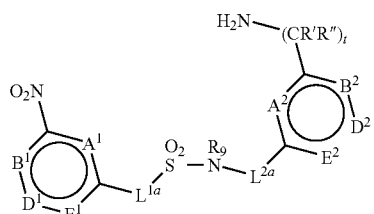

3-27b

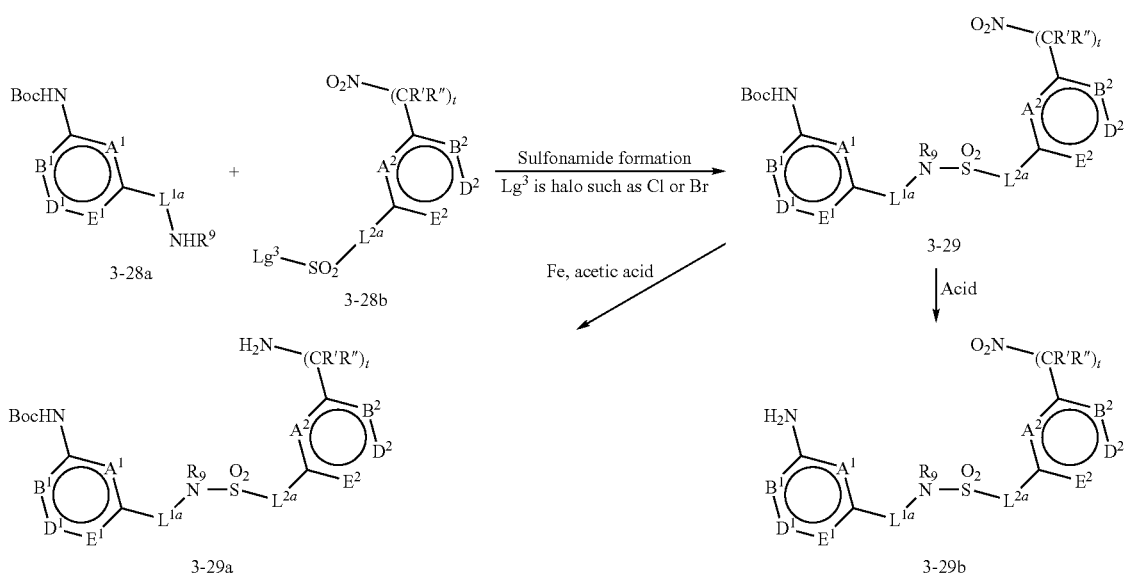

In Schemes 3a, 3b, 3b-1, 3c, 3c-1, 3d, 3e, 3e-1, and 3f wherein the compounds have a moiety of —(CR'R")$_t$—NO$_2$ [for example, —(CR'R")$_t$—R$^{252}$ wherein R$^{252}$ is NO$_2$; —(CR'R")$_t$—R$^{301}$ wherein R$^{301}$ is NO$_2$, or —(CR'R")$_t$—R$^{301a}$ wherein R$^{301a}$ is NO$_2$], the moiety —(CR'R")$_t$—NO$_2$ can be replaced with a moiety of —(CR'R")$_{ttt}$—CN (wherein ttt is 0, 1, or 2). Subsequently, the moiety of —(CR'R")$_{ttt}$—CN can be reduced to —(CR'R")$_{ttt}$—CH$_2$NH$_2$ under suitable conditions such as hydrogenation in the presence of Raney nickel, to provide additional useful intermediates.

As shown in Scheme 4, macrocycle 4-2 [wherein L$^{1a}$ and L$^{2a}$ can be the same as those in Scheme 3a] can be cyclized from acyclic precursor 4-1 by intramolecular Mitsunobu reaction/coupling. Preferably, one of L$^{1a}$ and L$^{2a}$ of acyclic precursor 4-1 is a bond in the intramolecular Mitsunobu reactions/couplings. Alternatively, one of the OH groups can be converted to a better leaving group such as halo or mesylate, and the intramolecular cyclization can be performed under suitable conditions.

Scheme 4

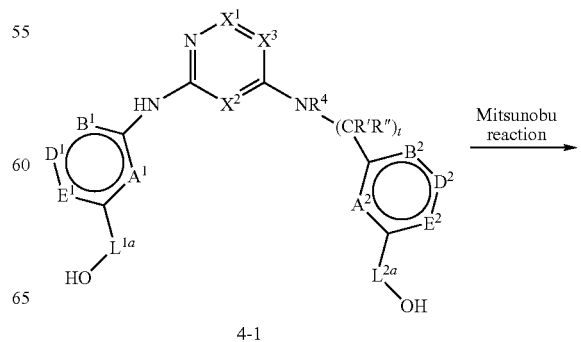

4-1

-continued

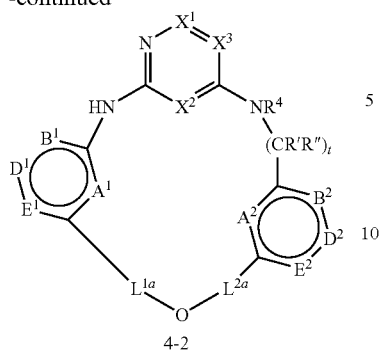

4-2

-continued

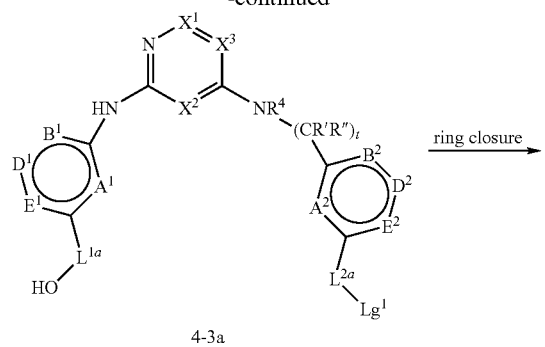

4-3a

As shown in Scheme 4-1, the free OH group of compound 4-1a (wherein $Pg^{100}$ is a hydroxyl protecting group such as methyl) can be converted to a better leaving group for example Br under suitable conditions (for example, using boron tribromide to convert OH to Br) to provide compound 4-2a. Removal of the protecting group $Pg^{100}$ of 4-2a provides acyclic precursor 4-3a. Macrocycle 4-4a [wherein $L^{1a}$ and $L^{2a}$ can be the same as those in Scheme 3a] can be cyclized from acyclic precursor 4-3a [wherein $Lg^1$ is a good leaving group such as halo (e.g Br)] under suitable conditions (such as in the presence of a base such as NaOH). Alternatively, the above described chemical transformation can be started with a compound similar to compound 4-1a, except that the hydroxyl protecting group $Pg^{100}$ is on the OH attached to $L^{2a}$; and that a free OH group (instead of $OPg^{100}$) is attached to $L^{1a}$.

Scheme 4-1

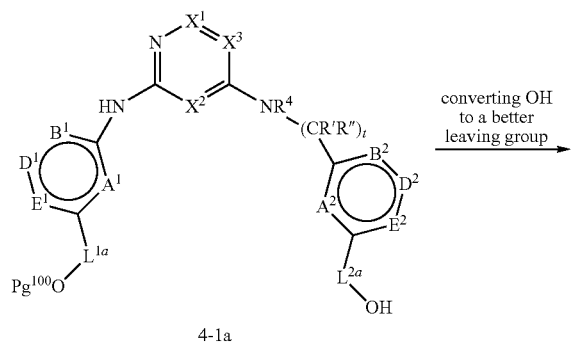

4-1a

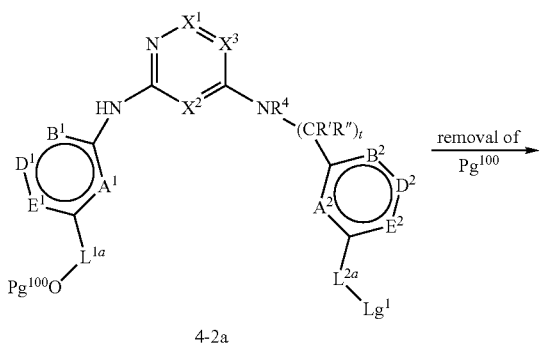

4-2a

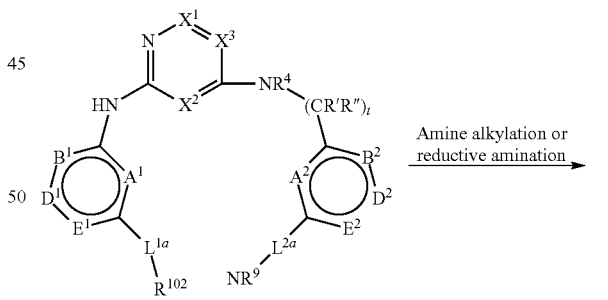

4-4a $Pg^{100}$ is a hydroxyl protecting group

In addition, many other intramolecular macrocyclizations can be useful for synthesizing the compounds of the present invention. For example, amine alkylations and reductive aminations can be useful for cyclizations as shown in Scheme 5a [wherein $L^{1a}$ and $L^{2a}$ can be the same as those in Scheme 3b].

Scheme 5a

-continued
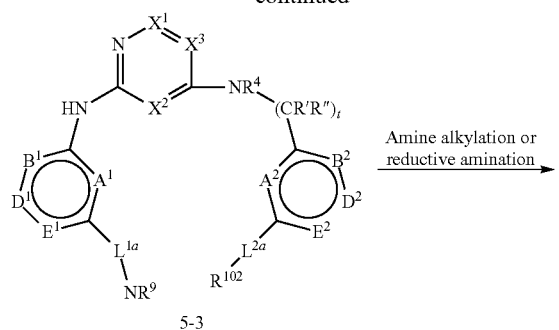
5-3
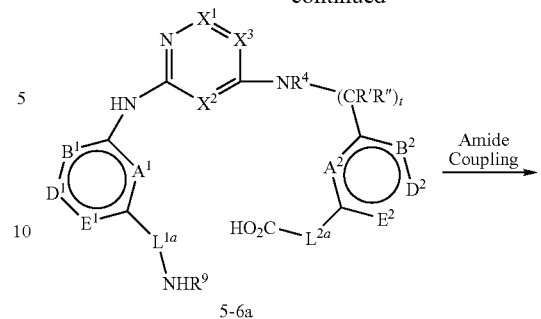
5-6a
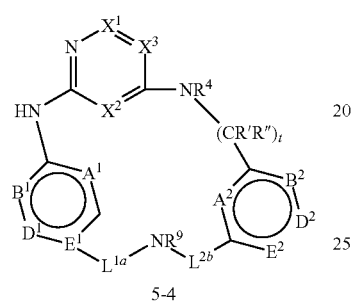
5-4
$R^{102}$ is $Lg^3$ or —C(=O)H;
$Lg^3$ is a leaving group such as halo (e.g., Br or Cl); and
$L^{1b}$ is $L^{1a}$ or $L^{1a}$-CH$_2$.
$L^{2b}$ is $L^{2a}$ or $L^{2a}$-CH$_2$.
Amide couplings can be useful for cyclizations as shown in Scheme 5b (similar to the reactions depicted in Scheme 3c, and wherein $L^{1a}$ and $L^{2a}$ can be the same as those in Scheme 3c).
Scheme 5b
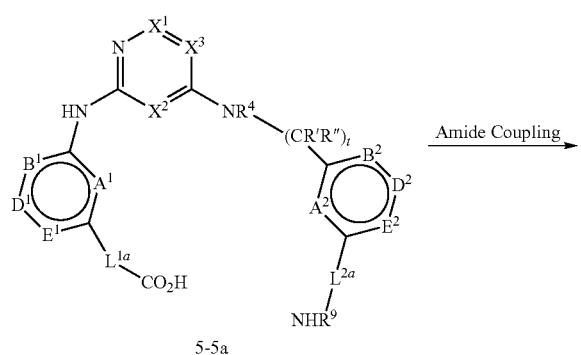
5-5a
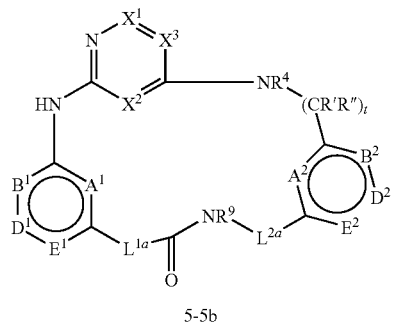
5-5b
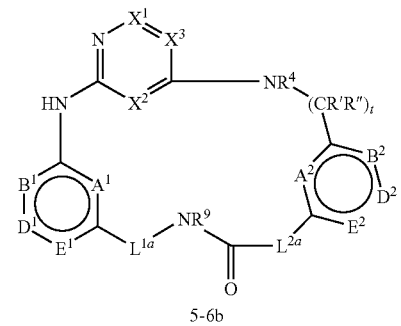
5-6b
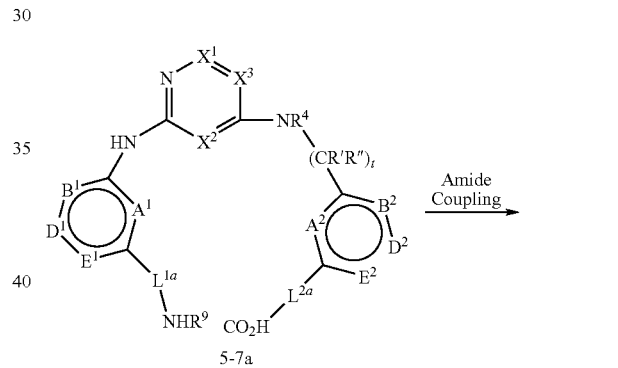
5-7a
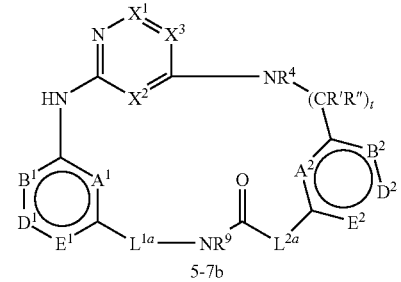
5-7b
5-8a -continued

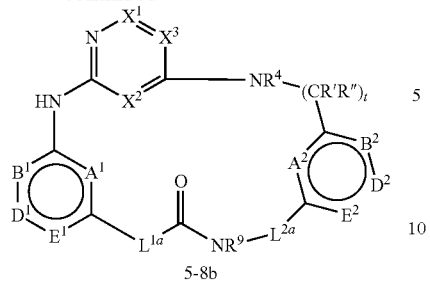

5-8b

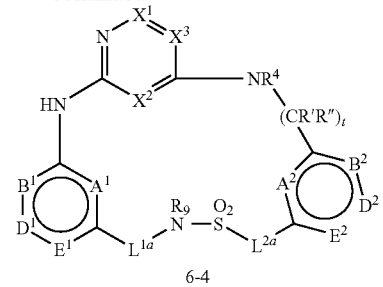

6-4

Sulfonamide formation can be useful for cyclization as shown in Scheme 6a (similar to the reactions depicted in Scheme 3d, and wherein $L^{1a}$ and $L^{2a}$ can be the same as those in Scheme 3d).

Urea formation and carbamate formation can be useful for cyclizations as shown in Scheme 6b (similar to the reactions depicted in Scheme 3e, and wherein $L^{1d}$ and $L^{2d}$ are the same as those in Scheme 3e).

Scheme 6a

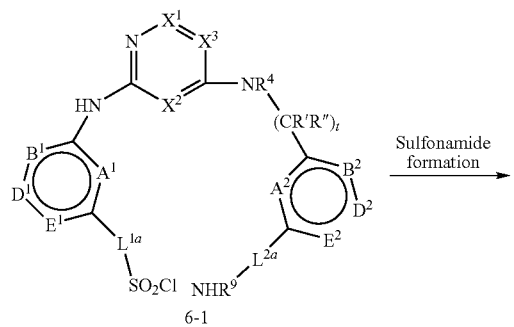

Scheme 6b

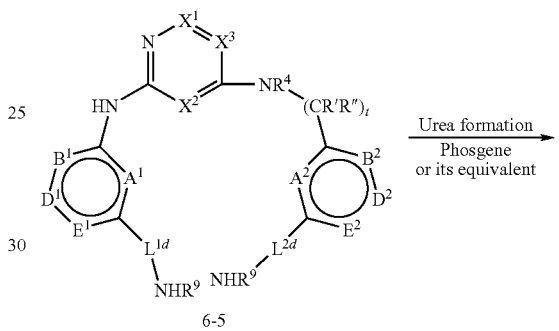

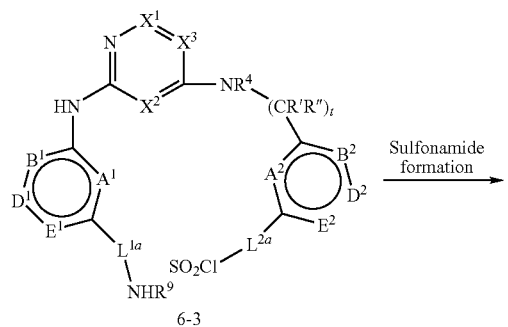

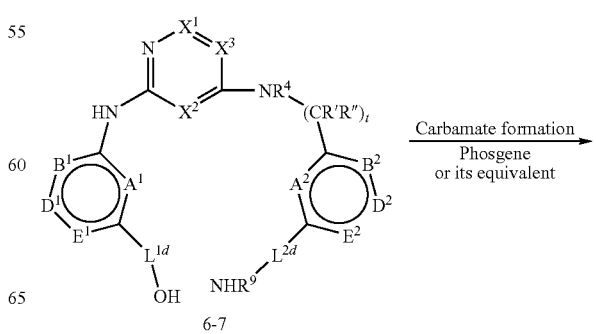

Scheme 7

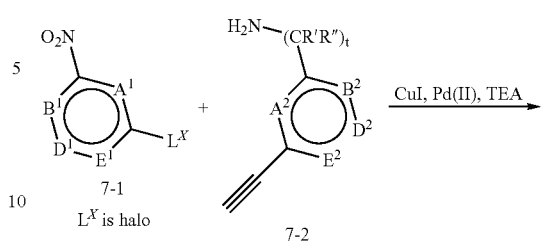

7-1

$L^X$ is halo 7-2

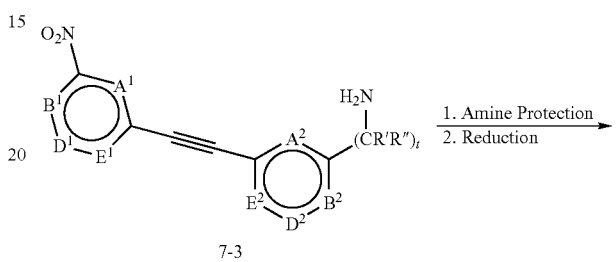

7-3

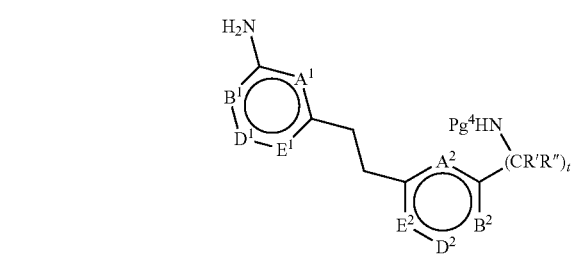

7-4

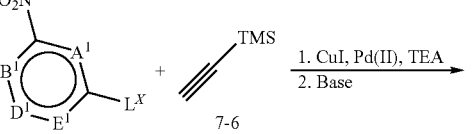

7-5

$L^X$ is halo 7-6

7-7

7-8

7-9

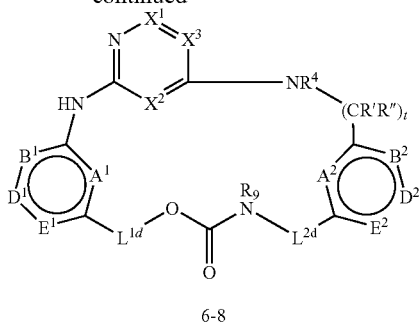

6-8

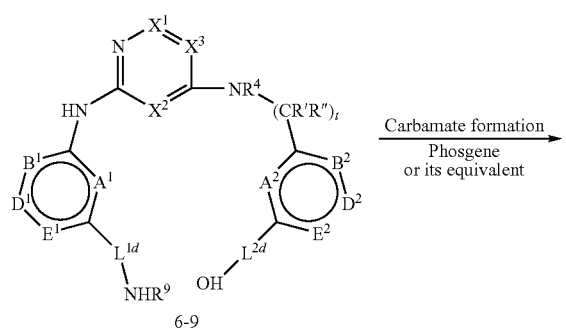

6-9

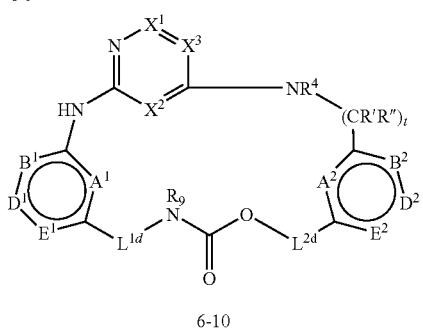

6-10

Useful intermediates 7-4, 7-10, and 7-13 can be made according to the methods outlined in Scheme 7. Aryl halide or heteroaryl halide 7-1 can be reacted with alkyne 7-2 under Sonogashira coupling reaction conditions to afford alkyne 7-3. [See, K. Sonogashira, Y. Tohda, N. Hagihara (1975). "A convenient synthesis of acetylenes: catalytic substitutions of acetylenic hydrogen with bromoalkenes, iodoarenes and bromopyridines". *Tetrahedron Letters* 16 (50): 4467-4470.]. The amino group of alkyne 7-3 can be protected with a protecting group $Pg^4$, followed by the C≡C bond being reduced to a saturated bond by hydrogenation to afford intermediate 7-4.

Aryl halide or heteroaryl halide 7-5 can be reacted with silyl substituted acetylene 7-6 [e.g. (trimethylsilyl)-acetylene] under Sonogashira coupling reaction conditions, followed by removal of the silyl group under suitable conditions [e.g., in the presence of a base (e.g., $K_2CO_3$)] to afford alkyne 7-7. Alkyne 7-7 can be reacted with aryl halide or heteroaryl halide 7-8 under Sonogashira coupling reaction condition to afford alkyne 7-9. Alkyne 7-9 can be reduced via hydrogenation to produce intermediate 7-10. Aryl halide or heteroaryl halide 7-11 can be reacted with alkyne 7-12 under Sonogashira coupling reaction conditions, followed by hydrogenation to reduce the C≡C bond, to afford alkyne 7-13.

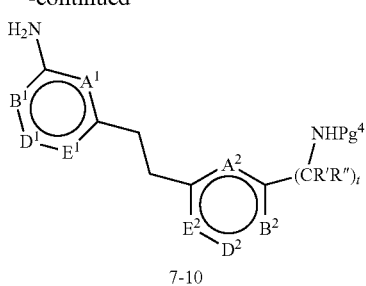

7-10

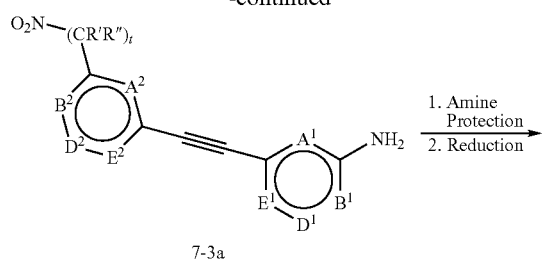

7-3a

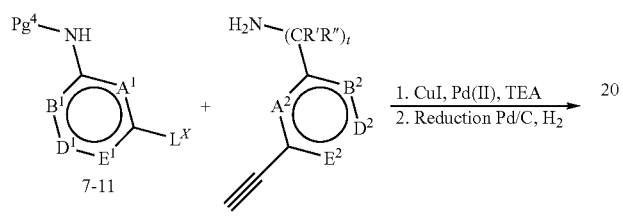

7-11    7-12

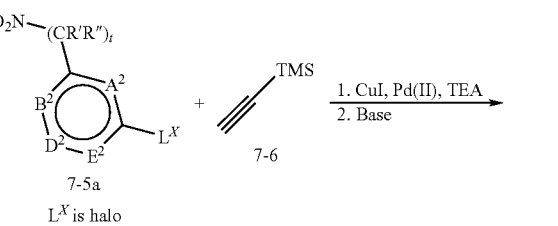

7-4a

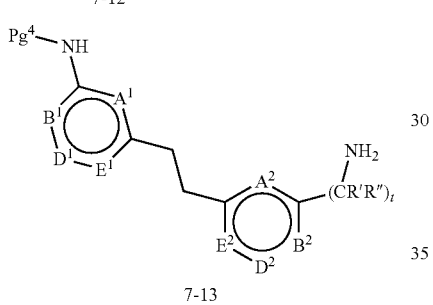

7-13

Pg$^4$ is an amine protecting group such as Boc

Useful intermediates 7-4a, 7-10a, and 7-13a can be made according to the methods outlined in Scheme 7-1 (similar to the reactions depicted in Scheme 7). Alternatively, in Scheme 7-1 wherein the compounds have a moiety of —(CR'R")$_t$—NO$_2$ (i.e. compounds 7-1a, 7-3a, 7-5a, 7-7a,), the moiety of —(CR'R")$_t$—NO$_2$ can be replaced with a moiety of —(CR'R")$_{ttt}$—CN (wherein ttt is 0, 1, or 2). Subsequently, the moiety of —(CR'R")$_{ttt}$—CN (such as those in compounds 7-3a and 7-7a) can be reduced to —(CR'R")$_{ttt}$—CH$_2$NH$_2$ under suitable conditions such as hydrogenation in the presence of Raney nickel, to provide additional useful intermediates.

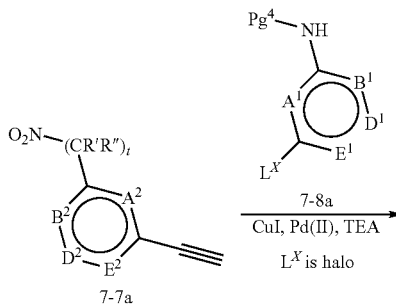

7-5a, L$^X$ is halo     7-6

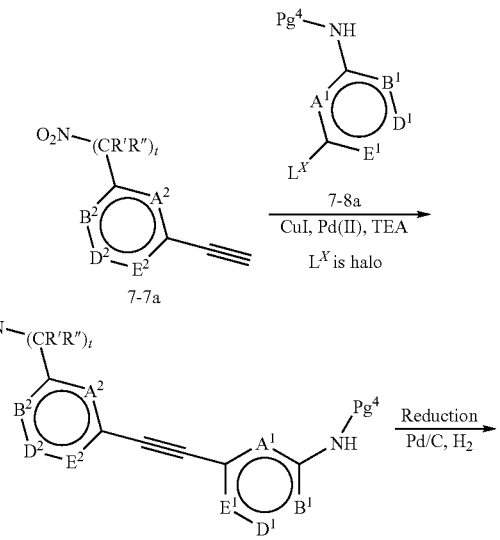

7-7a, L$^X$ is halo 7-8a, L$^X$ is halo 7-9a

Scheme 7-1

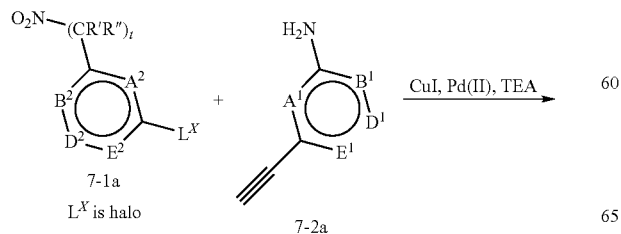

7-1a, L$^X$ is halo     7-2a 7-10a

Scheme 7-2

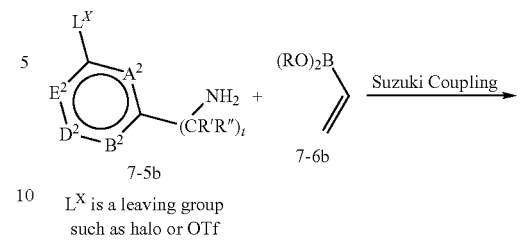

$L^X$ is a leaving group such as halo or OTf

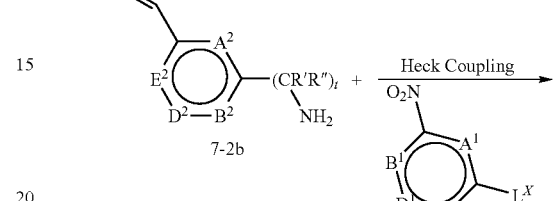

$L^X$ is, e.g., halo or OTf

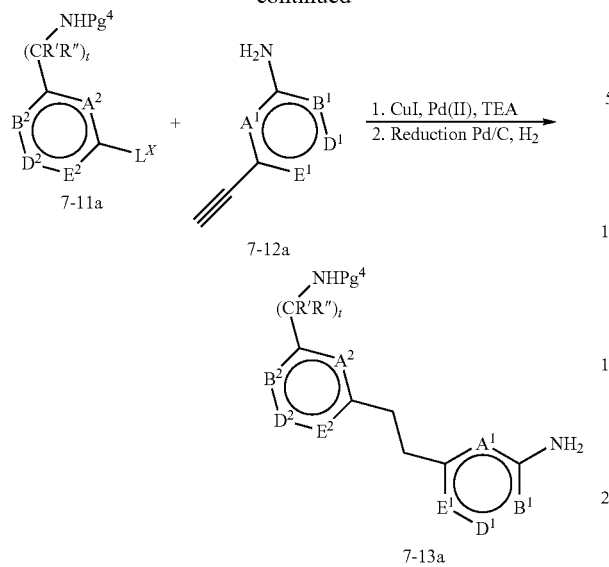

Pg⁴ is an amine protecting group such as Boc

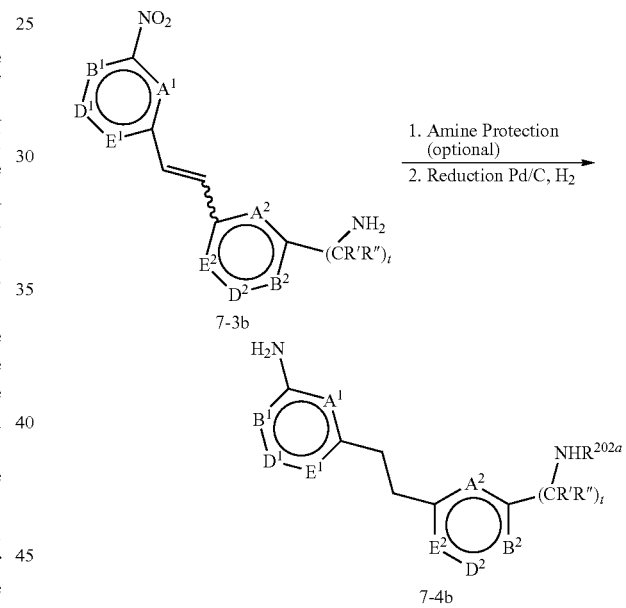

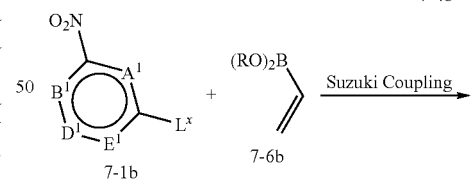

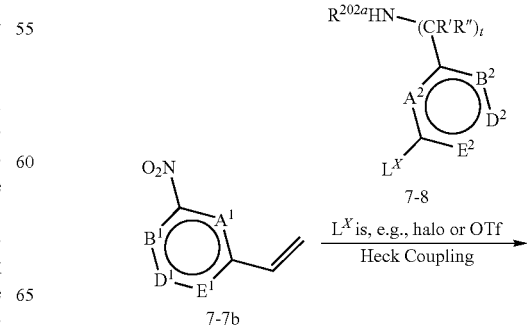

$L^X$ is, e.g., halo or OTf

Useful intermediates 7-4b, 7-10b, and 7-13b can be made according to the methods outlined in Scheme 7-2. Aryl halide/triflate or heteroaryl halide/triflate 7-5b can be reacted with vinylboronate 7-6b (R groups can be each, independently, H (e.g., compound 7-6b is a vinylboronic acid when both R are H) or alklyl; or together with the —O—B—O— to which they are attached form an optionally substituted heterocycloalkyl) under Suzuki-Miyaura reaction condition/Suzuki coupling to form alkene 7-2b [for reviews of the Suzuki-Miyaura reaction, see e.g. Miyaura, N; Suzuki, A. Chem. Rev., 1995, 95:2457-2483]. Alternatively, a vinyl stannane (such as tributyl(vinyl)stannane, equivalent to vinylboronate 7-6b in the Suzuki-Miyaura reaction described herein) can be used to react with aryl halide or heteroaryl halide 7-5b to form alkene 7-2b under Stille reaction conditions [See e.g. P. Espinet, A. M. Echavarren "The Mechanisms of the Stille Reaction"; Angewandte Chemie International Edition; 43 (36): 4704-4734 (2004)]. Aryl halide/triflate or heteroaryl halide/triflate 7-1b can be reacted with alkene 7-2b under Heck coupling reaction conditions to afford alkene 7-3b. [See e.g. Heck, R. F.; Nolley, Jr., J. P., "Palladium-catalyzed vinylic hydrogen substitution reactions with aryl, benzyl, and styryl halides"; J. Org. Chem., 37(14): 2320-2322 (1972)]. The amino group of alkene 7-3b can optionally be protected by an amine protecting group such as Boc group, followed by reduction of the C=C bond to a saturated bond via hydrogenation to afford intermediate 7-4b under an appropriate condition such as palladium catalyzed hydrogenation or using a hydrazine compound. [See e.g. Y. Imada, H. Iida, T. Naota, J. Am. Chem. Soc., 2005, 127, 14544-14545].

Intermediate 7-10b can be synthesized starting from aryl halide/triflate or heteroaryl halide/triflate 7-1b (also substituted with a nitro group) through similar chemical transformations to those described in the formation of intermediate 7-4b.

Alternatively, aryl halide/triflate or heteroaryl halide/triflate 7-11b can be reacted with alkene 7-12b under Heck coupling reaction conditions, followed by reduction of the C=C bond, for example, via hydrogenation, to afford intermediate 7-13b.

Scheme 7-3

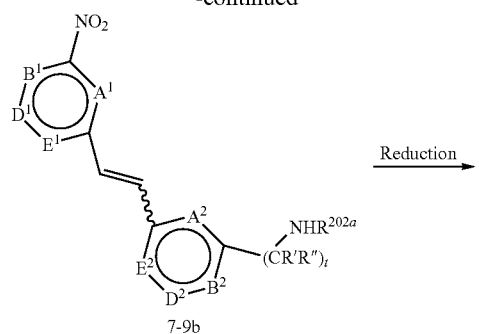

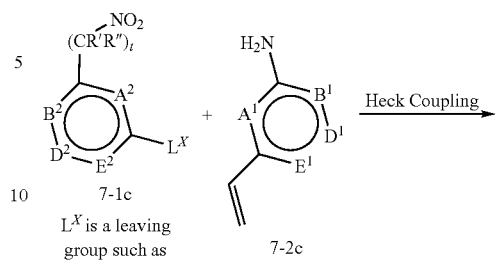

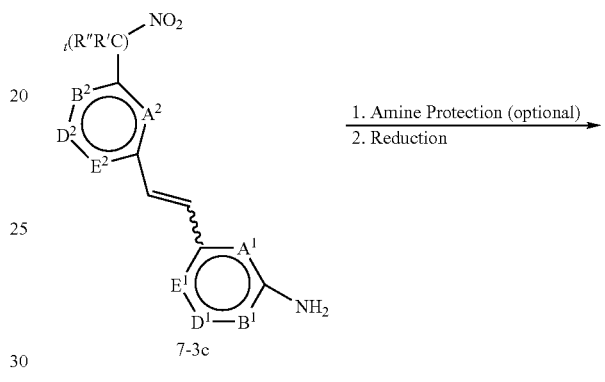

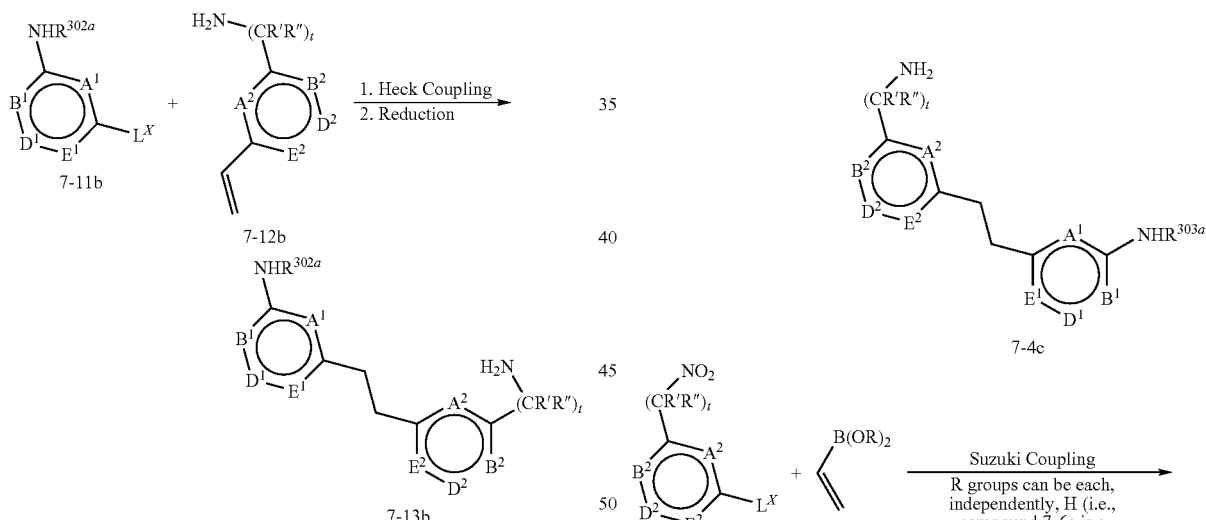

$R^{202a}$ is H or an amine protecting group such as Boc
$R^{302a}$ is H or an amine protecting group such as Boc Useful intermediates 7-4c, 7-10c, and 7-13c can be made according to the methods outlined in Scheme 7-3 (similar to those depicted in Scheme 7-2). Alternatively, in Scheme 7-1 wherein the compounds have a moiety of —(CR'R")$_t$—NO$_2$ (i.e. compounds 7-1c, 7-3c, 7-5c, 7-7c,), the moiety of —(CR'R")$_t$—NO$_2$ can be replaced with a moiety of —(CR'R")$_{ttt}$—CN (wherein ttt is 0, 1, or 2). Subsequently, the moiety of —(CR'R")$_{ttt}$—CN (such as those in compounds 7-3c and 7-7c) can be reduced to —(CR'R")$_{ttt}$—CH$_2$NH$_2$ under suitable conditions such as hydrogenation in the presence of Raney nickel, to provide additional useful intermediates.

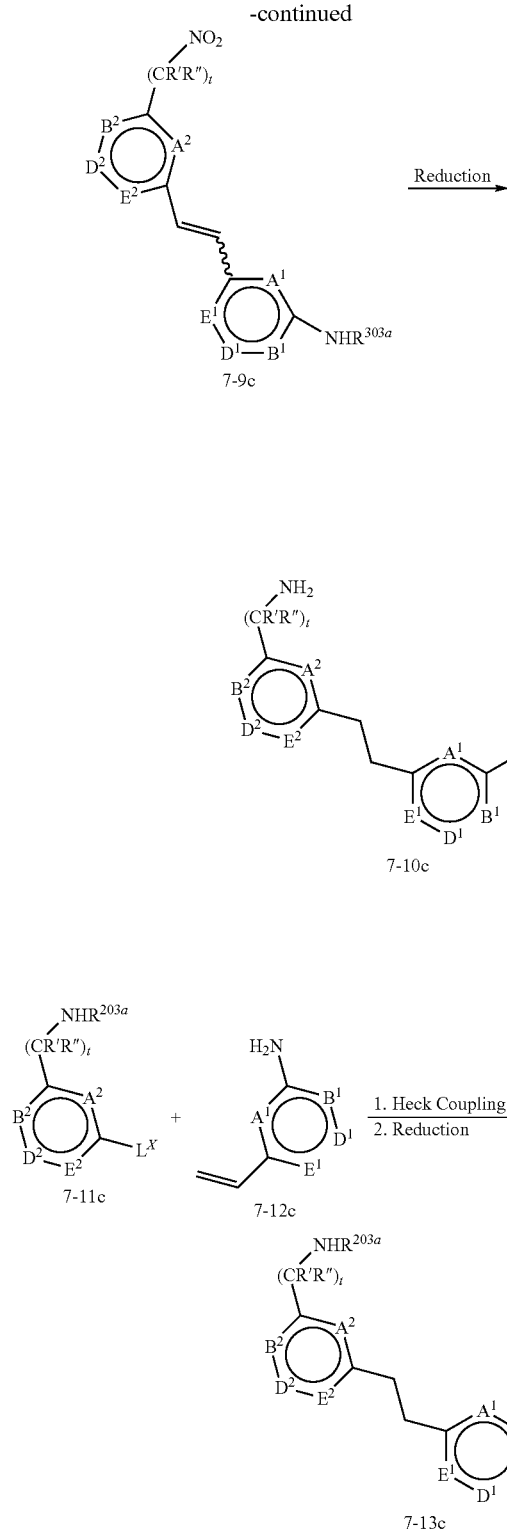
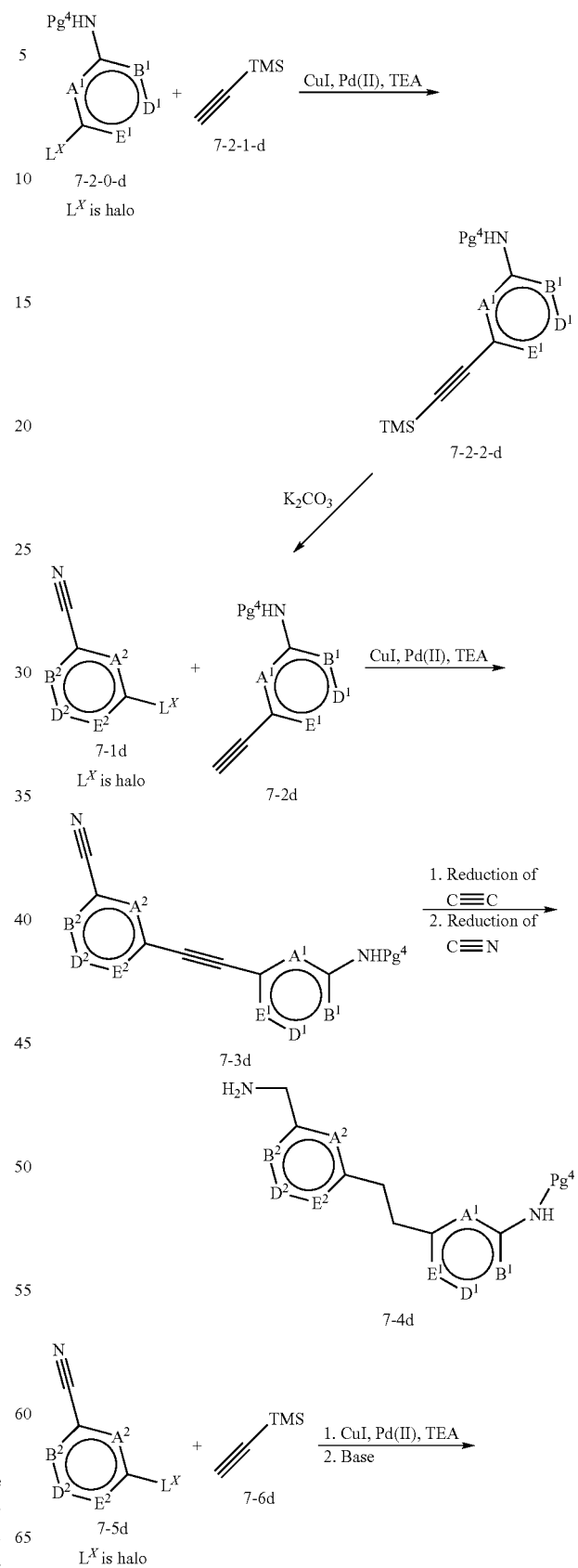
$R^{303a}$ is H or an amine protecting group such as Boc
$R^{203a}$ is H or an amine protecting group such as Boc
Useful intermediates 7-2d, 7-4d, 7-10d, and 7-13d can be made according to the methods outlined in Scheme 7-4 (similar to the reactions depicted in Scheme 7). The trimethylsilyl (TMS) group of 7-2-2-d can be removed in the presence of a base such as $K_2CO_3$ to give compound 7-2d.

-continued

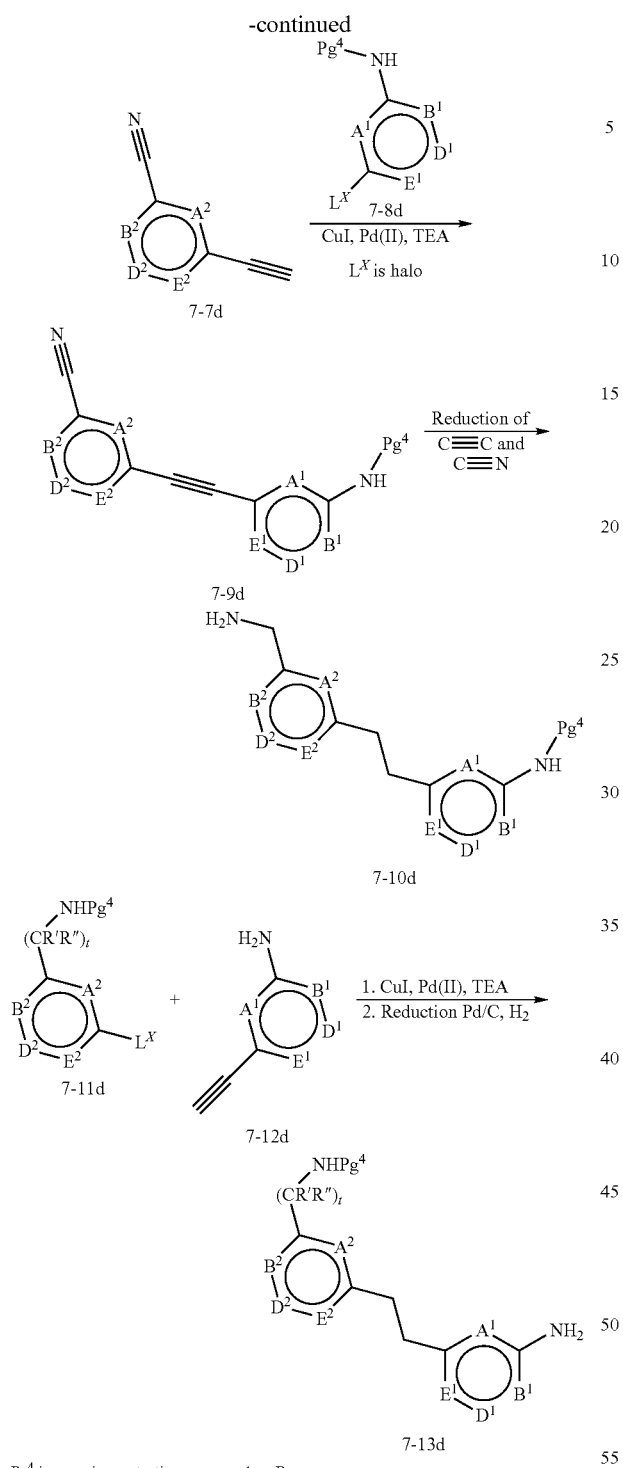

Pg⁴ is an amine protecting group such as Boc group can be reduced to $NH_2$; and a protected amino group can be de-protected to $NH_2$. Alternatively, in Scheme 8 wherein the compounds have a moiety of —$(CR'R'')_t$—$NO_2$ (i.e. $R^{301a}$ is $NO_2$), the moiety —$(CR'R'')_t$—$NO_2$ can be replaced with a moiety of —$(CR'R'')_{ttt}$—CN (wherein ttt is 0, 1, or 2). Subsequently, the moiety of —$(CR'R'')_{ttt}$—CN (such as those in compounds 8-3 and 8-5) can be reduced to —$(CR'R'')_{ttt}$—$CH_2NH_2$ under suitable conditions such as hydrogenation in the presence of Raney nickel, to provide additional useful intermediates.

Scheme 8

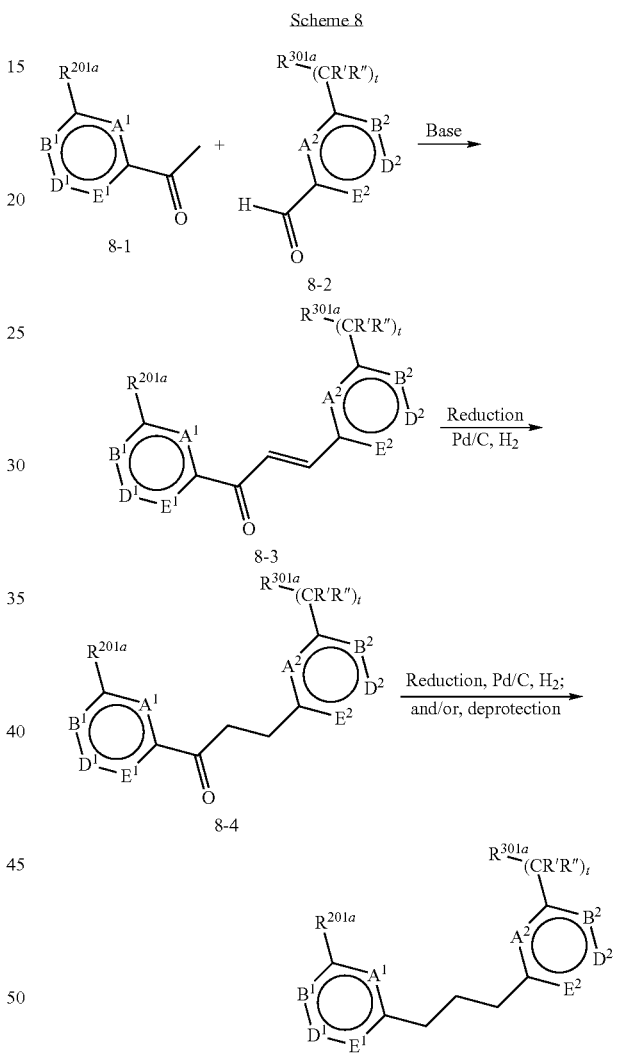

$R^{201a}$ is $NO_2$ or $NHPg^4$;
$R^{301a}$ is $NO_2$ or $NHPg^4$;
each Pg⁴ is independently an amine protecting group (such as tert-butyloxycarbonyl or BOC).

As shown in Scheme 8, aryl (or heteroaryl) methyl ketone 8-1 can be reacted with aryl (or heteroaryl) aldehyde 8-2 under basic conditions [(such as in the presence of an alkali metal hydroxide (e.g. NaOH)] to afford derivative 8-3. Intermediate 8-3 can be reduced via hydrogenation (such as in the presence of Pd/C, hydrogen and acetic acid) to afford compound 8-4, which further can be reduced to compound 8-5. $R^{201a}$ and $R^{301a}$ groups of compounds 8-4 or 8-5 can undergo further chemical transformations. For example, the $NO_2$ group can be reduced to $NH_2$; and a protected amino group can be de-protected to $NH_2$. Alternatively, in Scheme 8 wherein the compounds have a moiety of —$(CR'R'')_t$—$NO_2$ (i.e. $R^{201a}$ is $NO_2$), the moiety —$(CR'R'')_t$—$NO_2$ can be replaced with a moiety of —$(CR'R'')_{ttt}$—CN (wherein ttt is 0, 1, or 2). Subsequently, the moiety of —$(CR'R'')_{ttt}$—CN (such as those in compounds 8-3a and 8-5a) can be reduced to —$(CR'R'')_{ttt}$—$CH_2NH_2$ under suitable conditions such as Useful intermediates 8-3a, 8-4a, and 8-5a can be made according to the methods outlined in Scheme 8-1 (similar to the reactions depicted in Scheme 8). Alternatively, in Scheme 8-1 wherein the compounds have a moiety of —$(CR'R'')_t$—$NO_2$ (i.e. $R^{201a}$ is $NO_2$), the moiety —$(CR'R'')_t$—$NO_2$ can be replaced with a moiety of —$(CR'R'')_{ttt}$—CN (wherein ttt is 0, 1, or 2). Subsequently, the moiety of —$(CR'R'')_{ttt}$—CN (such as those in compounds 8-3a and 8-5a) can be reduced to —$(CR'R'')_{ttt}$—$CH_2NH_2$ under suitable conditions such as hydrogenation in the presence of Raney nickel, to provide additional useful intermediates.

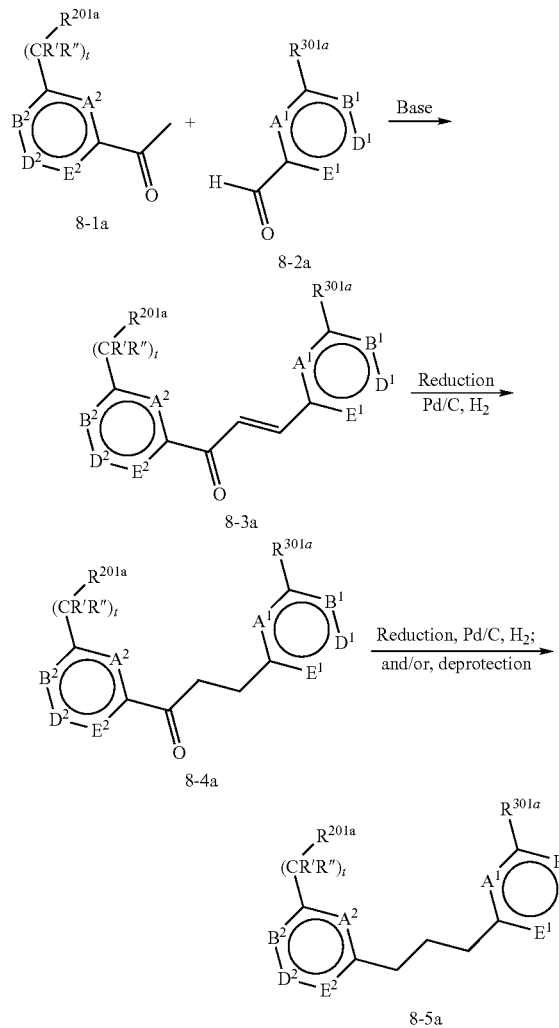

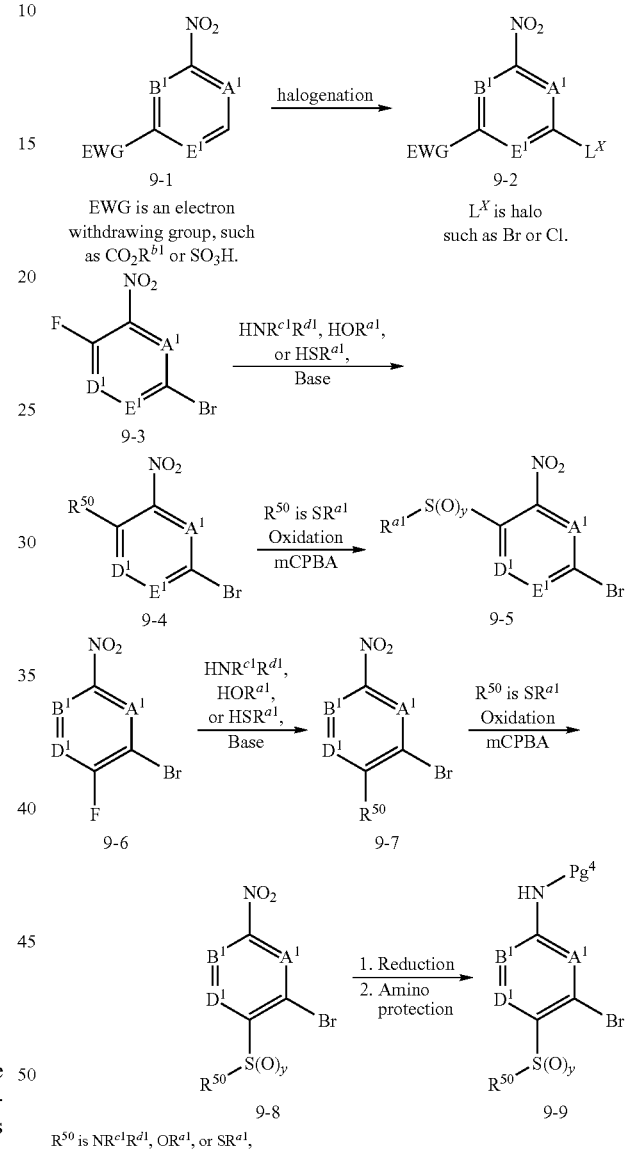

Some additional useful intermediates can be made by the methods outlined in Scheme 9. Aryl (or heteroaryl) compound 9-1 can be reacted with a halogenating reagent [such as bromine (Br$_2$), N-bromoacetamide (NBA), N-bromosuccinimide (NBS), 1,3-dibromo-5,5-dimethylhydantoin (DBDMH), 1,3-dichloro-5,5-dimethylhydantoin (DCDMH), N-chlorosuccinimide (NCS)] to afford halogenated compounds 9-2.

A fluorinated compound 9-3 can be reacted with an amine, an alcohol, or thioalcohol in the presence of a base (such as a tertiary amine, e.g., TEA) to form compound 9-4. Where $R^{50}$ is $SR^{a1}$, compound 9-4 can be oxidized to sulfinyl or sulfonyl compounds 9-5 (wherein y is 1 or 2), using an oxidizing reagent such as m-chloroperoxybenzoic acid (mCPBA).

A fluorinated compound 9-6 can be reacted with an amine, an alcohol, or thioalcohol in the presence of a base (such as a tertiary amine, e.g., triethylamine or TEA) to form compound 9-7. Where $R^{50}$ is $SR^{a1}$, compound 9-7 can be oxidized to sulfinyl or sulfonyl compound 9-8 (wherein y is 1 or 2), using an oxidizing reagent such as m-chloroperoxybenzoic acid (mCPBA). The nitro (NO$_2$) group of compound 9-8 can be reduced, for example, in the presence of Fe (or Zn) and acetic acid, followed by introduction of an amine protecting group (such as Boc), to afford compound 9-9.

As shown in Scheme 10, compound 10-1 [wherein $R^4$ can be H, methyl, ethyl, or the like; and $Lg^3$ is a leaving group such as halo (e.g., chloro)] can be reacted with substituted heteroaromatic compound 10-2 [wherein $Lg^1$ and $Lg^2$ are each, independently, a leaving group such as halo (e.g., chloro)] in the presence of a suitable base (such as an inorganic base, for example a metal carbonate (e.g., potassium carbonate), a metal hydride (e.g., sodium hydride), a metal hydroxide (e.g., sodium hydroxide), a metal alkoxide (e.g., sodium ethoxide)] and/or in the presence of a transition metal catalyst for example a palladium catalyst [e.g., Pd(PPh$_3$)$_4$] to afford compound 10-3. Reaction of compound 10-3 and alkene 10-4 under Heck coupling reaction conditions gives alkene compound 10-5. Reduction of the C=C bond (between the two aromatic rings) of compound 10-5 to a saturated bond under an appropriate condition such as palladium catalyzed hydrogenation or using a hydrazine compound, followed by optional deprotection (when $R^{101}$ is an amine protecting group) and ring closure step [in the presence of an acid (e.g. p-toluenesulfonic acid (PTSA) or HCl,) or a Pd catalyst], gives compound 10-6.

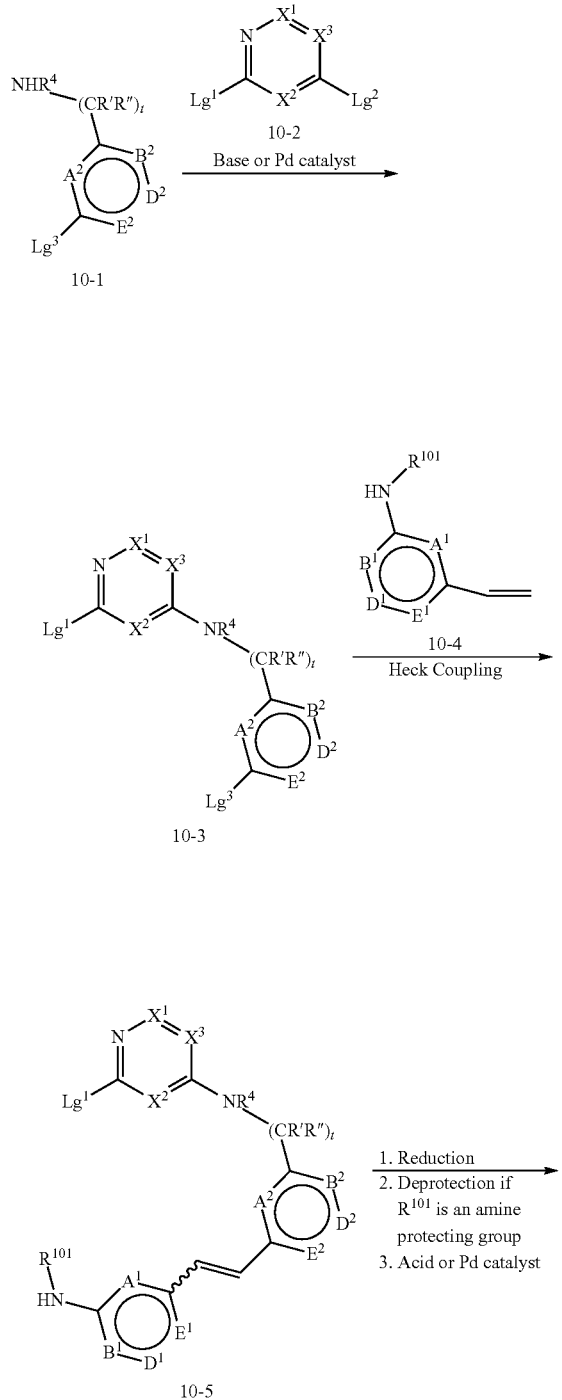

Scheme 10

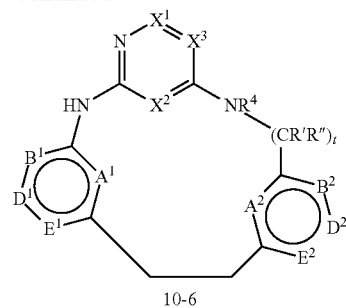

10-6

$R^{101}$ is H or an amine protecting group

Similar to the chemical reactions/transformations depicted in Scheme 10, compound 11-6 can be synthesized according to the methods shown in Scheme 11 wherein alkene 11-4 is substituted with a nitro group.

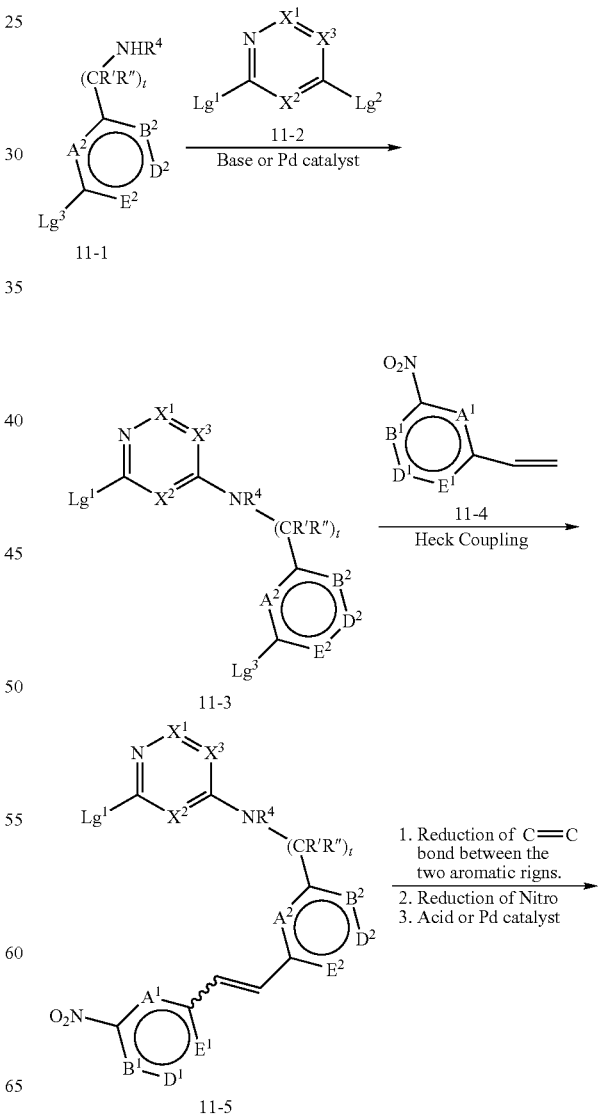

Scheme 11

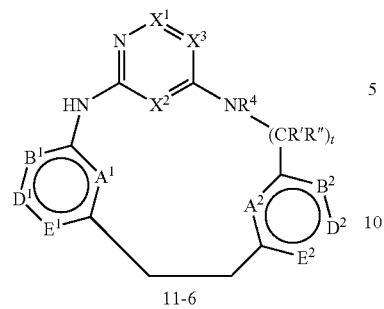

11-6

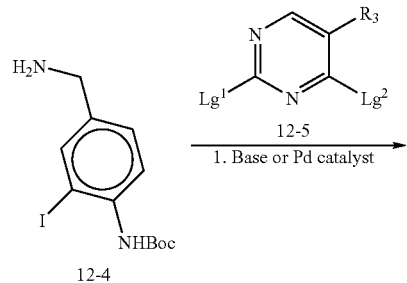

12-4

12-5
1. Base or Pd catalyst →

As shown in Scheme 12, arylamine 12-1 can be converted to its corresponding diazonium salt intermediate using $NaNO_2$ under acidic condition, followed by conversion of the diazonium salt to halide 12-2 [Se e.g., "The Chemistry of Functional Groups. The Chemistry of Diazonium and Diazo Groups" Wiley: New York, 1978, the articles by Hegarty, pt. 2, pp. 511-591, and Schank, pt. 2, pp. 645-657; See also, P. S. Kalsi, "Organic Reactions Stereochemistry and Mechanism: Through Solved Problems"; Chapter 6, page 362 (Sandmeyer Reaction), New Age Publishers, 4th edition, 2006]. The compound 12-2 can be converted to a carbamate compound such as the BOC-protected amine 12-3 via Curtis rearrangement [See Ende, D. J. a.; DeVries, K. M.; Clifford, P. J.; Brenek, S. J. Org. Proc. Res. Dev. 1998, 2, 382-392]. The CN group of compound 12-3 can be reduced to $CH_2NH_2$, followed by coupling to compound 12-5 (for example, in the presence of a base or a Pd catalyst), to afford compound 12-6. Compound 12-6 can be reacted with alkene 12-7 under Heck Reaction conditions to afford compound 12-8. Reduction of the C=C bond (between the two aromatic rings) of compound 12-8 to a saturated bond via hydrogenation, followed by ring closure step (for example in the presence of a Pd catalyst or an acid such as HCl or PTSA), gives compound 12-9. Optional deprotection (when $R^{101}$ is an amine protecting group) of compound 12-9, followed by further chemical modifications such as acylation (or sulfonylation, urea formation, carbamate formation, or arylation/heteraylation) can afford different compounds of invention such as compound 12-10.

Scheme 12

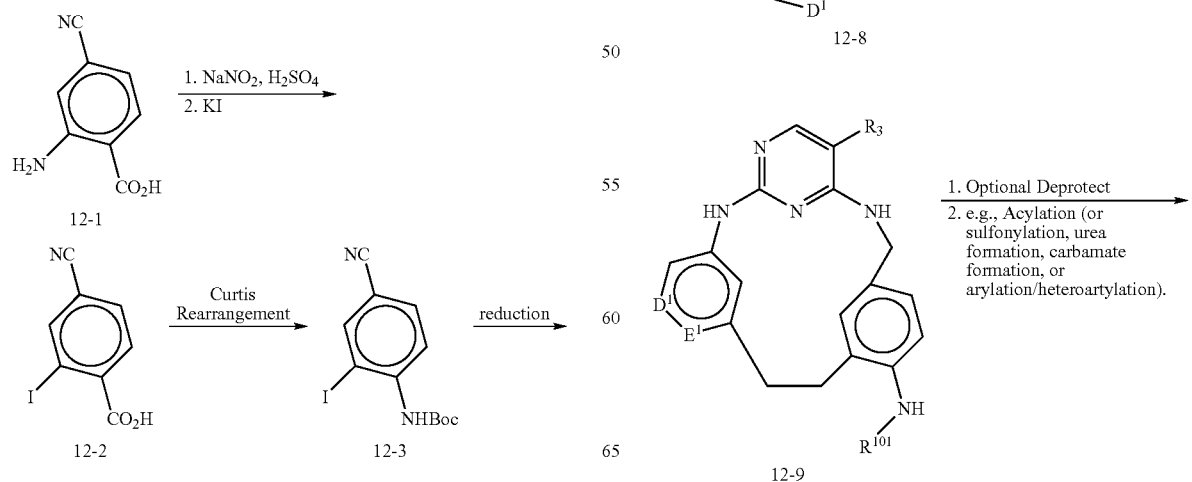

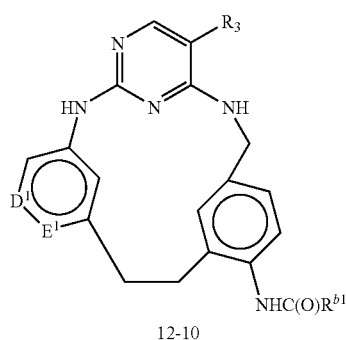

12-10

R[101] is H or an amine protecting group

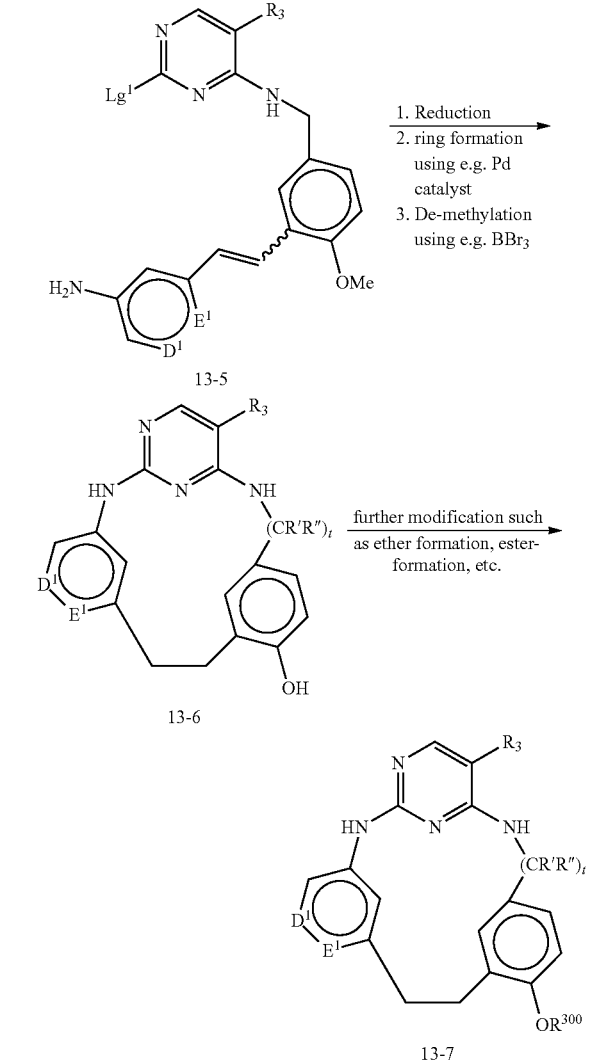

1. Reduction
2. ring formation using e.g. Pd catalyst
3. De-methylation using e.g. BBr₃

13-5 further modification such as ether formation, ester-formation, etc.

13-6

13-7

As shown in Scheme 13, compound 13-6 can be synthesized starting from amine 13-1, by chemical reactions similar to those for making compound 12-9 in Scheme 12. After the demethylation step (see. e.g. J. F. W. McOmie, M. L. Watts, and D. E. West, "Demethylation of aryl methyl ethers by boron tribromide"; Tetrahedron, Volume 24, Issue 5, 1968, Pages 2289-2292), the OH group of compound 13-6 can undergo further chemical modifications such as ether formation ($R^{300}$ can be, e.g., $C_{1-6}$ alkyl, arylalkyl, heteroarylalkyl, cycloalkylalkyl, or heterocycloalkylalkyl), ester formation ($R^{300}$ can be, e.g., $C(O)R^{b1}$), or carbamate formation ($R^{300}$ can be, e.g., $C(O)NR^{c1}R^{d1}$).

Scheme 13

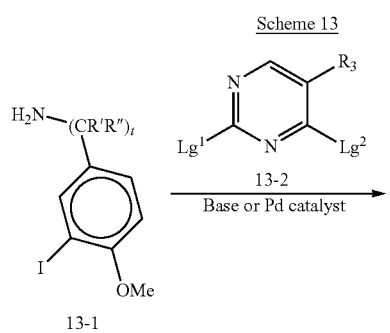

13-1

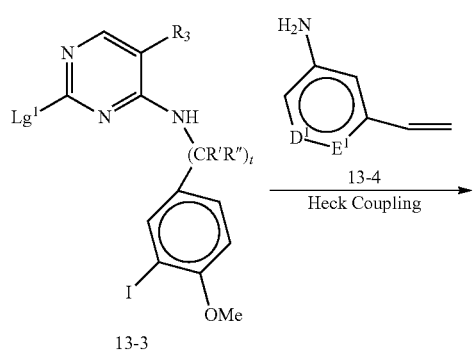

13-3

Additional starting materials and intermediates useful for making the compounds of the present invention can be obtained from chemical vendors such as Sigma-Aldrich or can be made according to methods described in the chemical art. For example, introducing pentafluorosulfanyl ($SF_5$) group to aromatic rings can be achieved according to the methods disclosed in U.S. Pat. No. 6,919,484 and/or the references cited therein.

Those skilled in the art can recognize that in all of the schemes described herein, if there are functional (reactive) groups present on a substituent group such as $R^1$, $R^2$, $R^3$, $R^4$, $R^5$, $R^6$, $R^7$, $R^8$, $R^9$, $R^{10}$, $L^1$, $L^2$, etc., further modification can be made if appropriate and/or desired. For example, a CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as mesylate, which in turn is suitable for nucleophilic substitution, such as by CN. For another example, an —S— can be oxidized to —S(O)— and/or —S(O)₂—. For yet another example, unsaturated bond such as C═C or C≡C can be reduced to saturated bond by hydrogenation. In some embodiments, a primary amine or a secondary amine moiety (present on a substituent group such as $R^1$, $R^2$, $R^3$, $R^4$, $R^5$, $R^6$, $R^7$, $R^8$, $R^9$, $R^{10}$, $L^1$, $L^2$, etc.) can be converted to amide, sulfonamide, urea, or thiourea moiety by reacting it with an appropriate reagent such as an acid chloride, a sulfonyl chloride, an isocyanate, or a thioisocyanate compound. In some embodiments, a primary amine, a secondary amine, or a tertiary amine moiety (present on a substituent group such as $R^1$, $R^2$, $R^3$, $R^4$, $R^5$, $R^6$, $R^7$, $R^8$, $R^9$, $R^{10}$, $L^1$, $L^2$, etc.) can be alkylated to form a quaternary ammonium salt. One skilled in the art will recognize further such modifications. Thus, a compound of Formula I (such as compound 1-2 of Scheme 1) having a substituent which contains a functional group can be converted to another compound of Formula I having a different substituent group.

As used herein, the term "reacting" refers to the bringing together of designated chemical reactants such that a chemical transformation takes place generating a compound different from any initially introduced into the system. Reacting can take place in the presence or absence of solvent.

Methods

Compounds of the invention can modulate activity of one or more Janus kinases (JAKs). The term "modulate" is meant to refer to an ability to increase or decrease the activity of one or more members of the JAK family of kinases. Accordingly, compounds of the invention can be used in methods of modulating a JAK by contacting the JAK with any one or more of the compounds or compositions described herein. In some embodiments, compounds of the present invention can act as inhibitors of one or more JAKs. In further embodiments, the compounds of the invention can be used to modulate activity of a JAK in an individual in need of modulation of the enzyme by administering a modulating amount of a compound of the invention.

JAKs to which the present compounds bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3. In some embodiments, the JAK is TYK2.

Another aspect of the present invention pertains to methods of treating a JAK-associated disease or disorder in an individual (e.g., patient) by administering to the individual a therapeutically effective amount or dose of a compound of the present invention or a pharmaceutical composition thereof. In some embodiments, the individual has been diagnosed to have a JAK-associated disease or disorder and is in need of treatment for the disease or disorder. A JAK-associated disease can include any disease, disorder or condition that is directly or indirectly linked to expression or activity of the JAK, including over expression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease (e.g, ulcerative colitis and Crohn's disease), ankylosing spondylitis, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP). In some embodiments, JAK-associated diseases include rheumatoid arthritis.

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, alopecia areata, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, colorectal cancer, pancreatic cancer, gastric cancer, breast cancer, lung cancer, cancers of the head and neck, thyroid cancer, glioblastoma, Kaposi's sarcoma, melanoma etc.), hematological cancers or malignancies [e.g., lymphoma, leukemia such as acute lymphoblastic leukemia, Chronic Lymphocytic Leukemia (CLL), myelodysplastic syndrome (MDS), acute myelogenous leukemia (AML), chronic myelogenous leukemia (CML), chronic myelomonocytic leukemia (CMML), or multiple myeloma, and other lymphoma related diseases including Castleman's disease, Waldenstrom's macroglobulinemia, and Poems syndrome], and skin cancer such as cutaneous T-cell lymphoma (CTCL) and cutaneous B-cell lymphoma. Examples of cutaneous T-cell lymphomas include Sezary syndrome and mycosis fungoides. Other kinase associated diseases may also include paraneoplastic syndromes associated with cytokine production in cancer.

JAK-associated diseases can further include those characterized by expression of a mutant JAK such as those having at least one mutation in the pseudo-kinase and/or kinase domain (e.g., JAK2V617F or JAK1R724H) or genetic or epigenetic alterations known or thought to result in dysregulated JAK activity (e.g. SOCS gene methylation or MPL mutation).

JAK-associated diseases can further include myeloproliferative disorders (MPDs) such as polycythemia vera (PV), essential thrombocythemia (ET), myelofibrosis with myeloid metaplasia (MMM), hypereosinophilic syndrome (HES), systemic mast cell disease (SMCD), and the like. In some embodiments, the myeloproliferative disorder is myelofibrosis with myeloid metaplasia (MMM). In some embodiments, the myeloproliferative disorder is selected from primary myelofibrosis (PMF). PMF has been known by a variety of terms including myelofibrosis with myeloid metaplasia (MMM), agnogenic myeloid metaplasia, and chronic idiopathic myelofibrosis. Myelofibrosis (MF) can present as a de novo disorder (PMF) or evolve from previous PV or ET [post-polycythemia vera myelofibrosis (Post-PV MF) or post-essential thrombocythemia myelofibrosis (Post-ET MF)]. Myelofibrosis develops in 10% to 20% of patients with PV (see e.g. J. L. Spivak, G. Barosi, G. Tognoni, T. Barbui, G. Finazzi, R. Marchioli, and M. Marchetti; "Chronic Myeloproliferative Disorders"; *Hematology*, January 2003; 2003: 200-224) and in 2% to 3% of patients with ET (See e.g. D. R.

Berk and A. Ahmed; "Portal, splenic, and superior mesenteric vein thrombosis in a patient with latent essential thrombocythemia and hyperhomocysteinemia"; *J. Clin. Gastroenterol.*, 2006; 40: 3: 227-8).

Further JAK-associated diseases include inflammation and inflammatory diseases. Examples of inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy (such as myocarditis), Systemic Inflammatory Response Syndrome (SIRS), septic shock, and other inflammatory diseases.

The JAK antagonists/inhibitors described herein can further be used to treat ischemia reperfusion injuries or a disease or condition related to an inflammatory ischemic event such as stroke or cardiac arrest. The JAK antagonists/inhibitors described herein can further be used to treat anorexia, cachexia, or fatigue such as that resulting from or associated with cancer. The JAK antagonists/inhibitors described herein can further be used to treat restenosis, sclerodermitis, or fibrosis. The JAK antagonists/inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2.

The JAK/ALK antagonists/inhibitors described herein can be used to treat any of the JAK-associated diseases, disorders or conditions and/or ALK-associated diseases, disorders or conditions, or any combination thereof. In some embodiments, the JAK antagonists/inhibitors described herein can be used to treat any of the JAK-associated diseases diseases, disorders or conditions, or any combination thereof.

The JAK antagonists/inhibitors described herein can further be used to treat any of the JAK-associated diseases or any combination thereof.

Certain compounds of the invention (the $IC_{50}$ of which with respect to ALK is less than about 10 µM) can also modulate activity of ALK kinases. The term "modulate" is meant to, in this context, refer to an ability to increase or decrease the activity of the ALK kinases. Certain compounds of the invention can be used in methods of modulating an ALK by contacting the ALK with any one or more of the compounds or compositions described herein. In some embodiments, certain compounds of the present invention (the $IC_{50}$ of which with respect to ALK is less than about 10 µM) can act as antagonists/inhibitors of ALK. Certain compounds of the invention (the $IC_{50}$ of which with respect to ALK is less than about 10 µM) can be used to modulate activity of an ALK in an individual in need of modulation of the enzyme by administering a modulating amount of a compound of the invention.

Another aspect of the present invention pertains to methods of treating an ALK-associated disease or disorder in an individual (e.g., patient) by administering to the individual a therapeutically effective amount or dose of a compound of the present invention (the $IC_{50}$ of which with respect to ALK is less than about 10 µM) or a pharmaceutical composition thereof. In some embodiments, the individual is diagnosed to have an ALK-associated disease or disorder and is in need of treatment for the disease or disorder. An ALK-associated disease can include any disease, disorder or condition that is directly or indirectly linked to expression or activity of the ALK, including over expression and/or abnormal activity levels. An ALK-associated disease can also include any disease, disorder or condition that can be prevented, ameliorated, or cured by modulating ALK activity. Examples of ALK-associated diseases include diseases involving ALK-related tumors including anaplastic large cell lymphomas and non-Hodgkin lymphomas in addition to lung cancers.

Treatment of the diseases/disorders herein includes treating one or more symptoms associated with the diseases/disorders. For example, symptoms of a JAK-associated skin disorder (such as psoriasis, atopic dermatitis, skin rash, skin irritation, or skin sensitization) include itching (prutitus).

As used herein, the term "contacting" refers to the bringing together of indicated moieties in an in vitro system or an in vivo system. For example, "contacting" a JAK/ALK with a compound of the invention includes the administration of a compound of the present invention to an individual or patient, such as a human, having a JAK/ALK, as well as, for example, introducing a compound of the invention into a sample containing a cellular or purified preparation containing the JAK/ALK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting/retarding the disease; for example, inhibiting/retarding a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or completely eliminating/curing the disease. As used herein, treating a disease further includes treating one or more symptoms associated with the disease.

Combination Therapies

One or more additional pharmaceutical agents such as, for example, chemotherapeutics, anti-inflammatory agents, steroids, immunosuppressants, as well as Bcr-Abl, Flt-3, RAF, IKK, EGFR, MET, IGF1R, and FAK, ALK kinase inhibitors such as, for example, those described in WO 2006/056399, or other agents can be used in combination with the compounds of the present invention for treatment of JAK/ALK-associated diseases, disorders or conditions. The one or more additional pharmaceutical agents can be administered to a patient simultaneously or sequentially.

Examples of chemotherapeutics include proteosome inhibitors (e.g., bortezomib), thalidomide, revlimid, pomalidomide, DNA-damaging agents such as melphalan, doxorubicin, cyclophosphamide, vincristine, etoposide, carmustine, tubulin targeted agents (e.g. taxanes and vincristine), topoisomerase inhibitors (e.g. irinotecan), enzymes (e.g. L-asparaginase), antimetabolites (e.g. gemcitabine and hyroxyurea), and the like.

Examples of steroids include coriticosteroids such as dexamethasone or prednisone.

Examples of Bcr-Abl inhibitors include the compounds, and pharmaceutically acceptable salts thereof, of the genera and species disclosed in U.S. Pat. No. 5,521,184, WO 04/005281, EP2005/009967, EP2005/010408, and U.S. Ser. No. 60/578,491.

Examples of suitable Flt-3 inhibitors include compounds, and their pharmaceutically acceptable salts, as disclosed in WO 03/037347, WO 03/099771, and WO 04/046120.

Examples of suitable RAF inhibitors include compounds, and their pharmaceutically acceptable salts, as disclosed in WO 00/09495 and WO 05/028444.

Examples of suitable FAK inhibitors include compounds, and their pharmaceutically acceptable salts, as disclosed in WO 04/080980, WO 04/056786, WO 03/024967, WO 01/064655, WO 00/053595, and WO 01/014402.

Examples of suitable ALK inhibitors include compounds, and their pharmaceutically acceptable salts, as disclosed in WO 04/079326.

In some embodiments, one or more of the compounds of the invention can be used in combination with one or more other kinase inhibitors including imatinib, particularly for treating patients resistant to imatinib or other kinase inhibitors.

In some embodiments, one or more JAK/ALK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, IGF1R, RAF and FAK kinase inhibitors. Additive or synergistic effects are desirable outcomes of combining a JAK/ALK inhibitor of the present invention with an additional agent. Furthermore, resistance of multiple myeloma cells to agents such as dexamethasone may be reversible upon treatment with a JAK/ALK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK/ALK inhibitor where the dexamethasone is administered intermittently as opposed to continuously.

In some further embodiments, combinations of one or more JAK/ALK inhibitors of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nano particulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a pharmaceutically effective amount. For example, the dosage of the active compounds of the invention as employed for the treatment of a patient in need thereof (such as an adult human) may range from 0.1 to 3000 mg per day, depending on the route and frequency of administration. Such a dosage corresponds to 0.001 to 50 mg/kg per day. In some embodiments, the dosage of the active compounds of the invention as employed for the treatment of a patient in need thereof (such as an adult human) may range from 1 to 2000 mg per day, from 1 to 1000 mg per day, from 10 to 1000 mg per day, or from 10 to 500 mg per day. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the radio-labeled compounds will depend on the specific application of that radio-labeled compound. For example, for in vitro receptor labeling and competition assays, compounds that incorporate $^{3}$H, $^{14}$C, $^{82}$Br, $^{125}$I, $^{131}$I, $^{35}$S or will generally be most useful. For radio imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from $^{3}$H, $^{14}$C, $^{125}$I, $^{35}$S and $^{82}$Br.

In some embodiments, the labeled compounds of the present invention contain a fluorescent label.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a JAK/ALK by monitoring its concentration variation when contacting with the JAK/ALK, through tracking the labeling. For another example, a test compound (labeled) can be evaluated for its ability to reduce binding of another compound which is known to bind to JAK/ALK (i.e., standard compound). Accordingly, the ability of a test compound to compete with the standard compound for binding to the JAK/ALK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK/ALK-associated diseases or disorders such as prostate cancer, renal cancer, hepatic cancer, breast cancer, lung cancer, and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. In some instances where the compounds of the examples were isolated by preparative HPLC in the presence of trifluoroacetic acid (TFA) or other acid, the compound may have been obtained as the corresponding salt. Certain compounds of the Examples were found to be inhibitors of JAK/ALK according to one or more of the assays provided herein. In some embodiments, the $IC_{50}$ value for the compound of invention with respect one or more of JAK/ALK is less than about 100, 80, 50, 20, 10, 8, 5, 2, or 1 µM. In some embodiments, the $IC_{50}$ value for the compound of invention with respect to one or more of ALK is less than about 100, 80, 50, 20, 10, 8, 5, 2, or 1 µM. In some embodiments, the $IC_{50}$ value for the compound of invention with respect to one or more of JAK is less than about 100, 80, 50, 20, 10, 8, 5, 2, or 1 µM. In some embodiments, the $IC_{50}$ value for the compound of invention with respect one or more of JAK/ALK is less than about 1000, 800, 500, 200, 100, 80, 50, 20, or 10 nM. Certain compounds described in Tables 1 and in the Example section were tested for inhibitory activity of JAK/ALK targets according to assays such as those described herein or those known in the art [e.g., ALK assays described in WO 04/079326; and TYK2 assays described by James E. Thompson et. al, "Photochemical preparation of a pyridone containing tetracycle: A JAK protein kinase inhibitor," *Bioorganic & Medicinal Chemistry Letters, Volume* 12, *Issue* 8, 22 Apr. 2002, Pages 1219-1223]. For instance, Examples 1-10 and 12-16 were found to have $IC_{50}$ values less than 1000 nM, 800 nM, 500 nM, 200 nM, or 100 nM for at least one of JAK1, JAK2, JAK3, TYK2, and ALK. Some exemplary data of the compounds of the invention are shown in Table 1 in the experimental section.

EXAMPLES

Experimental procedures for compounds of the invention are provided below. Some of the compounds prepared were separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 Tm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.,* 6, 874-883 (2004)].

pH=10 purifications: Waters XBridge $C_{18}$ 5 Tm, 19×100 mm column, eluting with mobile phase A: 0.15% NH$_4$OH in water and mobile phase B: 0.15% NH$_4$OH in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.,* 6, 874-883 (2004)].

The compounds separated were typically subjected to analytical liquid chromatography mass spectrometry (LCMS) for purity under the following conditions: Instrument; Agilent 1100 series, LC/MSD, Column: Waters Sunfire™ $C_{18}$ 5 Tm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Example 1

6-Chloro-15-oxa-2,4,8,23-tetraazatetracyclo[15.3.1.1 (3,7).1(10,14)]tricosa-1(21),3(23),4,6,10(22),11,13, 17,19-nonaene trifluoroacetate

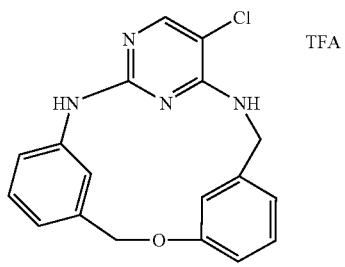 [SMILES: Clc1cnc2nc1NCc1cccc(c1)OCc1cccc(c1)N2]

Step A:
2,5-Dichloro-N-(3-methoxybenzyl)pyrimidin-4-amine

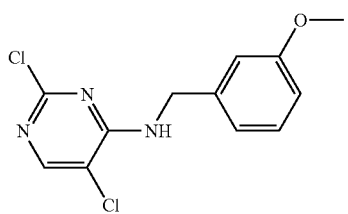 [SMILES: COc1cccc(CNc2nc(Cl)ncc2Cl)c1]

To a solution of 3-methoxybenzylamine (0.75 g, 5.4 mmol) and 2,4,5-trichloropyrimidine (1.1 g, 6.0 mmol) in N,N-dimethylformamide (20 mL) was added potassium carbonate (2.3 g, 16 mmol). The resulting mixture was stirred overnight at room temperature. The reaction was quenched with water. Ethyl acetate ("EtOAc") was added and the layers were separated. The aqueous layer was extracted with EtOAc once. The combined organic layers were washed with water and brine successively, then dried (Na$_2$SO$_4$), filtered, and concentrated. The crude product was purified by silica gel column chromatography to give the desired product as a white powder (1.43 g, 92%). LCMS for C$_{12}$H$_{12}$ClN$_3$O (M+H)$^+$: m/z=284.0, 286.0.

Step B: [3-({5-Chloro-4-[(3-methoxybenzyl)amino] pyrimidin-2-yl}amino)phenyl]methanol

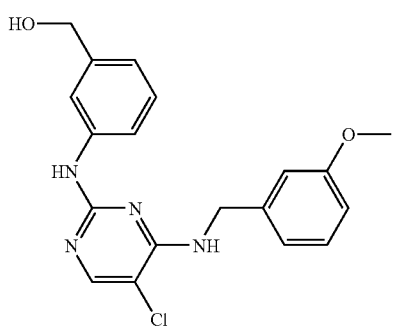 [SMILES: COc1cccc(CNc2nc(Nc3cccc(CO)c3)ncc2Cl)c1]

Into the reaction flask was added 2,5-dichloro-N-(3-methoxybenzyl)pyrimidin-4-amine (0.82 g, 2.9 mmol), 1,4-dioxane (20 mL), 3-aminobenzyl alcohol (0.53 g, 4.3 mmol), and p-toluenesulfonic acid monohydrate (0.22 g, 1.2 mmol). The mixture was heated at 105° C. for 3 hours and then was heated at 70° C. overnight. The reaction was quenched with NaHCO$_3$ (saturated). The organic solvent was removed under vacuum, followed by the addition of water and EtOAc. The aqueous layer was extracted with EtOAc twice. The organic layers were combined, dried over Na$_2$SO$_4$ and concentrated under vacuum to give the desired product as a brown powder (1.05 g, 98%). LCMS for C$_{19}$H$_{20}$N$_4$O$_2$ (M+H)$^+$: m/z=371.1, 373.0. $^1$H NMR (400 MHz, DMSO-d$_6$): δ 9.54 (s, 1H), 8.28 (s, 1H), 8.03 (s, 1H), 7.54 (s, 1H), 7.40 (d, J=8.3 Hz, 1H), 7.20 (t, J=8.3 Hz, 1H), 7.14 (t, J=7.9 Hz, 1H), 6.89 (m, 1H), 6.77 (ddd, J=8.3, 2.2, 1.4 Hz, 1H), 4.59 (d, J=6.2 Hz, 2H), 4.38 (s, 2H), 3.64 (s, 3H).

Step C: 3-{[(2-{[3-(Bromomethyl)phenyl]amino}-5-chloropyrimidin-4-yl)amino]methyl}phenol

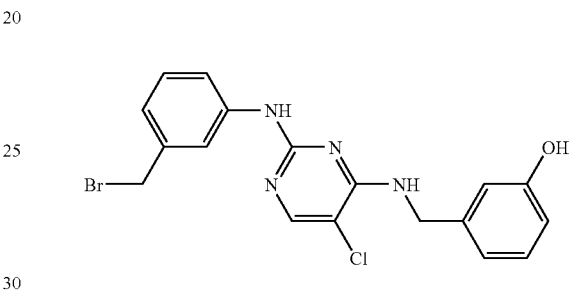

Into a 1-neck round-bottom flask were added [3-({5-chloro-4-[(3-methoxybenzyl)amino]pyrimidin-2-yl}amino) phenyl]methanol (0.66 g, 1.8 mmol) and 5 mL of methylene chloride. To the above mixture was slowly added a solution of boron tribromide in methylene chloride (2.7 mL, 2.7 mmol, 1.0 M) at 0° C. The mixture was allowed to warm up to room temperature ("rt") and stirred overnight. The resultant mixture was cooled in a dry ice bath when water (10 mL) was added. The mixture was allowed to warm up to rt, followed by an addition of EtOAc. The aqueous layer was extracted with EtOAc twice. The organic layers were combined and solvent removed under vacuum. The crude was purified by prep-HPLC to give the desired product (730 mg, 99%). LCMS for C$_{18}$H$_{17}$BrClN$_4$O (M+H)$^+$: m/z=418.9, 420.9. $^1$H NMR (400 MHz, DMSO-d$_6$): δ 9.55 (s, 1H), 9.34 (br s, 1H), 8.18 (s, 1H), 8.04 (s, 1H), 7.68 (t, J=1.7 Hz, 1H), 7.41 (m, 1H), 7.16 (t, J=7.9 Hz, 1H), 7.09 (t, J=7.9 Hz, 1H), 6.98 (d, J=7.7 Hz, 1H), 6.70 (m, 1H), 6.59 (m, 1H), 4.58 (d, J=6.6 Hz, 2H), 4.49 (s, 2H).

Step D: 6-Chloro-15-oxa-2,4,8,23-tetraazatetracyclo [15.3.1.1(3,7).1(10,14)]tricosa-1(21),3(23),4,6,10 (22),11,13,17,19-nonaene trifluoroacetate Into the reaction flask was added 3-{[(2-{[3-(bromomethyl)phenyl]amino}-5-chloropyrimidin-4-yl)amino] methyl}phenol (0.15 g, 0.36 mmol), DMF (5 mL), and potassium carbonate (0.20 g, 1.4 mmol). The reaction mixture was stirred at rt overnight and water (5 mL) was added. The aqueous layer was extracted with EtOAc twice. The combined organic layers were dried over Na$_2$SO$_4$, filtered, and concentrated under vacuum. The crude was purified by silica gel column chromatography to give the desired product as an off-white powder (10 mg, 8%). LCMS for C$_{18}$H$_{16}$ClN$_4$O (M+H)$^+$: m/z=339.0, 341.0. $^1$H NMR (400 MHz, DMSO-d$_6$): δ 9.00 (s, 1H), 7.87 (t, J=5.7 Hz, 1H), 7.85 (s, 1H), 7.45 (t, J=1.9 Hz, 1H), 7.21 (t, J=7.8 Hz, 1H), 7.17 (t, J=7.8 Hz, 1H), 6.97 (m, 2H), 6.73 (d, J=7.9 Hz, 1H), 5.13 (s, 2H), 4.23 (d, J=5.9 Hz, 2H).

Example 2

6-Chloro-15-oxa-2,4,8,24-tetraazatetracyclo[16.3.1.1(3,7).1(10,14)]tetracosa-1(22),3(24),4,6,10(23),11,13,18,20-nonaene trifluoroacetate

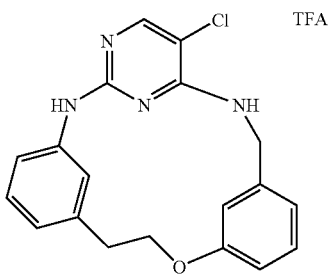 [SMILES: Clc1cnc2nc1NCc1cccc(c1)OCCc1cccc(c1)N2]

Step A: 2-(3-Aminophenyl)ethanol

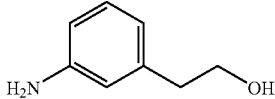

Into a pressure bottle were added 2-(3-nitrophenyl)ethanol (3.0 g, 18 mmol) and methanol (100 mL) and 10% palladium on carbon (0.1 g, 0.08 mmol). The reaction mixture was hydrogenated at 45 psi overnight. The resultant mixture was filtered and concentrated to provide the desired product (2.44 g, 99%) as a white solid. LCMS for $C_8H_{12}NO$ $(M+H)^+$: m/z=138.1.

Step B: 2-[3-({5-Chloro-4-[(3-methoxybenzyl)amino]pyrimidin-2-yl}amino)phenyl]ethanol

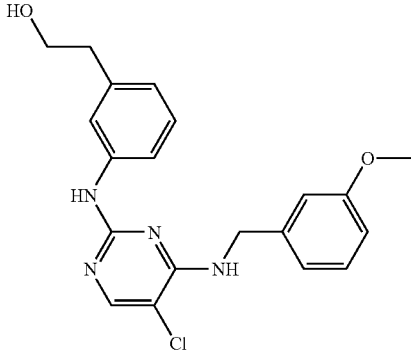 [SMILES: COc1cccc(CNc2nc(Nc3cccc(CCO)c3)ncc2Cl)c1]

Into a reaction flask were added 2,5-dichloro-N-(3-methoxybenzyl)pyrimidin-4-amine (0.33 g, 1.2 mmol) (prepared according to Example 1, step A), 1,4-dioxane (20 mL), 2-(3-aminophenyl)ethanol (0.22 g, 1.6 mmol), and p-toluenesulfonic acid monohydrate (0.080 g, 0.42 mmol). The mixture was heated at 105° C. for 3 hours and then an aqueous solution of $NaHCO_3$ (saturated) was added. The organic solvent was removed under vacuum followed by the addition of water and EtOAc. The aqueous layer was extracted with EtOAc twice. The organic layers were combined, dried over $Na_2SO_4$, and concentrated under vacuum. The crude was purified by silica gel column chromatography to provide the desired product as a white solid (0.33 g, 74% yield). LCMS for $C_{20}H_{22}ClN_4O_2$ $(M+H)^+$: m/z=385.1.

Step C: 3-{[(2-{[3-(2-Bromoethyl)phenyl]amino}-5-chloropyrimidin-4-yl)amino]methyl}phenol

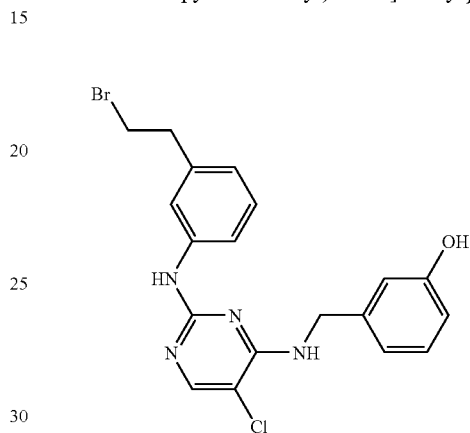

Into a 1-neck round-bottom flask were added 2-[3-({5-chloro-4-[(3-methoxybenzyl)amino]pyrimidin-2-yl}amino)phenyl]ethanol (0.20 g, 0.52 mmol) and dichloromethane ("DCM", 5 mL). To the reaction mixture was added a solution of boron tribromide in methylene chloride (1.6 mL, 1.6 mmol, 1.0 M) at 0° C. The resulting mixture was allowed to warm up to rt and stirred overnight. The resulted mixture was cooled in a dry ice bath when water (10 mL) was added. The mixture was allowed to warm up to rt and EtOAc was added. The aqueous layer was extracted with EtOAc twice. The organic layers were combined and concentrated under vacuum. The crude product was purified by silica gel column chromatography to give the desired product as a light brown powder (34 mg, 20%). LCMS for $C_{19}H_{19}BrClN_4O$ $(M+H)^+$: m/z=371.1, 373.1. $^1H$ NMR (400 MHz, DMSO-$d_6$): δ 9.30 (s, 1H), 9.11 (s, 1H), 7.95 (s, 1H), 7.74 (t, J=6.1 Hz, 1H), 7.42 (m, 1H), 7.08 (t, J=7.9 Hz, 1H), 7.03 (dd, J=8.7, 7.6 Hz, 1H), 6.71 (dd, J=11.5, 7.6 Hz, 1H), 6.69 (s, 1H), 6.58 (dd, J=8.0, 2.3 Hz, 1H), 4.56 (m, 2H), 3.50 (m, 2H), 2.56 (t, J=7.1 Hz, 2H).

Step D: 6-Chloro-15-oxa-2,4,8,24-tetraazatetracyclo[16.3.1.1(3,7).1(10,14)]tetracosa-1(22),3(24),4,6,10(23),11,13,18,20-nonaene trifluoroacetate Into a reaction flask were added 3-{[(2-{[3-(2-bromoethyl)phenyl]amino}-5-chloropyrimidin-4-yl)amino]methyl}phenol (36 mg, 0.083 mmol) and 1,4-dioxane (2.0 mL) and a solution of sodium hydroxide in water (1.0 mL, 3 M). The mixture was stirred at 70° C. for 3 hours. To the reaction mixture were added methanol (1 mL) and HCl aqueous solution (2 mL, 2 N). The resulted solution was filtered and purified by prep-HPLC to give the desired product as an off-white powder (5 mg, 18%). LCMS for $C_{19}H_{18}ClN_4O$ (M+H)$^+$: m/z=353.0, 355.0.

Example 3

6-Chloro-16-thia-2,4,8,15,23-pentaazatetracyclo [15.3.1.1(3,7).1(10,14)]tricosa-1(21),3(23),4,6,10 (22),11,13,17,19-nonaene 16,16-dioxide trifluoroacetate

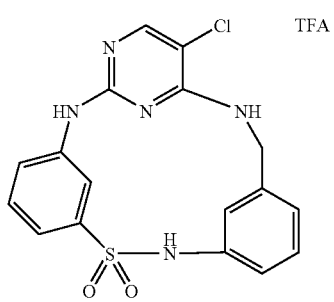 [SMILES: O=S1(=O)Nc2cccc(c2)CNc2nc(ncc2Cl)Nc2cccc1c2]

Step A: tert-Butyl(3-{[(2,5-dichloropyrimidin-4-yl) amino]methyl}phenyl)carbamate

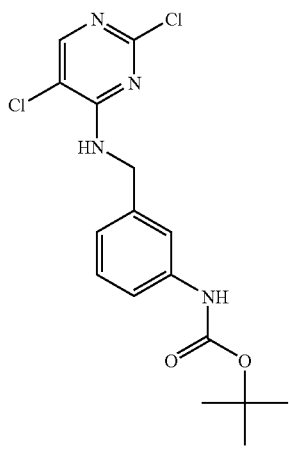 [SMILES: CC(C)(C)OC(=O)Nc1cccc(CNc2nc(Cl)ncc2Cl)c1]

To a solution of tert-butyl [3-(aminomethyl)phenyl]carbamate (0.50 g, 2.2 mmol) and 2,4,5-trichloropyrimidine (0.45 g, 2.5 mmol) in N,N-dimethylformamide (6 mL) was added potassium carbonate (0.62 g, 4.5 mmol). The resultant mixture was stirred overnight at room temperature. The reaction was quenched with water. EtOAc was added and the layers were separated. The aqueous layer was extracted with EtOAc twice. The combined organic layers were washed with water and brine successively, then dried (Na$_2$SO$_4$), filtered, and concentrated. The resulted residue was triturated with methylene chloride and hexanes to give the desired product as an off-white powder (0.75 g, 90%). LCMS for $C_{12}H_{11}Cl_2N_4O_2$ (M-tBu+H)$^+$: m/z=313.0, 315.0.

Step B: N-(3-Aminobenzyl)-2,5-dichloropyrimidin-4-amine.hydrogen chloride

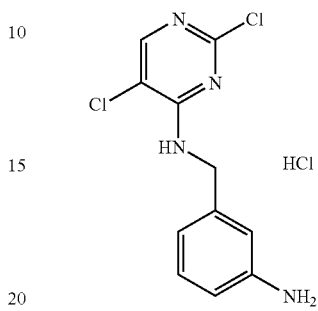

Into a reaction flask were added tert-butyl (3-{[(2,5-dichloropyrimidin-4-yl)amino]methyl}phenyl)carbamate (0.50 g, 1.4 mmol), 1,4-dioxane (7 mL), and a solution of hydrogen chloride in 1,4-dioxane (7 mL, 4.0 M). The reaction mixture was stirred at rt for 2 hours. After concentration, the crude off-white powder product (0.46 g, 99%) was used in the next step without further purification. LCMS for $C_{11}H_{11}Cl_2N_4$ (M+H)$^+$: m/z=269.0, 271.0.

Step C: N-(3-{[(2,5-Dichloropyrimidin-4-yl)amino] methyl}phenyl)-3-nitrobenzenesulfonamide

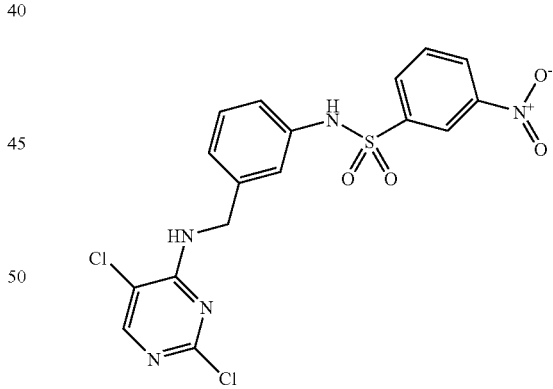

To a mixture of N-(3-aminobenzyl)-2,5-dichloropyrimidin-4-amine.hydrogen chloride (0.20 g, 0.58 mmol) and triethylamine (0.32 mL, 2.3 mmol) in THF (3 mL) was added slowly m-nitrobenzenesulfonyl chloride (0.13 g, 0.58 mmol). The resulting mixture was stirred at rt for 2 hours and the solvent was removed under vacuum. The residue was treated with EtOAc and water. The organic layer was dried over Na$_2$SO$_4$, filtered, and concentrated under vacuum to provide Step D: 3-Amino-N-(3-{[(2,5-dichloropyrimidin-4-yl)amino]methyl}phenyl)benzenesulfonamide

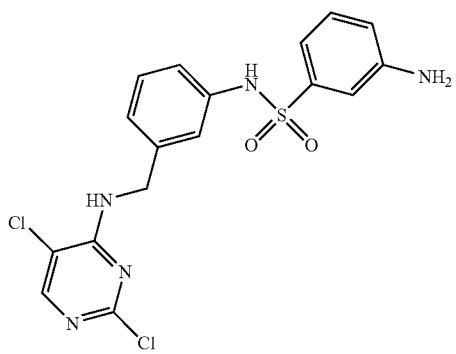 [SMILES: Nc1cccc(S(=O)(=O)Nc2cccc(CNc3nc(Cl)ncc3Cl)c2)c1]

Into a reaction flask was added N-(3-{[(2,5-dichloropyrimidin-4-yl)amino]methyl}phenyl)-3-nitrobenzenesulfonamide (0.20 g, 0.44 mmol), methanol (20 mL), acetic acid (2.0 mL), and water (1 mL). Then iron (0.25 g, 4.5 mmol) powder was added. The reaction mixture was heated at 70° C. for 2 hours. After cooling, the mixture was filtered and washed with EtOAc. The filtrate was concentrated under vacuum to give a residue, which was treated with NaHCO$_3$ (saturated aqueous solution) and EtOAc. The organic layer was dried and concentrated under vacuum. The resulting crude product was then purified by silica gel column chromatography to provide the desired product (46 mg, 25%). LCMS for $C_{17}H_{16}Cl_2N_5O_2S$ (M+H)$^+$: m/z=424.0, 426.0.

Step E: 6-Chloro-16-thia-2,4,8,15,23-pentaazatetracyclo[15.3.1.1(3,7).1(10,14)]tricosa-1(21),3(23),4,6,10(22),11,13,17,19-nonaene 16,16-dioxide trifluoroacetate To a solution of 3-amino-N-(3-{[(2,5-dichloropyrimidin-4-yl)amino]methyl}phenyl)benzenesulfonamide (46 mg, 0.11 mmol) in 2-methoxyethanol (1.5 mL) was added a solution of hydrogen chloride in 1,4-dioxane (0.072 mL, 4.00 M). The resultant mixture was heated at 150° C. in a microwave for 15 minutes. The mixture was concentrated and purified by prep-HPLC to give the desired product as a white powder (20 mg, 14%). LCMS for $C_{17}H_{15}ClN_5O_2S$ (M+H)$^+$: m/z=388.0. $^1$H NMR (400 MHz, DMSO-d$_6$): δ 9.78 (s, 1H), 9.49 (s, 1H), 8.49 (br, 1H), 8.01 (s, 1H), 7.59 (m, 1H), 7.55 (t, J=7.9 Hz, 1H), 7.33 (ddd, J=7.9, 1.9, 1.4 Hz, 1H), 7.27 (t, J=7.8 Hz, 2H), 7.16 (m, 2H), 6.98 (m, 1H), 4.22 (d, J=5.8 Hz, 2H).

Example 4

6-Chloro-2,4,8,15,23-pentaazatetracyclo[15.3.1.1(3,7).1(10,14)]tricosa-1(21),3(23),4,6,10(22),11,13,17,19-nonaen-16-one trifluoroacetate

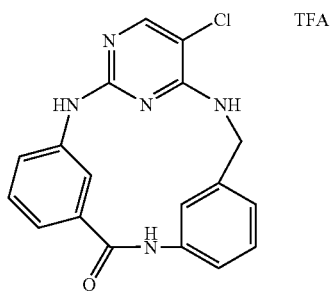 [SMILES: "TFA" ; O=C1Nc2cccc(c2)CNc2nc(ncc2Cl)Nc2cccc1c2]

Step A: N-(3-{[(2,5-Dichloropyrimidin-4-yl)amino]methyl}phenyl)-3-nitrobenzamide

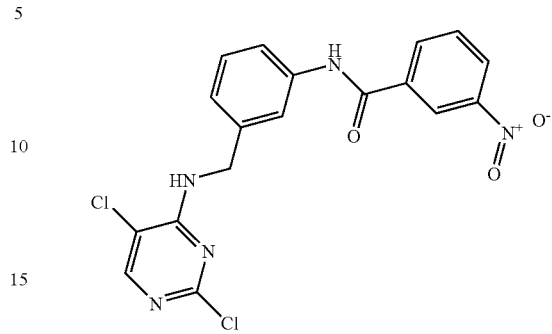

To a mixture of N-(3-aminobenzyl)-2,5-dichloropyrimidin-4-amine.hydrogen chloride (0.10 g, 0.29 mmol) (prepared according to Example 3, step B) and triethylamine (0.16 mL, 1.2 mmol) in THF (3 mL) was added slowly 3-nitrobenzoyl chloride (54 mg, 0.29 mmol). The resulting mixture was stirred at rt for 2 hours and concentrated under vacuum. The residue was partitioned in EtOAc and water. The organic layer was dried over Na$_2$SO$_4$, filtered, and concentrated under vacuum to give the desired product as a yellow solid (90 mg, 70%). LCMS for $C_{18}H_{14}Cl_2N_5O_3$ (M+H)$^+$: m/z=418.0, 420.0.

Step B: 3-Amino-N-(3-{[(2,5-dichloropyrimidin-4-yl)amino]methyl}phenyl)benzamide

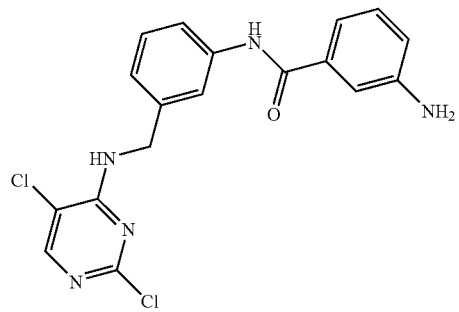 [SMILES: Nc1cccc(C(=O)Nc2cccc(CNc3nc(Cl)ncc3Cl)c2)c1]

Into a reaction flask were added N-(3-{[(2,5-dichloropyrimidin-4-yl)amino]methyl}phenyl)-3-nitrobenzamide (0.30 g, 0.72 mmol), methanol (20 mL), acetic acid (2.0 mL), and water (1 mL). Then iron (0.50 g, 9.0 mmol) powder was added. The reaction mixture was heated at 70° C. overnight. After cooling, the mixture was filtered and washed with EtOAc. The filtrate was concentrated under vacuum to give a residue, which was treated with NaHCO$_3$ (saturated aqueous solution) and EtOAc. The organic layer was dried and concentrated under vacuum to provide the desired product (0.27 g, 97%). LCMS for $C_{18}H_{16}Cl_2N_5O$ (M+H)$^+$: m/z=388.0, 390.0.

Step C: 6-Chloro-2,4,8,15,23-pentaazatetracyclo[15.3.1.1(3,7).1(10,14)]tricosa-1(21),3(23),4,6,10(22),11,13,17,19-nonaen-16-one trifluoroacetate To a solution of 3-amino-N-(3-{[(2,5-dichloropyrimidin-4-yl)amino]methyl}phenyl)benzamide (72 mg, 0.18 mmol) in 2-methoxyethanol (1.5 mL) was added a solution of hydrogen chloride in 1,4-dioxane (0.072 mL, 4.00 M). The resulting mixture was heated at 150° C. in a microwave for 15 minutes. The mixture was concentrated and purified by prep-HPLC to give the desired product as a white powder (6 mg, 10%). LCMS for $C_{18}H_{15}ClN_5O$ (M+H)$^+$: m/z=352.0.

Example 5

6-Chloro-15-oxa-2,4,8,25-tetraazatetracyclo[17.3.1.1(3,7).1(10,14)]pentacosa-1(23),3(25),4,6,10(24),11,13,19,21-nonaene trifluoroacetate

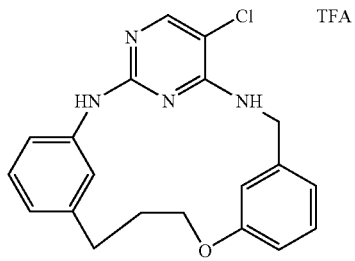 [SMILES: "TFA" ; Clc1cnc2nc1NCc1cccc(c1)OCCCc1cccc(c1)N2]

Step A: 3-[3-({5-Chloro-4-[(3-methoxybenzyl)amino]pyrimidin-2-yl}amino)phenyl]propan-1-ol

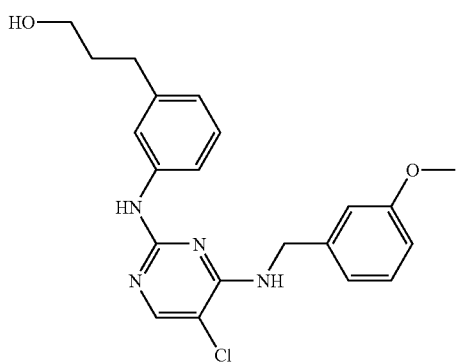 [SMILES: COc1cccc(CNc2nc(Nc3cccc(CCCO)c3)ncc2Cl)c1]

Into a reaction flask were added 2,5-dichloro-N-(3-methoxybenzyl)pyrimidin-4-amine (0.20 g, 0.70 mmol, prepared according to Example 1, step A), 1,4-dioxane (20 mL), 3-(3-aminophenyl)propan-1-ol (0.16 g, 1.0 mmol, prepared according to Example 12, step A & B), and p-toluenesulfonic acid monohydrate (0.049 g, 0.26 mmol). The mixture was heated at 105° C. for 2 days and NaHCO$_3$ (saturated aqueous solution) was added. The organic solvent was removed under vacuum followed by an addition of water and EtOAc. The aqueous layer was extracted with EtOAc twice. The organic layers were combined, dried over Na$_2$SO$_4$, filtered, and concentrated under vacuum. The crude product was purified by silica gel column chromatography to give the desired product (0.18 g, 64%) as a white solid. LCMS for $C_{21}H_{24}lN_4O_2$ (M+H)$^+$: m/z=399.1.

Step B: 3-{[(2-{[3-(3-Bromopropyl)phenyl]amino}-5-chloropyrimidin-4-yl)amino]methyl}phenol

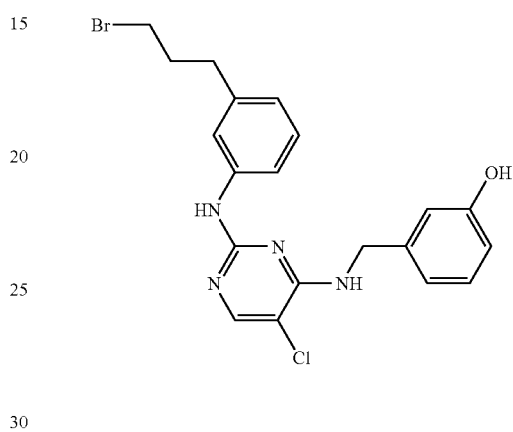

Into a 1-neck round-bottom flask were added 3-[3-({5-chloro-4-[(3-methoxybenzyl)amino]pyrimidin-2-yl}amino)phenyl]propan-1-ol (0.18 g, 0.45 mmol) and DCM (5 mL). To the reaction mixture was added a solution of boron tribromide in methylene chloride (3.0 mL, 3.0 mmol, 1.0 M) at 0° C. The mixture was allowed to warm up to rt and stirred overnight. The resultant mixture was cooled in a dry ice bath when NaHCO$_3$ (saturated aqueous solution, 10 mL) was added. The mixture was allowed to warm up to rt and DCM was added. The aqueous layer was extracted with DCM twice. The organic layers were combined, dried, filtered, and concentrated under vacuum to give the desired product as an off-white powder (150 mg, 74%). LCMS for $C_{20}H_{21}BrClN_4O$ (M+H)$^+$: m/z=447.0, 449.0.

Step C: 6-Chloro-15-oxa-2,4,8,25-tetraazatetracyclo[17.3.1.1(3,7).1(10,14)]pentacosa-1(23),3(25),4,6,10(24),11,13,19,21-nonaene trifluoroacetate Into a reaction flask were added 3-{[(2-{[3-(3-bromopropyl)phenyl]amino}-5-chloropyrimidin-4-yl)amino]methyl}phenol (0.053 g, 0.12 mmol), tetrahydrofuran (1.5 mL), and a solution of sodium hydroxide in water (1.0 mL, 0.5 M). The reaction mixture was stirred at rt overnight. To the reaction mixture was added an aqueous solution of HCl (0.5 mL, 2 N). The resultant mixture was filtered and the crude product was purified by prep-HPLC to give the desired product as an off-white powder (10 mg, 25%). LCMS for $C_{20}H_{20}ClN_4O$ (M+H)$^+$: m/z=367.0. $^1$H NMR (400 MHz, DMSO-d$_6$): δ 9.46 (s, 1H), 8.69 (br s, 1H), 8.05 (s, 1H), 7.23 (m, 1H), 7.20 (t, J=7.9 Hz, 1H), 6.98 (m, 1H), 6.80 (ddd, J=8.1, 2.4, 0.8 Hz, 1H), 6.52 (br, 1H), 4.34 (d, J=6.1 Hz, 2H), 4.12 (t, J=6.1 Hz, 2H), 2.67 (m, 2H), 1.76 (m, 2H).

Example 6

(9R)-6-Chloro-9-methyl-15-oxa-2,4,8,23-tetraazatetracyclo[15.3.1.1(3,7).1(10,14)]tricosa-1(21),3(23),4,6,10(22),11,13,17,19-nonaene trifluoroacetate

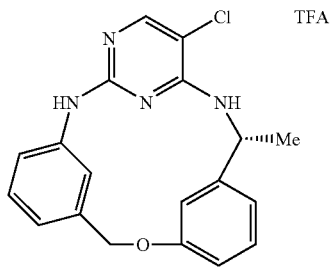 [SMILES: "TFA" ; C[C@H]1Nc2nc(ncc2Cl)Nc2cccc(c2)COc2cccc1c2]

Step A: 2,5-Dichloro-N-[(1R)-1-(3-methoxyphenyl)ethyl]pyrimidin-4-amine

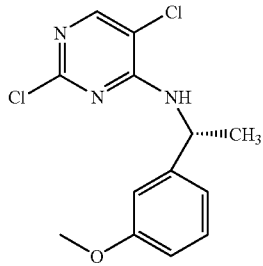 [SMILES: COc1cccc([C@@H](C)Nc2nc(Cl)ncc2Cl)c1]

To a solution of (1R)-1-(3-methoxyphenyl)ethanamine (1.50 g, 9.92 mol) (R-isomer, >98% ee purity) and 2,4,5-trichloropyrimidine (1.19 mL, 10.4 mmol) in N,N-dimethylformamide (30 mL) was added potassium carbonate (4.1 g, 30 mmol). The resultant mixture was stirred over two days at room temperature. The reaction was quenched with water. EtOAc was added and the layers were separated. The aqueous layer was extracted with EtOAc twice. The combined organic layers were washed with water and brine successively, then dried ($Na_2SO_4$), filtered, concentrated, and triturated with cold EtOAc to give the desired product as a light yellow gel (2.81 g, 95%). LCMS for $C_{13}H_{14}Cl_2N_3O$ (M+H)$^+$: m/z=298.0.

Step B: {3-[(5-Chloro-4-{[(1R)-1-(3-methoxyphenyl)ethyl]amino}pyrimidin-2-yl)amino]phenyl}methanol

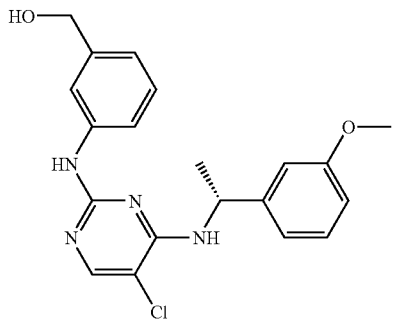 [SMILES: COc1cccc([C@@H](C)Nc2nc(Nc3cccc(CO)c3)ncc2Cl)c1]

Into a reaction flask were added 2,5-dichloro-N-[(1R)-1-(3-methoxyphenyl)ethyl]pyrimidin-4-amine (0.21 g, 0.70 mmol), 1,4-dioxane (20 mL), 3-aminobenzyl alcohol (0.13 g, 1.0 mmol), and p-toluenesulfonic acid monohydrate (0.049 g, 0.26 mmol). The mixture was heated at 105° C. for 2 days. To the reaction mixture was added $NaHCO_3$ (saturated aqueous solution) and the organic solvent was removed under vacuum. Water and EtOAc were added to the residue. The aqueous layer was extracted with EtOAc twice. The organic layers were combined, dried over $Na_2SO_4$, filtered, and concentrated. The crude product was purified by silica gel column chromatography to give the desired product (0.27 g, 96%). LCMS for $C_{20}H_{22}ClN_4O_2$ (M+H)$^+$: m/z=385.1.

Step C: 3-{(1R)-1-[(2-{[3-(Bromomethyl)phenyl]amino}-5-chloropyrimidin-4-yl)amino]ethyl}phenol

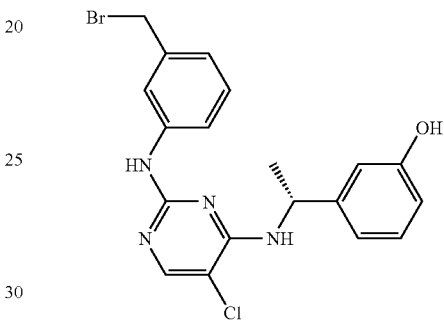

Into a 1-neck round-bottom flask were added {3-[(5-chloro-4-{[(1R)-1-(3-methoxyphenyl)ethyl]amino}pyrimidin-2-yl)amino]phenyl}methanol (0.26 g, 0.68 mmol) and methylene chloride (5 mL). To the mixture was added a solution of boron tribromide in methylene chloride (3.0 mL, 3.0 mmol, 1.0 M) at 0° C. The mixture was allowed to warm up to rt and stirred overnight. The resultant mixture was cooled in dry ice when $NaHCO_3$ (saturated aqueous solution, 10 mL) was added. The mixture was allowed to warm up to rt and DCM was added. The aqueous layer was extracted with DCM twice. The organic layers were combined, dried, filtered, and concentrated under vacuum. The crude product was purified by silica gel column chromatography to give the desired product (40 mg, 30%). LCMS for $C_{19}H_{19}BrClN_4O$ (M+H)$^+$: m/z=432.9, 434.9.

Step D: (9R)-6-Chloro-9-methyl-15-oxa-2,4,8,23-tetraazatetracyclo[15.3.1.1(3,7).1(10,14)]tricosa-1(21),3(23),4,6,10(22),11,13,17,19-nonaene trifluoroacetate Into a reaction flask were added 3-{(1R)-1-[(2-{[3-(bromomethyl)phenyl]amino}-5-chloropyrimidin-4-yl)amino]ethyl}phenol (40 mg, 0.09 mmol), tetrahydrofuran (1.5 mL), and a solution of sodium hydroxide in water (1.0 mL, 0.5 M). The reaction mixture was stirred at rt overnight. To the mixture was added an aqueous solution of HCl (0.5 mL, 2N). The resultant solution was filtered and purified by prep-HPLC to give the desired product (10 mg, 30%). LCMS for $C_{19}H_{18}ClN_4O$ (M+H)$^+$: m/z=353.0. $^1$H NMR (400 MHz, DMSO-$d_6$): δ 9.54 (s, 1H), 8.02 (s, 2H), 7.33 (t, J=7.9 Hz, 1H), 7.24 (t, J=7.6 Hz, 1H), 7.17 (d, J=7.6 Hz, 1H), 7.05 (m, 1H), 6.81 (ddd, J=7.9, 2.4, 0.9 Hz, 1H), 6.71 (s, 1H), 5.32 (d, J=13.2 Hz, 1H), 4.81 (d, J=13.3 Hz, 1H), 4.52 (q, J=6.9 Hz, 1H), 1.49 (d, J=7.2 Hz, 3H).

Example 7

6-Chloro-15,18-dioxa-2,4,8,25-tetraazatetracyclo[17.3.1.1(3,7).1(10,14)]pentacosa-1(23),3(25),4,6,10(24),11,13,19,21-nonaene trifluoroacetate

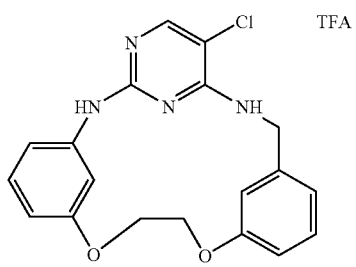 [SMILES: "TFA" ; Clc1cnc2nc1NCc1cccc(c1)OCCOc1cccc(c1)N2]

Step A: 5-Chloro-N(4)-(3-methoxybenzyl)-N(2)-(3-methoxyphenyl)pyrimidine-2,4-diamine

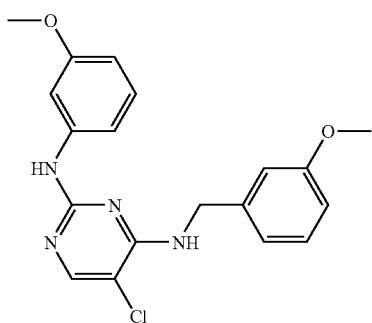

Into a reaction flask were added 2,5-dichloro-N-(3-methoxybenzyl)pyrimidin-4-amine (0.20 g, 0.70 mmol) (prepared according to Example 1, step A), 1,4-dioxane (20 mL), 3-methoxy-benzenamine (0.13 g, 1.0 mmol), and p-toluenesulfonic acid monohydrate (49 mg, 0.26 mmol). The mixture was heated at 105° C. for 2 days. To the mixture was added an aqueous solution of $NaHCO_3$ (saturated, 0.5 mL) and the organic solvent was removed under vacuum. The aqueous layer was extracted with DCM twice. The combined organic layers were dried, filtered and concentrated. The crude product was purified by silica gel column chromatography to provide the desired product (90 mg, 30%). LCMS for $C_{19}H_{20}ClN_4O_2$ $(M+H)^+$: m/z=371.1.

Step B: 3-({5-Chloro-4-[(3-hydroxybenzyl)amino]pyrimidin-2-yl}amino)phenol

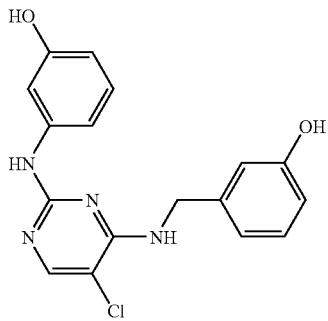 [SMILES: Oc1cccc(CNc2nc(Nc3cccc(O)c3)ncc2Cl)c1]

Into a 1-neck round-bottom flask were added 5-chloro-N(4)-(3-methoxybenzyl)-N(2)-(3-methoxyphenyl)pyrimidine-2,4-diamine (90 mg, 0.2 mmol) and methylene chloride (5 mL). To the mixture was added a solution of boron tribromide in methylene chloride (3.0 mL, 3.0 mmol, 1.0 M) at 0° C. The mixture was allowed to warm up to rt and stirred overnight. The resultant mixture was cooled in a dry ice bath when $NaHCO_3$ (saturated aqueous solution, 10 mL) was added. The mixture was allowed to warm up to rt and DCM was added. The aqueous layer was extracted with DCM twice. The organic layers were combined, dried, filtered, and concentrated under vacuum to give the desired product (40 mg, 50%). LCMS for $C_{17}H_{16}ClN_4O_2$ $(M+H)^+$: m/z=343.0.

Step C: 6-Chloro-15,18-dioxa-2,4,8,25-tetraazatetracyclo[17.3.1.1(3,7).1(10,14)]pentacosa-1(23),3(25),4,6,10(24),11,13,19,21-nonaene trifluoroacetate Into a reaction flask were added 3-[(5-chloro-4-[(3-hydroxyphenyl)amino]pyrimidin-2-yl)amino]phenol (40 mg, 0.12 mmol), 1,2-diiodoethane (0.34 g, 1.2 mmol), tetrahydrofuran (1.0 mL), and a solution of sodium hydroxide in water (1.0 mL, 0.5 M). The mixture was stirred at rt for 3 hours. To the mixture were added methanol (1 mL) and HCl (0.25 mL, 2 N aqueous solution). The resultant mixture was filtered and purified by prep-HPLC to give the desired product (4 mg, 5%). LCMS for $C_{19}H_{18}ClN_4O_2$ $(M+H)^+$: m/z=369.0.

Example 8

19-Chloro-9-oxa-2,17,21,22-tetraazatetracyclo[16.3.1.1(3,7).1(10,14)]tetracosa-1(22),3(24),4,6,10(23),11,13,18,20-nonaene

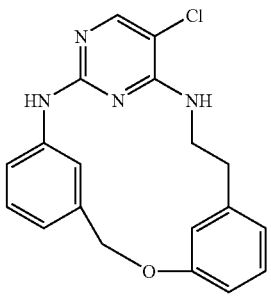 [SMILES: Clc1cnc2nc1NCCc1cccc(c1)OCc1cccc(c1)N2]

Step A: 2,5-Dichloro-N-[2-(3-methoxyphenyl)ethyl]pyrimidin-4-amine

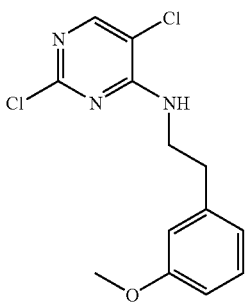 [SMILES: COc1cccc(CCNc2nc(Cl)ncc2Cl)c1]

To a solution of 3-methoxyphenethylamine (1.93 mL, 13.2 mmol) and 2,4,5-trichloropyrimidine (1.59 mL, 13.9 mmol) in N,N-dimethylformamide (40 mL) was added potassium carbonate (5.5 g, 40 mmol). The resultant mixture was stirred overnight at room temperature. The reaction was quenched with water. EtOAc was added and the layers were separated. The aqueous layer was extracted with EtOAc twice. The combined organic layers were washed with water and brine successively, then dried (Na₂SO₄), filtered, and concentrated to give the desired product as a yellow gel (3.74 g, 95%). LCMS for $C_{13}H_{14}Cl_2N_3O$ (M+H)⁺: m/z=298.0, 300.0.

Step B: {3-[(5-Chloro-4-{[2-(3-methoxyphenyl) ethyl]amino}pyrimidin-2-yl)amino]phenyl}methanol

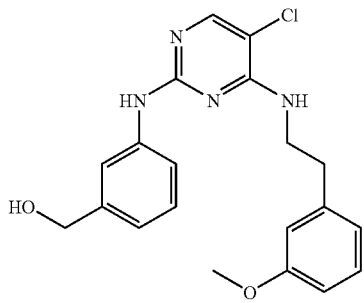 [SMILES: COc1cccc(CCNc2nc(Nc3cccc(CO)c3)ncc2Cl)c1]

To a solution of 2,5-dichloro-N-[2-(3-methoxyphenyl) ethyl]pyrimidin-4-amine (0.70 g, 2.3 mmol) and 3-aminobenzyl alcohol (0.39 g, 3.2 mmol) in 1,4-dioxane (20.0 mL) was added p-toluenesulfonic acid monohydrate (0.16 g, 0.85 mmol). The mixture was heated at 100° C. for 16 h and the reaction was complete. To the mixture was added NaHCO₃ (saturated aqueous solution) and the organic solvent was removed under vacuum, followed by the addition of water and EtOAc. The aqueous layer was extracted with EtOAc twice. The combined organic layers were dried over Na₂SO₄, filtered, and concentrated (then triturated with cold EtOAc) to give the desired product as an off-white powder (0.90 g, 100%). LCMS for $C_{20}H_{22}ClN_4O_2$ (M+H)⁺: m/z=385.1.

Step C: 3-{2-[(2-{[3-(Bromomethyl)phenyl]amino}-5-chloropyrimidin-4-yl)amino]ethyl}phenol

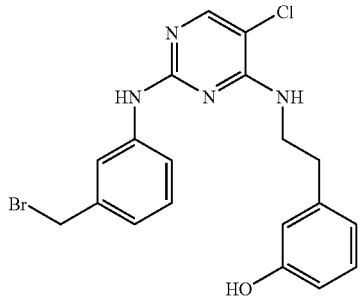 [SMILES: Oc1cccc(CCNc2nc(Nc3cccc(CBr)c3)ncc2Cl)c1]

To a solution of {3-[(5-chloro-4-{[2-(3-methoxyphenyl) ethyl]amino}pyrimidin-2-yl)amino]phenyl}methanol (0.30 g, 0.78 mmol) in methylene chloride (5.0 mL) was added slowly a solution of boron tribromide in methylene chloride (2.3 mL, 2.3 mmol, 1.0 M) at 0° C. The mixture was allowed to warm up to rt and stirred overnight. The resultant mixture was cooled in a dry ice bath when water was added. The mixture was allowed to warm up to rt. Both aqueous layer (no product in it) and organic layer (containing small amounts of product, plus byproducts) were checked and discarded. The remaining solid residue was triturated with cold EtOAc and then filtered. The cake was washed with cold EtOAc and then H₂O to give the desired product as a white powder (0.30 g, 89%). LCMS for $C_{19}H_{19}BrClN_4O$ (M+H)⁺: m/z=433.0, 435.0, 437.0. ¹H NMR (400 MHz, CD₃OD): δ 7.94 (s, 1H), 7.60 (s, 1H), 7.40 (m, 2H), 7.32 (m, 1H), 7.05 (m, 1H), 6.60 (m, 3H), 4.54 (s, 2H), 3.76 (t, J=6.4 Hz, 2H), 2.85 (t, J=7.6 Hz, 2H).

Step D: 19-Chloro-9-oxa-2,17,21,22-tetraazatetracyclo[16.3.1.1(3,7).1(10,14)]tetracosa-1(22),3(24),4,6,10(23),11,13,18,20-nonaene To a solution of 3-{2-[(2-{[3-(bromomethyl)phenyl] amino}-5-chloropyrimidin-4-yl)amino]ethyl}phenol (25.0 mg, 0.0576 mmol) in tetrahydrofuran (0.561 mL) was added a solution of sodium hydroxide in water (0.46 mL, 0.50 M). The resultant solution was stirred at rt for 16 hours until the reaction was complete. The reaction mixture was neutralized with aqueous HCl solution (3 M) to pH 7. The aqueous layer was extracted with EtOAc twice. The combined organic layers were dried over Na₂SO₄, filtered, and concentrated (then triturated with cold EtOAc) to give the desired product as an off-white powder (13 mg, 65%). LCMS for $C_{19}H_{18}ClN_4O$ (M+H)⁺: m/z=353.0. ¹H NMR (400 MHz, CD₃OD): δ 7.72 (s, 1H), 7.52 (s, 1H), 7.29 (t, J=7.6 Hz, 1H), 7.19 (s, 1H), 7.10 (dd, J=7.6, 0.8 Hz, 1H), 7.06 (t, J=7.2 Hz, 1H), 6.93 (dd, J=7.2, 0.8 Hz, 1H), 6.73 (dd, J=2.4, 0.8 Hz, 1H), 6.66 (d, J=7.2 Hz, 1H), 5.25 (s, 2H), 3.70 (m, 2H), 2.72 (t, J=6.8 Hz, 1H).

Example 9

6-Chloro-16-oxa-2,4,8,25-tetraazatetracyclo[17.3.1.1 (3,7).1(11,15)]pentacosa-1(23),3(25),4,6,11(24),12, 14,19,21-nonaene

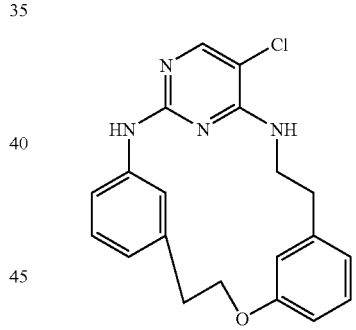

Step A: 2-{3-[(5-Chloro-4-{[2-(3-methoxyphenyl) ethyl]amino}pyrimidin-2-yl)amino]phenyl}ethanol

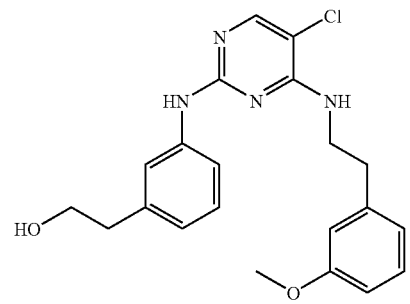 [SMILES: COc1cccc(CCNc2nc(Nc3cccc(CCO)c3)ncc2Cl)c1]

To a solution of 2,5-dichloro-N-[2-(3-methoxyphenyl)ethyl]pyrimidin-4-amine (0.50 g, 1.7 mmol) (prepared according to Example 8, step A) and 2-(3-aminophenyl)ethanol (0.31 g, 2.3 mmol) (prepared according to Example 22, Step B) in 1,4-dioxane (14.3 mL) was added p-toluenesulfonic acid monohydrate (0.12 g, 0.61 mmol). The mixture was heated at 100° C. for 16 h and the reaction was complete. To the mixture was added NaHCO$_3$ (saturated aqueous solution). The organic solvent was removed under vacuum and water/EtOAc was added. After layer separation, the aqueous layer was extracted with EtOAc twice. The combined organic layers were dried over Na$_2$SO$_4$, filtered, and concentrated (then triturated with cold EtOAc) to give the desired product as a light brown powder (0.64 g, 96%). LCMS for C$_{21}$H$_{24}$ClN$_4$O$_2$ (M+H)$^+$: m/z=399.1.

Step B: 3-{2-[(2-{[3-(2-Bromoethyl)phenyl]amino}-5-chloropyrimidin-4-yl)amino]ethyl}phenol

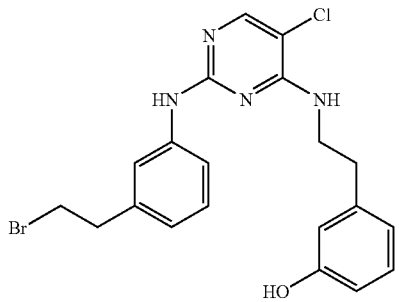 [SMILES: Oc1cccc(CCNc2nc(Nc3cccc(CCBr)c3)ncc2Cl)c1]

To a solution of 2-{3-[(5-chloro-4-{[2-(3-methoxyphenyl)ethyl]amino}pyrimidin-2-yl)amino]phenyl}ethanol (0.30 g, 0.75 mmol) in methylene chloride (4.8 mL) was added slowly a solution of boron tribromide in methylene chloride (2.2 mL, 2.2 mmol, 1.0 M) at 0° C. The mixture was allowed to warm up to rt and stirred overnight and the reaction was not complete. Thus additional 2 molar equivalents of BBr$_3$ (1.5 mL, 1.5 mmol, 1.0M) were added, and the reaction mixture was stirred at rt for one more day and then the reaction was complete. To the mixture was added NaHCO$_3$ (saturated aqueous solution). The organic solvent was removed under vacuum and water/EtOAc was added. The aqueous layer was extracted with EtOAc twice. The combined organic layers were dried over Na$_2$SO$_4$, filtered, and concentrated (then triturated with cold EtOAc) to give the desired product as an off-white powder (222 mg, 65%). LCMS for C$_{20}$H$_{21}$BrClN$_4$O (M+H)$^+$: m/z=447.0, 449.0. $^1$H NMR (400 MHz, CD$_3$OD): δ 7.92 (s, 1H), 7.37 (m, 3H), 7.20 (d, J=7.6 Hz, 1H), 7.04 (t, J=8.0 Hz, 1H), 6.58 (m, 3H), 3.74 (t, J=7.6 Hz, 2H), 3.61 (t, J=7.2 Hz, 2H), 3.14 (t, J=7.2 Hz, 2H), 2.83 (t, J=7.2 Hz, 2H).

Step C: 6-Chloro-16-oxa-2,4,8,25-tetraazatetracyclo[17.3.1.1(3,7).1(11,15)]pentacosa-1(23),3(25),4,6,11(24),12,14,19,21-nonaene To a solution of 3-{2-[(2-{[3-(2-bromoethyl)phenyl]amino}-5-chloropyrimidin-4-yl)amino]ethyl}phenol (50.0 mg, 0.112 mmol) in tetrahydrofuran (1.09 mL) was added a solution of sodium hydroxide in water (0.893 mL, 0.50 M). The resultant solution was stirred at rt for 2 days until the reaction was complete. The reaction was neutralized with HCl (3 M, aqueous solution) to pH 7. The aqueous layer was extracted with EtOAc twice. The combined organic layers were dried over Na$_2$SO$_4$, filtered, and concentrated to give the crude, which was purified by silica gel column chromatography to give the desired product as a white powder (8.5 mg, 21%). LCMS for C$_{20}$H$_{20}$ClN$_4$O (M+H)$^+$: m/z=367.0. $^1$H NMR (400 MHz, CD$_3$OD): δ 7.81 (s, 1H), 7.70 (s, 1H), 7.57 (m, 1H), 7.22 (t, J=8.0 Hz, 1H), 7.08 (m, 2H), 6.69 (s, 1H), 6.67 (m, 2H), 5.73 (dd, J=6.8, 0.8 Hz, 2H), 5.14 (dd, J=7.2, 1.2 Hz, 2H), 3.72 (t, J=7.6 Hz, 2H), 2.86 (t, J=7.6 Hz, 2H).

Example 10

20-Chloro-9-oxa-2,18,22,23-tetraazatetracyclo[17.3.1.1(3,7).1(10,14)]pentacosa-1(23),3(25),4,6,10(24),11,13,19,21-nonaene

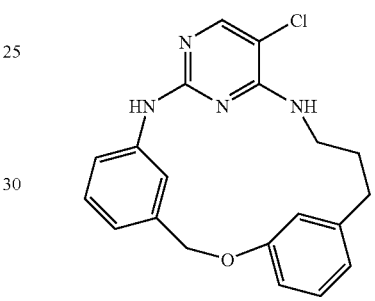

Step A: 2,5-Dichloro-N-[3-(3-methoxyphenyl)propyl]pyrimidin-4-amine

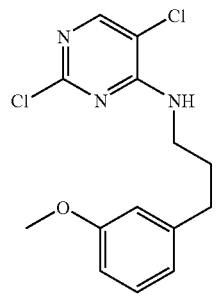 [SMILES: COc1cccc(CCCNc2nc(Cl)ncc2Cl)c1]

To a solution of 3-(3-methoxyphenyl)propan-1-amine hydrochloride (2.00 g, 9.92 mmol) and 2,4,5-trichloropyrimidine (1.19 mL, 10.4 mmol) in N,N-dimethylformamide (30 mL) was added potassium carbonate (4.80 g, 34.7 mmol). The resultant mixture was stirred overnight at room temperature. The reaction was quenched with water. EtOAc was added and the layers were separated. The aqueous layer was extracted with EtOAc twice. The combined organic layers were washed with water and brine successively, then dried (Na$_2$SO$_4$), filtered, and concentrated (then triturated with cold EtOAc) to give the desired product as a light brown gel (2.82 g, 91%). LCMS for $C_{14}H_{16}Cl_2N_3O$ (M+H)$^+$: m/z=312.0, 314.0.

Step B: {3-[(5-Chloro-4-{[3-(3-methoxyphenyl)propyl]amino}pyrimidin-2-yl)amino]phenyl}methanol

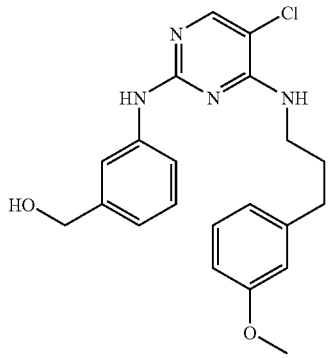 [SMILES: COc1cccc(CCCNc2nc(Nc3cccc(CO)c3)ncc2Cl)c1]

To a solution of 2,5-dichloro-N-[3-(3-methoxyphenyl)propyl]pyrimidin-4-amine (0.70 g, 2.2 mmol) and 3-aminobenzyl alcohol (0.38 g, 3.0 mmol) in 1,4-dioxane (19.1 mL) was added p-toluenesulfonic acid monohydrate (0.16 g, 0.82 mmol). The mixture was heated at 100° C. for 16 hours and the reaction was complete. After cooling, the mixture was filtered under vacuum. The cake was washed with cold EtOAc and then H$_2$O to give the desired product as an off-white powder (0.71 g, 79%). LCMS for $C_{21}H_{24}ClN_4O_2$ (M+H)$^+$: m/z=399.1.

Step C: 3-{3-[(2-{[3-(Bromomethyl)phenyl]amino}-5-chloropyrimidin-4-yl)amino]propyl}phenol

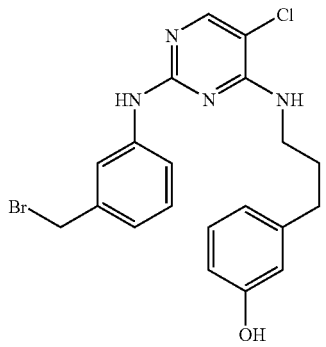 [SMILES: Oc1cccc(CCCNc2nc(Nc3cccc(CBr)c3)ncc2Cl)c1]

To a solution of {3-[(5-chloro-4-{[3-(3-methoxyphenyl) propyl]amino}pyrimidin-2-yl)amino]phenyl}methanol (0.30 g, 0.75 mmol) in methylene chloride (4.8 mL) was added slowly a solution of boron tribromide in methylene chloride (3.8 mL, 1.0 M) at 0° C. The mixture was allowed to warm up to rt and stirred overnight. The resultant mixture was cooled in a dry ice bath when water was added. The mixture was allowed to warm up to rt. After methylene chloride layer was separated, water and EtOAc were added. The aqueous layer was extracted with EtOAc twice. The combined organic layers were dried over Na$_2$SO$_4$, filtered, and concentrated (then triturated with cold EtOAc) to give the desired product as an off-white powder (252 mg, 75%). LCMS for $C_{20}H_{21}BrClN_4O$ (M+H)$^+$: m/z=447.0, 449.0. $^1$H NMR (400 MHz, CD$_3$OD): δ 7.92 (s, 1H), 7.63 (s, 1H), 7.39 (s, 1H), 7.38 (m, 2H), 7.03 (t, J=7.2 Hz, 1H), 6.61 (m, 2H), 6.58 (s, 1H), 4.56 (s, 2H), 3.60 (t, J=7.6 Hz, 2H), 2.58 (t, J=7.6 Hz, 2H), 1.96 (m, 2H).

Step D: 20-Chloro-9-oxa-2,18,22,23-tetraazatetracyclo[17.3.1.1(3,7).1(10,14)]pentacosa-1(23),3(25),4,6,10(24),11,13,19,21-nonaene To a solution of 3-{3-[(2-{[3-(bromomethyl)phenyl] amino}-5-chloropyrimidin-4-yl)amino]propyl}phenol (50.0 mg, 0.112 mmol) in tetrahydrofuran (1.09 mL) was added a solution of sodium hydroxide in water (0.893 mL, 0.50 M). The resultant solution was stirred at rt for 16 hours until the reaction was complete. The reaction mixture was neutralized with HCl (3 M aqueous solution) to pH=7. The aqueous layer was extracted with EtOAc twice. The combined organic layers were dried over Na$_2$SO$_4$, filtered, and concentrated to give the crude product, which was purified by silica gel column chromatography to give the desired product as a white powder (8 mg, 20%). LCMS for $C_{20}H_{20}ClN_4O$ (M+H)$^+$: m/z=367.0. $^1$H NMR (400 MHz, CD$_3$OD): δ 7.94 (s, 1H), 7.75 (s, 1H), 7.26 (m, 1H), 7.17 (m, 2H), 7.03 (t, J=7.6 Hz, 1H), 6.88 (m, 1H), 6.70 (m, 1H), 6.60 (m, 1H), 5.17 (s, 2H), 3.48 (t, J=7.6 Hz, 2H), 2.74 (t, J=6.8 Hz, 2H), 1.91 (m, 2H).

Example 11

(9S)-6-Chloro-9-methyl-15-oxa-2,4,8,23-tetraazatetracyclo[15.3.1.1(3,7).1(10,14)]tricosa-1(21),3(23),4,6,10(22),11,13,17,19-nonaene trifluoroacetate

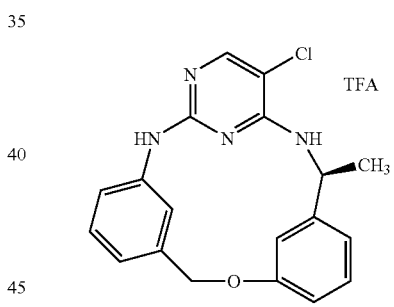

Step A: 2,5-Dichloro-N-[(1S)-1-(3-methoxyphenyl) ethyl]pyrimidin-4-amine

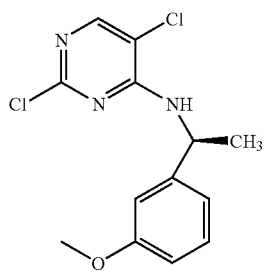 [SMILES: COc1cccc([C@H](C)Nc2nc(Cl)ncc2Cl)c1]

To a solution of (1S)-1-(3-methoxyphenyl)ethanamine (1.50 g, 9.92 mol) (S-isomer, >99% ee purity) and 2,4,5-trichloropyrimidine (1.19 mL, 10.4 mmol) in N,N-dimethylformamide (30 mL) was added potassium carbonate (4.1 g, 30 mmol). The resultant mixture was stirred overnight at room temperature. The reaction was quenched with water. Then EtOAc was added and the layers were separated. The aqueous layer was extracted with EtOAc twice. The combined organic layers were washed with water and then dried (Na$_2$SO$_4$), filtered, and concentrated to give the desired product as a light yellow thick oil (2.84 g, 96%). LCMS for C$_{13}$H$_{14}$Cl$_2$N$_3$O (M+H)$^+$: m/z=298.0, 300.0, 302.0 (9:6:1).

Step B: {3-[(5-Chloro-4-{[(1S)-1-(3-methoxyphenyl)ethyl]amino}pyrimidin-2-yl)amino]phenyl}methanol

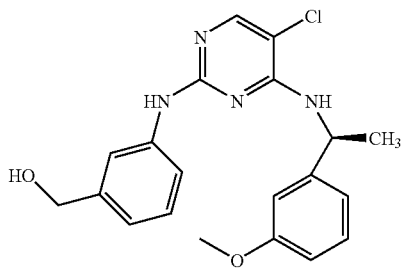 [SMILES: COc1cccc([C@H](C)Nc2nc(Nc3cccc(CO)c3)ncc2Cl)c1]

To a solution of 2,5-dichloro-N-[(1S)-1-(3-methoxyphenyl)ethyl]pyrimidin-4-amine (0.70 g, 2.3 mmol) and 3-aminobenzyl alcohol (0.39 g, 3.2 mmol) in 1,4-dioxane (20.0 mL) was added p-toluenesulfonic acid monohydrate (0.16 g, 0.85 mmol). The mixture was heated at 100° C. for 16 hours and NaHCO$_3$ (saturated aqueous solution) was added. The organic solvent was removed under vacuum and water/EtOAc was added. The aqueous layer was extracted with EtOAc twice. The combined organic layers were dried over Na$_2$SO$_4$, filtered, and concentrated (then triturated with cold EtOAc) to give the desired product as a light brown powder (0.81 g, 90%). LCMS for C$_{20}$H$_{22}$ClN$_4$O$_2$ (M+H)$^+$: m/z=385.1.

Step C: 3-{(1S)-1-[(2-{[3-(Bromomethyl)phenyl]amino}-5-chloropyrimidin-4-yl)amino]ethyl}phenol

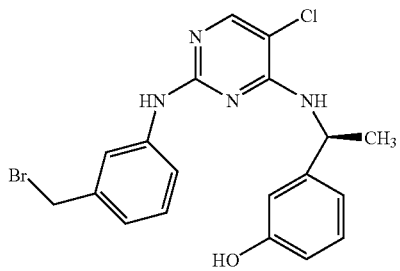 [SMILES: C[C@H](Nc1nc(Nc2cccc(CBr)c2)ncc1Cl)c1cccc(O)c1]

To a solution of {3-[(5-chloro-4-{[(1S)-1-(3-methoxyphenyl)ethyl]amino}pyrimidin-2-yl)amino]phenyl}methanol (0.30 g, 0.78 mmol) in methylene chloride (5.0 mL) was added slowly a solution of boron tribromide in methylene chloride (3.9 mL, 3.9 mmol, 1.0 M) at 0° C. The mixture was allowed to warm up to rt and stirred overnight. The resultant mixture was cooled in a dry ice bath when water was added. The mixture was allowed to warm up to rt. Water and EtOAc were added. The aqueous layer was extracted with EtOAc twice. The combined organic layers were dried over Na$_2$SO$_4$, filtered, and concentrated (then triturated with cold EtOAc) to give the desired product as a white powder (0.255 g, 75%). LCMS for C$_{19}$H$_{19}$BrClN$_4$O (M+H)$^+$: m/z=433.0, 435.0.

Step D: (9S)-6-Chloro-9-methyl-15-oxa-2,4,8,23-tetraazatetracyclo[15.3.1.1(3,7).1(10,14)]tricosa-1(21),3(23),4,6,10(22),11,13,17,19-nonaene trifluoroacetate To a solution of 3-{(1S)-1-[(2-{[3-(bromomethyl)phenyl]amino}-5-chloropyrimidin-4-yl)amino]ethyl}phenol (100 mg, 0.1 mmol) in tetrahydrofuran (2.24 mL) was added a solution of sodium hydroxide in water (1.84 mL, 0.50 M). The resultant solution was stirred at rt for 16 hours until the reaction was complete. The reaction mixture was neutralized with HCl (3 M aqueous solution) to pH=7. The aqueous layer was extracted with EtOAc twice. The combined organic layers were dried over Na$_2$SO$_4$, filtered, concentrated, and purified by prep-HPLC (pH2 method) to give the desired product as a white powder (5 mg, 8%). LCMS for C$_{19}$H$_{18}$BrClN$_4$O (M+H)$^+$: m/z=352.9.

Example 12

6-Chloro-16-oxa-2,4,8,26-tetraazatetracyclo[18.3.1.1(3,7).1(11,15)]hexacosa-1(24),3(26),4,6,11(25),12,14,20,22-nonaene

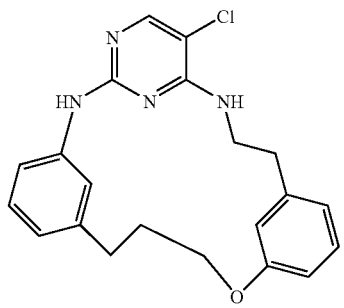 [SMILES: Clc1cnc2nc1NCCc1cccc(c1)OCCCc1cccc(c1)N2]

Step A: 3-(3-Nitrophenyl)propan-1-ol

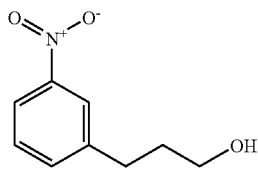

3-(3-Nitrophenyl)propanoic acid (3.0 g, 15 mmol) was dissolved in dry tetrahydrofuran (7.6 mL) in a flame-dried flask and cooled in an ice bath. A solution of borane in tetrahydrofuran (20 mL, 20 mmol, 1.0 M) was added dropwise over a period of 30 minutes. The reaction mixture was stirred for an additional 2 hours at rt, then quenched slowly with ice water, and followed by an addition of ether (40 mL).

The ether layer was washed with water and saturated aqueous solution of NaHCO₃ successively, dried, and concentrated to give the desired product as a yellow gel (2.7 g, 97%).

Step B: 3-(3-Aminophenyl)propan-1-ol

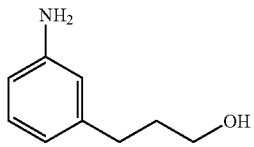 [SMILES: Nc1cccc(CCCO)c1]

To a solution of 3-(3-nitrophenyl)propan-1-ol (2.70 g, 14.9 mmol) in methanol (50.0 mL) was added 10% palladium on carbon (0.54 g, 0.46 mmol). The resultant mixture was hydrogenated at 50 psi overnight. The reaction mixture was then filtered and concentrated to give the desired product as a light brown thick oil (2.16 g, 96%). LCMS for $C_9H_{14}NO$ (M+H)⁺: m/z=152.1.

Step C: 3-{3-[(5-Chloro-4-{[2-(3-methoxyphenyl) ethyl]amino}pyrimidin-2-yl)amino]phenyl}propan-1-ol

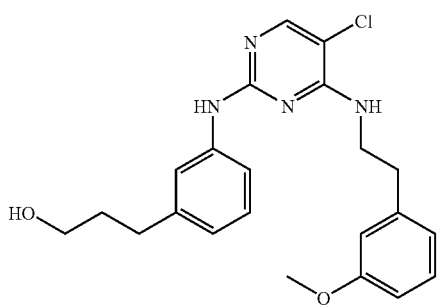 [SMILES: COc1cccc(CCNc2nc(Nc3cccc(CCCO)c3)ncc2Cl)c1]

To a solution of 2,5-dichloro-N-[2-(3-methoxyphenyl) ethyl]pyrimidin-4-amine (0.50 g, 1.7 mmol) (prepared according to Example 8, Step A) and 3-(3-aminophenyl)propan-1-ol (0.34 g, 2.3 mmol) in 1,4-dioxane (14.3 mL) was added p-toluenesulfonic acid monohydrate (0.12 g, 0.61 mmol). The mixture was heated at 100° C. for 16 hours and the reaction was complete. To the mixture was added NaHCO₃ aqueous solution (saturated). The organic solvent was removed under vacuum. Water and EtOAc were added to the residue. The aqueous layer was extracted with EtOAc twice. The combined organic layers were dried over Na₂SO₄, filtered, and concentrated (then triturated with cold EtOAc) to give the desired product as a light brown gel (0.634 g, 92%). LCMS for $C_{22}H_{26}ClN_4O_2$ (M+H)⁺: m/z=413.0.

Step D: 3-{2-[(2-{[3-(3-Bromopropyl)phenyl] amino}-5-chloropyrimidin-4-yl)amino]ethyl}phenol

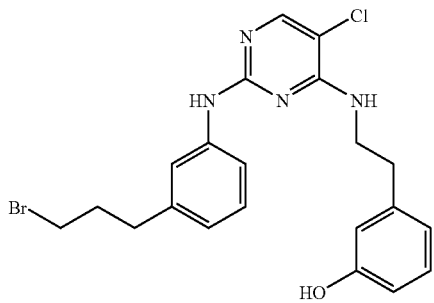 [SMILES: Oc1cccc(CCNc2nc(Nc3cccc(CCCBr)c3)ncc2Cl)c1]

To a solution of 3-{3-[(5-chloro-4-{[2-(3-methoxyphenyl) ethyl]amino}pyrimidin-2-yl)amino]phenyl}propan-1-ol (0.41 g, 0.73 mmol) in methylene chloride (4.7 mL) was added slowly a solution of boron tribromide in methylene chloride (3.6 mL, 3.6 mmol, 1.0 M) at 0° C. The mixture was allowed to warm up to rt and stirred overnight. The resultant mixture was cooled in dry ice when Na₂CO₃ (saturated aqueous solution) was added. The mixture was filtered and the solid collected was triturated with EtOAc, followed by washing with EtOAc and water successively to give the desired product as an off-white powder (322 mg, 96%). LCMS for $C_{21}H_{23}BrClN_4O$ (M+H)⁺: m/z=461.0, 463.0. ¹H NMR (400 MHz, CD₃OD): δ 7.96 (s, 1H), 7.92 (s, 1H), 7.37 (m, 3H), 7.16 (t, J=7.2 Hz, 1H), 6.94 (m, 1H), 6.62 (m, 2H), 3.75 (t, J=7.6 Hz, 2H), 3.43 (t, J=6.8 Hz, 2H), 2.84 (t, J=8.0 Hz, 2H), 2.76 (t, J=8.0 Hz, 2H), 2.15 (m, 2H).

Step E: 6-Chloro-16-oxa-2,4,8,26-tetraazatetracyclo [18.3.1.1(3,7).1(11,15)]hexacosa-1(24),3(26),4,6,11 (25),12,14,20,22-nonaene To a solution of 3-{2-[(2-{[3-(3-bromopropyl)phenyl] amino}-5-chloropyrimidin-4-yl)amino]ethyl}phenol (50.0 mg, 0.108 mmol) in tetrahydrofuran (1.0 mL) was added a solution of sodium hydroxide in water (1.0 mL, 1.0 M). The resultant solution was stirred at rt for 60 hours until the reaction was complete. The reaction mixture was neutralized with HCl (3 M aqueous solution) to pH=7. The aqueous layer was extracted with EtOAc twice. The combined organic layers were dried over Na₂SO₄, filtered, and concentrated to give a residue, which was purified by silica gel column chromatography to give the desired product as a white powder (4.0 mg, 10%). LCMS for $C_{21}H_{22}ClN_4O$ (M+H)⁺: m/z=381.0. ¹H NMR (400 MHz, CD₃OD): δ 7.95 (s, 1H), 7.90 (s, 1H), 7.30 (m, 3H), 7.12 (t, J=7.4 Hz, 1H), 6.94 (m, 1H), 6.65 (m, 2H), 3.70 (t, J=7.6 Hz, 2H), 3.48 (t, J=6.8 Hz, 2H), 2.80 (m, 2H), 2.72 (m, 2H), 2.10 (m, 2H).

Example 13

21-Chloro-10-oxa-2,19,23,24-tetraazatetracyclo [18.3.1.1(3,7).1(11,15)]hexacosa-1(24),3(26),4,6,11 (25),12,14,20,22-nonaene

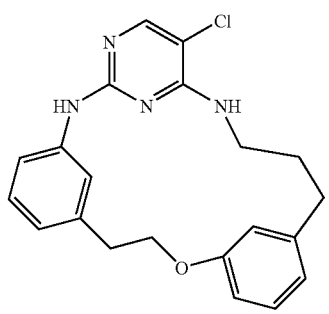 [SMILES: Clc1cnc2nc1NCCCc1cccc(c1)OCCc1cccc(c1)N2]

143

Step A: 2-{3-[(5-Chloro-4-{[3-(3-methoxyphenyl)propyl]amino}pyrimidin-2-yl)amino]phenyl}ethanol

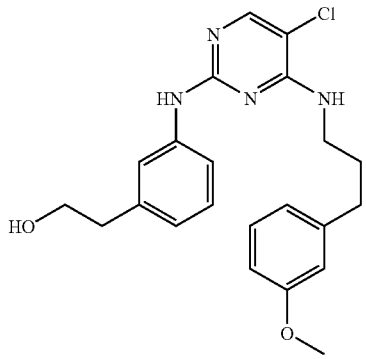 [SMILES: COc1cccc(CCCNc2nc(Nc3cccc(CCO)c3)ncc2Cl)c1]

To a solution of 2,5-dichloro-N-[3-(3-methoxyphenyl)propyl]pyrimidin-4-amine (0.50 g, 1.6 mmol) (prepared according to Example 10, Step A) and 2-(3-aminophenyl)ethanol (0.30 g, 2.2 mmol) (prepared according to Example 2, Step A) in 1,4-dioxane (13.6 mL) was added p-toluenesulfonic acid monohydrate (0.11 g, 0.58 mmol). The mixture was heated at 100° C. for 16 hours and the reaction was complete. After cooling, the mixture was filtered under vacuum. The cake was washed with cold EtOAc and H$_2$O successively to give the desired product as a light brown gum (0.61 g, 92%). LCMS for C$_{22}$H$_{26}$ClN$_4$O$_2$ (M+H)$^+$: m/z=413.1.

Step B: 3-{3-[(2-{[3-(2-Bromoethyl)phenyl]amino}-5-chloropyrimidin-4-yl)amino]propyl}phenol

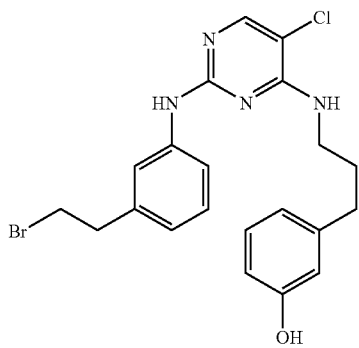 [SMILES: Oc1cccc(CCCNc2nc(Nc3cccc(CCBr)c3)ncc2Cl)c1]

To a solution of 2-{3-[(5-chloro-4-{[3-(3-methoxyphenyl)propyl]amino}pyrimidin-2-yl)amino]phenyl}ethanol (0.35 g, 0.73 mmol) in methylene chloride (4.7 mL) was added slowly a solution of boron tribromide in methylene chloride (3.6 mL, 3.6 mmol, 1.0 M) at 0° C. The mixture was allowed to warm up to rt and stirred overnight. The resultant mixture was cooled in dry ice when Na$_2$CO$_3$ (saturated aqueous solution) was added. The mixture was filtered and the solid collected was triturated with EtOAc, followed by washing with EtOAc and water successively to give the desired product as an off-white powder (303 mg, 90%). LCMS for C$_{21}$H$_{23}$BrClN$_4$O (M+H)$^+$: m/z=461.0, 463.0. $^1$H NMR (400 MHz, CD$_3$OD): δ 7.95 (s, 1H), 7.91 (s, 1H), 7.44 (d, J=7.2 Hz, 1H), 7.38 (m, 1H), 7.08 (m, 1H), 6.97 (s, 1H), 6.68 (d, J=2.8 Hz, 1H), 6.59 (m, 2H), 3.60 (m, 4H), 3.18 (m, 2H), 2.66 (t, J=7.6 Hz, 2H), 1.99 (t, J=7.6 Hz, 2H).

144

Step C: 21-Chloro-10-oxa-2,19,23,24-tetraazatetracyclo[18.3.1.1(3,7).1(11,15)]hexacosa-1(24),3(26),4,6,11(25),12,14,20,22-nonaene To a solution of 3-{3-[(2-{[3-(2-bromoethyl)phenyl]amino}-5-chloropyrimidin-4-yl)amino]propyl}phenol (50.0 mg, 0.108 mmol) in tetrahydrofuran (1.0 mL) was added a solution of sodium hydroxide in water (1.0 mL, 1.0 M). The resultant solution was stirred at rt for 60 hours until the reaction was complete. The reaction mixture was neutralized with HCl (3 M aqueous solution) to pH=7. The aqueous layer was extracted with EtOAc three times. The combined organic layers were dried over Na$_2$SO$_4$, filtered, and concentrated to give the crude, which was purified by silica gel column chromatography to give the desired product as a white powder (4.5 mg, 11%). LCMS for C$_{21}$H$_{22}$ClN$_4$O (M+H)$^+$: m/z=381.0. $^1$H NMR (400 MHz, CD$_3$OD): δ 7.98 (s, 1H), 7.92 (s, 1H), 7.48 (d, J=7.6 Hz, 1H), 7.40 (m, 1H), 7.06 (m, 1H), 6.97 (s, 1H), 6.70 (d, J=2.4 Hz, 1H), 6.62 (m, 2H), 3.60 (m, 4H), 3.20 (m, 2H), 2.68 (t, J=7.6 Hz, 2H), 2.02 (t, J=7.6 Hz, 2H).

Example 14

11-Bromo-6-chloro-15-oxa-2,4,8,25-tetraazatetracyclo[17.3.1.1(3,7).1(10,14)]pentacosa-1(23),3(25),4,6,10(24),11,13,19,21-nonaene

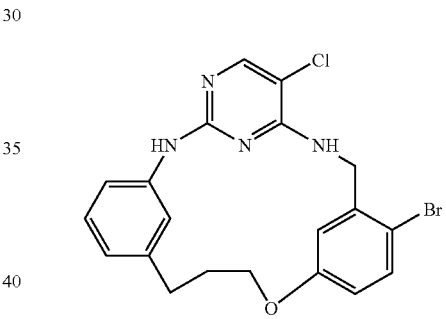

Step A: 1-(2-Bromo-5-methoxyphenyl)methanamine

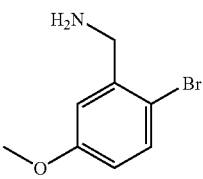

2-Bromo-5-methoxybenzonitrile (10.0 g, 47.2 mmol) was dissolved in dry tetrahydrofuran (100 mL) in a flame-dried flask and cooled in an ice bath. A solution of borane in tetrahydrofuran (75 mL, 75 mmol, 1.0 M) was added dropwise over a period of 30 minutes. The reaction mixture was stirred overnight at rt, then quenched slowly with ice water and Na$_2$CO$_3$ (saturated aqueous solution). After removal of THF, the residue was extracted with large amounts of EtOAc three times. The combined organic layers were washed with water, dried, and concentrated to give the crude, which was purified by silica gel column chromatography to give the desired product as a white powder (3.65 g, 36%). LCMS for $C_8H_{10}BrNO$ (M+H)+: m/z=216.9, 219.0.

Step B: N-(2-Bromo-5-methoxybenzyl)-2,5-dichloropyrimidin-4-amine

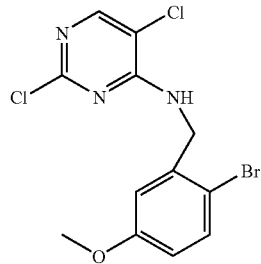 [SMILES: COc1ccc(Br)c(CNc2nc(Cl)ncc2Cl)c1]

To a solution of 1-(2-bromo-5-methoxyphenyl)methanamine (3.6 g, 13 mmol) and 2,4,5-trichloropyrimidine (1.60 mL, 14 mmol) in N,N-dimethylformamide (41.3 mL) was added potassium carbonate (5.53 g, 40 mmol). The resulting mixture was stirred overnight at room temperature. The reaction was quenched with water. EtOAc was added and the layers were separated. The aqueous layer was extracted with EtOAc twice. The combined organic layers were washed with water and brine successively, then dried ($Na_2SO_4$), filtered, and concentrated to give the desired product as a light yellow gel (4.65 g, 96%). LCMS for $C_{12}H_{10}BrCl_2N_3O$ (M+H)+: m/z=361.9, 363.9.

Step C: 3-[3-({4-[(2-Bromo-5-methoxybenzyl) amino]-5-chloropyrimidin-2-yl)amino] phenyl}propan-1-ol

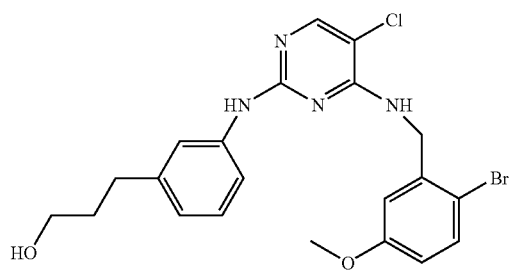 [SMILES: COc1ccc(Br)c(CNc2nc(Nc3cccc(CCCO)c3)ncc2Cl)c1]

To a solution of N-(2-bromo-5-methoxybenzyl)-2,5-dichloropyrimidin-4-amine (4.0 g, 11 mmol) and 3-(3-aminophenyl)propan-1-ol (2.3 g, 15 mmol, prepared according to Example 12, Step B) in 1,4-dioxane (90 mL) was added p-toluenesulfonic acid monohydrate (0.31 g, 1.6 mmol). The mixture was heated at 80° C. over two days and the reaction was complete. After cooling, the mixture was filtered under vacuum. The cake was washed with cold EtOAc to give the desired product as an off-white powder (4.35 g, 83%). LCMS for $C_{21}H_{22}BrClN_4O_2$ (M+H)+: m/z=477.0, 479.0.

Step D: 4-Bromo-3-{[(2-{[3-(3-bromopropyl)phenyl]amino}-5-chloropyrimidin-4-yl)amino] methyl}phenol

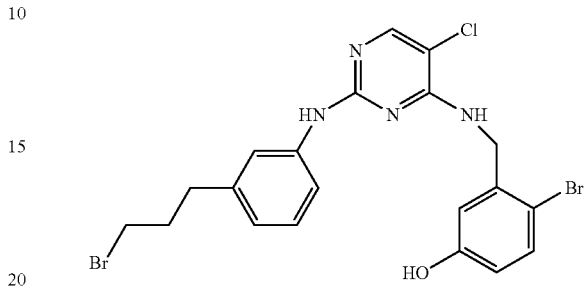

To a solution of 3-[3-({4-[(2-bromo-5-methoxybenzyl) amino]-5-chloropyrimidin-2-yl}amino)phenyl]propan-1-ol (3.0 g, 6.3 mmol) in methylene chloride (40 mL) was added slowly a solution of boron tribromide in methylene chloride (31 mL, 31 mmol, 1.0 M) at 0° C. The mixture was allowed to warm up to rt and stirred over the weekend. The resultant mixture was cooled in dry ice when $Na_2CO_3$ (saturated aqueous solution) was added. The mixture was filtered and the solid collected was triturated with EtOAc, followed by washing with cold water to give the desired product (3.0 grams, 91%) as an off-white powder. LCMS for $C_{20}H_{19}Br_2ClN_4O$ (M+H)+: m/z=524.8, 526.8, 528.7.

Step E: 11-Bromo-6-chloro-15-oxa-2,4,8,25-tetraazatetracyclo[17.3.1.1(3,7).1(10,14)]pentacosa-1 (23),3(25),4,6,10(24),11,13,19,21-nonaene To a solution of 4-bromo-3-{[(2-{[3-(3-bromopropyl)phenyl]amino}-5-chloropyrimidin-4-yl)amino]methyl}phenol (1.00 g, 1.90 mmol) in tetrahydrofuran (9.0 mL) was added a solution of sodium hydroxide in water (18 mL, 4.0 M). The resultant solution was then treated with benzyltriethylammonium chloride (30.0 mg, 0.13 mmol) and heated at 35° C. for 40 hours. The reaction mixture could not be purified by silica gel column chromatography or prep-HPLC. However, after cooling, THF and alkaline NaOH layers could be separated. THF layer was washed with brine and concentrated to give a light yellow solid residue, which was triturated with MeOH/EtOAc (90:10). After vacuum filtration, the cake was washed with MeOH to provide the desired pure product (300 mg, 35%) as an off-white powder. LCMS for $C_{20}H_{18}BrClN_4O$ (M+H)+: m/z=444.9, 446.9. $^1$H NMR (400 MHz, DMSO-$d_6$): δ 8.76 (s, 1H), 7.86 (s, 1H), 7.50 (s, 1H), 7.31 (d, J=8.8

Hz, 1H), 7.27 (m, 1H), 7.16 (m, 1H), 7.04 (m, 2H), 6.68 (m, 1H), 6.20 (m, 1H), 4.23 (m, 2H), 4.02 (t, 2H), 3.15 (m, 1H), 2.65 (m, 2H), 1.96 (m, 2H).

Example 15

6-Chloro-11-phenyl-15-oxa-2,4,8,25-tetraazatetracyclo[17.3.1.1(3,7).1(10,14)]pentacosa-1(23),3(25),4,6,10(24),11,13,19,21-nonaene

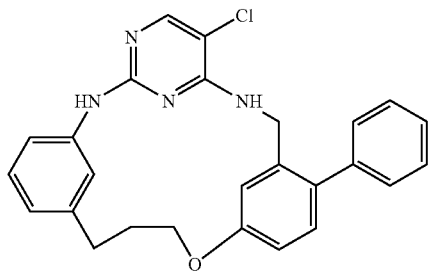 [SMILES: Clc1cnc2nc1NCc1cc(ccc1-c1ccccc1)OCCCc1cccc(c1)N2]

A mixture of 11-bromo-6-chloro-15-oxa-2,4,8,25-tetraazatetracyclo[17.3.1.1(3,7).1(10,14)]pentacosa-1(23),3(25),4,6,10(24),11,13,19,21-nonaene (30.0 mg, 0.067 mmol) (prepared according to Example 14, Step E), phenylboronic acid (9.8 mg, 0.081 mmol), tetrakis(triphenylphosphine)palladium(0) (7.8 mg, 0.0067 mmol), 1,2-dimethoxyethane (0.50 mL), and a solution of sodium carbonate in water (0.17 mL, 2.0 M) was sealed into a microwave vial and the resultant suspension was de-gassed by bubbling with $N_2$. After degassing, the vial was microwaved at 150° C. for 20 min. The reaction mixture was diluted with EtOAc, filtered, and concentrated to give a residue, which was purified by silica gel column chromatography to provide the desired product (8 mg, 27%) as a white powder. LCMS for $C_{26}H_{23}ClN_4O$ (M+H)+: m/z=443.1. $^1$H NMR (400 MHz, DMSO-$d_6$): δ 8.96 (s, 1H), 7.78 (s, 1H), 7.56 (s, 1H), 7.41 (dd, J=6.0, 1.2 Hz, 2H), 7.32 (m, 2H), 7.14 (m, 1H), 7.05 (m, 1H), 6.96 (m, 1H), 6.87 (m, 2H), 6.75 (m, 1H), 5.70 (t, 2H), 4.62 (m, 2H), 4.16 (m, 1H), 4.04 (m, 1H), 2.68 (m, 2H), 1.84 (m, 2H).

Example 16

12-Bromo-6-chloro-15-oxa-2,4,8,25-tetraazatetracyclo[17.3.1.1(3,7).1(10,14)]pentacosa-1(23),3(25),4,6,10(24),11,13,19,21-nonaene

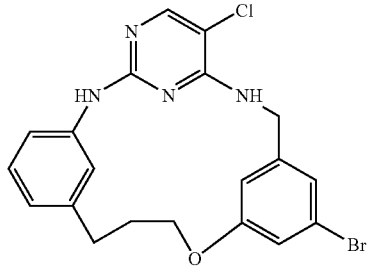 [SMILES: Clc1cnc2nc1NCc1cc(Br)cc(c1)OCCCc1cccc(c1)N2]

Step A: 1-(3-Bromo-5-methoxyphenyl)methanamine

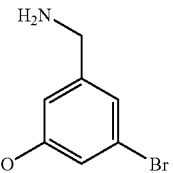

3-Bromo-5-methoxybenzonitrile (13.1 g, 61.8 mmol) was dissolved in dry tetrahydrofuran (100 mL) in a flame-dried flask and cooled in an ice bath. A solution of borane in tetrahydrofuran (100 mL, 0.10 mol, 1.0 M) was slowly added over a period of 30 minutes. After the addition was complete, the mixture was heated at 70° C. overnight and quenched slowly with ice water and $Na_2CO_3$ (saturated aqueous solution). After removal of THF, the residue was extracted with large amounts of EtOAc three times. The combined organic layers were washed with water, dried, and concentrated to give the crude product, which was purified by silica gel column chromatography to give the desired product as a white powder (2.57 g, 19%). LCMS for $C_8H_{10}BrNO$ (M+H)+: m/z=216.9, 218.9.

Step B: N-(3-Bromo-5-methoxybenzyl)-2,5-dichloropyrimidin-4-amine

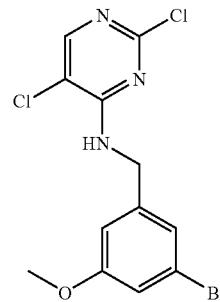

To a solution of 1-(3-bromo-5-methoxyphenyl)methanamine (2.57 g, 11.9 mmol) and 2,4,5-trichloropyrimidine (2.4 g, 13 mmol) in N,N-dimethylformamide (30 mL) was added potassium carbonate (3.3 g, 24 mmol). The resultant mixture was stirred overnight at room temperature. The reaction mixture was quenched with water. EtOAc was added and the layers were separated. The aqueous layer was extracted with EtOAc twice. The combined organic layers were washed with water and brine successively, then dried ($Na_2SO_4$), filtered, and concentrated. The residue was purified by silica gel column chromatography to give the desired product (3.7 g, 87%). LCMS for $C_{12}H_{10}BrCl_2N_3O$ (M+H)+: m/z=361.9, 363.9.

Step C: 3-[3-({4-[(3-Bromo-5-methoxybenzyl)amino]-5-chloropyrimidin-2-yl}amino)phenyl]propan-1-ol

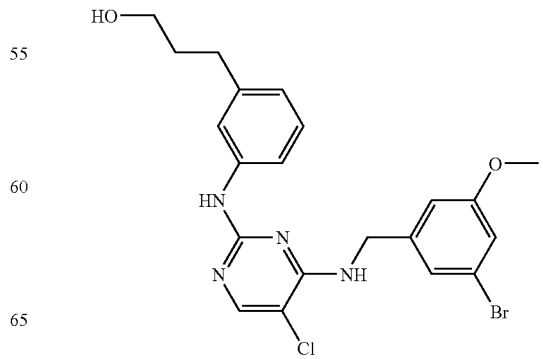

Into a reaction flask were added N-(3-bromo-5-methoxybenzyl)-2,5-dichloropyrimidin-4-amine (2.0 g, 5.5 mmol), 1,4-dioxane (30 mL), 3-(3-aminophenyl)propan-1-ol (1.2 g, 8.3 mmol, prepared according to Example 12, Step B), and p-toluenesulfonic acid monohydrate (0.12 g, 0.63 mmol). The mixture was heated at 70° C. over two days and NaHCO$_3$ (saturated aqueous solution) was added. After removal of the organic solvent, the aqueous layer was extracted with methylene chloride twice. The combined organic layers were washed with water and brine successively, then dried (Na$_2$SO$_4$), filtered, and concentrated to give the desired product as a white powder (2.6 g, 99%). LCMS for C$_{21}$H$_{22}$BrClN$_4$O$_2$ (M+H)$^+$: m/z=477.0, 479.0.

Step D: 3-Bromo-5-{[(2-{[3-(3-bromopropyl)phenyl]amino}-5-chloropyrimidin-4-yl)amino]methyl}phenol

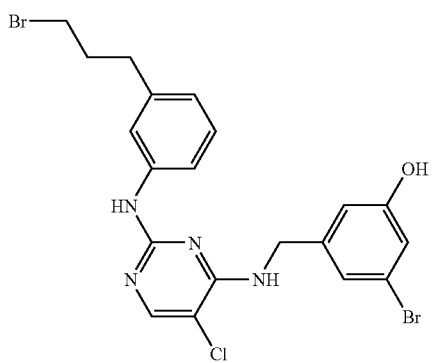 [SMILES: Oc1cc(Br)cc(CNc2nc(Nc3cccc(CCCBr)c3)ncc2Cl)c1]

Into a reaction flask was added 3-[3-({4-[(3-bromo-5-methoxybenzyl)amino]-5-chloropyrimidin-2-yl}amino)phenyl]propan-1-ol (2.70 g, 5.65 mmol), methylene chloride (30 mL), and a solution of boron tribromide in methylene chloride (17.0 mL, 17.0 mmol, 1.0 M). The mixture was stirred at rt overnight. The resultant mixture was cooled in dry ice when NaHCO$_3$ (saturated aqueous solution) was added. After removal of the organic solvent, the aqueous layer was extracted with methylene chloride twice. The combined organic layers were washed with water and brine successively, then dried (Na$_2$SO$_4$), filtered, and concentrated to give the desired product (2.97 g, 100%). LCMS for C$_{20}$H$_{19}$Br$_2$ClN$_4$O (M+H)$^+$: m/z=526.9, 528.8.

Step E: 12-Bromo-6-chloro-15-oxa-2,4,8,25-tetraazatetracyclo[17.3.1.1(3,7).1(10,14)]pentacosa-1(23),3(25),4,6,10(24),11,13,19,21-nonaene Into a reaction flask were added 3-bromo-5-{[(2-{[3-(3-bromopropyl)phenyl]amino}-5-chloropyrimidin-4-yl)amino]methyl}phenol (2.97 g, 5.64 mmol), tetrahydrofuran (30 mL), and a solution of sodium hydroxide in water (33.8 mL, 1.0 M). The reaction mixture was stirred at rt over two days. The mixture was filtered, and then the cake was washed with water, MeOH, and EtOAc successively to provide the desired product (1.33 g, 53%) as an off-white powder. LCMS for C$_{20}$H$_{18}$BrClN$_4$O (M+H)$^+$: m/z=444.9, 446.9. $^1$H NMR (400 MHz, DMSO-d$_6$): δ 9.04 (s, 1H), 7.95 (s, 1H), 7.93 (s, 1H), 7.36 (s, 1H), 7.10 (m, 1H), 7.07 (m, 1H), 6.92 (d, J=7.9 Hz, 1H), 6.86 (s, 1H), 6.78 (d, J=7.5 Hz, 1H), 4.42 (d, J=5.5 Hz, 2H), 4.18 (t, 2H), 3.60 (m, 1H), 2.65 (m, 2H), 1.65 (m, 2H).

Example 17

6-Chloro-2,4,8,19,23-pentaazatetracyclo[15.3.1.1(3,7).1(10,14)]tricosa-1(21),3(23),4,6,10(22),11,13,17,19-nonaen-13-amine

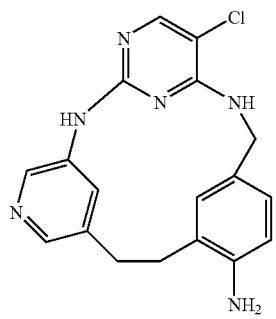 [SMILES: Nc1ccc2cc1CCc1cncc(c1)Nc1ncc(Cl)c(n1)NC2]

Step A: tert-Butyl {5-[(trimethylsilyl)ethynyl]pyridin-3-yl}carbamate

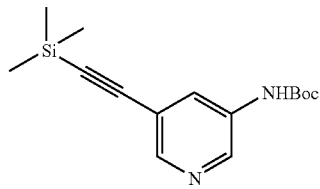 [SMILES: CC(C)(C)OC(=O)Nc1cncc(C#C[Si](C)(C)C)c1]

Into a reaction flask were added tert-butyl (5-bromopyridin-3-yl)carbamate (3.0 g, 11.0 mmol), tetrahydrofuran (30 mL), and triethylamine (1.7 mL, 12 mmol). The reaction mixture was stirred under N$_2$ bubbling for 5 min. (Trimethylsilyl)acetylene (1.60 g, 16.3 mmol), copper(I) iodide (84 mg, 0.44 mmol), and bis(triphenylphosphine)palladium(II) chloride (0.31 g, 0.44 mmol) were then added. The resultant mixture was heated at 50° C. overnight. The solvent was removed under vacuum and the residue was diluted with EtOAc and water. After separation, the organic layer was dried over Na$_2$SO$_4$ and concentrated under vacuum. The crude product was purified by silica gel column chromatography to give the desired product as a white powder (2.0 g, 63%). LCMS for C$_{15}$H$_{23}$N$_2$O$_2$Si (M+H)$^+$: m/z=291.1.

Step B: tert-Butyl (5-ethynylpyridin-3-yl)carbamate

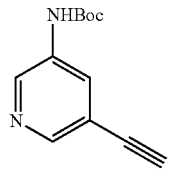 [SMILES: C#Cc1cncc(NC(=O)OC(C)(C)C)c1]

Into a reaction flask were added tert-butyl {5-[(trimethylsilyl)ethynyl]pyridin-3-yl}carbamate (2.0 g, 6.9 mmol), methanol (25 mL), and a solution of potassium carbonate (7.1 g, 52 mmol) in water (25 mL). The reaction mixture was stirred at rt overnight. The solvent was removed under vacuum and the residue was diluted with EtOAc and water. After separation, the organic layer was dried over $Na_2SO_4$ and concentrated under vacuum. The crude product was purified by silica gel column chromatography to give the desired product as a white powder (1.0 g, 67%). LCMS for $C_{12}H_{15}N_2O_2$ (M+H)$^+$: m/z=219.0.

Step C: tert-Butyl (4-cyano-2-iodophenyl)carbamate

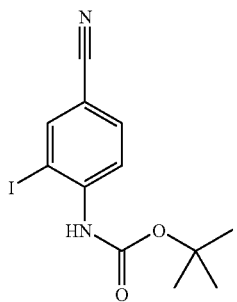 [SMILES: CC(C)(C)OC(=O)Nc1ccc(C#N)cc1I]

Sodium hydride (0.59 g, 24 mmol) was added slowly to a stirring solution of 4-amino-3-iodobenzonitrile (5.0 g, 20 mmol) in N,N-dimethylformamide (90 mL) at 0° C., followed by an addition of di-tert-butyldicarbonate (4.9 g, 22 mmol). The mixture was slowly warmed up to rt and stirred overnight. The reaction mixture was diluted with EtOAc and water. The aqueous layer was extracted with EtOAc twice. The combined organic layers were dried over $Na_2SO_4$ and concentrated under vacuum. The crude product was purified by silica gel column chromatography to give the desired product as a white powder (4.0 g, 57%). LCMS for $C_{12}H_{14}IN_2O_2$ (M+H)$^+$: m/z=344.6.

Step D: tert-Butyl [5-({2-[(tert-butoxycarbonyl)amino]-5-cyanophenyl}ethynyl)pyridin-3-yl]carbamate

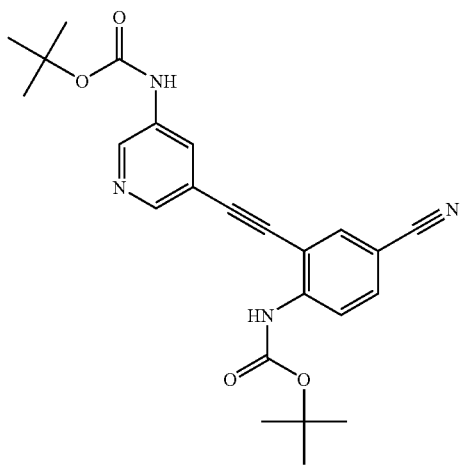 [SMILES: CC(C)(C)OC(=O)Nc1cncc(C#Cc2cc(C#N)ccc2NC(=O)OC(C)(C)C)c1]

Into a reaction flask were added tert-butyl (4-cyano-2-iodophenyl)carbamate (1.4 g, 4.1 mmol), copper(I) iodide (31 mg, 0.16 mmol), bis(triphenylphosphine)palladium(II) chloride (0.12 g, 0.16 mmol), tetrahydrofuran (10 mL), and triethylamine (0.63 mL, 4.5 mmol). The mixture was stirred under $N_2$ bubbling for 5 minutes and tert-butyl (5-ethynylpyridin-3-yl)carbamate (0.90 g, 4.1 mmol) (prepared according to Example 17, Step B) was then added. The reaction mixture was stirred at 65° C. for 2 hours. The solvent was removed under vacuum and the residue was diluted with EtOAc and water. After separation, the organic layer was dried over $Na_2SO_4$ and concentrated under vacuum. The crude was purified by silica gel column chromatography to give the desired product (0.94 g, 52%). LCMS for $C_{24}H_{27}N_4O_4$ (M+H)$^+$: m/z=435.2.

Step E: tert-Butyl [5-(2-{2-[(tert-butoxycarbonyl)amino]-5-cyanophenyl}ethyl)pyridin-3-yl]carbamate

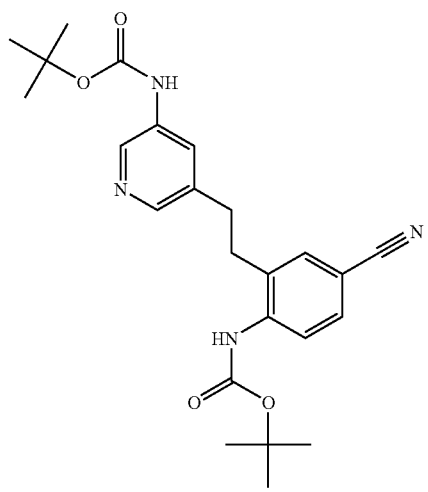 [SMILES: CC(C)(C)OC(=O)Nc1cncc(CCc2cc(C#N)ccc2NC(=O)OC(C)(C)C)c1]

Into a reaction flask were added tert-butyl [5-({2-[(tert-butoxycarbonyl)amino]-5-cyanophenyl}ethynyl)pyridin-3-yl]carbamate (0.94 g, 2.2 mmol), methanol (50 mL), and 10% palladium on carbon (0.40 g, 0.38 mmol). The mixture was hydrogenated at 60 psi for 6 hours. After filtration to remove the catalyst, the mixture was concentrated under vacuum to give the desired product as an off-white powder (0.94 g, 99%). LCMS for $C_{24}H_{31}N_4O_4$ (M+H)$^+$: m/z=439.2.

Step F: tert-Butyl [5-(2-{5-(aminomethyl)-2-[(tert-butoxycarbonyl)amino]phenyl}ethyl)pyridin-3-yl]carbamate

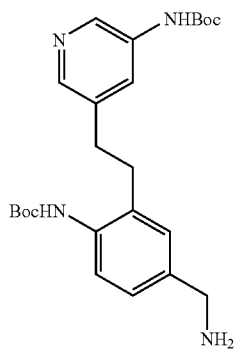 [SMILES: CC(C)(C)OC(=O)Nc1cncc(CCc2cc(CN)ccc2NC(=O)OC(C)(C)C)c1]

Into a pressure bottle were added tert-butyl [5-(2-{2-[(tert-butoxycarbonyl)amino]-5-cyanophenyl}ethyl)pyridin-3-yl] carbamate (0.80 g, 1.8 mmol), tetrahydrofuran (3 mL), methanol (10 mL), and Raney nickel (0.30 g, 5 mmol). The reaction mixture was hydrogenated at 45 psi for 2 hours. After filtration to remove the catalyst, the mixture was concentrated under vacuum to give the desired product as an off-white powder (0.30 g, 99%). LCMS for $C_{24}H_{35}N_4O_4$ (M+H)$^+$: m/z=443.2.

Step G: tert-Butyl {5-[2-(2-[(tert-butoxycarbonyl)amino]-5-{[(2,5-dichloropyrimidin-4-yl)amino]methyl}phenyl)ethyl]pyridin-3-yl}carbamate

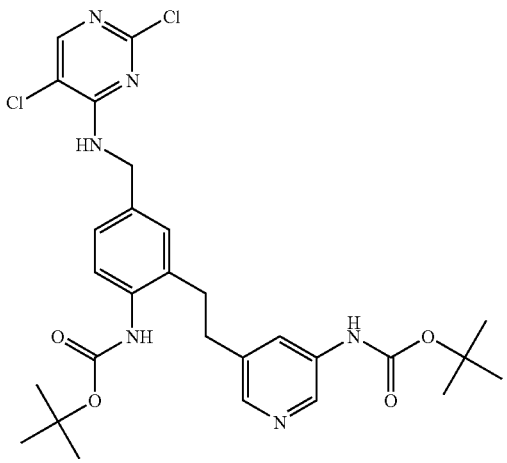 [SMILES: CC(C)(C)OC(=O)Nc1cncc(CCc2cc(CNc3nc(Cl)ncc3Cl)ccc2NC(=O)OC(C)(C)C)c1]

To a solution of tert-butyl [5-(2-{5-(aminomethyl)-2-[(tert-butoxycarbonyl)amino]phenyl}ethyl)pyridin-3-yl]carbamate (0.81 g, 1.8 mmol) and 2,4,5-trichloropyrimidine (0.45 g, 2.4 mmol) in N,N-dimethylformamide (10 mL) was added potassium carbonate (1.30 g, 9.37 mmol). The resultant mixture was stirred overnight at 45° C. The reaction was quenched with water. EtOAc was added and the layers were separated. The aqueous layer was extracted with EtOAc once. The combined organic layers were washed with water, and then dried (Na$_2$SO$_4$), filtered, and concentrated under vacuum. The crude product was purified by silica gel column chromatography to give the desired product as a white powder (0.44 g, 40%). LCMS for $C_{28}H_{35}Cl_2N_6O_4$ (M+H)$^+$: m/z=589.1, 591.1.

Step H: N-{4-Amino-3-[2-(5-aminopyridin-3-yl)ethyl]benzyl}-2,5-dichloropyrimidin-4-amine trihydrochloride

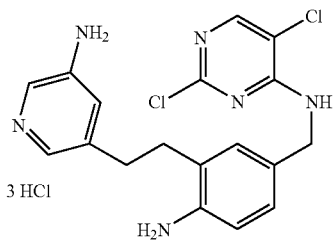 [SMILES: "3 HCl" ; Nc1cncc(CCc2cc(CNc3nc(Cl)ncc3Cl)ccc2N)c1]

Into a reaction flask were added tert-butyl {5-[2-(2-[(tert-butoxycarbonyl)amino]-5-{[(2,5-dichloropyrimidin-4-yl)amino]methyl}phenyl)ethyl]pyridin-3-yl}carbamate (0.44 g, 0.75 mmol), methanol (3 mL), and a solution of hydrogen chloride in 1,4-dioxane (5 mL, 4.0 M). The reaction mixture was stirred at rt overnight and concentrated under vacuum to give the desired product as a white powder (0.40 g, 98%). LCMS for $C_{18}H_{19}Cl_2N_6$ (M+H)$^+$: m/z=389.0, 391.0.

Step I: 6-Chloro-2,4,8,19,23-pentaazatetracyclo[15.3.1.1(3,7).1(10,14)]tricosa-1(21),3(23),4,6,10(22),11,13,17,19-nonaen-13-amine Into a reaction flask were added N-{4-amino-3-[2-(5-aminopyridin-3-yl)ethyl]benzyl}-2,5-dichloropyrimidin-4-amine trihydrochloride (0.29 g, 0.74 mmol), 1,4-dioxane (5 mL), and triethylamine (0.31 mL, 2.2 mmol). The mixture was stirred at rt under N$_2$ for 5 minutes, followed by an addition of palladium acetate (5 mg, 0.02 mmol), (9,9-dimethyl-9H-xanthene-4,5-diyl)bis(diphenylphosphine) (12.9 mg, 0.02 mmol), and cesium carbonate (500 mg, 2.0 mmol). The reaction mixture was degassed with N$_2$ bubbling. The tube was then sealed and heated at 160° C. for 2 hours. After concentration, the crude product was purified by silica gel column chromatography to give the desired product as a white powder (100 mg, 42%). LCMS for $C_{18}H_{18}ClN_6$ (M+H)$^+$: m/z=353.0. $^1$H NMR (400 MHz, DMSO-d$_6$): δ 9.65 (s, 1H), 8.44 (d, J=1.6 Hz, 2H), 8.16 (d, J=2.3 Hz, 1H), 8.01 (s, 1H), 7.11 (m, 2H), 7.03 (m, 2H), 6.69 (s, 1H), 4.14 (d, J=5.8 Hz, 2H), 2.88 (m, 4H).

Example 18

N-[6-Chloro-2,4,8,19,23-pentaazatetracyclo[15.3.1.1(3,7).1(10,14)]tricosa-1(21),3(23),4,6,10(22),11,13,17,19-nonaen-13-yl]benzamide bis(trifluoroacetate)

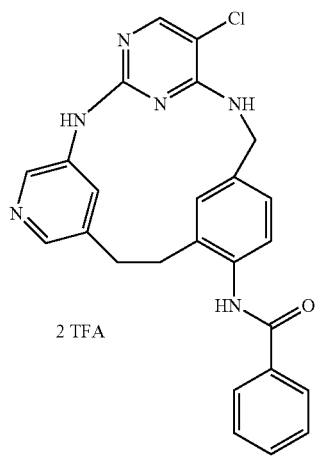 [SMILES: "2 TFA" ; O=C(Nc1ccc2cc1CCc1cncc(c1)Nc1ncc(Cl)c(n1)NC2)c1ccccc1]

Into a reaction flask were added 6-chloro-2,4,8,19,23-pentaazatetracyclo[15.3.1.1(3,7).1(10,14)]tricosa-1(21),3(23),4,6,10(22),11,13,17,19-nonaen-13-amine (20 mg, 0.06 mmol), N,N-dimethylformamide ("DMF", 1.0 mL), triethylamine (11 mg, 0.11 mmol), and benzoyl chloride (10 mg, 0.074 mmol). The reaction mixture was stirred at rt for 5 minutes. The mixture was diluted with DMF and was purified directly on prep-HPLC to provide the desired product (2.4 mg, 19%) as a white solid. LCMS for $C_{25}H_{22}ClN_6O$ (M+H)$^+$:

m/z=457.2. $^1$H NMR (400 MHz, DMSO-d$_6$): δ 9.95 (s, 1H), 9.53 (s, 1H), 8.35 (d, J=1.5 Hz, 1H), 8.24 (d, J=2.3 Hz, 1H), 8.01 (s, 1H), 7.94 (m, 2H), 7.48-7.62 (m, 4H), 7.16-7.25 (m, 3H), 4.25 (d, J=5.7 Hz, 2H), 2.88 (m, 4H).

Example 19

N-[6-Chloro-2,4,8,19,23-pentaazatetracyclo[15.3.1.1 (3,7).1(10,14)]tricosa-1(21),3(23),4,6,10(22),11,13, 17,19-nonaen-13-yl]-2-cyanobenzenesulfonamide bis(trifluoroacetate)

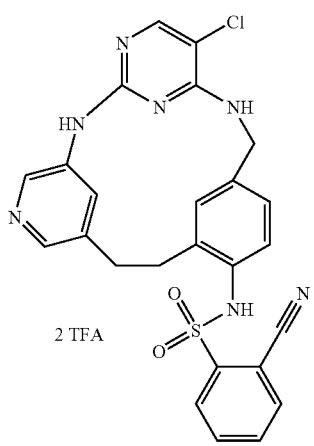 [SMILES: "2 TFA" ; N#Cc1ccccc1S(=O)(=O)Nc1ccc2cc1CCc1cncc(c1)Nc1ncc(Cl)c(n1)NC2]

Into a reaction flask were added 6-chloro-2,4,8,19,23-pentaazatetracyclo[15.3.1.1(3,7).1(10,14)]tricosa-1(21),3(23), 4,6,10(22),11,13,17,19-nonaen-13-amine (20 mg, 0.06 mmol), N,N-dimethylformamide (1.0 mL), triethylamine (11 mg, 0.11 mmol), and 2-cyanobenzenesulfonyl chloride (15 mg, 0.074 mmol). The reaction mixture was stirred at rt for 5 minutes. The mixture was diluted with DMF and was purified directly on prep-HPLC to provide the desired product (4.5 mg, 30%) as a white solid. LCMS for $C_{25}H_{19}ClN_7O_2S$ (M+H)$^+$: m/z=519.0.

Example AA

In Vitro JAK Kinase Assay

One or more compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). IC$_{50}$s of compounds were measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 μM for JAK1, 30 μM for JAK2 and 3 μM for JAK3. Reactions were carried out at room temperature for 1 hr and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.).

Example BB

Cellular Assays

One or more compounds herein were tested for inhibitory activity of JAK targets according to at least one of the following cellular assays.

Cancer cell lines dependent on cytokines and hence JAK/STAT signal transduction, for growth, were plated at 6000 cells per well (96 well plate format) in RPMI 1640, 10% FBS, and 1 nG/mL of appropriate cytokine. Compounds were added to the cells in DMSO/media (final concentration 0.2% DMSO) and incubated for 72 hours at 37° C., 5% CO$_2$. The effect of compound on cell viability was assessed using the CellTiter-Glo Luminescent Cell Viability Assay (Promega) followed by TopCount (Perkin Elmer, Boston, Mass.) quantitation. Potential off-target effects of compounds were measured in parallel using a non-JAK driven cell line with the same assay readout. All experiments were performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. *JBC* 280:41893-41899). Endpoints include the effects of compounds on cell survival, proliferation, and phosphorylated JAK, STAT, Akt, or Erk proteins.

Certain compounds herein have been or can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/mL penicillin, 100 µg/mL streptomycin) at a density of 2×10⁶ cells/mL at 37° C. for up to 2 days. For IL-2 stimulated cell proliferation analysis, T-cells are first treated with Phytohemagglutinin (PHA) at a final concentration of 10 µg/mL for 72 hours. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 hours and the proliferation index is assessed using CellTiter-Glo Luminescent reagents following the manufactory suggested protocol (Promega; Madison, Wis.).

Example CC

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J*. 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example DD

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today*. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds is given throughout the sensitization and challenge phases (day-1 to day 7) or prior to and throughout the challenge phase (usually afternoon of day 4 to day 7). Treatment of the test compounds (in different concentration) was administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example EE

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example FF pALK Assay

To determine the activity of numerous compounds on the phosphorylation of ALK in cells, an ELISA method testing lymphoma cell lysates was developed. Human lymphoma cells were treated with examples for 4 hours. Cells were lysed in lysis buffer (Cell Signaling #9803, Danvers, Mass.) supplemented with complete mini protease inhibitor cocktail tablets (Roche Applied Science, Indianapolis, Ind.) on ice and after 15 minutes, lysates were cleared by centrifugation. According to the manufacturer's instructions, lysates were placed in wells precoated with anti-phospho-ALK antibody (Cell Signaling #7324, Danvers, Mass.) and allowed to incubate overnight at 4° C. After washing, an anti-ALK antibody is added to wells. Colorimetric (TMB) detection of HRP-linked anti-mouse IgG is used to quantify relative levels of phospho-ALK.

Example GG

Cell Proliferation Assay

The activity of numerous compounds on ALK driven proliferation was assessed using Karpas-299 human anaplastic lymphoma cells. Cells were seeded at 2500 cells per well in clear bottom 96 well plates. On the first day, replicate plates were treated with various concentrations of compounds or processed using the manufacturer's instructions for Cell Titer Glo (Promega, Madison, Wis.) to determine baseline levels. After 72 hours, the dosed plate was processed using Cell Titer Glo. After calculating the specific proliferation of cells in the presence of compounds, $IC_{50}$s were determined using Prism software (GraphPad Software, San Diego, Calif.).

Example HH

ALK HTRF Kinase Assay

Materials: Recombinant Human Anaplastic Lymphoma Kinase was purchased from Invitrogen, Carlsbad, Calif. Peptide substrate (Biotin-KKKGPWLEEEEEAYGWLDF-amide) was custom synthesized at EZBiolab, Westfield, Ind. Streptavidin conjugated SureLight-Allophycocyania and LANCE Eu-W1024 labeled anti-phosphotyrosine antibody were from Perkin-Elmer, Boston, Mass. Microplates were from Corning Inc., Acton, Mass. All other reagents were from Sigma, St. Louis, Mo.

HTRF kinase assay: 40 µL reactions were run in black 384 well polystyrene plates in assay buffer (50 mM Tris, pH 7.8, 100 mM NaCl, 0.1 mg/mL BSA, 5 mM DTT), containing 0.5 µM Biotinylated peptide substrate, 10 mM $MgCl_2$, 90 µM ATP, and 0.25 nM enzyme for 2 hours at 25° C. Reactions were stopped by addition of 20 µL assay buffer supplemented with an additional 50 mM NaCl, 0.4 mg/mL BSA, 45 mM EDTA, 4.5 nM LANCE Eu-W1024 labeled anti-phosphotyrosine antibody and 200 nM streptavidin conjugated SureLight-allophycocyanin. Plates were read in Fusion α-FP instrument (Perkin-Elmer). The concentrations needed to reach 50% inhibition, the $IC_{50}$ value, were determined by fitting the assay signal to the following equation using Graphpad Prizm.

Signal=Bottom+(Top−Bottom)/(1+10^((Log(IC50)−Log [$I$])*Hill Slope)

Bottom and Top refer to the post and pre-transition baselines, respectively.

The $IC_{50}$ value for the example compounds of invention with respect one or more of JAK/ALK are provided in Table 1 as follows.

TABLE 1

| Example Number | JAK1 $IC_{50}$ (nM) | JAK2 $IC_{50}$ (nM) | JAK3 $IC_{50}$ (nM) | TYK2 $IC_{50}$ (nM) | ALK $IC_{50}$ (nM) |
|---|---|---|---|---|---|
| Example 1 | 51 | 49 | 17 | 400 | >1,000 |
| Example 2 | 13 | 10 | 9.2 | 35 | 1530 |
| Example 3 | 300 | 589 | 325 | 830 | >10,000 |
| Example 4 | 96 | 104 | 21 | >1,000 | >10,000 |

TABLE 1-continued

| Example Number | JAK1 $IC_{50}$ (nM) | JAK2 $IC_{50}$ (nM) | JAK3 $IC_{50}$ (nM) | TYK2 $IC_{50}$ (nM) | ALK $IC_{50}$ (nM) |
|---|---|---|---|---|---|
| Example 5 | 4.2 | 1.9 | 2.4 | 25 | 706 |
| Example 6 | 346 | 350 | 140 | >1,000 | >10,000 |
| Example 7 | 16 | 8.3 | 6.4 | 43 | 2,050 |
| Example 8 | 600 | 333 | 300 | 438 | >10,000 |
| Example 9 | 28 | 23 | 55 | 53 | 1,230 |
| Example 10 | 122 | 117 | 180 | 237 | >1,000 |
| Example 11 | >1,000 | >1,000 | >1,000 | >1,000 | >10,000 |
| Example 12 | 300 | 120 | 315 | 400 | >10,000 |
| Example 13 | 32 | 25 | 62 | 106 | >10,000 |
| Example 14 | 100 | 91 | 57 | 300 | 8200 |
| Example 15 | 81 | 41 | 31 | 400 | >1,000 |
| Example 16 | 15 | 5 | 15 | 149 | 280 |
| Example 17 | 102 | 447 | 114 | 386 | >1000 |
| Example 18 | >1,000 | >1,000 | >1,000 | >1,000 | >1,000 |
| Example 19 | >1,000 | >1,000 | >1,000 | >1,000 | >1,000 | a. when the experiment limit is set as "a" and the $IC_{50}$ measurement of the example compound exceeds the limit, then the $IC_{50}$ data is shown as ">a"

Various modifications of the invention, in addition to those described herein, will be apparent to those skilled in the art from the foregoing description. Such modifications are also intended to fall within the scope of the appended claims. Each reference cited in the present application is herein incorporated by reference in its entirety.

What is claimed is:
1. A compound of Formula I:

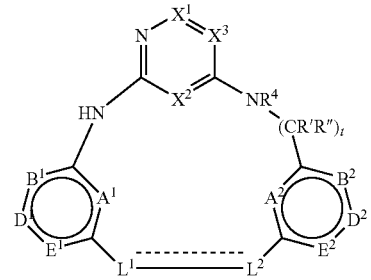

I or pharmaceutically acceptable salt thereof or quaternary ammonium salt thereof, wherein:

----- represents a single bond or a double bond;
$X^1$ is N or $CR^1$;
$X^2$ is N or $CR^2$;
$X^3$ is N or $CR^3$;
$A^1$ and $A^2$ are each, independently, selected from $CR^2$;
$B^1$, $B^2$, $E^1$, and $E^2$ are each, independently, selected from $CR^5$;
$D^1$ and $D^2$ are each, independently, selected from $CR^5$;
$L^1$ and $L^2$ are each, independently selected from a bond, —$(CR^7R^8)_n$—, —O—$(CR^7R^8)_m$—$CR^{10}$=, —S—$(CR^7R^8)_m$—$CR^{10}$=, —$(CR^7R^8)_m$—$CR^{10}$=, —$(CR^7R^8)_m$—$NR^9$—, —$(CR^7R^8)_m$—N=, —$(CR^7R^8)_m$—O—, —$(CR^7R^8)_m$—S—, —$(CR^7R^8)_m$—S(O)—, —$(CR^7R^8)_m$—S(O)$_2$—, —$(CR^7R^8)_m$—C(O)—, —C(O)$NR^9$—, —$(CR^7R^8)_m$—C(O)O—, —$(CR^7R^8)_m$—$NR^9$C(O)$NR^9$—, —$(CR^7R^8)_m$—OC(O)$NR^9$—, —$(CR^7R^8)_m$—$NR^9$C(O)O—, —$(CR^7R^8)_m$—$NR^9$—S(O)$_2$$NR^9$—, —$(CR^7R^8)_m$—S(O)$NR^9$—, and —$(CR^7R^8)_m$—S(O)$_2$$NR^9$—;

wherein at least one of $L^1$ and $L^2$ is other than a bond;
R' and R'' are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, C(O)

OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

or R' and R" together with the C atom to which they are attached form a 3-, 4-, 5-, 6-, 7-, 8-, 9- or 10-membered cycloalkyl group or heterocycloalkyl group, each optionally substituted with 1, 2, or 3 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

R$^1$ and R$^3$ are each, independently, selected from H, halo, C$_{1-6}$ alkyl, C$_{2-6}$ alkenyl, C$_{2-6}$ alkynyl, C$_{1-6}$ haloalkyl, CN, NO$_2$, SF$_5$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

each R$^2$ is, independently, selected from H, halo, C$_{1-6}$ alkyl, C$_{2-6}$ alkenyl, C$_{2-6}$ alkynyl, C$_{1-6}$ haloalkyl, CN, NO$_2$, SF$_5$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^{g2}$)NR$^{c2}$R$^{d2}$, NR$^{c2}$C(=NR$^{g2}$)NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$^2$R$^{b2}$, NR$^{c2}$S(O)$_2$R$^{b2}$, and S(O)$_2$NR$^{c2}$R$^{d2}$;

each R$^5$ is, independently, H, Cy$^1$, halo, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, halosulfanyl, CN, NO$_2$, SF$_5$, OR$^{a2}$, SR$^{a2}$, C(O)R$^{b1}$, C(O)NR$^{c1}$R$^{d1}$, C(S)R$^{b1}$, C(S)NR$^{c1}$R$^{d1}$, C(O)OR$^{a1}$, OC(O)R$^{b1}$, —W$^1$-Q$^1$-Y$^1$—Z$^1$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(S)R$^{b1}$, NR$^{c1}$C(S)NR$^{c1}$R$^{d1}$, NR$^{c1}$C(O)OR$^{a1}$, C(=NR$^{g1}$)NR$^{c1}$R$^{d1}$, NR$^{c2}$C(=NR$^{g1}$)NR$^{c2}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, or P(O)OR$^{e1}$OR$^{f1}$, wherein each of said C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, or heterocycloalkylalkyl, is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, Cy$^1$, halosulfanyl, CN, NO$_2$, SF$_5$, OR$^{a1}$, SR$^{a1}$, C(O)R$^{b1}$, C(O)NR$^{c1}$R$^{d1}$, C(S)R$^{b1}$, C(S)NR$^{c1}$R$^{d1}$, C(O)OR$^{a1}$, OC(O)R$^{b1}$, —W$^1$-Q$^1$-Y$^1$—Z$^1$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(S)R$^{b1}$, NR$^{c1}$C(S)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$; or two adjacent R$^5$ on the same ring can link to form a fused cycloalkyl or fused heterocycloalkyl group, each optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, halosulfanyl, Cy$^1$, CN, NO$_2$, OR$^{a1}$, SR$^{a1}$, C(O)R$^{b1}$, C(O)NR$^{c1}$R$^{d1}$, SF$_5$, C(S)R$^{b1}$, C(S)NR$^{c1}$R$^{d1}$, C(O)OR$^{a1}$, OC(O)R$^{b1}$, —W$^1$-Q$^1$-Y$^1$—Z$^1$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(S)R$^{b1}$, NR$^{c1}$C(S)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$, wherein each of said C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, or heterocycloalkylalkyl, is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, Cy$^1$, —W$^1$-Q$^1$-Y$^1$—Z$^1$, halosulfanyl, CN, NO$_2$, SF$_5$, OR$^{a1}$, SR$^{a1}$, C(O)R$^{b1}$, C(O)NR$^{c1}$R$^{d1}$, C(O)OR$^{a1}$, OC(O)R$^{b1}$, OCH$_2$C(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)$_2$R$^{b1}$, NR$^{c1}$S(O)$_2$ R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$;

R$^4$ and R$^6$ are each, independently, selected from H, Cy$^2$, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, —W$^2$—X$^2$—Y$^2$—Z$^2$, C(O)R$^{b1}$, C(O)NR$^{c1}$R$^{d1}$, C(O)OR$^{a1}$, C(=NR$^{g1}$)NR$^{c1}$R$^{d1}$, S(O)R$^{b1}$, S(O)NR$^{c1}$R$^{d1}$, S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$, wherein each of said C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, Cy$^2$, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, —W$^2$-Q$^2$-Y$^2$—Z$^2$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$;

R$^7$, R$^8$, and R$^{10}$ are each, independently, selected from H, Cy$^3$, halo, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, —W$^3$-Q$^3$-Y$^3$—Z$^3$, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$ R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^1$, wherein each of said C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a2}$, C(O)R$^{b1}$, C(O)NR$^{c1}$R$^{d1}$, C(O)OR$^{a1}$, OC(O)R$^{b1}$, Cy$^3$, —W$^3$-Q$^3$-Y$^3$—Z$^3$, —C(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$;

each R$^9$ is, independently, H, Cy$^4$, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, —W$^4$-Q$^4$-Y$^4$—Z$^4$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{g1}$)NR$^{c1}$R$^{d1}$, S(O)R$^{b1}$, S(O)NR$^{c1}$R$^{d1}$, S(O)$_2$R$^{b1}$, S(O)$_2$NR$^{c1}$R$^{d1}$, P(R$^{f1}$)$_2$, P(OR$^{e1}$)$_2$, $P(O)R^{e1}R^{f1}$, or $P(O)OR^{e1}OR^{f1}$ wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $Cy^4$, $-W^4-Q^4-Y^4-Z^4$, $-C(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$R^{11a}$, $R^{11b}$, $R^{12a}$, $R^{12b}$, and $R^{13}$ are each, independently, selected from H, $Cy^3$, halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $Cy^3$, $-W^3-Q^3-Y^3-Z^3$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$W^1$, $W^2$, $W^3$, $W^4$, and $W^5$ are each, independently, selected from absent, $W^6$, $C_{1-6}$ alkylenyl, $C_{2-6}$ alkenylenyl, $C_{2-6}$ alkynylenyl, $(CR^{11a}R^{11b})_{p1}O(CR^{11a}R^{11b})_{p2}$, $(CR^{11a}R^{11b})_{p1}S(CR^{11a}R^{11b})_{p2}$, $(CR^{11a}R^{11b})_{p1}NR^{e}(CR^{11a}R^{11b})_{p2}$, $(CR^{11a}R^{11b})_{p1}C(O)(CR^{11a}R^{11b})_{p2}$, $(CR^{11a}R^{11b})_{p1}C(S)(CR^{11a}R^{11b})_{p2}$, $(CR^{11a}R^{11b})_{p1}C(O)O(CR^{11a}R^{11b})_{p2}$, $(CR^{11a}R^{11b})_{p1}C(O)NR^{e}(CR^{11a}R^{11b})_{p2}$, $(CR^{11a}R^{11b})_{p1}C(S)NR^{e}(CR^{11a}R^{11b})_{p2}$, $(CR^{11a}R^{11b})_{p1}S(O)(CR^{11a}R^{11b})_{p2}$, $(CR^{11a}R^{11b})_{p1}S(O)_2(CR^{11a}R^{11b})_{p2}$, $(CR^{11a}R^{11b})_{p1}S(O)NR^{e}(CR^{11a}R^{11b})_{p2}$, $(CR^{11a}R^{11b})_{p1}S(O)_2NR^{e}(CR^{11a}R^{11b})_{p2}$, $(CR^{11a}R^{11b})_{p1}NR^{e}C(O)NR^{f}(CR^{11a}R^{11b})_{p2}$, $(CR^{11a}R^{11b})_{p1}NR^{e}C(S)NR^{f}(CR^{11a}R^{11b})_{p2}$, $(CR^{11a}R^{11b})_{p1}NR^{e}S(O)_2NR^{f}(CR^{11a}R^{11b})_{p2}$, $(CR^{11a}R^{11b})_{p1}C(=NR^{g})NR^{e}(CR^{11a}R^{11b})_{p2}$, $(CR^{11a}R^{11b})_{p1}NR^{e}C(=NR^{g})NR^{f}(CR^{11a}R^{11b})_{p2}$, $O(CR^{11a}R^{11b})_{q1}C(O)$, $S(CR^{11a}R^{11b})_{q1}C(O)$, $NR^{e}(CR^{11a}R^{11b})_{q1}C(O)$, $C(O)(CR^{11a}R^{11b})_{q1}C(O)$, $NR^{e}(CR^{11a}C^{11b})_{q1}NR^{f}$, $O(CR^{11a}R^{11b})_{q1}NR^{f}$, and $O(CR^{11a}R^{11b})_{q1}O$, wherein each of the $C_{1-6}$ alkylenyl, $C_{2-6}$ alkenylenyl and $C_{2-6}$ alkynylenyl is optionally substituted by 1, 2, or 3 substituents independently selected from halo, CN, $NO_2$, $OR^{a}$, $SR^{a}$, $C(O)R^{b}$, $C(O)NR^{c}R^{d}$, $C(O)OR^{a}$, $OC(O)R^{b}$, $OC(O)NR^{c}R^{d}$, $NR^{c}R^{d}$, $NR^{c}C(O)R^{b}$, $NR^{c}C(O)NR^{c}R^{d}$, $NR^{c}C(O)OR^{a}$, $C(=NR^{g})NR^{c}R^{d}$, $NR^{c}C(=NR^{g})NR^{c}R^{d}$, $NR^{c}S(O)_2NR^{c}R^{d}$, $S(O)R^{b}$, $S(O)NR^{c}R^{d}$, $S(O)_2R^{b}$, $NR^{c}S(O)_2R^{b}$, and $S(O)_2NR^{c}R^{d}$;

each $W^6$ is independently selected from $NR^{e100}C(O)NR^{f100}$ and $NR^{e200}C(O)CR^{13}R^{f200}$, wherein $R^{e100}$ and $R^{f100}$ together with the intervening NC(O)N moiety to which they are attached form a 4-7 membered heterocycloalkyl group which is optionally substituted by 1, 2, or 3 substituents each independently selected from $C_{1-6}$ alkyl, $C_{1-6}$ haloalkyl, $C_{2-6}$ alkenyl, $C_{2-6}$ alkynyl, halo, CN, $NO_2$, $OR^{a}$, $SR^{a}$, $C(O)R^{b}$, $C(O)NR^{c}R^{d}$, $C(O)OR^{a}$, $OC(O)R^{b}$, $OC(O)NR^{c}R^{d}$, $NR^{c}R^{d}$, $NR^{c}C(O)R^{b}$, $NR^{c}C(O)NR^{c}R^{d}$, $NR^{c}C(O)OR^{a}$, $C(=NR^{g})NR^{c}R^{d}$, $NR^{c}C(=NR^{g})NR^{c}R^{d}$, $NR^{c}S(O)_2NR^{c}R^{d}$, $S(O)R^{b}$, $S(O)NR^{c}R^{d}$, $S(O)_2R^{b}$, $NR^{c}$, $S(O)_2R^{b}$, and $S(O)_2NR^{c}R^{d}$, and wherein $R^{e200}$ and $R^{f200}$ together with the intervening $NC(O)CR^{13}$ moiety to which they are attached form a 4-7 membered heterocycloalkyl group which is optionally substituted by 1, 2, or 3 substituents each independently selected from $C_{1-6}$ alkyl, $C_{1-6}$ haloalkyl, $C_{2-6}$ alkenyl, $C_{2-6}$ alkynyl, halo, CN, $NO_2$, $OR^{a}$, $SR^{a}$, $C(O)R^{b}$, $C(O)NR^{c}R^{d}$, $C(O)OR^{a}$, $OC(O)R^{b}$, $OC(O)NR^{c}R^{d}$, $NR^{c}R^{d}$, $NR^{c}C(O)R^{b}$, $NR^{c}C(O)NR^{c}R^{d}$, $NR^{c}C(O)OR^{a}$, $C(=NR^{g})NR^{c}R^{d}$, $NR^{c}C(=NR^{g})NR^{c}R^{d}$, $NR^{c}S(O)_2NR^{c}R^{d}$, $S(O)R^{b}$, $S(O)NR^{c}R^{d}$, $S(O)_2R^{b}$, $NR^{c}S(O)_2R^{b}$, and $S(O)_2NR^{c}R^{d}$;

$Q^1$, $Q^2$, $Q^3$, $Q^4$, and $Q^5$ are each, independently, selected from aryl, cycloalkyl, heteroaryl, heterocycloalkyl, arylalkyl, heteroarylalkyl, cycloalkylalkyl, and heterocycloalkylalkyl, each optionally substituted by 1, 2, 3, 4, or 5 substituents independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, $NO_2$, $OR^{a}$, $SR^{a}$, $SF_5$, $C(O)R^{b}$, $C(O)NR^{c}R^{d}$, $C(O)OR^{a}$, $OC(O)R^{b}$, $OC(O)NR^{c}R^{d}$, $NR^{c}R^{d}$, $NR^{c}C(O)R^{b}$, $NR^{c}C(O)NR^{c}R^{d}$, $NR^{c}C(O)OR^{a}$, $C(=NR^{g})NR^{c}R^{d}$, $NR^{c}C(=NR^{g})NR^{c}R^{d}$, $NR^{c}S(O)_2NR^{c}R^{d}$, $S(O)R^{b}$, $S(O)NR^{c}R^{d}$, $S(O)_2R^{b}$, $NR^{c}S(O)_2R^{b}$, and $S(O)_2NR^{c}R^{d}$;

$Y^1$, $Y^2$, $Y^3$, $Y^4$, and $Y^5$ are each, independently, selected from absent, $C_{1-6}$ alkylenyl, $C_{2-6}$ alkenylenyl, $C_{2-6}$ alkynylenyl, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^{e}(CR^{12a}R^{12b})_{p4}$, $(CR^{12a}R^{12b})_{p3}C(O)(CR^{12a}R^{12b})_{p4}$, $(CR^{12a}R^{12b})_{p3}C(S)(CR^{12a}R^{12b})_{p4}$, $(CR^{12a}R^{12b})_{p3}C(O)O(CR^{12a}R^{12b})_{p4}$, $(CR^{12a}R^{12b})_{p3}C(O)NR^{e}(CR^{12a}R^{12b})_{p4}$, $(CR^{12a}R^{12b})_{p3}C(S)NR^{e}(CR^{12a}R^{12b})_{p4}$, $(CR^{12a}R^{12b})_{p3}S(O)(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)NR^{e}(CR^{12a}R^{12b})_{p4}$, $(CR^{12a}R^{12b})_{p3}S(O)_2NR^{e}(CR^{12a}R^{12b})_{p4}$, $(CR^{12a}R^{12b})_{p3}NR^{e}C(O)NR^{f}(CR^{12a}R^{12b})_{p4}$, $(CR^{12a}R^{12b})_{p3}NR^{e}C(O)NR^{f}(CR^{12a}R^{12b})_{p4}$, $(CR^{12a}R^{12b})_{p3}NR^{e}C(S)NR^{f}(CR^{12a}R^{12b})_{p4}$, $(CR^{12a}R^{12b})_{p3}NR^{e}S(O)_2NR^{f}(CR^{12a}R^{12b})_{p4}$, $(CR^{12a}R^{12})_{p3}C(=NR^{g})NR^{e}(CR^{12a}R^{12b})_{p4}$, $(CR^{12a}R^{12b})_{p3}NR^{e}C(=NR^{g})NR^{f}(CR^{12}R^{12b})_{p4}$, $O(CR^{12a}R^{12b})_{q2}C(O)$, $S(CR^{12a}R^{12b})_{q2}C(O)$, $NR^{e}(CR^{12a}R^{12b})_{q2}C(O)$, $NR^{e}(CR^{12a}R^{12b})_{q2}NR^{f}$, $O(CR^{12a}R^{12b})_{q2}NR^{f}$, and $O(CR^{12a}R^{12b})_{q2}O$, wherein each of the $C_{1-6}$ alkylenyl, $C_{2-6}$ alkenylenyl and $C_{2-6}$ alkynylenyl is optionally substituted by 1, 2 or 3 substituents independently selected from $C_{1-6}$ alkyl, $C_{1-6}$ haloalkyl, $C_{2-6}$ alkenyl, $C_{2-6}$ alkynyl, halo, CN, $NO_2$, $OR^{a}$, $SR^{a}$, $SF_5$, $C(O)R^{b}$, $C(O)NR^{c}R^{d}$, $C(O)OR^{a}$, $OC(O)R^{b}$, $OC(O)NR^{c}R^{d}$, $NR^{c}R^{d}$, $NR^{c}C(O)R^{b}$, $NR^{c}C(O)NR^{c}R^{d}$, $NR^{c}C(O)OR^{a}$, $C(=NR^{g})NR^{c}R^{d}$, $NR^{c}C(=NR^{g})NR^{c}R^{d}$, $NR^{c}S(O)_2NR^{c}R^{d}$, $S(O)R^{b}$, $S(O)NR^{c}R^{d}$, $S(O)_2R^{b}$, $NR^{c}S(O)_2R^{b}$, and $S(O)_2NR^{c}R^{d}$;

$Z^1$, $Z^2$, $Z^3$, $Z^4$, and $Z^5$ are each, independently, selected from H, halo, CN, $NO_2$, OH, $C_{1-6}$ alkoxy, $C_{1-6}$ haloalkoxy, amino, $C_{1-6}$ alkylamino, $C_{2-8}$ dialkylamino, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)R^b$, $NR^cC(O)NR^cR^d$, $NR^cC(O)OR^a$, $NR^cS(O)_2R^b$, $NR^cS(O)_2NR^cR^d$; $S(O)R^b$, $S(O)NR^cR^d$, $S(O)_2R^b$, and $S(O)_2NR^cR^d$;

$Cy^1$, $Cy^2$, $Cy^3$, and $Cy^4$ are each, independently, selected from aryl, cycloalkyl, heteroaryl, and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $SF_5$, $Cy^5$, $-L^{b1}-Cy^5$, $-W^5-Q^5-Y^5-Z^5$, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$Cy^5$ and $Cy^6$ are each, independently, selected from aryl, cycloalkyl, heteroaryl, and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, arylalkyl, heteroarylalkyl, cycloalkylalkyl, heterocycloalkylalkyl, halosulfanyl, CN, $NO_2$, $OR^{a2}$, $SR^{a2}$, $SF_5$, $C(O)R^{b2}$, $C(O)NR^{c2}R^{d2}$, $C(S)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$L^{b1}$ and $L^{b2}$ are each, independently, selected from $C_{1-4}$ alkylenyl, O, S, C(O), C(S), $C(O)NR^{c2}$, $C(S)NR^{c2}$, C(O)O, $OC(O)NR^{c2}$, $NR^{c2}$, $NR^{c2}C(O)NR^{d2}$, $NR^{c2}C(S)NR^{d2}$, $C(=NR^g)NR^{c2}$, $NR^{c2}C(=NR^g)NR^{d2}$, $NR^{c2}S(O)_2NR^{d2}$, S(O), $S(O)NR^{c2}$, $S(O)_2$, and $S(O)_2NR^{c2}$, wherein said $C_{1-4}$ alkylenyl is optionally substituted by 1, 2, 3, 4, 5, 6, 7, or 8 substituents each independently selected from halo, CN, $C_{1-6}$ alkyl, $C_{1-6}$ haloalkyl, OH, $C_{1-6}$ alkoxy, $C_{1-6}$ haloalkoxy, $NH_2$, $NH(C_{1-4}$ alkyl), and $N(C_{1-4}$ alkyl$)_2$;

$R^{a1}$, $R^{b1}$, $R^{c1}$, and $R^{d1}$ are each, independently, selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from $C_{1-6}$ alkyl, halo, CN, $Cy^6$, $-L^{b2}-Cy^6$, $OR^{a2}$, $SR^{a2}$, $SF_5$, $C(O)R^{b2}$, $C(O)NR^{c2}R^{d2}$, $C(S)R^{b2}$, $C(S)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(S)R^{b2}$, $NR^{c2}C(S)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from $C_{1-6}$ alkyl, $C_{1-6}$ haloalkyl, halo, CN, $Cy^6$, $-L^{b2}-Cy^6$, $OR^{a2}$, $SR^{a2}$, $SF_5$, $C(O)R^{b2}$, $C(O)NR^{c2}R^{d2}$, $C(S)R^{b2}$, $C(S)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(S)R^{b2}$, $NR^{c2}C(S)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{e1}$ is, independently, H, $C_{1-6}$ alkyl, $C_{1-6}$ haloalkyl, $C_{2-6}$ alkenyl, $(C_{1-6}$ alkoxy$)-C_{1-6}$ alkyl, $C_{2-6}$ alkynyl, aryl, cycloalkyl, heteroaryl, heterocycloalkyl, arylalkyl, cycloalkylalkyl, heteroarylalkyl, or heterocycloalkylalkyl;

each $R^{f1}$ is, independently, H, $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl;

$R^{a2}$, $R^{b2}$, $R^{c2}$, and $R^{d2}$ are each, independently, selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^a$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents independently selected from OH, CN, amino, halo, $C_{1-6}$ alkyl, $C_{1-6}$ haloalkyl, $C_{1-6}$ hydroxyalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

each $R^b$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, CN, amino, halo, $C_{1-6}$ alkyl, $C_{1-6}$ haloalkyl, $C_{1-6}$ hydroxyalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^c$ and $R^d$ are independently selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents independently selected from OH, CN, amino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^c$ and $R^d$ together with the N atom to which they are attached form a 4-, 5-, 6- or 7-membered heterocycloalkyl group that is optionally substituted with 1, 2, 3, 4, or 5 substituents independently selected from OH, CN, amino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl; and $R^e$ and $R^f$ are each, independently, selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted by OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, or heterocycloalkyl;

$R^g$, $R^{g1}$, and $R^{g2}$ are each, independently, H, CN, or $NO_2$;
each p1 is, independently, 0, 1, or 2;
each p2 is, independently, 0, 1, or 2;
each p3 is, independently, 0, 1, or 2;
each p4 is, independently, 0, 1, or 2;
each q1 is, independently, 1 or 2;
each q2 is, independently, 1 or 2;
each n is, independently, 1, 2, or 3;
each m is, independently, 0, 1, or 2; and
t is 1, 2, 3, or 4.

2. The compound of claim 1, or pharmaceutically acceptable salt thereof or quaternary ammonium salt thereof, wherein $X^2$ is N.

3. The compound of claim 1, or pharmaceutically acceptable salt thereof or quaternary ammonium salt thereof, wherein $X^3$ is $CR^3$.

4. The compound of claim 1, or pharmaceutically acceptable salt thereof or quaternary ammonium salt thereof, wherein $X^3$ is C-halo.

5. The compound of claim 1, or pharmaceutically acceptable salt thereof or quaternary ammonium salt thereof, wherein $X^3$ is C—Cl.

6. The compound of claim 1, or pharmaceutically acceptable salt thereof or quaternary ammonium salt thereof, wherein $X^1$ is $CR^1$; $X^2$ is N; and $X^3$ is $CR^3$.

7. The compound of claim 1, or pharmaceutically acceptable salt thereof or quaternary ammonium salt thereof, wherein $L^1$ and $L^2$ are each, independently, selected from a bond, —$(CR^7R^8)_n$—, —O—$(CR^7R^8)_m$—$CR^{10}$=, —S—$(CR^7R^8)_m$—$CR^{10}$=, —$(CR^7R^8)_m$—$CR^{10}$=, —$(CR^7R^8)_m$—$NR^9$—, —$(CR^7R^8)_m$—O—, —$(CR^7R^8)_m$—S—, —$(CR^7R^8)_m$—S(O)—, —$(CR^7R^8)_m$—S(O)$_2$—, —$(CR^7R^8)_m$—C(O)—, —C(O)$NR^9$—, —$(CR^7R^8)_m$—C(O)O—, —$(CR^7R^8)_m$—$NR^9$C(O)$NR^9$—, —$(CR^7R^8)_m$—OC(O)$NR^9$—, —$(CR^7R^8)_m$—$NR^9$C(O)O—, —$(CR^7R^8)_m$—$NR^9$—S(O)$_2$$NR^9$—, —$(CR^7R^8)_m$—S(O)$NR^9$—, and —$(CR^7R^8)_m$—S(O)$_2$$NR^9$—.

8. The compound of claim 1, or pharmaceutically acceptable salt thereof or quaternary ammonium salt thereof, wherein $L^1$ and $L^2$ together form —$(CR^7R^8)_m$—$CR^{10}CR^{10}$—$(CR^7R^8)_m$— or —$(CR^7R^8)_m$—$(CR^7R^8)_n$—.

9. The compound of claim 1, or pharmaceutically acceptable salt thereof or quaternary ammonium salt thereof, wherein $L^1$ and $L^2$ together form —$(CR^7R^8)$—, —$(CR^7R^8)_2$—, or —$(CR^7R^8)_3$—.

10. The compound of claim 1, or pharmaceutically acceptable salt thereof or quaternary ammonium salt thereof, wherein $L^1$ and $L^2$ together form —$CH_2$—, —$(CH_2)_2$—, or —$(CH_2)_3$—.

11. The compound of claim 1, or pharmaceutically acceptable salt thereof or quaternary ammonium salt thereof, wherein one of $L^1$ and $L^2$ is selected from —$(CR^7R^8)_m$—O—, —$(CR^7R^8)_m$—S—, —$(CR^7R^8)_m$—S(O)—, and —$(CR^7R^8)_m$—S(O)$_2$—; and the other is selected from a bond, —$(CR^7R^8)_n$—, —$(CR^7R^8)_m$—O—, —$(CR^7R^8)_m$—S—, —$(CR^7R^8)_m$—S(O)—, and —$(CR^7R^8)_m$—S(O)$_2$—.

12. The compound of claim 1, or pharmaceutically acceptable salt thereof or quaternary ammonium salt thereof, wherein:

$L^1$ and $L^2$ together form —$(CR^7R^8)_{t1}$—S—, —$(CR^7R^8)_{t1}$—O—, —$(CR^7R^8)_{t1}$—S(O)—, —$(CR^7R^8)_{t1}$—S(O)$_2$—, —S—$(CR^7R^8)_{t2}$—S—, —O—$(CR^7R^8)_{t2}$—S—, —O—$(CR^7R^8)_{t2}$—S(O)—, —O—$(CR^7R^8)_{t2}$—S(O)$_2$—, —S—S—, —$(CR^7R^8)_{t3}$—O—$(CR^7R^8)_{t4}$—, —$(CR^7R^8)_{t3}$—S—$(CR^7R^8)_{t4}$—, —$(CR^7R^8)_{t3}$—S(O)—$(CR^7R^8)_{t4}$—, or —$(CR^7R^8)_{t3}$—S(O)$_2$—$(CR^7R^8)_{t4}$—;

t1 is 1, 2, or 3;
t2 is 1 2, 3, or 4;
t3 is 1, 2, or 3; and
t4 is 1 or 2.

13. The compound of claim 1, or pharmaceutically acceptable salt thereof or quaternary ammonium salt thereof, wherein $L^1$ and $L^2$ together form —O—$(CR^7R^8)$—, —O—$(CR^7R^8)_2$—, or —O—$(CR^7R^8)_3$—.

14. The compound of claim 1, or pharmaceutically acceptable salt thereof or quaternary ammonium salt thereof, wherein $L^1$ and $L^2$ together form —O—$CH_2$—, —O—$(CH_2)_2$—, or —O—$(CH_2)_3$—.

15. The compound of claim 1, or pharmaceutically acceptable salt thereof or quaternary ammonium salt thereof, wherein $L^1$ is —$(CR^7R^8)$—, —$(CR^7R^8)_2$—, or —$(CR^7R^8)_3$—; and $L^2$ is —O—.

16. The compound of claim 1, or pharmaceutically acceptable salt thereof or quaternary ammonium salt thereof, wherein $L^1$ and $L^2$ together form —O—$(CR^7R^8)$—O—, —O—$(CR^7R^8)_2$—O—, or —O—$(CR^7R^8)_3$—O—.

17. The compound of claim 1, or pharmaceutically acceptable salt thereof or quaternary ammonium salt thereof, wherein $L^1$ and $L^2$ together form —$(CH_2)$—S—, —$(CH_2)$—S(O)—, —$(CH_2)$—S(O)$_2$—, —$(CH_2)$—O—, —$(CH_2)_2$—O—, —$(CH_2)_3$—O—, —O—$(CH_2)_2$—O—, —O—$(CH_2)_2$—S—, —O—$(CH_2)_2$—S(O)—, or —O—$(CH_2)_2$—S(O)$_2$—.

18. The compound of claim 1, or pharmaceutically acceptable salt thereof or quaternary ammonium salt thereof, wherein one of $L^1$ and $L^2$ is selected from —$(CR^7R^8)_m$—$NR^9$—, —$(CR^7R^8)_m$—S(O)$_2$—, —$(CR^7R^8)_m$—C(O)—, —C(O)$NR^9$—, —$(CR^7R^8)_m$—$NR^9$C(O)$NR^9$—, —$(CR^7R^8)_m$—OC(O)$NR^9$—, —$(CR^7R^8)_m$—$NR^9$C(O)O—, —$(CR^7R^8)_m$—$NR^9$—S(O)$_2$$NR^9$—, —$(CR^7R^8)_m$—S(O)

NR$^9$—, and —(CR$^7$R$^8$)$_m$—S(O)$_2$NR$^9$—; and the other is selected from a bond, —(CR$^7$R$^8$)$_n$—, —(CR$^7$R$^8$)$_m$—NR$^9$—, —(CR$^7$R$^8$)$_m$—S(O)$_2$—, —(CR$^7$R$^8$)$_m$—C(O)—, —C(O)NR$^9$—, —(CR$^7$R$^8$)$_m$—S(O)NR$^9$—, and —(CR$^7$R$^8$)$_m$—S(O)$_2$NR$^9$—.

19. The compound of claim 1, or pharmaceutically acceptable salt thereof or quaternary ammonium salt thereof, wherein L$^1$ and L$^2$ together form —(CR$^7$R$^8$)$_2$—C(O)—, —C(O)NR$^9$—(CR$^7$R$^8$)—, —C(O)NR$^9$—, —(CR$^7$R$^8$)—S(O)$_2$NR$^9$—, —S(O)$_2$NR$^9$—(CR$^7$R$^8$)—, or —S(O)$_2$NR$^9$—.

20. The compound of claim 1, or pharmaceutically acceptable salt thereof or quaternary ammonium salt thereof, wherein L$^1$ and L$^2$ together form —C(O)NH— or —S(O)$_2$NH—.

21. The compound of claim 1, or pharmaceutically acceptable salt thereof or quaternary ammonium salt thereof, wherein R$^1$ and R$^3$ are each, independently, selected from H, halo, C$_{1-3}$ alkyl, and C$_{1-3}$ haloalkyl.

22. The compound of claim 1, or pharmaceutically acceptable salt thereof or quaternary ammonium salt thereof, wherein R$^1$ is selected from H and C$_{1-3}$ alkyl; and R$^3$ is selected from halo, C$_{1-3}$ alkyl, and C$_{1-3}$ haloalkyl.

23. The compound of claim 1, or pharmaceutically acceptable salt thereof or quaternary ammonium salt thereof, wherein R$^1$ is H; and R$^3$ is selected from halo and C$_{1-3}$ alkyl.

24. The compound of claim 1, or pharmaceutically acceptable salt thereof or quaternary ammonium salt thereof, wherein R$^1$ is H; and R$^3$ is halo.

25. The compound of claim 1, or pharmaceutically acceptable salt thereof or quaternary ammonium salt thereof, wherein each R$^2$ is, independently, selected from H, F, Cl, CH$_3$, and CF$_3$.

26. The compound of claim 1, or pharmaceutically acceptable salt thereof or quaternary ammonium salt thereof, wherein each R$^2$ is H.

27. The compound of claim 1, or pharmaceutically acceptable salt thereof or quaternary ammonium salt thereof, wherein R$^4$ is H or C$_{1-6}$ alkyl.

28. The compound of claim 1, or pharmaceutically acceptable salt thereof or quaternary ammonium salt thereof, wherein R$^4$ is H.

29. The compound of claim 1, or pharmaceutically acceptable salt thereof or quaternary ammonium salt thereof, wherein each R$^5$ is, independently, selected from H, halo, C$_{1-6}$ alkyl, C$_{1-6}$ haloalkyl, Cy$^1$, —W$^1$-Q$^1$-Y$^1$—Z$^1$, CN, NO$_2$, SF$_5$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)NR$^{c1}$R$^{d1}$, S(O)R$^{b1}$, S(O)$_2$R$^{b1}$, NR$^{c1}$S(O)$_2$NR$^{c1}$R$^{d1}$, NR$^{c1}$S(O)$_2$R$^{b1}$, and S(O)$_2$NR$^{c1}$R$^{d1}$, wherein each of said C$_{1-6}$ alkyl, C$_{2-6}$ alkenyl, C$_{2-6}$ alkynyl, or C$_{1-6}$ haloalkyl is optionally substituted by 1, 2, 3, 4, or 5 substituents each independently selected from halo, C$_{1-6}$ alkyl, C$_{2-6}$ alkenyl, C$_{2-6}$ alkynyl, C$_{1-6}$ haloalkyl, halosulfanyl, Cy$^1$, —W$^1$-Q$^1$-Y$^1$—Z$^1$, CN, NO$_2$, SF$_5$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^1$.

30. The compound of claim 1, or pharmaceutically acceptable salt thereof or quaternary ammonium salt thereof, wherein each R$^5$ is, independently, selected from H, halo, C$_{1-6}$ alkyl, C$_{1-6}$ haloalkyl, CN, NO$_2$, SF$_5$, OR$^{a1}$, C(O)R$^{b1}$, C(O)NR$^{c1}$R$^{d1}$, C(O)OR$^{a1}$, NR$^{c1}$R$^{d1}$, NR$_{c1}$C(O)R$^{b1}$, NR$^{c1}$C(O)NR$^{c1}$R$^{d1}$, NR$^{c1}$S(O)$_2$NR$^{c1}$R$^{d1}$, S(O)R$^{b1}$, S(O)$_2$R$^{b1}$, NR$^{c1}$S(O)$_2$R$^{b1}$, and S(O)$_2$NR$^{c1}$R$^{d1}$.

31. The compound of claim 1, or pharmaceutically acceptable salt thereof or quaternary ammonium salt thereof, wherein:
each R$^5$ is, independently, selected from H, halo, C$_{1-6}$ alkyl, C$_{2-6}$ alkenyl, C$_{2-6}$ alkynyl, C$_{1-6}$ haloalkyl, Cy$^1$, —W$^1$-Q$^1$-Y$^1$—Z$^1$, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)NR$^{c1}$R$^{d1}$, NR$^{c1}$S(O)$_2$NR$^{c1}$R$^{d1}$, S(O)$_2$R$^{b1}$, NR$^{c1}$S(O)$_2$R$^{b1}$, and S(O)$_2$NR$^{c1}$R$^{d1}$, wherein each of said C$_{1-6}$ alkyl, C$_{2-6}$ alkenyl, C$_{2-6}$ alkynyl, or C$_{1-6}$ haloalkyl, is optionally substituted by 1, 2, 3, 4 or 5 substituents each independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, SF$_5$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$;

R$^{a1}$, R$^{b1}$, R$^{c1}$, and R$^{d1}$ are each, independently, selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, C$_{1-4}$ alkyl, C$_{1-4}$ haloalkyl, C$_{1-4}$ hydroxylalkyl, C$_{1-4}$ cyanoalkyl, aryl, cycloalkyl, heteroaryl, heterocycloalkyl, CN, NO$_2$, OH, SH, O(C$_{1-4}$ alkyl), O(C$_{1-4}$ haloalkyl), O(aryl), O(arylalkyl), S(C$_{1-4}$ alkyl), S(C$_{1-4}$ haloalkyl), S(aryl), S(arylalkyl), amino, C$_{1-4}$ alkylamino, C$_{2-8}$ dialkylamino, C(=O)H, C(=O)—(C$_{1-4}$ alkyl), C(=O)-(arylalkyl), C(=O)NH$_2$, C(=O)NH(C$_{1-4}$ alkyl), C(=O)N(C$_{1-4}$ alkyl)$_2$, C(=O)OH, C(=O)O—(C$_{1-4}$ alkyl), C(=O)O-(arylalkyl), OC(=O)H, OC(=O)—(C$_{1-4}$ alkyl), OC(=O)-(arylalkyl), OC(=O)NH$_2$, OC(=O)NH(C$_{1-4}$ alkyl), OC(=O)NH-(arylalkyl), OC(=O)N(C$_{1-4}$ alkyl)$_2$, NHC(=O)—(C$_{1-4}$ alkyl), NHC(=O)O-(arylalkyl), NHC(=O)O—(C$_{1-4}$ alkyl), NHC(=O)O-(arylalkyl), NHS(=O)$_2$—(C$_{1-4}$ alkyl), NHS(=O)$_2$-(arylalkyl), NHS(=O)$_2$—NH(C$_{1-4}$ alkyl), NHS(=O)$_2$—N(C$_{1-4}$ alkyl)$_2$, NHS(=O)$_2$—NH (arylalkyl), S(=O)$_2$—(C$_{1-4}$ alkyl), S(=O)$_2$-(arylalkyl), S(=O)$_2$NH$_2$, S(=O)$_2$NH(C$_{1-4}$ alkyl), and S(=O)$_2$NH (arylalkyl);

or R$^{c1}$ and R$^{d1}$ together with the N atom to which they are attached form a 4-, 5-, 6- or 7-membered heterocycloalkyl group or heteroaryl group, each optionally substituted with 1, 2, or 3 substituents independently selected from halo, C$_{1-4}$ alkyl, C$_{1-4}$ haloalkyl, C$_{1-4}$ hydroxylalkyl, C$_{1-4}$ cyanoalkyl, aryl, cycloalkyl, heteroaryl, heterocycloalkyl, CN, NO$_2$, OH, SH, O(C$_{1-4}$ alkyl), O(C$_{1-4}$ haloalkyl), O(aryl), O(arylalkyl), S(C$_{1-4}$ alkyl), S(C$_{1-4}$ haloalkyl), S(aryl), S(arylalkyl), amino, C$_{1-4}$ alkylamino, C$_{2-8}$ dialkylamino, C(=O)H, C(=O)—(C$_{1-4}$ alkyl), C(=O)-(arylalkyl), C(=O)NH$_2$, C(=O)NH(C$_{1-4}$ alkyl), C(=O)N(C$_{1-4}$ alkyl)$_2$, C(=O)OH, C(=O)O—(C$_{1-4}$ alkyl), C(=O)O-(arylalkyl), OC(=O)H, OC(=O)—(C$_{1-4}$ alkyl), OC(=O)-(arylalkyl), OC(=O)NH$_2$, OC(=O)NH(C$_{1-4}$ alkyl), OC(=O)NH-(arylalkyl), OC(=O)N(C$_{1-4}$ alkyl)$_2$, NHC(=O)—(C$_{1-4}$ alkyl), NHC(=O)O-(arylalkyl), NHC(=O)O—(C$_{1-4}$ alkyl), NHC(=O)O-(arylalkyl), NHS(=O)$_2$—(C$_{1-4}$ alkyl), NHS(=O)$_2$-(arylalkyl), NHS(=O)$_2$—NH(C$_{1-4}$ alkyl), NHS(=O)$_2$—N(C$_{1-4}$ alkyl)$_2$, NHS(=O)$_2$—NH(arylalkyl), S(=O)$_2$—(C$_{1-4}$ alkyl), S(=O)$_2$-(arylalkyl), S(=O)$_2$NH$_2$, S(=O)$_2$NH(C$_{1-4}$ alkyl), and S(=O)$_2$NH(arylalkyl).

32. The compound of claim 1, or pharmaceutically acceptable salt thereof or quaternary ammonium salt thereof, wherein at least one R$^5$ is Cy$^1$.

33. The compound of claim 1, or pharmaceutically acceptable salt thereof or quaternary ammonium salt thereof, wherein at least one R$^5$ is —W$^1$-Q$^1$-Y$^1$—Z$^1$.

34. The compound of claim 1, or pharmaceutically acceptable salt thereof or quaternary ammonium salt thereof, wherein at least one R$^5$ is —(CR$^{11a}$R$^{11b}$)$_{p1}$O(CR$^{11a}$R$^{11b}$)$_{p2}$-Q$^1$-Y$^1$—Z$^1$, —(CR$^{11a}$R$^{11b}$)$_{p1}$S(CR$^{11a}$R$^{11b}$)$_{p2}$-Q$^1$-Y$^1$—Z$^1$, —(CR$^{11a}$R$^{11b}$)$_{p1}$S(O)(CR$^{11a}$R$^{11b}$)$_{p2}$-Q$^1$-Y$^1$—Z$^1$, —(CR$^{11a}$R$^{11b}$)$_{p1}$S(O)$_2$(CR$^{11a}$R$^{11b}$)$_{p2}$-Q$^1$-Y$^1$—Z$^1$, —(CR$^{11a}$R$^{11b}$)$_{p1}$NR$^e$(CR$^{11a}$R$^{11b}$)$_{p2}$-Q$^1$-Y$^1$—Z$^1$, NR$^e$S(O)(CR$^{11a}$R$^{11b}$)$_{p1}$-Q$^1$-Y$^1$—Z$^1$, —S(O)NR$^e$(CR$^{11a}$R$^{11b}$)$_{p2}$-Q$^1$-Y$^1$—Z$^1$, —NR$^e$S(O)$_2$(CR$^{11a}$R$^{11b}$)$_{p1}$-Q$^1$-Y$^1$—Z$^1$, —S(O)$_2$NR$^e$(CR$^{11a}$R$^{11b}$)$_{p2}$-Q$^1$-Y$^1$—Z$^1$, —NR$^e$C(O)(CR$^{11a}$R$^{11b}$)$_{p1}$-Q$^1$-Y$^1$—Z$^1$, —C(O)NR$^e$(CR$^{11a}$R$^{11b}$)$_{p2}$-Q$^1$-Y$^1$—Z$^1$, or —NR$^e$C(O)NR$^f$(CR$^{11a}$R$^{11b}$)$_{p2}$-Q$^1$-Y$^1$—Z$^1$.

35. The compound of claim 1, or pharmaceutically acceptable salt thereof or quaternary ammonium salt thereof, wherein at least one R$^5$ is —W$^6$-Q$^1$-Y$^1$—Z$^1$.

36. The compound of claim 33, or pharmaceutically acceptable salt thereof or quaternary ammonium salt thereof, wherein each Y$^1$ is independently selected from absent, (CR$^{12a}$R$^{12b}$)$_{p3}$O(CR$^{12a}$R$^{12b}$)$_{p4}$, (CR$^{12a}$R$^{12b}$)$_{p3}$S(CR$^{12a}$R$^{12b}$)$_{p4}$, (CR$^{12a}$R$^{12b}$)$_{p3}$NR$^e$(CR$^{12a}$R$^{12b}$)$_{p4}$, (CR$^{12a}$R$^{12b}$)$_{p3}$C(O)(CR$^{12a}$R$^{12b}$)$_{p4}$, (CR$^{12a}$R$^{12b}$)$_{p3}$C(O)NR$^e$(CR$^{12a}$R$^{12b}$)$_{p4}$, (CR$^{12a}$R$^{12b}$)$_{p3}$S(O)(CR$^{12a}$R$^{12b}$)$_{p4}$, (CR$^{12a}$R$^{12b}$)$_{p3}$S(O)$_2$NR$^e$(CR$^{12a}$R$^{12b}$)$_{p4}$, and (CR$^{12a}$R$^{12b}$)$_{p3}$NR$^e$C(O)NR$^f$(CR$^{12a}$R$^{12b}$)$_{p4}$.

37. The compound of claim 33, or pharmaceutically acceptable salt thereof or quaternary ammonium salt thereof, wherein each Z$^1$ is independently selected from aryl, cycloalkyl, heteroaryl and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

38. The compound of claim 1, or pharmaceutically acceptable salt thereof or quaternary ammonium salt thereof, wherein R$^7$, R$^8$, and R$^{10}$ are each, independently, selected from H, halo, C$_{1-6}$ alkyl, C$_{2-6}$ alkenyl, C$_{2-6}$ alkynyl, C$_{1-6}$ haloalkyl, cycloalkyl, CN, NO$_2$, OR$^{a1}$, SR$^{a1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, C(O)R$^{b1}$, C(O)NR$^{c1}$R$^{d1}$, C(O)OR$^{a1}$, NR$^{c1}$C(O)R$^{b1}$, NR$^{c1}$C(O)NR$^{c1}$R$^{d1}$, and NR$^{c1}$R$^{d1}$, wherein each of said C$_{1-6}$ alkyl, C$_{2-6}$ alkenyl, C$_{2-6}$ alkynyl, C$_{1-6}$ haloalkyl and cycloalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, cycloalkyl, CN, NO$_2$, OR$^{a1}$, SR$^{a1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, C(O)R$^{b1}$, C(O)NR$^{c1}$R$^{d1}$, C(O)OR$^{a1}$, NR$^{c1}$C(O)R$^{b1}$, NR$^{c1}$C(O)NR$^{c1}$R$^{d1}$, and NR$^{c1}$R$^{d1}$.

39. The compound of claim 1, or pharmaceutically acceptable salt thereof or quaternary ammonium salt thereof, wherein R$^7$, R$^8$, and R$^{10}$ are each, independently, selected from H, halo, C$_{1-6}$ alkyl, C$_{1-6}$ haloalkyl, CN, NO$_2$, OR$^{a1}$, and SR$^{a1}$.

40. The compound of claim 1, or pharmaceutically acceptable salt thereof or quaternary ammonium salt thereof, wherein R' and R" are each, independently, selected from H, C$_{1-4}$ alkyl, and C$_{1-4}$ haloalkyl.

41. The compound of claim 1, or pharmaceutically acceptable salt thereof or quaternary ammonium salt thereof, wherein R' and R" are each, independently, selected from H and C$_{1-4}$ alkyl.

42. The compound of claim 1, or pharmaceutically acceptable salt thereof or quaternary ammonium salt thereof, wherein R' and R" are each, independently, selected from H and methyl.

43. The compound of claim 1, or pharmaceutically acceptable salt thereof or quaternary ammonium salt thereof, wherein at least one of R' and R" is methyl.

44. The compound of claim 1, or pharmaceutically acceptable salt thereof or quaternary ammonium salt thereof, wherein R' and R" are each H.

45. The compound of claim 1, or pharmaceutically acceptable salt thereof or quaternary ammonium salt thereof, wherein each n is, independently, 1 or 2.

46. The compound of claim 1, or pharmaceutically acceptable salt thereof or quaternary ammonium salt thereof, wherein each m is, independently, 0 or 1.

47. The compound of claim 1, or pharmaceutically acceptable salt thereof or quaternary ammonium salt thereof, wherein t is 1.

48. The compound of claim 1, or pharmaceutically acceptable salt thereof or quaternary ammonium salt thereof, wherein t is 2.

49. The compound of claim 1, or pharmaceutically acceptable salt thereof or quaternary ammonium salt thereof, wherein t is 3.

50. The compound of claim 1, or pharmaceutically acceptable salt thereof or quaternary ammonium salt thereof, wherein —(CR'R")$_t$— is —CH$_2$—, —CH(CH$_3$)—, —(CH$_2$)$_2$—, or —(CH$_2$)$_3$—.

51. The compound of claim 1 or pharmaceutically acceptable salt thereof or quaternary ammonium salt thereof, wherein each R$^5$ is, independently, selected from H, halo, C$_{1-6}$ alkyl, C$_{1-6}$ haloalkyl, CN, NO$_2$, SF$_5$, Cy$^1$, —W$^1$-Q$^1$-Y$^1$—Z$^1$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$S(O)$_2$R$^{b1}$, NR$^{c1}$C(O)NR$^{c1}$R$^{d1}$, NR$^{c1}$S(O)$_2$NR$^{c1}$R$^{d1}$, S(O)R$^{b1}$, S(O)$_2$R$^{b1}$, and S(O)$_2$NR$^{c1}$R$^{d1}$.

52. The compound of claim 1, or pharmaceutically acceptable salt thereof or quaternary ammonium salt thereof, wherein:
each R$^5$ is, independently, H, Cy$^1$, halo, C$_{1-6}$ alkyl, C$_{2-6}$ alkenyl, C$_{2-6}$ alkynyl, C$_{1-6}$ haloalkyl, halosulfanyl, CN, NO$_2$, SF$_5$, OR$^{a1}$, SR$^{a1}$, C(O)R$^{b1}$, C(O)NR$^{c1}$R$^{d1}$, C(S)R$^{b1}$, C(S)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(S)R$^{b1}$, NR$^{c1}$C(S)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, or —W$^1$-Q$^1$-Y$^1$—Z$^1$;
or two adjacent R$^5$ on the same ring link to form a fused cycloalkyl or fused heterocycloalkyl group, each optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, arylalkyl, heteroarylalkyl, cycloalkylalkyl, heterocycloalkylalkyl, halosulfanyl, Cy$^1$, CN, NO$_2$, OR$^{a1}$, C(O)R$^{b1}$, C(O)NR$^{c1}$R$^{d1}$, C(S)R$^{b1}$, C(S)NR$^{c1}$R$^{d1}$, C(O)OR$^{a1}$, OC(O)R$^{b1}$, —W$^1$-Q$^1$-Y$^1$—Z$^1$, OC(O)NR$^{c1}$R$^{d1}$, NR$^{c1}$R$^{d1}$, NR$^{c1}$C(O)R$^{b1}$.

53. The compound of claim 1, or pharmaceutically acceptable salt thereof or quaternary ammonium salt thereof, wherein at least one R$^5$ is —W$^1$-Q$^1$-Y$^1$—Z$^1$.

54. The compound of claim 1, or pharmaceutically acceptable salt thereof or quaternary ammonium salt thereof, wherein R$^1$ is H; X$_3$ is —CR$^3$; and R$^4$ is H.

55. The compound of claim 54, or pharmaceutically acceptable salt thereof or quaternary ammonium salt thereof, wherein:

each $R^5$ is, independently, H, $Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, OR $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, or —$W^1$-$Q^1$-$Y^1$—$Z^1$;

or two adjacent $R^5$ on the same ring link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, halosulfanyl, $Cy^1$, CN, $NO_2$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, —$W^1$-$Q^1$-$Y^1$—$Z^1$, $OC(O)NR^{c1}R^{d1}$, $NR^{c1}R^{d1}$, $NR^{c1}C(O)R^{b1}$.

56. The compound of claim 54, or pharmaceutically acceptable salt thereof or quaternary ammonium salt thereof, wherein at least one $R^5$ is —$W^1$-$Q^1$-$Y^1$—$Z^1$.

57. The compound of claim 1, or pharmaceutically acceptable salt thereof or quaternary ammonium salt thereof, wherein $R^1$ is selected from H and $C_{1-3}$ alkyl;

each $R^2$ is, independently, selected from H, F, Cl, $CH_3$, and $CF_3$;

$R^3$ is selected from halo, $C_{1-3}$ alkyl, and $C_{1-3}$ haloalkyl;

$R^4$ is H or methyl;

R' and R" are each, independently, H or methyl; and t is 1, 2, or 3.

58. The compound of claim 1, or pharmaceutically acceptable salt thereof or quaternary ammonium salt thereof, wherein $R^1$ is selected from H and methyl;

each $R^2$ is H;

$R^3$ is halo;

$R^4$ is H or methyl;

R' and R" are each, independently, H or methyl; and t is 1, 2, or 3.

59. A compound selected from:

6-Chloro-15-oxa-2,4,8,23-tetraazatetracyclo[15.3.1.1(3,7).1(10,14)]tricosa-1(21),3(23),4,6,10(22),11,13,17,19-nonaene;

6-Chloro-15-oxa-2,4,8,24-tetraazatetracyclo[16.3.1.1(3,7).1(10,14)]tetracosa-1(22),3(24),4,6,10(23),11,13,18,20-nonaene;

6-Chloro-16-thia-2,4,8,15,23-pentaazatetracyclo[15.3.1.1(3,7).1(10,14)]tricosa-1(21),3(23),4,6,10(22),11,13,17,19-nonaene 16,16-dioxide;

6-Chloro-2,4,8,15,23-pentaazatetracyclo [15.3.1.1(3,7).1(10,14)]tricosa-1(21),3(23),4,6,10(22),11,13,17,19-nonaen-16-one;

6-Chloro-15-oxa-2,4,8,25-tetraazatetracyclo[17.3.1.1(3,7).1(10,14)]pentacosa-1(23),3(25),4,6,10(24),11,13,19,21-nonaene;

(9R)-6-Chloro-9-methyl-15-oxa-2,4,8,23-tetraazatetracyclo [15.3.1.1(3,7).1(10,14)]tricosa-1(21),3 (23),4,6,10(22),11,13,17,19-nonaene;

6-Chloro-15,18-dioxa-2,4,8,25-tetraazatetracyclo [17.3.1.1(3,7).1(10,14)]pentacosa-1(23),3(25),4,6,10(24),11,13,19,21-nonaene;

19-Chloro-9-oxa-2,17,21,22-tetraazatetracyclo[16.3.1.1(3,7).1(10,14)]tetracosa-1(22),3(24),4,6,10(23),11,13,18,20-nonaene;

6-Chloro-16-oxa-2,4,8,25-tetraazatetracyclo[17.3.1.1(3,7).1(11,15)]pentacosa-1(23),3(25),4,6,11(24),12,14,19,21-nonaene;

20-Chloro-9-oxa-2,18,22,23-tetraazatetracyclo[17.3.1.1(3,7).1(10,14)]pentacosa-1(23),3(25),4,6,10(24),11,13,19,21-nonaene;

6-Chloro-16-oxa-2,4,8,26-tetraazatetracyclo[18.3.1.1(3,7).1(11,15)]hexacosa-1(24),3(26),4,6,11(25),12,14,20,22-nonaene;

21-Chloro-10-oxa-2,19,23,24-tetraazatetracyclo[18.3.1.1(3,7).1(11,15)]hexacosa-1(24),3(26),4,6,11(25),12,14,20,22-nonaene 11-Bromo-6-chloro-15-oxa-2,4,8,25-tetraazatetracyclo [17.3.1.1(3,7).1(10,14)]pentacosa-1(23),3(25),4,6,10(24),11,13,19,21-nonaene;

6-Chloro-11-phenyl-15-oxa-2,4,8,25-tetraazatetracyclo [17.3.1.1(3,7).1(10,14)]pentacosa-1(23),3(25),4,6,10(24),11,13,19,21-nonaene;

12-Bromo-6-chloro-15-oxa-2,4,8,25-tetraazatetracyclo [17.3.1.1(3,7).1(10,14)]pentacosa-1(23),3(25),4,6,10(24),11,13,19,21-nonaene; and or pharmaceutically acceptable salt thereof or quaternary ammonium salt thereof.

60. A composition comprising a compound according to claim 1, or pharmaceutically acceptable salt thereof or quaternary ammonium salt thereof, and at least one pharmaceutically acceptable carrier.

61. The compound of claim 1, wherein $X^2$ is N and $X^3$ is $CR^3$.

62. The compound of claim 1, wherein $X^2$ is N, $R^1$ is H and $X^3$ is $CR^3$.

63. The compound of claim 54, wherein $X^2$ is N.

64. The compound of claim 63, wherein $L_1$-$L_2$ is —$CH_2$—$CH_2$—.

* * * * *